US011084812B2

(12) United States Patent
Castro et al.

(10) Patent No.: US 11,084,812 B2
(45) Date of Patent: *Aug. 10, 2021

(54) RAD51 INHIBITORS

(71) Applicant: Cyteir Therapeutics, Inc., Lexington, MA (US)

(72) Inventors: Alfredo C. Castro, Woburn, MA (US); Casey Cameron McComas, Phoenixville, PA (US); Joseph Vacca, Telford, PA (US); Tyler Maclay, Somerville, MA (US)

(73) Assignee: Cyteir Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,566

(22) Filed: Jan. 6, 2020

(65) Prior Publication Data
US 2020/0216437 A1   Jul. 9, 2020

Related U.S. Application Data

(62) Division of application No. 16/127,229, filed on Sep. 11, 2018, now Pat. No. 10,590,122.

(60) Provisional application No. 62/711,959, filed on Jul. 30, 2018, provisional application No. 62/556,763, filed on Sep. 11, 2017.

(51) Int. Cl.
| | |
|---|---|
| *C07D 417/14* | (2006.01) |
| *C07D 277/28* | (2006.01) |
| *C07D 277/42* | (2006.01) |
| *A61P 37/00* | (2006.01) |
| *A61K 31/426* | (2006.01) |
| *A61P 37/02* | (2006.01) |
| *A61P 25/28* | (2006.01) |
| *A61P 35/00* | (2006.01) |
| *C07D 277/30* | (2006.01) |
| *C07D 417/04* | (2006.01) |
| *C07D 417/12* | (2006.01) |

(52) U.S. Cl.
CPC .......... *C07D 417/14* (2013.01); *A61K 31/426* (2013.01); *A61P 25/28* (2018.01); *A61P 35/00* (2018.01); *A61P 37/00* (2018.01); *A61P 37/02* (2018.01); *C07D 277/28* (2013.01); *C07D 277/30* (2013.01); *C07D 277/42* (2013.01); *C07D 417/04* (2013.01); *C07D 417/12* (2013.01)

(58) Field of Classification Search
CPC ..... C07D 417/14; C07D 277/28; A61P 37/00; A61P 37/02; A61P 25/28; A61P 35/00; A61K 31/426
USPC ................................................ 514/326, 365
See application file for complete search history.

(56) References Cited

U.S. PATENT DOCUMENTS

| | | |
|---|---|---|
| 5,837,832 A | 11/1998 | Chee et al. |
| 8,551,984 B2 | 10/2013 | Altman et al. |
| 10,336,746 B1 | 7/2019 | Castro et al. |
| 10,590,122 B2 | 3/2020 | Castro et al. |
| 2020/0129484 A1 | 4/2020 | Castro et al. |
| 2020/0291014 A1 | 9/2020 | Lapierre et al. |

FOREIGN PATENT DOCUMENTS

| | | |
|---|---|---|
| EP | 0834575 B1 | 11/2001 |
| EP | 0834576 B1 | 1/2002 |
| WO | WO 1996/31622 A1 | 10/1996 |
| WO | WO 1997/10365 A1 | 3/1997 |
| WO | WO 1998/30883 A2 | 7/1998 |
| WO | WO 2008/082856 A1 | 7/2008 |
| WO | WO 2014/085545 A1 | 6/2014 |
| WO | WO 2016/094897 A1 | 6/2016 |
| WO | WO 2016/140971 A1 | 9/2016 |
| WO | WO 2016/196955 A1 | 12/2016 |

OTHER PUBLICATIONS

Fei Huang et al A small molecule Inhibitor of Human RAD51 Potentiates Breast Cancer Cell killing by Therapeutic Agents in Mouse Xenografts. (Year: 2014).*
Yanning Gao et al , Sensitivity of Epstein-Barr Virus Positive Tumor Line, Daudi, to alpha interferon Correlates with Expression of a GC-rich viral Transcript (Year: 1999).*
Mariam Gachechechiadze et al. RAD51 as a potential surrogate marker for DNA repair capacity in solid malignancies. (Year: 2017).*
Borchert, G.M. et al. (2011) "Repression of human activation induced cytidine deaminase by miR-93 and miR-155" BMC Cancer, 11:347, 9 pages.
Chaudhuri, J. et al. (2004) "Class-Switch Recombination: Interplay of Transcription, DNA Deamination and DNA Repair" Nature Reviews, Immunology, 4:541-552.
Chaudhuri, J. et al. (2004) "Replication protein A interacts with AID to promote deamination of somatic hypermutation targets" Nature, 430:992-998.

(Continued)

*Primary Examiner* — Rita J Desai
(74) *Attorney, Agent, or Firm* — Cooley LLP; Matthew Pavao; Chen Chen

(57) ABSTRACT

This application is directed to inhibitors of RAD51 represented by the following structural formula,

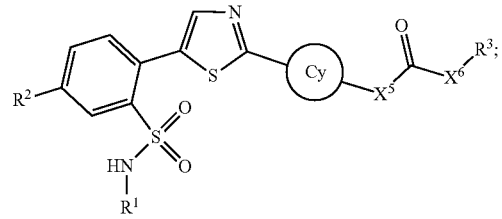

and methods for their use, such as to treat cancer, autoimmune diseases, immune deficiencies, or neurodegenerative diseases.

23 Claims, No Drawings

(56) References Cited

OTHER PUBLICATIONS

Chaudhuri, J. et al. (2007) "Evolution of the Immunoglobulin Heavy Chain Class Switch Recombination Mechanism" Advances in Immunology, 94:157-214.
Chen, C-F. et al. (1999) "Expression of BRC Repeats in Breast Cancer Cells Disrupts the BRCA2-Rad51 Complex and Leads to Radiation Hypersensitivity and Loss of G2/M Checkpoint Control" J Biol Chem, 274(46):32931-32935.
Collis, S.J. et al. (2001) "Ribozyme minigene-mediated RAD51 down-regulation increases radiosensitivity of human prostate cancer cells" Nucleic Acids Res, 29(7):1534-1538.
Connell, P.P. (2004) "A Hot Spot for RAD51C Interaction Revealed by a Peptide That Sensitizes Cells to Cisplatin" Cancer Research, 64:3002-3005.
Crouch, E.E. et al. (2007) "Regulation of AID expression in the immune response" The Journal of Experimental Medicine, 204(5):1145-1156.
Engels, K. et al. (2008) "Expression of Activation-induced Cytidine Deaminase in Malignant Lymphomas Infiltrating the Bone Marrow" Appl Immunohistochem Mol Morphol, 16(6):521-529.
Feldhahn, N. et al. (2007) "Activation-induced cytidine deaminase acts as a mutator in BCR-ABL1-transformed acute lymphoblastic leukemia cells" J Exp Med, 204:1157-1166.
Gatehouse, J. et al. (1995) "Nuclear "Run-On" Transcription Assays" in Methods in Molecular Biology, vol. 49, Plant Gene Transfer and Expression Protocols. H. Jones (Ed.) Totowa, NJ: Humana Press Inc.; Chapter 19, pp. 229-238.
Gene ID 23626 (Feb. 13, 2019) "SPO11 initiator of meiotic double stranded breaks [*Homo sapiens* (human)]" National Center for Biotechnology Information (NCBI) [online]. Retrieved from: https://www.ncbi.nlm.nih.gov/gene?cmd=Retrieve&dopt=full_report&list_uids=23626; retrieved on Feb. 25, 2019, 6 pages.
Godthelp, B.C. et al. (2002) "Mammalian Rad51C contributes to DNA cross-link resistance, sister chromatid cohesion and genomic stability" Nucleic Acids Res, 30(10):2172-2182.
Greeve, J. et al. (May 1, 2003) "Expression of activation-induced cytidine deaminase in human B-cell non-Hodgkin lymphomas" Blood, 101(9):3574-3580.
Gruber, T.A. et al. (2010) "Activation-Induced Cytidine Deaminase Accelerates Clonal Evolution in BCR-ABL1-Driven B-Cell Lineage Acute Lymphoblastic Leukemia" Cancer Res, 70:7411-7420.
Hancer, V. S. et al. (Jan. 2011) "Activation-induced cytidine deaminase mRNA levels in chronic lymphocytic leukemia" Leuk Lymphoma, 52(1):79-84.
Hansen, L.T. et al. (2003) "The Role of RAD41 in etoposide (VP16) Resistance in Small Cell Lung Cancer" Int J Cancer, 105:472-479.
Hardianti, M.S. et al. (2004) "Activation-induced cytidine deaminase expression in follicular lymphoma: association between AID expression and ongoing mutation in FL" Leukemia 18:826-831.
Heintel, D. et al. (2004) "High expression of activation-induced cytidine deaminase (AID) mRNA is associated with unmutated IGVH gene status and unfavourable cytogenetic aberrations in patients with chronic lymphocytic leukaemia" Leukemia, 18:756-762.
Hockley, S. L. et al. (2010) "Higher expression levels of activation-induced cytidine deaminase distinguish hairy cell leukemia from hairy cell leukemia-variant and splenic marginal zone lymphoma" Leukemia, 24:1084-1086.
Houllenberghs, H. et al. (May 2017) "Suspected Lynch syndrome associated MSH6 variants: A functional assay to determine their pathogenicity" PLOS Genetics, 13(5):e1006765, 18 pages.
Huang, F. et al. (2014) "A Small Molecule Inhibitor of Human RAD51 Potentiates Breast Cancer Cell Killing by Therapeutic Agents in Mouse Xenografts" PLOS ONE, 9(6):e100993, 12 pages.
Ito, M. et al. (2005) "Rad51 siRNA delivered by HVJ envelope vector enhances the anti-cancer effect of cisplatin" The Journal of Gene Medicine, 7:1044-1052.
Klemm, L. et al. (2009) "The B Cell Mutator AID Promotes B Lymphoid Blast Crisis and Dmg Resistance in Chronic Myeloid Leukemia" Cancer Cell, 16:232-245.
Komori, J. et al. (2008) "Activation-Induced Cytidine Deaminase Links Bile Duct Inflammation to Human Cholangiocarcinoma" Hepatology, 47(3):888-896.
Kotani, A. et al. (Jan. 30, 2007) "Activation-induced cytidine deaminase (AID) promotes B cell lymphomagenesis in Emu-cmyc transgenic mice" PNAS, 104(5):1616-1620.
Kovalchuk, A.L. et al. (2007) "AID-deficient Bcl-xL transgenic mice develop delayed atypical plasma cell tumors with unusual Ig/Myc chromosomal rearrangements" J Exp Med, 204(12):2989-3001.
Kumari, S. et al. (2008) "DNA Damage: Detection Strategies" EXCLI Journal, 7:44-62.
Küppers, R. et al. (2001) "Mechanisms of chromosomal translocations in B cell lymphomas" Oncogene, 20:5580-5594.
Leuenberger, M. et al. (2010) "AID protein expression in chronic lymphocytic leukemia/small lymphocytic lymphoma is associated with poor prognosis and complex genetic alterations" Modern Pathology, 23:177-186.
Liu, M. et al. (Feb. 14, 2008) "Two levels of protection for the B cell genome during somatic hypermutation" Nature, 451:841-845, including "Methods", 1 page.
Liu, M. et al. (2009) "Balancing AID and DNA repair during somatic hypermutation" Trends in Immunology, 30(4):173-181.
Liu, N. et al. (May 1998) "XRCC2 and XRCC3, New Human Rad51-Family Members, Promote Chromosome Stability and Protect against DNA Cross-Links and Other Damages" Molecular Cell, 1:783-793.
Longerich, S. et al. (2006) "AID in somatic hypermutation and class switch recombination" Curr Opin Immunol, 18:164-176.
Manis, J.P. et al. (2002) "Mechanism and control of class-switch recombination" Trends Immunol, 23(1):31-39.
Mao, X. et al. (2001) "A case of adult T-cell leukaemia/lymphoma characterized by multiplex-fluorescence in situ hybridization, comparative genomic hybridization, fluorescence in situ hybridization and cytogenetics" Br J Dermatol, 145:117-122.
Marusawa, H. (2008) "Aberrant AID expression and human cancer development" Int J Biochem Cell Biol, 40:1399-1402.
Marusawa, H. et al. (2011) "Role of Activation-Induced Cytidine Deaminase in Inflammation-Associated Cancer Development" Advances in Immunology, 111:109-141.
Mills, K.D. et al. (2003) "The role of DNA breaks in genomic instability and tumorigenesis" Immunological Reviews, 194:77-95.
Motalleb, G. et al. (Jul. 1, 2012) "Methods for DNA Strand Breaks Detection" Research Journal of Applied Sciences, Engineering and Technology, 4(13):1888-1894.
Muramatsu, M. et al. (Jun. 25, 1999) "Specific Expression of Activation-induced Cytidine Deaminase (AID), a Novel Member of the RNA-editing Deaminase Family in Germinal Center B Cells" J Biol Chem, 274(26):18470-18476.
Muto, T. et al. (Feb. 21, 2006) "Negative regulation of activation-induced cytidine deaminase in B cells" PNAS, 103(8):2752-2757.
Nakamura, M. et al. (2011) "High levels of activation-induced cytidine deaminase expression in adult T-cell leukaemia/lymphoma" Br J Dermatol, 165(2):437-439.
Ohnishi, T. et al. (1998) "In Vitro and in Vivo Potentiation of Radiosensitivity of Malignant Gliomas by Antisense Inhibition of the RAD51 Gene" Biochem Biophys Res Commun, 245:319-324.
Okazaki, I. (May 5, 2003) "Constitutive Expression of AID Leads to Tumorigenesis" The Journal of Experimental Medicine, 197(9):1173-1181.
Palacios, F. et al. (Jun. 3, 2010) "High expression of AID and active class switch recombination might account for a more aggressive disease in unmutated CLL patients: link with an activated microenvironment in CLL disease" Blood, 115(22):4488-4496.
Pasqualucci, L. et al. (Jan. 2008) "AID is required for germinal center-derived lymphomagenesis" Nature Genetics, 40(1):108-112.
Pérez-Durán, P. et al. (2007) "Oncogenic events triggered by AID, the adverse effect of antibody diversification" Carcinogenesis, 28(12):2427-2433.
Qui, Y. et al. (2012) "Immunoglobulin G expression and its colocalization with complement proteins in papillary thyroid cancer" Modern Pathology, 25:36-45.

(56) References Cited

OTHER PUBLICATIONS

Reina-San-Martin, B. et al. (Nov. 2004) "ATM is Required for Efficient Recombination between Immunoglobulin Switch Regions" The Journal of Experimental Medicine, 200(9):1103-1110.
Robbiani, D.F. (Nov. 25, 2009) "AID Produces DNA Double-Strand Breaks in Non-Ig Genes and Mature B Cell Lymphomas with Reciprocal Chromosome Translocations" Molecular Cell, 36:631-641.
Russell, J. S. et al. (Nov. 1, 2003) "Gleevec-Mediated Inhibition of Rad51 Expression and Enhancement of Tumor Cell Radiosensitivity" Cancer Research, 63:7377-7383.
Shen, H.M. et al. (2008) "Expression of AID transgene is regulated in activated B cells but not in resting B cells and kidney" Molecular Immunology, 45:1883-1892.
Shikata, H. et al. (Mar. 2012) "Role of activation-induced cytidine deaminase in the progression of follicular lymphoma" Cancer Sci, 103(3):415-421.
Takata, M. et al. (2001) "Chromosome Instability and Defective Recombinational Repair in Knockout Mutants of the Five Rad51 Paralogs" Molecular and Cellular Biology, 21(8):2858-2866.
Tebbs, R.S. et al. (Jul. 1995) "Correction of chromosomal instability and sensitivity to diverse mutagens by a cloned cDNA of the XRCC3 DNA repair gene" Proc Natl Acad Sci USA, 92:6354-6358.
Volpi, E.V. et al. (Oct. 2008) "FISH glossary: an overview of the fluorescence in situ hybridization technique" BioTechniques, 45(4):385-409.
White, C.A. et al. (2011) "AID dysregulation in lupus-prone MRL/Faslpr/lpr mice increases class switch DNA recombination and promotes interchromosomal c-Myc/IgH loci translocations: Modulation by HoxC4" Autoimmunity, 44(8):585-598.
Xu, X. et al. (2009) "Increased Expression of Activation-Induced Cytidine Deaminase is Associated with Anti-CCP and Rheumatoid Factor in Rheumatoid Arthritis" Scand J Immunol, 70:309-316.
Yoshikawa, K. et al. (Jun. 2002) "AID Enzyme-Induced Hypermutation in an Actively Transcribed Gene in Fibroblasts" Science, 296(5575):2033-2036.
Zhang, L. et al. (2012) "Expression of immunoglobulin G in esophageal squamous cell carcinomas and its association with tumor grade and Ki67" Human Pathology, 43:423-434.

* cited by examiner

RAD51 INHIBITORS

CROSS-REFERENCES TO RELATED APPLICATIONS

This application is a division of U.S. application Ser. No. 16/127,229, filed on Sep. 11, 2018 (now allowed), which claims the benefit of U.S. Provisional Application No. 62/556,763, filed on Sep. 11, 2017; and U.S. Provisional Application No. 62/711,959, filed on Jul. 30, 2018. The entire teachings of the aforementioned applications are incorporated herein by reference.

FIELD OF THE INVENTION

This application is directed to inhibitors of RAD51, and methods for their use, such as to treat conditions including cancers, autoimmune diseases, immune deficiencies, and neurodegenerative diseases.

BACKGROUND OF THE INVENTION

RAD51 is a eukaryote gene. The protein encoded by this gene is a member of the RAD51 protein family which assists in repair of DNA double strand breaks. RAD51 family members are homologous to the bacterial RecA, Archaeal RadA and yeast RAD51. The protein is highly conserved in most eukaryotes, from yeast to humans. In humans, RAD51 is a 339-amino acid protein that plays a major role in homologous recombination of DNA during double strand break (DSB) repair. RAD51 catalyzes strand transfer between a broken sequence and its undamaged homologue to allow re-synthesis of the damaged region (see homologous recombination models).

Studies have demonstrated a sensitization to certain DNA damaging therapies associated with cellular defects in proteins that promote HR DNA repair. This sensitization is particularly dramatic for DNA cross-linking chemotherapeutic drugs (30-100 times) and ionizing radiation (3-5 times) (Godthelp et al., "Mammalian Rad51C contributes to DNA cross-link resistance, sister chromatid cohesion and genomic stability," Nucleic Acids Res., 30:2172-2182, 2002; Tebbs et al., "Correction of chromosomal instability and sensitivity to diverse mutagens by a cloned cDNA of the XRCC3 DNA repair gene," Proc. Natl. Acad. Sci. USA, 92:6354-6358, 1995; Takata et al., "Chromosome instability and defective recombinational repair in knockout mutants of the five Rad51 paralogs," Mol. Cell Biol., 21:2858-2866, 2001; Liu et al., "XRCC2 and XRCC3, new human Rad51-family members, promote chromosome stability and protect against DNA cross-links and other damages," Mol. Cell, 1:783-793, 1998).

Several groups have recently demonstrated that HR can be partially inhibited in order to sensitize cells to DNA damaging therapies. Inhibition of XRCC3 (a RAD51 paralog protein), has been demonstrated using a synthetic peptide corresponding to another paralog protein. This peptide sensitized Chinese Hamster Ovary (CHO) cells to cisplatin and inhibited the formation of sub-nuclear RAD51 foci in response to DNA damage (Connell et al., Cancer Res., 64:3002-3005, 2004). Other researchers have inhibited the expression of the RAD51 protein itself (Russell et al., Cancer Res., 63:7377-7383, 2003; Hansen et al., Int. J. Cancer, 105:472-479, 2003; Ohnishi et al., Biochem. Biophys. Res. Commun., 245:319-324, 1998; Ito et al., J. Gene Med., 7(8):1044-1052, 2005; Collins et al., Nucleic Acids Res., 29:1534-1538, 2001) or blocked its function by overexpressing a dominant negative BRC peptide fragment derived from BRCA2 (Chen et al., J. Biol. Chem., 274: 32931-32935, 1999). In view of the connection between increased sensitivity to certain DNA damaging therapies and cellular defects in HR DNA repair-related proteins, there is a need for additional compounds that inhibit RAD51.

SUMMARY OF THE INVENTION

Applicant has now discovered novel compounds which are effective inhibitors of RAD51 (see Examples 1-75). The RAD51 inhibitors of the present invention inhibit homologous recombination by altering the nucleocytoplasmic distribution of RAD51 following DNA damage induction. The RAD51 inhibitors of the present invention reduce the repair of AID-induced DNA double strand breaks, leading to AID-dependent cytotoxicity in both normal and malignant B-lymphocytes. Certain of these RAD51 inhibitors have superior cell permeability as measured in Caco-2 cells (see Example 76). Among the RAD51 inhibitors with good cell permeability, several have superior metabolic stability (as measured by a liver microsome assay, see Example 77) and exposure, including oral exposure (see Example 79).

The present invention provides a compound represented by Structural Formula I:

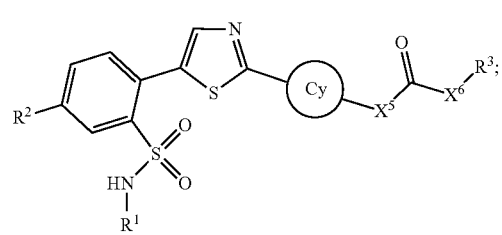

or a pharmaceutically acceptable salt thereof. The definition of each variable is provided below.

The present invention also provides a pharmaceutical composition comprising a compound as described herein or a pharmaceutically acceptable salt thereof and a pharmaceutically acceptable carrier or diluent.

The present invention further provides a method of treating a cancer, an autoimmune disease, an immune deficiency, or a neurodegenerative disease. The method comprises administering to a subject in need thereof an effective amount of a compound of disclosed herein or a pharmaceutically acceptable salt thereof or a pharmaceutical composition disclosed herein.

Also provided is the use of a compound disclosed herein, or a pharmaceutically acceptable salt thereof, or a pharmaceutical compositions disclosed herein for the preparation of a medicament for the treatment of a cancer, an autoimmune disease, an immune deficiency, or a neurodegenerative disease.

Also provided is a compound disclosed herein, or a pharmaceutically acceptable salt thereof, or a pharmaceutical composition disclosed herein for use in treating a cancer, an autoimmune disease, an immune deficiency, or a neurodegenerative disease.

Although Applicant does not wish to be bound by any mechanism, it is believed that the compounds of the invention inhibit RAD51 by binding to MDC1 and causing reduced ability to form active complexes of RAD51.

DETAILED DESCRIPTION

In a first embodiment, the invention provides a compound represented by Structural Formula I:

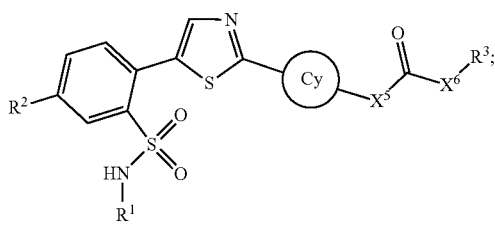

I or a pharmaceutically acceptable salt thereof, wherein:

the thiazole ring is optionally substituted with —F or —Cl;

Cy is —$(C_3\text{-}C_7)$cycloalkyl, bridged $(C_6\text{-}C_{12})$ cycloalkyl, or a 4-12 membered heterocyclic ring, each of which is optionally substituted with one or more groups selected from the group consisting of halogen, —OH, $(C_1\text{-}C_4)$alkyl, and $(C_1\text{-}C_4)$alkoxy;

when $X^5$ is connected with a nitrogen ring atom of Cy, $X^5$ is absent;

when $X^5$ is connected with a carbon ring atom of Cy, $X^5$ is $NR^a$ or O;

$X^6$ is $NR^a$ or O;

$R^1$ is $(C_1\text{-}C_5)$alkyl;

$R^3$ is $(C_1\text{-}C_5)$alkyl, —$CH_2$-phenyl, —$(C_3\text{-}C_7)$cycloalkyl, —$CH_2$—$(C_3\text{-}C_7)$cycloalkyl, —$CH_2$-monocyclic 3-7 membered heterocyclic ring, or monocyclic 3-7 membered heterocyclic ring, wherein the $(C_1\text{-}C_5)$alkyl, —$(C_3\text{-}C_7)$cycloalkyl, phenyl or monocyclic 3-7 membered heterocyclic ring represented by $R^3$ or in the group represented by $R^3$ is optionally substituted with one or more groups selected from the group consisting of halogen, —OH, $(C_1\text{-}C_4)$alkyl, halomethyl, halomethoxy, —CN, and $(C_1\text{-}C_4)$alkoxy; $R^2$ is —$NR^aC(O)O(C_1\text{-}C_4)$alkyl; —$NR^aC(O)NR^a(C_1\text{-}C_4)$alkyl; —$NR^aC(O)O(C_2\text{-}C_4)$alkenyl; —$NR^aC(O)NR^a(C_2\text{-}C_4)$alkenyl; —$NR^aC(O)O$—$(C_3\text{-}C_6)$cycloalkyl; —$NR^aC(O)NR^a$—$(C_3\text{-}C_7)$cycloalkyl; —$NR^aC(O)O$-phenyl; —$NR^aC(O)NR^a$-phenyl; —$NR^aC(O)O$-monocyclic 3-7 membered heterocyclic ring; —$NR^aC(O)NR^a$-monocyclic 3-7 membered heterocyclic ring; —$NR^aC(O)O$-monocyclic 5-6 membered heteroaromatic ring; —$NR^aC(O)NR^a$-monocyclic 5-6 membered heteroaromatic ring;

wherein the $(C_1\text{-}C_4)$alkyl and the $(C_2\text{-}C_4)$alkenyl in the group represented by $R^2$ are each optionally and independently substituted with one or more groups selected from the group consisting of halogen, $N_3$, —$OR^a$, —$NR^aR^a$, —$(C_3\text{-}C_6)$cycloalkyl, phenyl, a monocyclic 3-7 membered heterocyclic ring, and a monocyclic 5-6 membered heteroaromatic ring; wherein the $(C_3\text{-}C_7)$cycloalkyl in the group represented by $R^2$ is optionally substituted with one or more groups selected from the group consisting of halogen, —$CH_3$, =O, —$OR^a$ and —$NR^aR^a$;

wherein the phenyl in the group represented by $R^2$ is optionally substituted with one or more groups selected from the group consisting of halogen, —$CH_3$, halomethyl, halomethoxy, —CN, —$OR^a$, and —$N_3$;

wherein the heterocyclic ring in the group represented by $R^2$ is optionally substituted with one or more groups selected from the group consisting of =O, halogen, —$OR^a$, —$CH_3$, halomethyl, and halomethoxy;

wherein the heteroaromatic ring in the group represented by $R^2$ is optionally substituted with one or more groups selected from the group consisting of halogen, —CN, —$CH_3$, halomethyl, halomethoxy, —$OR^a$ and —$NR^aR^a$; and each $R^a$ is independently —H or —$CH_3$.

In a second embodiment, the invention provides a compound represented by Structural Formula II:

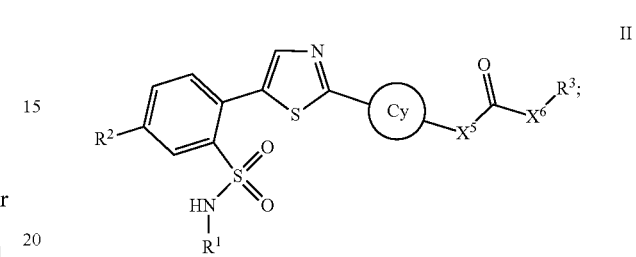

II or a pharmaceutically acceptable salt thereof, wherein the thiazole ring is optionally substituted with —F or —Cl;

Cy is cyclohexyl or a 6-membered monocyclic heterocyclic ring;

$X^5$ and $X^6$ are each independently $NR^a$ or O;

$R^1$ is $(C_1\text{-}C_5)$alkyl;

$R^3$ is $(C_1\text{-}C_5)$alkyl or monocyclic 3-7-membered heterocyclic ring;

$R^2$ is —$NR^aC(O)O(C_1\text{-}C_4)$alkyl; —$NR^aC(O)NR^a(C_1\text{-}C_4)$alkyl; —$NR^aC(O)O(C_2\text{-}C_4)$alkenyl; —$NR^aC(O)NR^a(C_2\text{-}C_4)$alkenyl; —$NR^aC(O)$—$O(C_3\text{-}C_6)$cycloalkyl; —$NR^aC(O)NR^a$—$(C_3\text{-}C_6)$cycloalkyl; —$NR^aC(O)O$-phenyl; —$NR^aC(O)NR^a$-phenyl; —$NR^aC(O)O$-monocyclic 3-7 membered heterocyclic ring; —$NR^aC(O)NR^a$-monocyclic 3-7 membered heterocyclic ring; —$NR^aC(O)O$-monocyclic 5-6 membered heteroaromatic ring; —$NR^aC(O)NR^a$-monocyclic 5-6 membered heteroaromatic ring;

wherein the $(C_1\text{-}C_4)$alkyl and the $(C_2\text{-}C_4)$alkenyl in the group represented by $R^2$ are each optionally and independently substituted with one or more halogen, $N_3$, —$OR^a$, —$NR^aR^a$, —$(C_3\text{-}C_6)$cycloalkyl, phenyl, monocyclic 3-7-membered heterocyclic ring, or monocyclic 5-6-membered heteroaromatic ring;

wherein the —$(C_3\text{-}C_6)$cycloalkyl in the group represented by $R^2$ is optionally substituted with one or more halogen, —$CH_3$, —$OR^a$ or —$NR^aR^a$;

wherein the phenyl in the group represented by $R^2$ is optionally substituted with one or more halogen, —$CH_3$, halomethyl, halomethoxy, —$OR^a$, or —$N_3$;

wherein the heterocyclic ring in the group represented by $R^2$ is optionally substituted with one or more =O, halogen, —$CH_3$, halomethyl, or halomethoxy;

wherein the heteroaromatic ring in the group represented by $R^2$ is optionally substituted with one or more halogen, —$CH_3$, halomethyl, halomethoxy, —$OR^a$ or —$NR^aR^a$; and each $R^a$ is independently —H or —$CH_3$.

In a third embodiment, the invention provides a compound according to Structural Formula I, or a pharmaceutically acceptable salt thereof, wherein Cy is cyclopropyl, cyclobutyl, cyclopentyl, cyclohexyl, cycloheptyl; azetidinyl, azepanyl, diazaspiro[4.4]nonyl, diazaspiro[3.5]nonyl, diazepanyl, dihydroimidazole, dihydrofuranyl, dihydropyranyl, dihydropyridinyl, dihydropyrimidinyl, dihydrothienyl, dihydrothiophenyl, dihydrothiopyranyl, hexahydropyridazinyl, hexahydropyrimidinyl, hydantoinyl, indolinyl, isoindolinyl, morpholinyl, oxiranyl, oxetanyl, piperidinyl, piperazinyl, pyrrolidinonyl, pyrrolidinyl, tetrahydrofuranyl, tetrahydroimidazole, tetrahydroindolyl, tetrahydropyranyl, tetrahydrothienyl, tetrahydropyridinyl, tetrahydropyrimidinyl, tetrahydrothiophenyl, tetrahydrothiopyranyl, thiomorpholinyl, tropanyl, valerolactamyl; bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, adamantly; azanorbornyl, quinuclidinyl, isoquinuclidinyl, tropanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, azabicyclo[3.3.1]nonanyl, diazabicyclo[2.2.1]heptanyl, diazabicyclo[3.2.1]octanyl, octahydropyrrolo[3,4-b]pyrrolyl, octahydropyrrolo[3,4-c]pyrrolyl; and the remaining variables are as defined in the first embodiment.

In a fourth embodiment, the invention provides a compound according to Structural Formula I or II, or a pharmaceutically acceptable salt thereof, wherein Cy is cyclohexyl, morpholinyl, thiomorpholinyl, piperidinyl, piperazinyl, hexahydropyridazinyl, hexahydropyrimidinyl, valerolactamyl, dihydropyranyl, dihydropyridinyl, dihydropyrimidinyl, dihydrothiopyranyl, tetrahydropyranyl, tetrahydropyridinyl, tetrahydropyrimidinyl, or tetrahydrothiopyranyl; and the remaining variables are as defined in the first, second, and/or third embodiments.

In a fifth embodiment, the invention provides a compound represented by Structural Formula III,

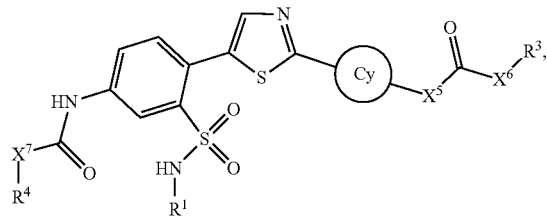

or a pharmaceutically acceptable salt thereof, wherein:

$X^7$ is NH or O;

$R^4$ is $(C_1-C_4)$alkyl, $(C_3-C_6)$cycloalkyl, or a monocyclic 3-7 membered heterocyclic ring;

wherein the $(C_1-C_4)$alkyl represented by $R^4$ is optionally substituted with one or more groups selected from the group consisting of halogen, $N_3$, —$OR^a$, —$NR^aR^a$, —$(C_3-C_6)$cycloalkyl, phenyl, a monocyclic 3-7 membered heterocyclic ring, and a monocyclic 5-6 membered heteroaromatic ring, wherein the $(C_3-C_6)$cycloalkyl or the monocyclic 3-7 membered heterocyclic ring represented by $R^4$, the $(C_3-C_6)$cycloalkyl or the monocyclic 3-7 membered heterocyclic ring in the group represented by $R^4$ is optionally substituted with one or more groups selected from the group consisting of halogen, —$OR^a$, ═O, and —$CH_3$, wherein the phenyl in the group represented by $R^4$ is optionally substituted with one or more groups selected from the group consisting of halogen, —$CH_3$, halomethyl, halomethoxy, —$OR^a$, and —$N_3$;

wherein the heteroaromatic ring in the group represented by $R^4$ is optionally substituted with one or more groups selected from the group consisting of halogen and —$CH_3$; and the remaining variables are as defined in the first, second, third, and/or fourth embodiments.

In a sixth embodiment, the invention provides a compound according to Structural Formula III, or a pharmaceutically acceptable salt thereof, wherein $X^7$ is NH or O; $R^3$ is $(C_1-C_5)$alkyl; and $R^4$ is $(C_1-C_4)$alkyl wherein the $(C_1-C_4)$alkyl represented by $R^4$ is optionally substituted with one or more halogen, —$OR^a$, —$NR^aR^a$, —$(C_3-C_6)$cycloalkyl, phenyl (optionally substituted by one or more halogen, —$CH_3$, halomethyl, halomethoxy, $OR^a$ or $N_3$), monocyclic 3-7-membered heterocyclic ring (optionally substituted by ═O, halogen or —$CH_3$), or monocyclic 5-6-membered heteroaromatic ring (optionally substituted by halogen or —$CH_3$); and the remaining variables are as defined in the first, second, third, fourth and/or fifth embodiments.

In a seventh embodiment, the invention provides a compound represented by Structural Formula IV,

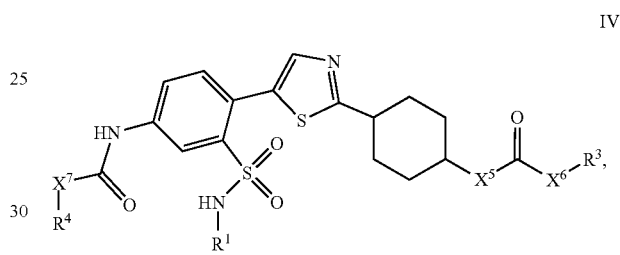

or a pharmaceutically acceptable salt thereof; and the variables are as defined in the first, second, third, fourth, fifth and/or sixth embodiments.

In an eighth embodiment, the invention provides a compound represented by Structural Formula V,

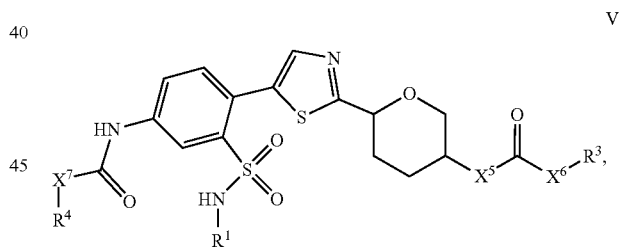

or a pharmaceutically acceptable salt thereof; and the variables are as defined in the first, second, third, fourth, fifth and/or sixth embodiments.

In a ninth embodiment, the invention provides a compound represented by Structural Formula VI:

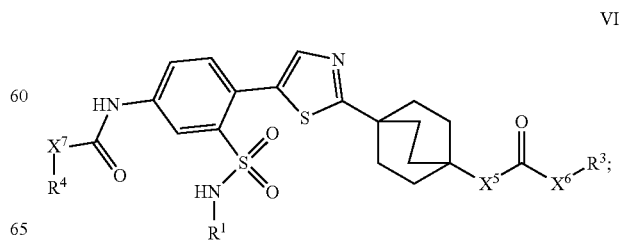

or a pharmaceutically acceptable salt thereof; and the variables are as defined in the first, second, third, fourth, fifth and/or sixth embodiments.

In a tenth embodiment, the invention provides a compound represented by Structural Formula VII:

VII

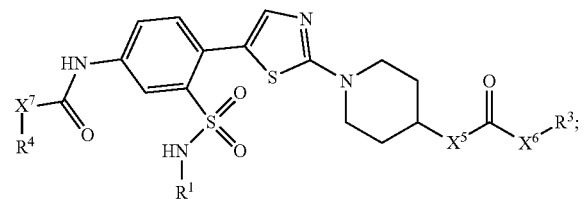

or a pharmaceutically acceptable salt thereof; and the variables are as defined in the first, second, third, fourth, fifth and/or sixth embodiments.

In an eleventh embodiment, the invention provides a compound represented by Structural Formula VIII:

VIII

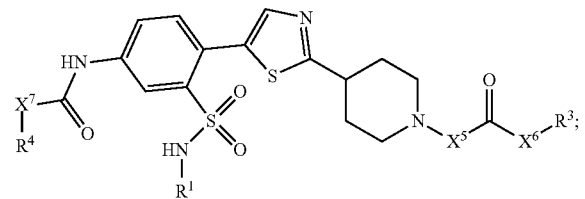

or a pharmaceutically acceptable salt thereof; and the variables are as defined in the first, second, third, fourth, fifth and/or sixth embodiments.

In a twelfth embodiment, the invention provides a compound represented by Structural Formula IX:

IX

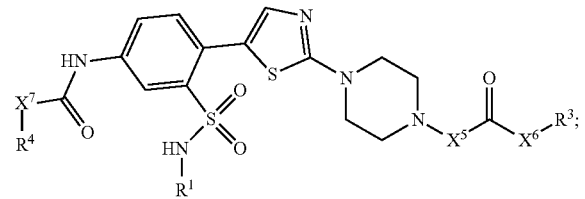

or a pharmaceutically acceptable salt thereof; and the variables are as defined in the first, second, third, fourth, fifth and/or sixth embodiments.

In a thirteenth embodiment, the invention provides a compound according to Structural Formula I, II, or III, or a pharmaceutically acceptable salt thereof, wherein Cy is azetidinyl or pyrrolidinyl, and the nitrogen ring atom is connected with the thiazole ring; and the remaining variables are as defined in the first, second, third, fourth, fifth and/or sixth embodiments.

In a fourteenth embodiment, the invention provides a compound according to Structural Formula I, II, or III, or a pharmaceutically acceptable salt thereof, wherein Cy is 1,7-diazaspiro[4.4]nonyl, 2,7-diazaspiro[4.4]nonyl, 2,7-diazaspiro[3.5]nonyl, 1,4-diazepanyl, 2,5-diazabicyclo[2.2.1]heptanyl, 3,8-diazabicyclo[3.2.1]octanyl, octahydropyrrolo[3,4-b]pyrrolyl, or octahydropyrrolo[3,4-c]pyrrolyl, and the two nitrogen ring atoms are connected with the thiazole ring and the $-X^5C(O)X^6R^3$ moiety, respectively; and the remaining variables are as defined in the first, second, third, fourth, fifth and/or sixth embodiments.

In a fifteenth embodiment, the invention provides a compound according to Structural Formula III, IV, V, VI, VII, VIII, or IX, or a pharmaceutically acceptable salt thereof, wherein $R^4$ is $-(C_1-C_3)$alkyl, $(C_3-C_6)$cycloalkyl, or a monocyclic 3-7 membered heterocyclic ring, wherein the $-(C_1-C_3)$alkyl is optionally substituted with (i) phenyl optionally substituted by one or more halogen or $-CH_3$; (ii) a monocyclic 5-6 membered heteroaromatic ring optionally substituted by one or more halogen or $-CH_3$; or (iii) a monocyclic 3-7 membered heterocyclic ring optionally substituted by one or more groups selected from the group consisting of halogen and $-CH_3$; and the remaining variables are as defined in the first, second, third, fourth, fifth, seventh, eighth, ninth, tenth, eleventh, twelfth, thirteenth, and/or fourteenth embodiments.

In a sixteenth embodiment, the invention provides a compound according to Structural Formula III, IV, V, VI, VII, VIII, or IX, or a pharmaceutically acceptable salt thereof, wherein $R^4$ is $-(C_1-C_3)$alkyl, $-CHR^a$-phenyl, $-CHR^a$-5-6 membered heteroaromatic ring, or $-CHR^a$-3-7 membered monocyclic heterocyclic ring, wherein the phenyl, 5-6 membered heteroaromatic ring or 3-7 membered monocyclic heterocyclic ring in the group represented by $R^4$ is optionally substituted one or more groups selected from the group consisting of halogen and $-CH_3$; and the remaining variables are as defined in the first, second, third, fourth, fifth, seventh, eighth, ninth, tenth, eleventh, twelfth, thirteenth, and/or fourteenth embodiments.

In a seventeenth embodiment, the invention provides a compound according to Structural Formula III, IV, V, VI, VII, VIII, or IX, or a pharmaceutically acceptable salt thereof, wherein $R^4$ is $-(C_1-C_3)$alkyl, optionally substituted with (i) phenyl optionally substituted by one or more halogen, $-CH_3$, halomethyl, halomethoxy, $OR^a$, or $N_3$; (ii) a monocyclic 5-6-membered heteroaromatic ring optionally substituted by one or more halogen or $-CH_3$; or (iii) a monocyclic 3-7-membered heterocyclic ring optionally substituted by one or more $=O$ or $-CH_3$; and the remaining variables are as defined in the first, second, third, fourth, fifth, sixth, seventh, eighth, ninth, tenth, eleventh, twelfth, thirteenth, and/or fourteenth embodiments.

In an eighteenth embodiment, the invention provides a compound according to Structural Formula III, IV, V, VI, VII, VIII, or IX, or a pharmaceutically acceptable salt thereof, wherein $R^4$ is $-(C_1-C_3)$alkyl, optionally substituted with (i) phenyl optionally substituted by one or more halogen, $-CH_3$, halomethyl, halomethoxy, $OR^a$, or $N_3$; (ii) a monocyclic 5-6-membered heteroaromatic ring optionally substituted by one or more halogen or $-CH_3$; or (iii) a monocyclic 3-7-membered heterocyclic ring optionally substituted by one or more $=O$ or $-CH_3$; and the remaining variables are as defined in the first, second, third, fourth, fifth, sixth, seventh, eighth, ninth, tenth, eleventh, twelfth, thirteenth, fourteenth, and/or seventeenth embodiments.

In a nineteenth embodiment, the invention provides a compound according to Structural Formula I, III, IV, V, VI, VII, VIII, or IX, or a pharmaceutically acceptable salt thereof, wherein $R^3$ is $(C_1-C_4)$alkyl, $-(C_4-C_6)$cycloalkyl, $-CH_2$-phenyl, $-CH_2$-monocyclic 4-6 membered heterocyclic ring, or monocyclic 4-6 membered heterocyclic ring, wherein the phenyl or monocyclic 4-6 membered heterocyclic ring represented by R³ or in the group represented by R³ is optionally substituted with one or more groups selected from the group consisting of halogen, —ORᵃ, and —CH₃; and the remaining variables are as defined in the first, third, fourth, fifth, seventh, eighth, ninth, tenth, eleventh, twelfth, thirteenth, fourteenth, fifteenth, sixteenth, seventeenth, and/or eighteenth embodiments.

In a twentieth embodiment, the invention provides a compound represented by Structural Formula X:

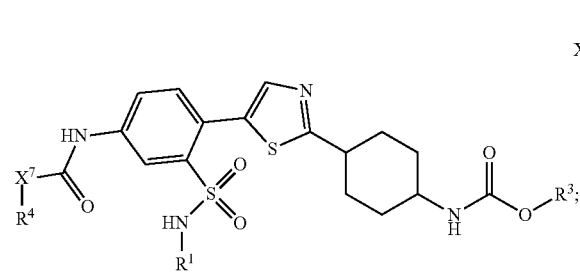

X or a pharmaceutically acceptable salt thereof; and the variables are as defined in the first, second, third, fourth, fifth, sixth, seventh, fifteenth, sixteenth, seventeenth, eighteenth, and/or nineteenth embodiments.

In a twenty first embodiment, the invention provides a compound represented by Structural Formula XI:

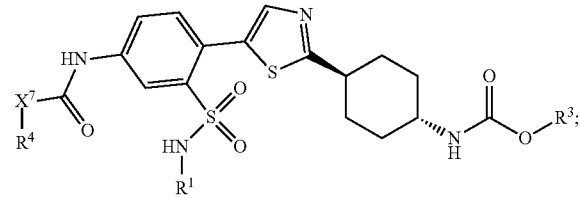

XI or a pharmaceutically acceptable salt thereof; and the variables are as defined in the first, second, third, fourth, fifth, sixth, seventh, fifteenth, sixteenth, seventeenth, eighteenth, and/or nineteenth embodiments.

In a twenty second embodiment, the invention provides a compound represented by Structural Formula XII:

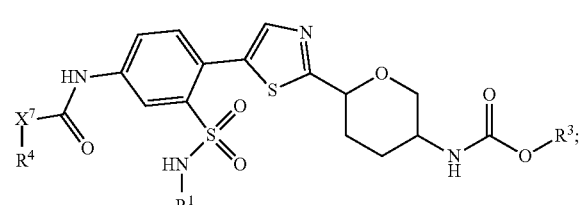

XII or a pharmaceutically acceptable salt thereof; and the variables are as defined in the first, second, third, fourth, fifth, sixth, eighth, fifteenth, sixteenth, seventeenth, eighteenth, and/or nineteenth embodiments.

In a twenty third embodiment, the invention provides a compound represented by Structural Formula XIII(a) or XIII(b):

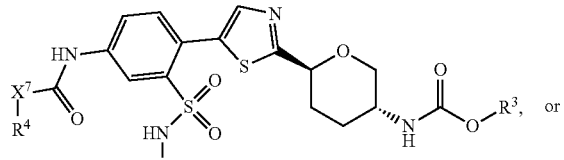

XIII(a)

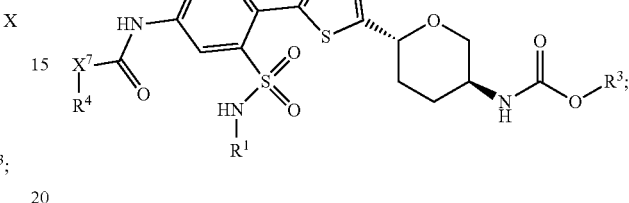

XIII(b)

or a pharmaceutically acceptable salt thereof; and the variables are as defined in the first, second, third, fourth, fifth, sixth, eighth, fifteenth, sixteenth, seventeenth, eighteenth, and/or nineteenth embodiments.

In a twenty fourth embodiment, the invention provides a compound represented by Structural Formula XIV:

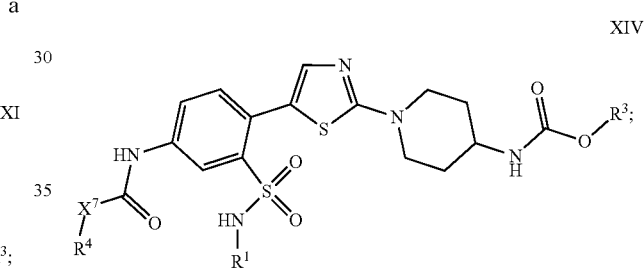

XIV or a pharmaceutically acceptable salt thereof; and the variables are as defined in the first, second, third, fourth, fifth, sixth, tenth, fifteenth, sixteenth, seventeenth, eighteenth, and/or nineteenth embodiments.

In a twenty fifth embodiment, the invention provides a compound according to Structural Formula I, II, III, IV, V, VI, VII, VIII, IX, X, XI, XII, XIII(a), XIII(b), XIV, or a pharmaceutically acceptable salt thereof, wherein R³ is isopropyl, tert-butyl, cyclobutyl, cyclopentyl, benzyl, oxetanyl, tetrahydro-2H-pyranyl, or

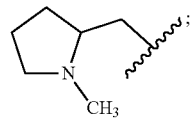

and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third and/or twenty fourth embodiments. In an alternative embodiment, R³ is isopropyl or oxetanyl. In another alternative embodiment, R³ is isopropyl.

In a twenty sixth embodiment, the invention provides a compound according to Structural Formula I, II, III, IV, V, VI, VII, VIII, IX, X, XI, XII, XIII(a), XIII(b), XIV, or a pharmaceutically acceptable salt thereof, wherein $R^1$ is tert-butyl; and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, and/or twenty fifth embodiments.

In a twenty seventh embodiment, the invention provides a compound according to Structural Formula III, IV, V, VI, VII, VIII, IX, X, XI, XII, XIII(a), XIII(b), XIV, or a pharmaceutically acceptable salt thereof, wherein $R^4$ is

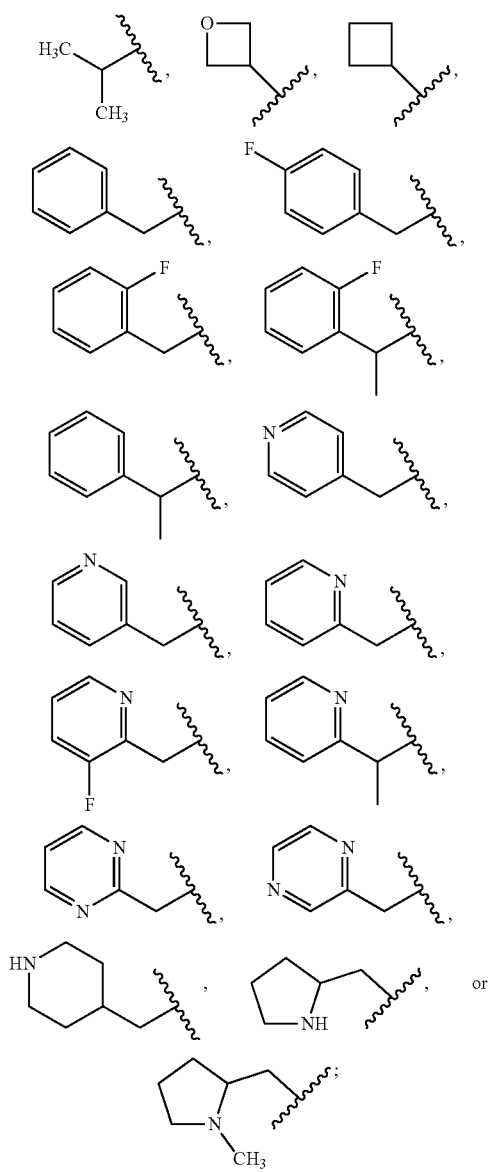

and the variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty first, twenty second, twenty third, twenty fourth, twenty fifth, and/or twenty sixth embodiments. In an alternative embodiment, $R^4$ is

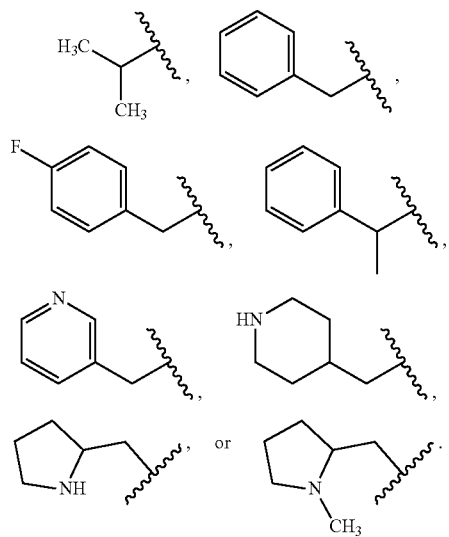

In another alternative embodiment, $R^4$ is

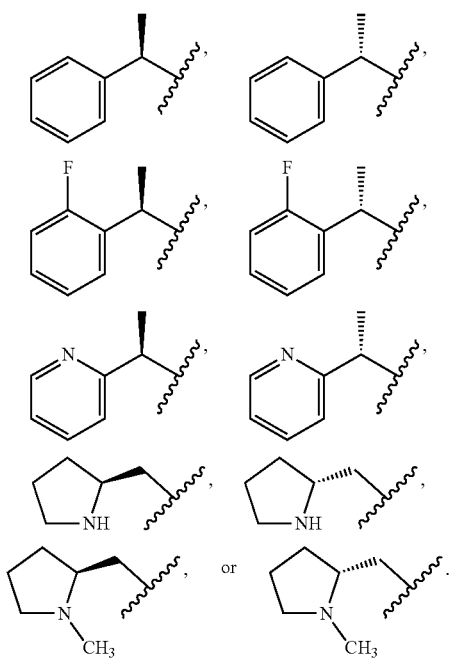

In another alternative embodiment, $R^4$ is

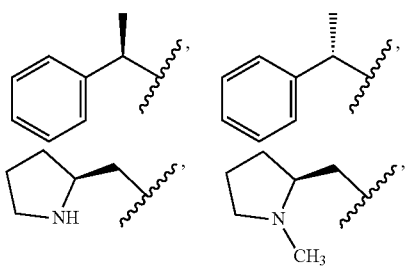

13
-continued

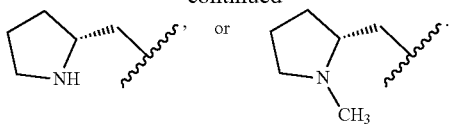

Still in another alternative embodiment, R⁴ is

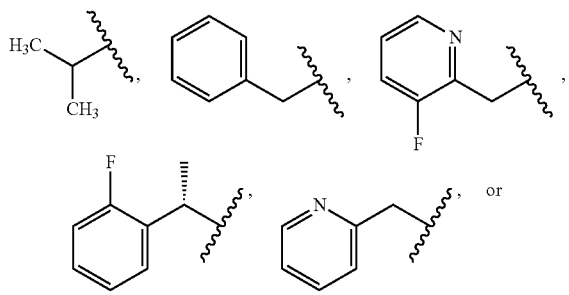

14
-continued

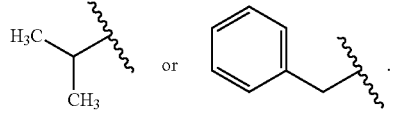

Still in another alternative embodiment, R⁴ is

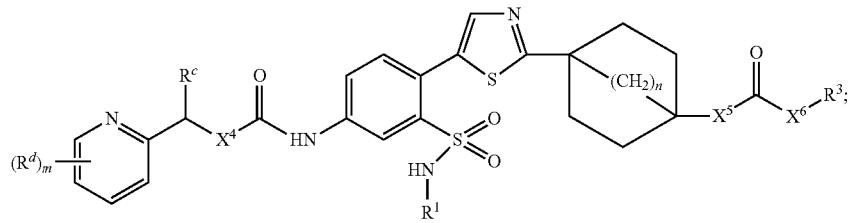

The present invention provides a compound represented by Structural Formula I'.

In a first embodiment, the invention provides a compound represented by Structural Formula I':

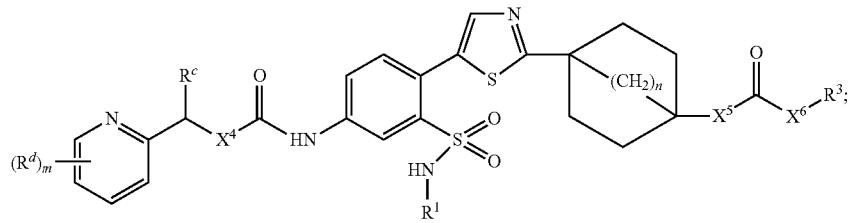

or a pharmaceutically acceptable salt thereof, wherein:
the thiazole ring is optionally substituted with —F or —Cl;
$X^4$ is $NR^a$ or O;
$X^5$ and $X^6$ are each independently $NR^b$ or O;
$R^1$ is $(C_1-C_5)$alkyl;
$R^3$ is $(C_1-C_5)$alkyl, $—(C_3-C_7)$cycloalkyl, or $—(CH_2)_q$heterocyclyl (wherein the heterocyclyl is a monocyclic 3-7-membered heterocyclic ring optionally substituted with one or more occurrences of methyl), or benzyl (wherein the benzyl ring is optionally substituted with one or more occurrences of halogen, methoxy, halomethoxy, methyl, halomethyl, or cyano);
each of $R^a$, $R^b$, and $R^c$ is independently hydrogen or methyl;
$R^d$ is independently halogen, methoxy, halomethoxy, methyl, halomethyl, or cyano;
m is 0, 1, 2, or 3;
n is 0, 1, or 2; and
q is 0 or 1.
In a second embodiment, the invention provides a compound represented by Structural Formula I'-1:

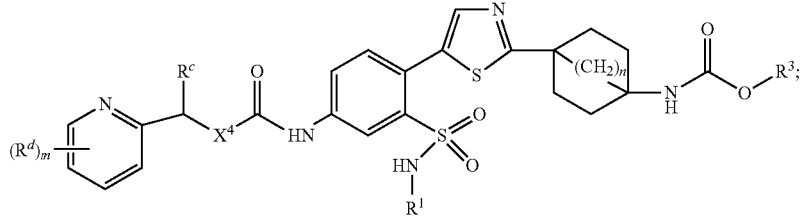

or a pharmaceutically acceptable salt thereof, and the variables are as defined in the first embodiment.

In a third embodiment, the invention provides a compound represented by Structural Formula I'-2:

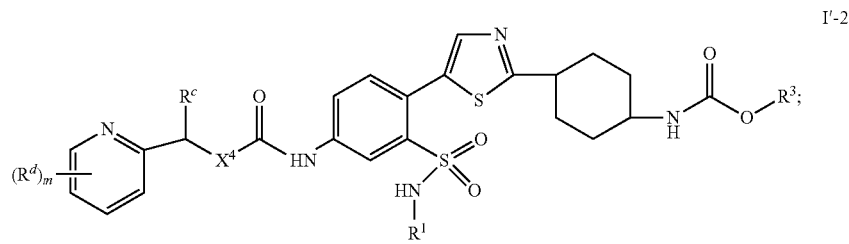

I'-2 or a pharmaceutically acceptable salt thereof, and the variables are as defined in the first embodiment.

In a forth embodiment, the invention provides a compound represented by Structural Formula I'-3:

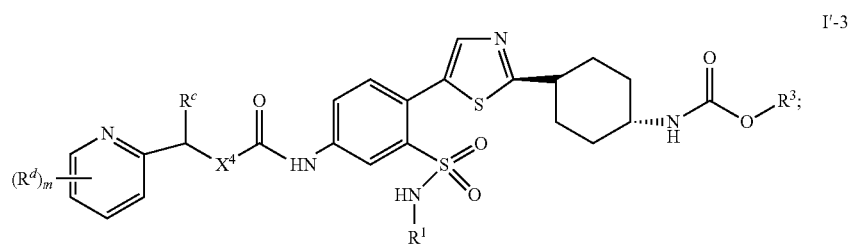

I'-3 or a pharmaceutically acceptable salt thereof, and the variables are as defined in the first embodiment.

In a fifth embodiment, the invention provides a compound represented by Structural Formula I'-4:

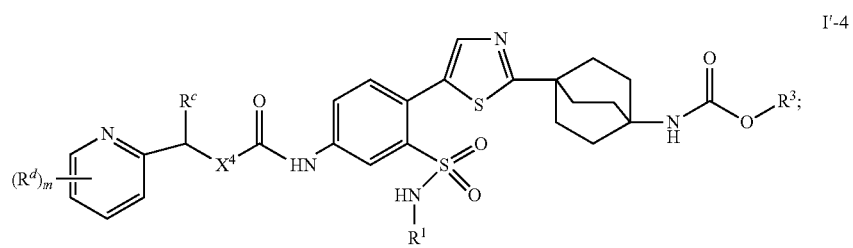

I'-4 or a pharmaceutically acceptable salt thereof, and the variables are as defined in the first embodiment.

In a sixth embodiment, the invention provides a compound according to Structural Formula I', I'-1, I'-2, I'-3, or I'-4, or a pharmaceutically acceptable salt thereof, wherein $X^4$ is NH, and the remaining variables are as defined in the first embodiment.

In a seventh embodiment, the invention provides a compound according to Structural Formula I', I'-1, I'-2, I'-3, or I'-4, or a pharmaceutically acceptable salt thereof, wherein $R^3$ is $(C_1-C_4)$alkyl, —$(C_4-C_6)$cycloalkyl, —$(CH_2)_q$heterocyclyl (wherein the heterocyclyl is a monocyclic 4-6-membered heterocyclic ring optionally substituted with one methyl), or benzyl, and the remaining variables are as defined in the first and/or sixth embodiments. In one specific embodiment, $R^3$ is isopropyl, tert-butyl, cyclobutyl, cyclopentyl, oxetanyl, benzyl, tetrahydro-2H-pyranyl, or

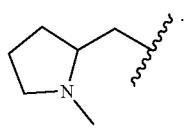 [SMILES: *CC1CCCN1C]

In another specific embodiment, $R^3$ is isopropyl or oxetanyl.

In an eighth embodiment, the invention provides a compound according to Structural Formula I', I'-1, I'-2, I'-3, or I'-4, or a pharmaceutically acceptable salt thereof, wherein $R^d$ is halogen, and m is 0 or 1, and the remaining variables are as defined in the first, sixth, and/or seventh embodiments. In one specific embodiment, is

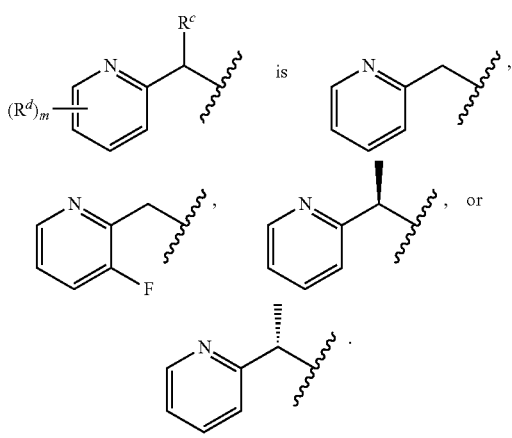

In a ninth embodiment, the invention provides a compound according to Structural Formula I', I'-1, I'-2, I'-3, or I'-4, or a pharmaceutically acceptable salt thereof, wherein $R^1$ is tert-butyl, and the remaining variables are as defined in the first, sixth, seventh, and/or eighth embodiments.

In a tenth embodiment, the invention provides a compound, or a pharmaceutically acceptable salt thereof, wherein the compound is selected from the group consisting of:

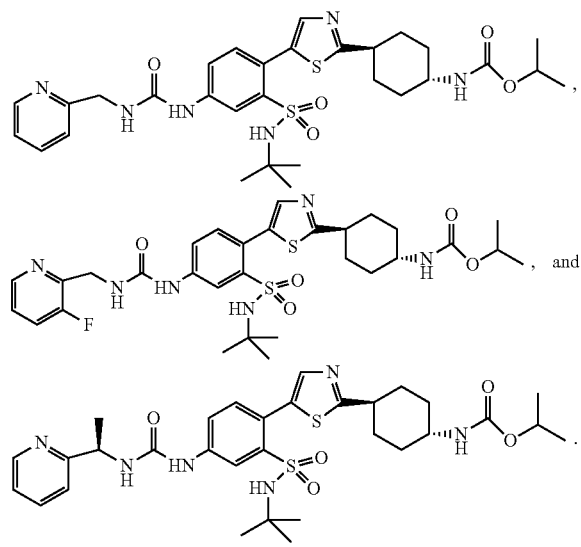

In an eleventh embodiment, the invention provides a compound represented by Structural Formula II':

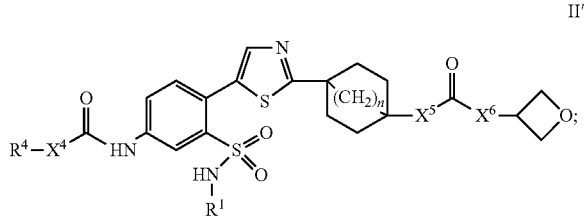

or a pharmaceutically acceptable salt thereof, wherein:

the thiazole ring is optionally substituted with —F or —Cl;

$X^4$ is $NR^a$ or O;

$X^5$ and $X^6$ are each independently $NR^b$ or O;

$R^1$ is $(C_1\text{-}C_5)$alkyl;

$R^4$ is $(C_1\text{-}C_4)$alkyl, —$(C_3\text{-}C_7)$cycloalkyl, —$(CH(R^c))_q$-heterocycyl (wherein the heterocycyl is a monocyclic 3-7-membered heterocyclic ring optionally substituted with one or more occurrences of methyl), —$(CH(R^c))_q$-phenyl (wherein the phenyl ring is optionally substituted with one or more occurrences of halogen, methoxy, halomethoxy, methyl, halomethyl, or cyano), or —$(CH(R^c))_q$-2-pyridinyl (wherein the 2-pyridinyl ring is optionally substituted with one or more occurrences of halogen, methoxy, halomethoxy, methyl, halomethyl, or cyano);

each of $R^a$, $R^b$, and $R^c$ is independently hydrogen or methyl;

n is 0, 1, or 2; and q is 0 or 1.

In a twelfth embodiment, the invention provides a compound represented by Structural Formula II'-1:

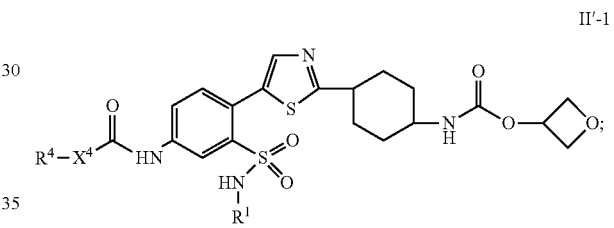

or a pharmaceutically acceptable salt thereof, and the variables are as defined in the eleventh embodiment.

In a thirteenth embodiment, the invention provides a compound represented by Structural Formula II'-2:

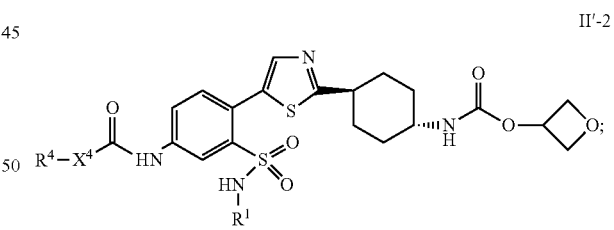

or a pharmaceutically acceptable salt thereof, and the variables are as defined in the eleventh embodiment.

In a fourteenth embodiment, the invention provides a compound according to Structural Formula II', II'-1 or II'-2, or a pharmaceutically acceptable salt thereof, wherein $R^4$ is isopropyl, oxetanyl, cyclobutyl, —$CH_2$-2-pyrrolidinyl, —$CH_2$—N-methyl-2-pyrrolidinyl, —$CH_2$-3-piperidinyl, —$CH_2$-2-pyrazinyl, —$CH_2$-2-pyrimidinyl, —$CH(R^c)$-phenyl, or —$CH(R^c)$-2-pyridinyl, and that the phenyl and 2-pyridinyl rings are each independently and optionally substituted with one or more occurrences of halogen, and the remaining variables are as defined in the eleventh embodiment. In one specific embodiment, $R^4$ is

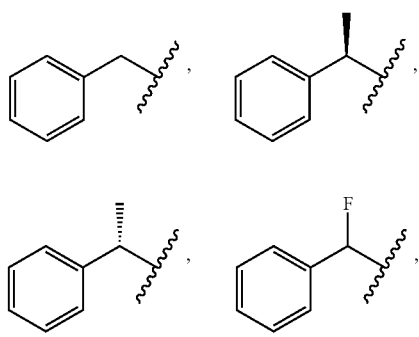

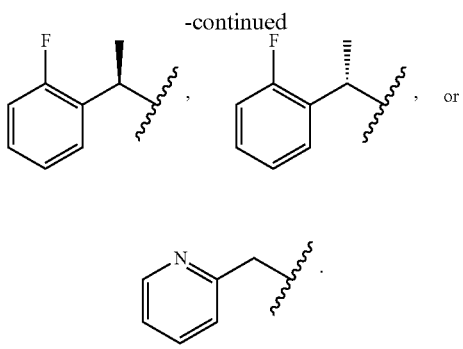
-continued

In another specific embodiment, R⁴ is or

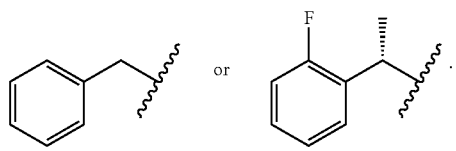

In a fifteenth embodiment, the invention provides a compound according to Structural Formula II', II'-1 or II'-2, or a pharmaceutically acceptable salt thereof, wherein $X^4$ is NH, and the remaining variables are as defined in the eleventh and/or fourteenth embodiments.

In a sixteenth embodiment, the invention provides a compound according to Structural Formula II', II'-1 or II'-2, or a pharmaceutically acceptable salt thereof, wherein $R^1$ is tert-butyl, and the remaining variables are as defined in the eleventh, fourteenth, and fifteenth embodiments.

In a seventeenth embodiment, the invention provides a compound, or a pharmaceutically acceptable salt thereof, wherein the compound is selected from the group consisting of:

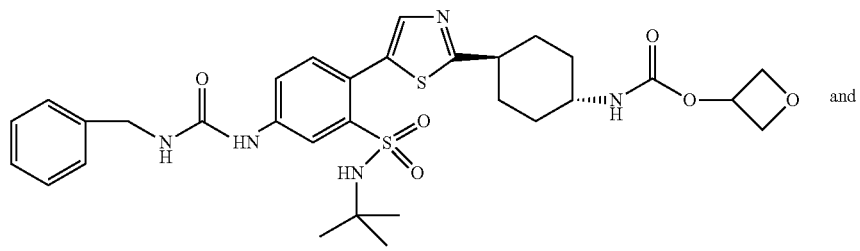 and

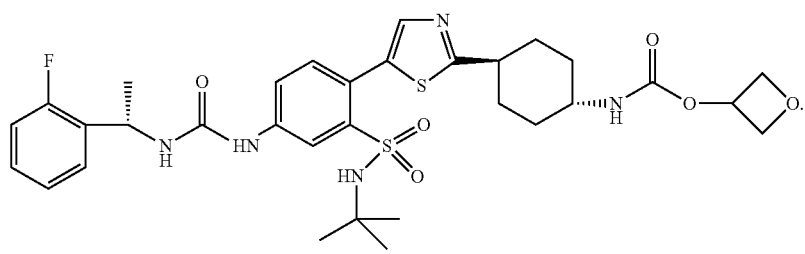

Also included are the compounds disclosed in the Exemplification, both in the pharmaceutically acceptable salt form and in the neutral form.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Definitions

The term "halo" as used herein means halogen and includes fluoro, chloro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. $(C_1$-$C_5)$alkyl. As used herein, a "$(C_1$-$C_5)$alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "$(C_1$-$C_4)$alkoxy" includes methoxy, ethoxy, propoxy, and butoxy.

The terms "haloalkyl" and "haloalkoxy" means alkyl or alkoxy, as the case may be, substituted with one or more halogen atoms.

An "alkylene group" is a saturated aliphatic branched or straight-chain divalent hydrocarbon radical. Unless otherwise specified, an alkylene group typically has 2-6 carbon atoms, e.g. $(C_2$-$C_6)$alkylene.

The term "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e., $(C_2$-$C_6)$alkenyl. For example, "$(C_2$-$C_4)$alkenyl" means a radical having from 2-4 carbon atoms in a linear or branched arrangement.

The term "cycloalkyl" means a monocyclic saturated hydrocarbon ring system. For example, a $C_3$-$C_6$ cycloalkyl includes cyclopropyl, cyclobutyl, cyclopentyl and cyclohexyl. Unless otherwise described, a "cycloalkyl" has from three to seven ring carbon atoms.

A bridged cycloalkyl means a bicyclic non-aromatic hydrocarbon ring system in which the two rings share at least three adjacent ring carbon atoms. A bridged cycloalkyl typically has 6-12 ring carbon atoms. Examples include, but are not limited to, bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

The terms "heterocyclyl", "heterocyclic ring", and "heterocyclic group", are used interchangeably herein, and means a saturated or unsaturated non-aromatic 4-10 membered ring radical containing from 1 to 4 ring heteroatoms, which may be the same or different, selected from N, O, or S. It can be monocyclic, bicyclic or tricyclic (e.g., a fused or bridged bicyclic or tricyclic ring). Examples of include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. A heterocyclic ring optionally contains one or more double bonds and/or is optionally fused with one or more aromatic rings (for example, tetrahydronaphthyridine, indolinone, dihydropyrrolotriazole, imidazopyrimidine, quinolinone, dioxaspirodecane).

Examples of 3-7 membered monocyclic heterocyclic ring include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

A bridged heterocyclyl means a bicyclic non-aromatic ring system containing from 1 to 4 ring heteroatoms in which the two rings share at least three adjacent ring atoms. A bridged heterocyclyl typically has 6-12 ring atoms. Examples include, but are not limited to, azanorbomyl, quinuclidinyl, isoquinuclidinyl, tropanyl, azabicyclo[3.2.1]octanyl, azabicyclo[2.2.1]heptany 1,2-azabicyclo[3.2.1]octanyl, azabicyclo[3.2.1]octanyl, azabicyclo[3.2.2]nonanyl, azabicyclo[3.3.0]nonanyl, and azabicyclo[3.3.1]nonanyl.

The terms "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to ten ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. "Heteroaryl" includes monocyclic and bicyclic ring systems.

"Monocyclic 5-6 membered heteroaromatic ring (or heteroaryl)" means a monocyclic heteroaromatic ring having five or six ring atoms selected from carbon and at least one (typically 1 to 3, more typically 1 or 2) heteroatoms (e.g., oxygen, nitrogen or sulfur). Examples of monocyclic 5-6 membered heteroaromatic ring groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl).

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, cycloalkyl, or a heterocyclic ring) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant disclosure. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art. When a group is described as being optionally substituted by "one or more" substituents, it denotes that the group is optionally substituted by one, two, three, four, five or six substituents. In one embodiment, a group is optionally substituted by 1-3 substituents. In one embodiment, a group is optionally substituted by 1-2 substituents. In one embodiment, a group is optionally substituted by one substituent.

Suitable substituents are those which do not have a significant adverse effect on the ability of the compound to inhibit RAD51. Where suitable substituents are not specifically enumerated, exemplary substituents include, but are not limited to, halo, —CN, alkyl, alkoxy, halomethyl, halomethoxy, $(C_1-C_5)$alkyl, halo$(C_1-C_5)$alkyl, $(C_1-C_5)$alkoxy, —$NO_2$, —$OR^c$, —$NR^{a'}R^{b'}$, —$S(O)_iR^{a'}$, —$NR^aS(O)_i$ $R^{b'}$, —$S(O)_iNR^{a'}R^{b'}$, —$C(=O)OR^{a'}$, —$OC(=O)OR^{a'}$, —$C(=S)OR^{a'}$, —$O(C=S)R^{a'}$, —$C(=O)NR^{a'}R^{b'}$, —$NR^{a'}C(=O)R^{b'}$, —$C(=S)NR^{a'}R^{b'}$, —$NR^{a'}C(=S)R^{b'}$, —$NR^{a'}(C=O)OR^{b'}$, —$O(C=O)NR^{a'}R^{b'}$, —$NR^{a'}(C=S)OR^{b'}$, —$O(C=S)NR^{a'}R^{b'}$, —$NR^{a'}(C=O)NR^{a'}R^{b'}$, —$NR^{a'}(C=S)NR^{a'}R^{b'}$, —$C(=S)R^{a'}$, —$C(=O)R^{a'}$, $(C_3-C_6)$cycloalkyl, monocyclic heteroaryl and phenyl, wherein the $(C_3-C_6)$cycloalkyl, monocyclic heteroaryl and phenyl substituents are optionally and independently substituted with —$CH_3$, halomethyl, halo, methoxy or halomethoxy. Each $R^{a'}$ and each $R^{b'}$ are independently selected from —H and $(C_1-C_5)$alkyl, wherein the $(C_1-C_5)$alkyl group represented by $R^{a'}$ or $R^{b'}$ is optionally substituted with hydroxyl or $(C_1-C_3)$alkoxy; $R^c$ is —H, halo$(C_1-C_5)$alkyl or $(C_1-C_5)$alkyl, wherein the $(C_1-C_5)$alkyl group represented by $R^c$ is optionally substituted with hydroxyl or $(C_1-C_3)$alkoxy; and i is 0, 1, or 2. $=O$ is also a suitable substituent for alkyl, cycloalkyl, and a heterocyclic ring.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diastereomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Pharmaceutical Compositions

The compounds disclosed therein are RAD51 inhibitors. The pharmaceutical composition of the present invention comprises one or more RAD51 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present invention provides a method of treating a subject with a disease which can be ameliorated by inhibition of RAD51, by administering to the subject an effective amount of one or more disclosed compounds, or a pharmaceutically acceptable salt thereof, or the corresponding pharmaceutical composition. Diseases which can be ameliorated by inhibition of RAD51 include treating cancer, autoimmune disease, immune deficiency, or neurodegenerative disease.

In one aspect, described herein is a method of treating cancer, autoimmune disease, immune deficiency, or neurodegenerative disease, the method comprising administering a therapeutically effective dose of a composition as described herein, e.g., a composition comprising a compound of the present invention, to a subject in need of treatment for cancer, autoimmune disease, immune deficiency, or neurodegenerative disease.

In some embodiments, the subject can be a subject determined to have an increased level of DNA damage occurring in one or more cell types relative to a reference level. As used herein, "DNA damage" refers to breaks, nicks, and mutations of the DNA present in a cell. In some embodiments, the DNA damage can comprise one or more of single-strand breaks (e.g., "nicks"), double strand breaks (DSBs), and mutations. In some embodiments, the DNA damage can be one or more DSBs. As used herein, "mutation" refers to a change or difference in the genetic material of a cell as compared to a reference wildtype cell, e.g. a deletion, an insertion, a SNP, a gene rearrangement, and/or the introduction of an exogenous gene or sequence.

In some embodiments, the subject can be determined to have an increased level of DNA damage if the subject is determined to have an increased level and/or activity of a DNA damage process or DNA editing enzyme. As used herein, "DNA damage process" refers to any activity or process in a cell which causes one or more types of DNA damage to occur.

In some embodiments, an increased level of DNA damage can be an increased level of mutations, e.g., by determining the overall mutation status in all or a portion of the genome of a cell. An overall mutation status at least 2% greater, e.g. 2% greater or more, 3% greater or more, 5% greater or more, 10% greater or more, or 20% greater or more than the overall mutation status in a reference cell can be indicative of an increased, elevated, and/or significant level of a DNA editing enzyme activity. In some embodiments, the level of hyper mutations can be determined. In some embodiments, the overall mutation status in the whole genome or a portion thereof can be determined using FISH, whole genome sequencing, high throughput sequencing, exome sequencing, hybridization, and/or PCR. In some embodiments the activity of a DNA editing enzyme can be measured by determining the level of hypermutations in the specific target genes including, but not limited to IGH, BCL6, MYC, BCL1 1A, CD93, PIMI and/or PAX5. In certain embodiments the DNA editing enzyme is AID. In some embodiments, a level of mutation in specific target genes including IGH, BCL6, MYC, BCL1 1A, CD93, PIMI and/or PAX5 which is at least 2% greater, e.g. 2% greater or more, 3% greater or more, 5% greater or more, 10% greater or more, or 20% greater or more than the level of mutation in IGH, BCL6, MYC, BCL1 1A, CD93, PIMI and/or PAX5 in a reference cell can be indicative of an increased, elevated, and/or significant level of AID activity.

In some embodiments, an increased level of DNA damage can be an increased level of double strand breaks (DSBs). The level of DSBs can be determined, by way of non-limiting example, by karyotyping, by γ-H2AX foci formation, and/or by using FISH analysis to detect DNA double strand breaks, e.g. DNA breakage detection fish (DBD-FISH) (Volpi and Bridger, BioTechniques, Vol. 45, No. 4, October 2008, pp. 385-409).

In some embodiments, an increased level of DNA damage can be an increased level of single strand breaks. The level of single-strand breaks in DNA can be determined, by way of non-limiting example, by COMET assays, FISH, or the use of single-strand break-specific probes. Detection of DNA breaks, both single and double-stranded is known in the art and described further, at, e.g., Kumari et al. EXCLI Journal 2009 7:44-62 and Motalleb et al. Research Journal of Applied Sciences, Engineering and Technology. 2012 4: 1888-1894; each of which is incorporated by reference herein in its entirety.

In some embodiments, an increased level of activity of a DNA damage process can comprise an increased level and/or activity of a DNA editing enzyme. In some embodiments, the technology described herein is directed to treating cells having an active DNA editing enzyme with a compound of the present invention. In some embodiments, the technology described herein is directed to treating cells having an increased level and/or activity of a DNA editing enzyme with a compound of the present invention. As used herein, "DNA editing enzyme" refers to an enzyme which normally catalyzes the mutation, exchange or excision of DNA segments, particularly enzymes which can generate or promote the generation of point mutations, DNA single strand breaks, DNA double-strand breaks or protein-DNA adducts. A DNA editing enzyme, as referred to herein, is not necessarily site-specific in its action. Similarly, it is not necessarily cell specific. In some embodiments, the cell is a B cell expressing a detectable amount of such an enzyme.

Non-limiting examples of DNA editing enzymes include, but are not limited to Recombination Activating Gene 1 (RAG1; NCBI Gene ID: 5896), Recombination Activating Gene 1 (RAG2; NCBI Gene ID: 5897), Sporulation-specific protein 11 (SPO11; NCBI Gene ID: 23626), APOBEC family members a Type 1 Topoisomerase; a Type 2 Topoisomerase; and/or AID. In some embodiments, the DNA editing enzyme can be AID.

In some embodiments, the DNA editing enzyme can be a member of the APOBEC (apolipoprotein B mRNA editing enzyme, catalytic polypeptide-like) family. As used herein "APOBEC family" refers to a family of cytidine deaminase enzymes having an N-terminal zinc-dependent cytidine deaminase catalytic domain comprising and a C-terminal pseudocatalytic domain. Non-limiting examples of APOBEC family members include AID, APOBEC 1 (e.g., NCBI Gene ID: 339), APOBEC2 (e.g., NCBI Gene ID: 10930), APOBEC3A (e.g., NCBI Gene ID: 200315), APOBEC3C (e.g., NCBI Gene ID: 27350), APOBEC3E (e.g., NCBI Gene ID: 140564), APOBEC3F (e.g., NCBI Gene ID:200316), APOBEC3G (e.g., NCBI Gene ID: 60489), APOBEC3H (e.g., NCBI Gene ID: 164668), and APOBEC4 (e.g., NCBI Gene ID: 403314).

In some embodiments, the DNA editing enzyme can be a Type 1 topoisomerase. In some embodiments, the DNA editing enzyme can be a Type 2 topoisomerase. Topoisomerases generate breaks in DNA to help uncoil or relax the strand. Type II topoisomerases hydrolyze ATP to generate DSB cuts, while Type I topoisomerases generate single-stranded breaks. Non-limiting examples of Type II topoisomerases can include topoisomerase II (e.g., NCBI Gene ID: 7153 and 7155). Non-limiting examples of Type I topoisomerases can include topoisomerase I (e.g., NCBI Gene ID: 7150).

Embodiments of the technology described herein are based on the discovery that the compounds described herein can inhibit DNA repair mechanisms, e.g., homologous repair. Activation-induced cytidine deaminase (AID, or AICDA, also known as ARP2, CDA2 or HIGM2), a DNA-editing enzyme that is a member of the apolipoprotein B mRNA editing enzymes, catalytic polypeptide-like (APOBEC), will cause widespread genomic breaks and cell death in cells with diminished homologous recombination ability (e.g. cells with diminished DNA double strand break repair abilities). Accordingly, provided herein is a method of causing cell death comprising detecting increased expression of a DNA-editing enzyme (e.g. AID) in a cell and thereafter contacting the cell with a compound of the present invention; thereby resulting in cell death. Accordingly, provided herein is a method of causing cell death comprising increasing expression of a DNA-editing enzyme (e.g. AID) in a cell and thereafter contacting the cell with a compound of the present invention; thereby resulting in cell death. Accordingly, provided herein is a method of causing cell death comprising administering to a cell a therapeutically effective amount of a DNA editing enzyme (e.g. AID) and thereafter contacting the cell with a compound of the present invention; thereby resulting in cell death.

AID, encoded by the AICDA gene (NCBI Gene ID: 57379), is required for proper B-cell function and is most prominently expressed in centroblast B-cells. The protein is involved in somatic hypermutation, gene conversion, and class-switch recombination of immunoglobulin genes. AID is normally expressed almost exclusively in antigen-activated germinal center B-cells, where it initiates immunoglobulin isotype class switching (Manis et al. 2002, Trends Immunol, 23, 31-39; Chaudhuri and Alt, Nat Rev Immunol, 2004, 4, 541-552; Longerich et al., Curr Opin Immunol, 2006, 18, 164-174; Chaudhuri et al., Adv Immunol 2007, 94, 157-214). AID is required for somatic hypermutation and immunoglobulin class switching in activated B cells. AID expression is regulated by CD40 ligand, B-cell receptor, IL4R, or Toll-like receptor stimulation (Crouch et al., J Exp Med 2007 204: 1145-1156; Muramatsu et al., J Biol Chem 1999 274: 18470-6). After activation, AID is transiently upregulated, induces point mutations or DNA double strand breaks in a sequence nonspecific manner within immunoglobulin genes, and is then downregulated (Longerich et al., Curr Opin Immunol, 2006, 18, 164-176; Chaudhuri et al., Adv Immunol 2007, 94, 157-214). Overall, AID is active in only a tiny population of normal cells (antigen-activated B-cells) at any given time. The genomic rearrangements and mutations controlled by AID lead to the development of antigen-recognition diversity, receptor editing and lymphoid effector function required for functional adaptive immunity (Mills, et al. Immunol Rev 2003 194:77-95). Recently it has been reported that AID has off-target point mutation activities (Liu, M. et al., Nature 2008, 451, 841-845; Liu and Schatz, Trends Immunol. 2009, 30, 173-181; Perez-Duran et al., Carcinogenesis. 2007, 28(12):2427-33). Robbiani et al. has reported off-target activities of AID in B-cells, especially c-myc/IgH translocations (Robbiani et al., Mol Cell 2009, 36(4):631-41). AID expression accelerates the rate of tumor development in Bcl6 transgenic mice (Pasqualucci et al., 2008, Nat. Genet. 40, 108-112). However, deregulated AID does not necessarily cause malignancy or translocation-associated cancer on its own in B cells (Muto et al., 2006, Proc. Natl. Acad. Sci. USA 103, 2752-2757; Okazaki et al., 2003, J. Exp. Med. 197, 1173-1181; Shen et al., 2008, Mol. Immunol. 45, 1883-1892). In addition, despite its obligate role in c-myc/IgH translocation, AID is not required for the development of plasmacytosis or plasmacytoma in IL-6 transgenic or pristane-treated mice, respectively (Kovalchuk et al., 2007, J. Exp. Med. 204, 2989-3001; Ramiro et al., 2004, J. Exp. Med. 200, 1103-1110). However, most human B cell lymphoma-associated translocations do not involve c-myc, and many do not involve Ig genes (Kuppers, 2005, Oncogene 20, 5580-5594).

Overexpression of AID has been reported in chronic lymphocytic leukemia (CLL) (Hancer et al. Leuk Lymphoma. 2011 January; 52(1):79-84; Heintel et al., Leukemia. 2004 April; 18(4):756-62). Further, AID expression has been shown to be correlated with blast crisis B lineage leukemia and therapy resistance in myeloid leukemia and to be associated with generally poor prognosis in chronic B lymphocytic leukemia (Mao et al., Br J Dermatol 2001, 145: 117-122; Chaudhuri et al., Nature 2004, 430:992-8). Further expression of AID in tumor cells from a variety of cancers has been reported including but not limited to lung, breast, gastric, colon, intestinal, liver cancer and choriangiocarcinoma (Greeve et al., Blood 2003, 1010, 3574-3580; Feldhahn et al., J Exp Med 2007, 204, 1157-1166; Kotani et al., PNAS USA 2007, 104, 1616-1620; Engels et al., 2008, Appl Immunohistochem Mol Morphol 16, 521-529; Klemm et al., 2009, Cancer Cell 6, 232-245; Palacios et al., 2010, Blood 115(22), 4488-4496; Leuenberger et al., 2009, Mod Pathol 32, 177-186; Gruber et al., 2010, Cancer Res 70, 7411-7420; inflammatory cancer (Marusawa 2008, Int J Biochem Cell Biol. 40, 399-402); follicular lymphoma (Hardianti et al., 2004, Leukemia 18, 826-831; Shikata et al., 2012, Cancer Sci. 103(3):415-21); thyroid cancer (Qiu et al. 2012, Mod Pathol 25(1), 36-45); breast cancer (Borchert et al. 2011, BMC Cancer 11:347); Marusawa, et al., 2011, Adv Immunol 111: 109-41; Zhang et al. 2012, Hum Pathol 43(3):423-34; Komori et al., 2008, Hepatology 47(3):888-896; Hockley 2010, Leukemia 24(5): 1084-6; adult T-cell leukemia (Nakamura et al., 2011, Br J Dermatol. 165(2):437-9). All of the references in the foregoing paragraph are incorporated by reference herein in their entireties.

Elevated levels of AID have been reported in arthritis (Xu et al. Scand. J. Immunol. 2009, 296, 2033-6) and in the MRL/Fas(lpr/lpr) mouse lupus model (White et al. 2011, Autoimmunity 44(8), 585-98). All of the references in the foregoing paragraph are incorporated by reference herein in their entireties.

When DSB repair is inhibited, the extent of the DSBs generated by AID is much higher than previously suspected and the extent of genomic damage is so severe as to result in cell death. Accordingly, in one embodiment of the technology described herein, there is provided a method of treatment comprising; (a) selecting a subject having cells that express elevated levels of activation-induced cytidine deaminase (AID); and (b) administering a therapeutically effective amount of an inhibitor of double strand break repair (e.g. a compound of the present invention) to the subject; wherein an elevated level of AID is a level of AID that is higher than the level of AID in cells of the same type from a healthy individual. In some embodiments, the cells expressing elevated levels of AID are B cells. In some embodiments, the B cell expressing elevated levels of AID is a cancerous B cells or a B cell associated with autoimmune disease. In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

In some embodiments, an increased level and/or activity of a DNA editing enzyme can be an increased level of DNA editing enzyme mRNA. mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In one embodiment, nuclear "run-on" (or "run-off") transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In some embodiments, a subject can be determined to have an increased level of DNA damage occurring in one or more cell types relative to a reference level if the subject has been exposed to an agent that is known to cause such DNA damage. Non-limiting examples of such agents can include a viral infection with a DNA integrating virus (e.g. adeno-associated virus, retrovirus, human T-lymphotropic virus, HIV-1, oncovirus, hepatitis virus, hepatitis B virus); DNA damaging chemicals (e.g. acetaldehyde, polycyclic aromatic hydrocarbons, benzenes, nitrosamines, tobacco smoke, aflatoxin, and the like); DNA damaging chemotherapeutic agents (e.g. bleomycin, mitomycin, nitrogen mustards (e.g. mechlorethamine, cyclophosphamide, melphalan, chlorambucil, ifosfamide and busulfan), nitrosoureas (e.g., N-Nitroso-N-methylurea (MNU), carmustine (BCNU), lomustine (CCNU) and semustine (MeCCNU), fotemustine and streptozotocin), tetrazines (e.g., dacarbazine, mitozolomide and temozolomide), aziridines (e.g., thiotepa, mytomycin and diaziquone (AZQ)), cisplatins (e.g., cisplatin, carboplatin and oxaliplatin) procarbazine and hexamethylmelamine); and ionizing or ultraviolet radiation. Exposure to such agents can be the result of an accident, infection and/or environmental exposure or the result of a therapeutic administration of such agents.

In some embodiments, the increased level of DNA damage can be occurring in a cell type affected by the cancer, autoimmune disease, and/or neurodegenerative disease. In some embodiments, the subject is determined to have an increased level of DNA damage occurring in a cell selected from the group consisting of: a cancer cell; an immune system cell; or a nervous system cell.

In some embodiments, the DNA editing enzyme can be AID. In some embodiments, the level of AID can be the level of AID in a blood cell. In some embodiments, the level of AID can be the level of AID in a B cell.

In some embodiments, an increased level of AID can be a detectable level of AID, e.g., as described below herein.

In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is a provided a treatment paradigm that selectively induces self-destruction of certain diseased cells, while reducing the unintended side effects in healthy tissues.

Methods of defecting cancers in patients with increased levels of DNA damage or increased levels of DNA editing enzymes are disclosed in WO2016/094897, incorporated herein by reference.

In certain embodiments, the cancer to be treated is a type with high expression of a DNA editing enzyme. In certain embodiments, the cancer to be treated is a B-cell neoplasm.

Another embodiment is a method of treating a cancer by administering to the subject an effective amount of one or more disclosed compounds, or a pharmaceutically acceptable salt thereof, or the corresponding pharmaceutical composition. In one aspect, the cancer is selected from the group consisting of lymphoma, leukemia, and a plasma cell neoplasm. In another aspect, the cancer selected from the group consisting of carcinoma and sarcoma.

In certain embodiments, the cancer to be treated is a lymphoma. Lymphomas which can be treated by the disclosed methods include Non-Hodgkin's lymphoma; Burkitt's lymphoma; small lymphocytic lymphoma; lymphoplasmacytic lymphoma; MALT lymphoma; follicular lymphoma; diffuse large B-cell lymphoma; and T-cell lymphoma.

Lymphoma is a malignancy in the lymphatic cells of the immune system (e.g. B cells, T cells, or natural killer (NK) cells). Lymphomas often originate in the lymph nodes and present as solid tumors. They can metastasize to other organs such as the brain, bone, or skin. Extranodal sites are often located in the abdomen. Lymphomas are closely related to the lymphoid leukemia and in some cases a particular form of cancer is categorized as both a lymphoma and a leukemia.

Leukemias which can be treated by the disclosed methods include acute lymphoblastic leukemia (ALL); Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

In certain embodiments the cancer to be treated is B-cell neoplasms, B-cell leukemia, B-cell acute lymphoblastic leukemia, chronic lymphocytic leukemia, chronic myelogenous leukemia, Burkitt's leukemia, acute myelogenous leukemia and/or T-ALL. The maturation of B cells most typically ceases or substantially decreases when the foreign antigen has been neutralized. Occasionally, however, proliferation of a particular B cell will continue unabated; such proliferation can result in a cancer referred to as "B-cell lymphoma" or a "B-cell leukemia." In certain embodiments the cancer to be treated is chronic lymphocytic leukemia (CLL) or chronic myelogenous leukemia (CML).

In certain embodiments the cancer to be treated is a plasma cell neoplasm. Examples for plasma cell neoplasms include multiple myeloma; plasma cell myeloma; plasma cell leukemia and plasmacytoma.

Carcinomas which can be treated by the disclosed methods include colon cancer; liver cancer; gastric cancer; intestinal cancer; esophageal cancer; breast cancer; ovarian cancer; head and neck cancer; lung cancer; and thyroid cancer.

Sarcomas which can be treated by the disclosed methods include soft tissue sarcoma and bone sarcoma.

Any cancer characterized by high levels of DNA damage and/or DNA editing enzyme expression can be treated with a compound as described herein, e.g. a compound of the present invention. For example, sarcomas, epithelial cell cancer (carcinomas), colon cancer, gastric cancer, intestinal cancer, liver cancer, hepatocellular cancer, breast cancer, thyroid cancer, esophageal cancer, lung cancer, brain cancer, head and neck cancer, melanoma, renal cancer, prostate cancer, hemangioma, rhabdomyosarcoma, chondrosarcoma, osteosarcoma, fibrosarcoma and cholangiocarcinoma may be characterized by high levels of a DNA editing enzyme expression, e.g. AID. In certain embodiments the cancer to be treated is colon cancer, liver cancer, gastric cancer, intestinal cancer, breast cancer, lung cancer, thyroid cancer and/or cholangiocarcinoma.

Specific cancers that can be treated by the disclosed methods include cancer of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; sarcomas; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another embodiment for the disclosed method, the cancer is characterized by mutations in the mutS homologues (e.g., MSH2, MSH3, and MSH6), mutL homologues (e.g. MLH1), or mismatch repair endonuclease PMS2. Mutations are changes in the genetic code. They include point mutations and frameshift mutations. In a point mutation, one nucleotide is swapped out for another. Therefore, the mutation occurs at a single point or location within the DNA strand. Frameshift mutations are due to either insertions or deletions of nucleotides. This causes the entire DNA strand to elongate or to shrink in size. Thus, frameshift mutations may alter all of the codons that occur after the deletion or insertion. The mutations referred to herein include, but are not limited to, insertions, deletions, duplications, inversions, or other recognized point mutations. It has now been found that RAD51 inhibitors are particularly effective in treating cancers with mutations in MSH (e.g. MSH6), MLH, or PMS2.

MutS Homolog 2 (MSH2) is a protein that in humans is encoded by the MSH2 gene, which is located on chromosome 2. MSH2 is a tumor suppressor gene and more specifically a caretaker gene that codes for a DNA mismatch repair (MMR) protein, MSH2, which forms a heterodimer with MSH6 to make the human MutSα mismatch repair complex. It also dimerizes with MSH3 to form the MutSβ DNA repair complex. MSH2 is involved in many different forms of DNA repair, including transcription-coupled repair, homologous recombination, and base excision repair. Examples of the mutations in MSH2 include, but are not limited to, g.47630253_47630254del, g.47702411_47702421del, g.47709913_47709915inv, g.47635629_47635634del, g.47637227_47637236dup, g.47639550_47639561del, g.(?_47630206)_(47710367_?)del, g.(?_47630206)_(47643569_47656880)del, g.47630263_47643568del, g.(?_47630206)_(47657081_47672686)del, g.47630263_47657080del, g.(?_47630206)_(47672797_47690169)del, g.47630263_47672796del, g.(?_47630206)_(47672797_47690169)del, g.(?_47630206)_(47693948_47698103)del, g.47630263_47693947del, g.(?_47630206)_(47698202_47702163)del, g.(?_47630206)_(47630542_47635539)del, g.(?_47630206)_(47708011_47709917)del, g.(?_47630206)_(47635695_47637232)del, g.(?_47630206)_(47635695_47637232)del, g.(?_47630206)_(47637512_47639552)del, g.(?_47630206)_(47639700_47641407)del, g.(?_47630206)_(47641558_47643434)del, g.47618487_47650860delins(155), g.47628578_47638433del, g.47595033_47662777del, g.47583175_47667707del, g.47625602_47636880del, g.47554933_47699909de, g.47629508_47649552del, g.47629375_47651274del, g.(?_47630206)_(47630542_47635539)del, g.(?_47630206)_(47635695_47637232)del, g.47643509_47643510del, g.47643529_47643530dup, g.47656746_47657199dup, g.47656661_47663325del, g.(47643569_47656880)_(47710367_?)del, g.(47643569_47656880)_(47710367_?)del, g.47643569_47656881_47657080del, g.(47643569_47656880)_(47657081_47672686)del, g.(47643569_47656880)_(47657081_47672686)del, g.(47643569_47656880)_(47657081_47672686)del, g.(47643569_47656880)_(47657081_47672686)dup, g.(47643569_47656880)_(47657081_47672686)dup, g.(47643569_47656880)_(47672797_47690169)del, g.(47643569_47656880)_(47693948_47698103)del, g.47656881_47693947del, g.(47643569_47656880)_(47702410_47703505) del, g.47656881_47656882ins(173), g.47656901_47656902insA, g.47656903del, g.47656912del, g.47630440del, g.47656923del, g.47656931_47656932dup, g.47656943del, g.47656943_47656949delinsCCCAGA, g.47656948dup, g.47656996dup, g.47657000_47657001dup, g.47630449del, g.47657007dup, g.47657008del, g.47657020_47657023dup, g.47657025_47657026del, g.47657026dup, g.47657030_47657031 del, g.47657047_47657050del, g.47657053del, g.47657053_47657057057de, g.47657064del, g.47657073dup, g.47657312_47676594del, g.47668611_47674615del, g.47672116_47675123del, g.47666463_47677632del, g.47666403_47677572del, g.(47657081_47672686)_(47710367_?)del, g.(47657081_47672686)_(47710367_?)inv, g.47671507_47675022deinsCATTCTCTTTGAAAA, g.47657278_47676557del, g.47672687_47672796de, g.(47657081_47672686)_(47672797_47690169)del, g.(47657081_47672686)_(47672797_47690169)del, g.(47657081_47672686)_(47693948_47698103)del, g.(47657081_47672686)_(47698202_47702163)del, g.(47657081_47672686)_(47708011_47709917)del, g.47672691dup, g.47672697dup, g.47672721_47672744 delins47672748_47672771inv, g.47672728_47672729del, g.47672731dup, g.47672750_47672751 insGG, g.47672755_47672758del, g.47672762_47672763del, g.47630466_47630494del, g.47686194_47697740del, g.(47672797_47690169)_(47710367_?)del, g.(47672797_47690169)_(47690294_47693796)del, g.(47672797_47690169)_(47693948_47698103)del, g.47690170_47693947del, g.(47672797_47690169)_(47693948_47698103)del, g.(47672797_47690169)_(47693948_47698103)dup, g.(47672797_47690169)_(47705659_47707834)del, g.47690173del, g.47690191del, g.47690216_47690217dup, g.47690227del, g.47690227dup, g.47690228_47690232del, g.47690230_47690231 del, g.47690240del, g.47690240_47690243del, g.47630475del, g.47630475_47630476del, g.47690259_47690260delins CT, g.47690277dup, g.47690280del, g.47690283dup, g.(47690294_47693796)_(47702410_47703505)del, g. 47630484_47630485insG, g.47693838_47693839del, g.47693862del, g.47693864del, g.47693873del, g.47693880dup, g.47693913del, g.47693924_47693925dup, g.47630493del, g.47697730_47706125de, g.(47693948_47698103)_(47710367_?)del, g.(47693948_47698103)_(47698202_47702163)del, g.(47693948_47698103)_(47705659_47707834)del, g.47698107del, g.47698109del, g.47698109_47698110insA, g.47630496del, g.47698118del, g.47698125del, g.47698129dup, g.47698138_47698139del, g.47698142_47698146del, g.47698144dup, g.47698147_47698148del, g.47698147_47698148dup, g.47698147_47698148insT, g.47698159del, g.47698162del, g.47698506_47703472de, g.47701803_47708848del, g.(47698202_47702163)_(47710367_?)del, g.(47698202_47702163)_(47702410_47703505)del, g.(47698202_47702163)_(47703711_47705410)del, g.(47698202_47702163)_(47705659_47707834)del, g.47702164del, g.47702175_47702176insA, g.47702183_47702186del, g.47702185_47702186insCT, g.47702190_47702192del, g.47702191dup, g.47702192_47702193del, g.47702213del, g.47702231del, g.47702242dup, g.47702257del, g.47702262_47702263dup, g.47630516_47630517dup, g.47630517del, g.47630517dup, g.47702289_47702290inv, g.47702293_47702296del, g.47702301dup, g.47702315del, g.47702315del, g.47702328_47702329del, g.47630522dup, g.47702339del, g.47702371_47702374dup, g.47702384_47702385del, g.47702386_47702389del, g.47702388del, g.47702388_47702389del, g.47702390del, g.47702390_47702391del, g.47702400_47702401del, g.47703506_47703710del, g.47703506_47708010del, g.47703510del, g.47703515del, g.47703521_47703522de, g.47703535_47703536del, g.47703546_47703547de, g.47703548_4770361 Idup, g.47630534del, g.47703571dup, g.47703574_4770358 Idel, g.47703585dup, g.47630350del, g.47632107_47668733del, g.47703613del, g.(47630542_47635539)_(47643569_47656880)del, g.(47630542_47635539)_(47643569_47656880)inv, g.(47630542_47635539)_(47657081_47672686)del, g.47635540_47657080del, g.(47630542_47635539)_(47672797_47690169) del, g.(47630542_47635539)_(47690294_47693796)del, g.(47630542_47635539)_(47705659_47707834)del, g.47635540_47635694del, g.(47630542_47635539)_(47635695_47637232)del, g.(47630542_47635539)_

(47635695_47637232)del, g.(47630542_47635539)_(47637512_47639552)del, g.47703635dup, g.47703641dup, g.47635542_47635549del, g.47703660_47703663del, g.47703667dup, g.47630351dup, g.47703704del, g.47703826_47707938del, g.(47703711_47705410)_(477055659_47707834)del, g.47705428_47705431 del, g.47705437_47705438insA, g.47635551_47635552del, g.47705440_47705441 del, g.47705461del, g.47705490del, g.47705494del, g.47705495del, g.47635557_47635558del, g.47705505del, g.47705535dup, g.47705547del, g.47705560_47705561dup, g.47705561dup, g.47705562dup, g.47705588del, g.47705608_47705609del, g.47705618dup, g.47705627dup, g.47635571_47635601delins(217), g.(47705659_47707834)_(47710367_?)del, g.(47705659_47707834)_(47708011_47709917)del, g.47707842_47707843del, g.47707861del, g.47707861_47707874dup, g.47707878_47707884del, g.47707878_47707884de, g.47707883del, g.47707895_47707905de, g.47707897del, g.47707901_47707902del, g.47707905_47707906de, g.47707921del, g.47635583dup, g.47635583_47635584del, g.47707969_47707973de, g.47707996_47707997ins(115), g.47708009_47708010del, g.(47708011_47709917)_(47710367_?)del, g.47635591_47635592del, g.47635597_47635618dup, g.47635606_47635607del, g.47630359dup, g.47635672del, g.47635675_47635678del, g.47630364dup, g.47635680dup, g.47636862_47639040del, g.47636781_47638831del, g.47636753_47638155del, g.47636552_47638597del, g.(47635695_47637232)_(47643569_47656880)del, g.(47635695_47637232)_(47643569_47656880)del, g.(47635695_47637232)_(47657081_47672686)del, g.(47635695_47637232)_(47672797_47690169)del, g.(47635695_47637232)_(47698202_47702163)del, g.(47635695_47637232)_(47637512_47639552)del, g.(47635695_47637232)_(47641558 47643434)del, g.47637234del, g.47637246_47637247del, g.47637253_47637254del, g.47637254_47637255del, g.47637254_47637255del, g.47637265del, g.47637274del, g.47637282del, g.47637320del, g.47637372_47637375de, g.47637377_47637449dup, g.47637379del, g.47637384del, g.47637394_47637395del, g.47637396_47637397del, g.47637417del, g.47637427_47637435del, g.47637437_47637439del, g.47637453del, g.47637458dup, g.47637479_47637482dup, g.47637482dup, g.47637504_47637505del, g.47637508_47637511del, g.47638050_47653430del, g.47638302_47648462del, g.47638478_47648643del, g.(47637512_47639552)_(47710367_?)del, g.(47637512_47639552)(47643569_47656880)del, g.47639553_47643568del, g.(47637512_47639552)_(47657081_47672686)del, g.(47637512_47639552)_(47657081_47672686)del, g.(47637512_47639552)_(47672797_47690169)del, g.(47637512_47639552)_(47639700_47641407)del, g.(47637512_47639552)(47641558_47643434)del, g.47639557_47639561del, g.47639582_47639586delinsTAAT, g.47639583_47639584del, g.47639594del, g.47639594dup, g.47639598del, g.47639603_47639604del, g.47639611_47639612del, g.47639612del, g.47639618_47639621del, g.47639624_47639628delinsTTA, g.47630401dup, g.47639632dup, g.47639638_47639641dup, g.47639638_47639641dup, g.47639639del, g.47639639del, g.47639642dup, g.47630403_47630404insC, g.47639653del, g.47639666del, g.47639666_47639669del, g.47639668del, g.47639670_47639673delinsTT, g.47639674_47639675dup, g.47639695_47639696del, g.47639707_47642985del, g.47641402_47642007del, g.(47639700_47641407)(47643569 47656880)del, g.47641408_47643568del, g.(47639700_47641407)_(47657081_47672686)del, g.(47639700_47641407)_(47672797_47690169)del, g.(47639700_47641407)_(47641558_47643434)del, g.(47639700_47641407)_(47641558_47643434)del, g.47641410del, g.47641425_47641426del, g.47641426_47641429del, g.47630412del, g.47641451del, g.47641454dup, g.47641455dup, g.47641469del, g.47641478del, g.47641488_47641491del, g.47641496_47641497del, g.47641503del, g.47641513_47641514dup, g.47641530_47641537dup, g.47642509_47655432del, g.(47641558_47643434)(47643569_47656880)del, g.(47641558_47643434)_(47693948_47698103)del, g.47630424_47630433del, g.47643450dup, g.47643462_47643463del, g.47643462_47643463ins(4), g.47643464_47643465insNC_000022.10:35788169_35788352, g.47643465dup.

MutS Homolog 3 (MSH3) is a human homologue of the bacterial mismatch repair protein MutS that participates in the mismatch repair (MMR) system. MSH3 typically forms the heterodimer MutSβ3 with MSH2 in order to correct long insertion/deletion loops and base-base mispairs in microsatellites during DNA synthesis. Deficient capacity for MMR is found in approximately 15% of colorectal cancers, and somatic mutations in the MSH3 gene can be found in nearly 50% of MMR-deficient colorectal cancers. Examples of the mutations in MSH3 include, but are not limited to, g.79970809del.

MSH6 encodes MutS homologue 6 (MSH6), a member of the Mutator S (MutS) family of proteins that are involved in DNA mismatch repair (MMR). The MSH6 protein forms a heterodimer with MutS homologue 2 (MSH2) in both human and yeast. Human MSH2/6 recognizes single base-base mismatches and short insertion/deletion loops. Upon recognition of a mismatch, MSH2/6 complex binds and exchanges ADP for ATP, resulting in a conformational change to the complex that precedes base pair dissolution, base excision, and repair.

MSH6 mutations include frameshift and/or nonsense mutations and can result in non-functional MSH6 and loss of protein expression. Examples include a frameshift mutation at MSH6 amino acid residue 290 and a compounding missense T1189I.

Inactivating MSH6 mutations can be detected in cancers by routine diagnostics methods. These methods include, but are not limited to, obtaining cancer cells and other diagnostic indicators such as peripheral blood mononuclear cells (PBMCs), PBMC subpopulations, circulating blasts (CD34+ cells), circulating tumor cells and circulating exosomescancer cells by biopsy and blood tests and by obtaining lymphatic or other bodily fluids. It is then determined from the cancer cells or other diagnostic indicators whether the cancer exhibits an inactivating MSH6 mutation is by methodology known in the art, for example, direct DNA sequencing and multiplex ligation dependent probe amplification, RNA sequencing (RNA-Seq), microarray, quantitative PCR, or NanoString™ gene expression panels, or MSH6 protein by immunohistochemistry, flow cytometry, immunocytochemistry or Western blot. Methods for identifying inactivating MSH6 mutations are disclosed in Houlleberghs H, Goverde A, Lusseveld J, Dekker M, Bruno M J, et al. (2017) Suspected Lynch syndrome associated MSH6 variants: A functional assay to determine their pathogenicity. PLOS Genetics 13(5): e1006765. https://doi.org/10.1371/journal.pgen.1006765.

Examples of the mutations in MSH6 include, but are not limited to, g.48032846_48032849del, g.48032846_48032849del, g.48032846_48032849del, g.48033337_48033342del, g.48033420_48033422del, g.(?_48010221)_(48034092)del, g.(?_48010221)_(48018263_48023032)del, g.47998510_48020183del, g.48007276_48020272del, g.48026207del, g.48026223del, g.48026223del, g.48026257_48026261del, g.48026261_48026265del, g.48026312_48026313del, g.48026398del, g.48026543_48026544dup, g.48026693dup, g.48026702del, g.48026712del, g.48026718dup, g.48026736_48026737delinsAG, g.48026736_48026737delinsG, g.48026750_48026751 del, g.48026754_48026757del, g.48026756_48026759del, g.48026759_48026760del, g.48026906del, g.48026928_48026931del, g.48026941dup, g.48026991del, g.48027023_48027024del, g.48027079del, g.48027079_48027082dup, g.48027167_48027168del, g.48027172_48027173dup, g.48027178_48027185del, g.48027184_48027185del, g.48027272_48027275del, g.48027470_48027471 del, g.48027501_48027502del, g.48027501_48027502delTG, g.48027657dup, g.48027691_48027694del, g.48027733_48027736dup, g.48027794_48027796delinsC, g.48027841_48027842del, g.48027887del, g.48027890dup, g.48027973_48027980del, g.48028067del, g.48028098del, g.48028106del, g.48028175_48028176del, g.48028241_48028242del, g.48028241_48028242delTT, g.48028272_48028284dup, g.48028277_48028278del, g.48030558_48030559de, g.48030126_48032394del, g.48030568del, g.48030581_48030584del, g.48030584_48030585dup, g.48030607del, g.48030645_48030646insT, g.48030647del, g.48030647dup, g.48030649dup, g.48030654_48030660del, g.48030659dup, g.48030697_48030698del, g.48030698del, g.48030706del, g.48030710dup, g.48030727_48030728insC, g.48030765_48030829del, c.3438+797 3438+798insTA-Tins1839_3439-428, c.3438+797_3438+798insTA-Tins1839_3439-428, g.48032121_48032122del, g.48032123_48032124del, g.48032124dup, g.48032126_48032129del, g.48032129_48032130insA, g.48032129_48032132dup, g.(48032167_48032756)_(48034092_?)del, g.48032809_48032812del, g.48032835dup, g.48032846_48032849del, g.48033374_48033402dup, g.48033395_48033398del, g.48033421_48033433del, g.48033425_48033428dup, g.48033453_48033454insA, g.48033494_48033523del, g.48033495_48033496del, g.48033593dup, g.48033610_48033613dup, g.48033629_48033635del, g.48033636_48033639dup, g.48033676_48033682del, g.48033707dup, g.48033709_48033716dup, g.48033721_48033724dup, g.48033727_48033730dup, g.48033728_48033746dup, g.(48033742_48033743)_(48033742_48033743)ins(32), g.48033746dup, g.48033748_48033751del, g.48033758_48033768del, g.48033773_48033774insATCA, g.48033773_48033776dup, g.48033785_48033789dup, g.48033887_48033910inv, g.(48018263_48023032)_(48032167_48032756)del, g.(48018263_48023032)_(48023203_48025749)del, g.48023097_48023098del, g.48025773dup, g.48025832del, g.48025860_48025861insT, g.48025884_48025885del, g.48025967dup.

MutL homolog 1, colon cancer, nonpolyposis type 2 (*E. coli*) is a protein that in humans is encoded by the MLH1 gene located on Chromosome 3. It is a gene commonly associated with hereditary nonpolyposis colorectal cancer.

Examples of the mutations in MSH6 include, but are not limited to, g.37089113_37089115del, g.37089175del, g.37090379_37090393del, g.37038201_37038202del, g.37042531_37042542del, g.37053339_37053355del, g.37053354del, g.37053590_37053591insT, g.37034841_37092337del, g.(?_37034841)_(37092337_?)del, g.(?_37034841)_(37061955_37067127)del, g.(?_37034841)_(37035155_37038109)del, g.(?_37034841)_(37035155_37038109)del, g.(?_37034841)_(37070424_37081676)del, g.(?_37034841)_(37083823_37089009)del, g.37034841_37083822del, g.(?_37034841)_(37038201_37042445)del, g.(?_37034841)_(37042545_37045891)del, g.37034841_37042544del, g.(?_37034841)_(37042545_37045891)del, g.(?_37034841)_(37042545_37045891)del, g.(?_37034841)_(37045966_37048481)del, g.(?_37034841)_(37050397_37053310)del, g.(?_37034841)_(37059091_37061800)del, g.37034658_37038806del, g.36961079_37138741del, g.37061923del, g.37061927del, g.37061933del, g.37061939del, g.37061942dup, g.37035140_37035141del, g.37070417del, g.37070417_37070418insT, g.37070419dup, g.37070422_37070423insT, g.37080355_37083368del, g.(37070424_37081676)_(37092337_?)del, g.(37070424_37081676)_(37081786_37083758)del, g.(37070424_37081676)_(37083823_37089009)del, g.37038148_37038151del, g.37038149del, g.37038149dup, g.37081690_37081691del, g.37081691_37081692del, g.37081706_37081708del, g.37081710_37081711del, g.37035053_37035066del, g.37038154del, g.37038154_37038157del, g.37081738_37081739del, g.37081740del, g.37081753dup, g.37081757_37081761dup, g.37081782_37081783insAAGT, g.37081787_37081793delinsATTT, g.(37081786_37083758)_(37083823_37089009)del, g.(37081786_37083758)_(37089175_37090007)del, g.37083759del, g.37083780dup, g.37083781_37083784del, g.37083781_37083784delCTCA, g.37083808_37083809del, g.37083816del, g.37086069_37089606del, g.37084092_37089247del, g.37084590_37089786del, g.(37083823_37089009)_(37092337_?)del, g.(37083823_37089009)_(37089175_37090007)del, g.37089010_37089174del, g.(37083823_37089009)_(37090509_37091976)del, g.37089023del, g.37089026_37089027del, g.37089027del, g.37089036del, g.37089036dup, g.37038168dup, g.37089042del, g.37089047del, g.37089050_37089053del, g.37089056_37089057del, g.37089061_37089062del, g.37089078_37089096del, g.37089090dup, g.37089099dup, g.37089107_37089110dup, g.37089109_37089110del, g.37089130_37089132del, g.37089130_37089132delAAG, g.37089131delinsTTCTT, g.37089133del, g.37089133delG, g.37089144del, g.37089155del, g.37089155_37089161del, g.37089158_37089161del, g.37089162_37089166del, g.37089171del, g.(37089175_37090007)_(37090101_37090394)del, g.37035056_37035072del, g.37090013del, g.37090015dup, g.37038183_37038184del, g.37090024_37090037dup, g.37090025_37090053dup, g.37090027dup, g.37038184dup, g.37090031_37090032insT, g.37090041del, g.37090057del, g.37090064_37090067del, g.37038188del, g.37090082del, g.37090086_37090087del, g.37090087_37090088del, g.37090097_37090101delinsC, g.37090099del, g.37038191dup, g.(37090101_37090394)_(37092337_?)del, g.37035057_37035073del, g.37090405dup, g.37090411_37090415del, g.37090414del, g.37038194del, g.37038198del, g.37090472_37090478del, g.37039445_37059613dup, g.37039760_37052440del, g.37090481_37090482del, g.37090483_37090484del, g.37090483_37092045del, g.37040732_37043185delinsACATAGTA, g.37042445_37042446del, g.(37038201_37042445)_(37042545_37045891)del, g.(37038201_37042445)_(37048555_37050304)del, g.(37038201_37042445)_(37050397_37053310)del, g.(37038201_37042445)_(37053591_37055922)del, g.37090497_37090498del, g.37090497_37090498delTC, g.37090504_37090507del, g.(37090509_37091976)(3709 2337_?)del, g.(37090509_37091976)_(37092337_?)dup, g.37091977_37091978del, g.37091978_37091987del, g.37042448_37042451del, g.37091984_37091990del, g.37042451_37042453del, g.37092020_37092021del, g.37092022_37092068dup, g.37092027_37092028del, g.37092027_37092028dup, g.37092030dup, g.37092052_37092055del, g.37092054_37092055del, g.37092068_37092071dup, g.37092091dup, g.37092094_37092097deins(30), g.37092096_37092106del, g.37092097del, g.37092125_37092126delAA, g.37092125_37092126del, g.37092139_37092142dup, g.37092142dup, g.37035060dup, g.37042469_37042470del, g.37042470del, g.37042482dup, g.37042485del, g.37042499del, g.37042546dup, g.37044472_37046589del, g.37045648_37049941del, g.37045095_37054651del, g.37045072_37046861del, g.(37042545_37045891)(37045966_37044481)del, g.(37042545_37045891)_(37092337_?)del, g.(37042545_37045891)_(37048555_37050304)del, g.(37042545_37045891)_(37050397_37053310)del, g.37045892_37050396del, g.37035069del, g.37045926del, g.37045931del, g.37045939_37045940dup, g.37045957_37045958del, g.37045963del, g.37035075del, g.37048067_37049287del, g.(37045966_37048481)_(37048555_37050304)del, g.(37045966_37048481)_(37050397_37053310)del, g.37048483del, g.37048483_37048503delinsT, g.37048486_37048487delinsGTT, g.37048489del, g.37048490del, g.37035076_37035077insCCCA, g.37035077_37035078dup, g.37048505_37048508del, g.37048521del, g.37048529dup, g.37035082dup, g.37049873_37052281del, g.37049839_37052249del, g.37049800_37052209del, g.37049640_37050445del, g.37050305_37050396del, g.(37048555_37050304)_(37050397_37053310)del, g.37050305_37050396del, g.37050319_37050320del, g.37050339del, g.37050348del, g.37050353_37050354del, g.37050354dup, g.37050364del, g.37050375_37050376insGA, g.37035090del, g.37050382_37050383delinsAT, g.37050382_37050383delinsCT, g.37050390_37050396del, g.37052950_37060990del, g.(37050397_37053310)_(37067499_37070274)dup, g.(37050397_37053310)_(37053591_37055922)del, g.(37050397_37053310)_(37056036_37058996)del, g.37053353del, g.37053510_37053511del, g.37035099del, g.37053545_37053546insT, g.37053562del, g.37053578del, g.37053578dup, g.37053585del, g.37053586_37053589del, g.37053591del, g.37053590_37053591delinsAT, g.37055920_37055921del, g.37055914_37055938del, g.(37053591_37055922)_(37070424_37081676)del, g.(37053591_37055922)_(37083823_37089009)del, g.(37053591_37055922)_(37059091_37061800)del, g.37035105del, g.37055928dup, g.37035106_37035116del, g.37055938del, g.37035108del, g.37055972_37055975del, g.37055976_37055979de, g.37035111del, g.37055990dup, g.37035114del, g.37035116del, g.37056036del, g.37056037dup, g.37058993_37059001del, g.(37056036_37058996)_(37070424_37081676)del, g.(37056036_37058996)_(37059091_37061800)del, g.37058997_37059000del, g.37059014_37059017del, g.37059017_37059021de, g.37059027_37059030dup, g.37035122del, g.37059062_37059063insT, g.37059065_37059066del, g.37059066del, g.37059066dup, g.37059072_37059073del, g.37059072_37059073dup, g.37059090_37059093de, g.37061595_37061913de, g.37061308_37066756del, g.37061207_37063077de, g.(37059091_37061800)_(37092337_?)del, g.(37059091_37061800)_(37061955_37067127)del, g.37061801_37061954del, g.(37059091_37061800)_(37083823_37089009)del, g.37061803dup, g.37061804del, g.37061817del, g.37061837_37061838dup, g.37061844del, g.37061851dup, g.37061855dup, g.37061870del, g.37061904_37061906del, g.37061910del, g.37035047del, g.[37049179_37051317delinsTG; 37051667_37054327delinsCA].

Human PMS2 related genes are located at bands 7p12, 7p13, 7q11, and 7q22. Exons 1 through 5 of these homologues share high degree of identity to human PMS2. The product of this gene is involved in DNA mismatch repair. The protein forms a heterodimer with MLH1 and this complex interacts with MSH2 bound to mismatched bases. Defects in this gene are associated with hereditary nonpolyposis colorectal cancer, with Turcot syndrome, and are a cause of supratentorial primitive neuroectodermal tumors.

Examples of the mutations in PMS2 include, but are not limited to, g.(?_6012870)_(6048737_?)del, g.6012870_6048737del, g.(6027252_6029430)_(6048737_?)del, g.(6045663_6048627)_(6048737_?)del, g.6029554del, g.6029499dup, g.6029495_6029496del, g.6029462_6029463delinsTAAA, g.5992485_6028601del, g.(6018328_6022454)_(6027252_6029430)del, g.(6013174_6017218)_(6027252_6029430)del, g.6027226_6027227ins(20), g.6027175del, g.6027090dup, g.6036705_6044207delinsCG, g.6026666dup, g.6026628del, g.6043671del, g.6026565dup, g.6026565dupT, g.6018315_6018316del, g.6018306_6018310del, g.6018306_6018310delAGTTA, g.6043633_6043634dup, g.6018256_6018259del, g.6015623_6017501del, g.6016429_6017479del, g.6017300_6017303del, g.6045579_6045674delinsATTT, g.(6043690_6045522)_(6045663_6048627)del, g.(?_6012870)_(6042268_6043320)del, g.(6035265_6036956)_(60422686043320)del, g.6038283_6039384del, g.6038901del, g.6038851dup, g.(6035265_6036956)_(6037055_6038738)del, g.6037019_6037024delinsCTTCACACACA, g.6036980del, g.6036958dup, g.6035323_6035324insJN866832.1, g.(6022623_6026389)_(6035265_6036956)del, g.(6031689_6035164)_(6035265_6036956)del, g.6035204_6035207del, g.6035205_6035206del, g.(?_6012870)_(6031689_6035164)del, g.(6027252_6029430)_(6031689_6035164)del, g.(6029587_6031603)_(6031689_6035164)del, g.6028725_6029882del, g.(?_6012870)_(6029587_6031603)del.

The present invention provides a method of treating patients with Lynch syndrome to reduce the likelihood of from developing or treating cancers derived from Lynch syndrome, by administering to the subject an effective amount of one or more disclosed compounds, or a pharmaceutically acceptable salt thereof, or the corresponding pharmaceutical composition.

Lynch syndrome is a hereditary disorder caused by a mutation in a mismatch repair gene in which affected individuals have a higher than normal chance of developing colorectal cancer, endometrial cancer, and various other types of aggressive cancers, often at a young age—also called hereditary nonpolyposis colon cancer (HNPCC).

The mutations of specific mismatch repair (MMR) genes including but not limited to MLH1, MSH2, MSH6, PMS2, and EPCAM-TACSTD1 deletions are responsible for Lynch syndrome. These genes work in repairing mistakes made when DNA is copied in preparation for cell division. The defects in the genes disallow repair of DNA mistakes and as cells divide, errors stack and uncontrollable cell growth may result in cancer.

Those with Lynch syndrome carry up to an 85% risk of contracting colon cancer as well as a higher than average risk for endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

Thus, in one embodiment for the disclosed method, the method is a method of treating cancer derived from Lynch syndrome, selected from the group consisting of colon cancer, endometrial cancer, stomach cancer, pancreatic cancer, kidney/ureter tract cancer, hepatobiliary tract cancer, gastric tract cancer, prostate cancer, ovarian cancer, gallbladder duct cancer, brain cancer, small intestine cancer, breast cancer, and skin cancer.

In yet another embodiment, the method is a method of treating autoimmune disease. Exemplary autoimmune diseases include lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; inflammatory chronic rhinosinusitis; colitis; celiac disease; inflammatory bowel disease; Barrett's esophagus; inflammatory gastritis; autoimmune nephritis; autoimmune vasculitis; autoimmune hepatitis; autoimmune carditis; autoimmune encephalitis; autoimmune diabetes; autoimmune diabetes nephritis; psoriasis; Graft-versus-host disease (GvHD); and autoimmune mediated hematological disease.

In one aspect of this embodiment, the method is a method of treating immune deficiency selected from the group consisting of Autoimmune Lymphoproliferative Syndrome (ALPS), Autoimmune polyglandular syndrome type 1 (APS-1), BENTA Disease, Caspase Eight Deficiency State (CEDS), Chronic Granulomatous Disease (CGD), Common Variable Immunodeficiency (CVID), Congenital Neutropenia Syndromes, CTLA4 Deficiency, DOCK8 Deficiency, GATA2 Deficiency, Glycosylation Disorders With Immunodeficiency, hyper-immunoglobulin E syndrome (HIES), Hyper-Immunoglobulin M (Hyper-IgM) Syndromes, Leukocyte adhesion deficiency (LAD), LRBA deficiency, PI3 Kinase disease, PLCG2-associated antibody deficiency and immune dysregulation (PLAID), severe combined immunodeficiency (SCID), STAT3 gain-of-function disease, Warts, Hypogammaglobulinemia, Infections, and Myelokathexis Syndrome (WHIMS), X-Linked Agammaglobulinemia (XLA), X-Linked Lymphoproliferative Disease (XLP), and XMEN Disease.

As used herein, the term "immune deficiency" refers to a condition in which a portion or some portions of cell components constituting an immune system are defective or dysfunction, so that a normal immune mechanism is damaged. In other words, "immune deficiency" means a condition under which: congenital immunity and/or acquired immunity are suppressed and/or decreased. In some embodiments, the immune-deficiency subject is an immunocompromised subject. Non-limiting examples of immune deficiencies can include AIDS, hypogammaglobulinemia, agammaglobulinemia, granulocyte deficiency, chronic granulomatous disease, asplenia, SCID, complement deficiency, and/or sickle cell anemia.

In another aspect of this embodiment, the method is a method of treating a neurodegenerative disorder selected from the group consisting of multiple sclerosis, Parkinson's disease (PD), Alzheimer's disease (AD), Dentatorubropallidoluysian atrophy (DRPLA), Huntington's Disease (HD), Spinocerebellar ataxia Type 1 (SCA1), Spinocerebellar ataxia Type 2 (SCA2), Spinocerebellar ataxia Type 3 (SCA3), Spinocerebellar ataxia 6 (SCA6), Spinocerebellar ataxia Type 7 (SCA7), Spinocerebellar ataxia Type 8 (SCA8), Spinocerebellar ataxia Type 12 (SCA12), Spinocerebellar ataxia Type 17 (SCA17), Spinobulbar Muscular Ataxia/Kennedy Disease (SBMA), Fargile X syndrome (FRAXA), Fragile XE mental retardation (FRAXE), and Myotonic dystrophy (DM).

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In certain embodiments, the methods disclosed herein further comprise co-administering an effective amount of a DNA repair inhibitor, a DNA damage response (DDR) inhibitor, a DNA damaging agent or an immunomodulatory agent to the subject being treated for cancer, in addition to an effective amount of a disclosed RAD51 inhibitor.

The term "DNA repair inhibitor" refers to any agent that targets components/processes which a cell uses to repair mutations or changes in DNA and restore the DNA to its original state and prevents the repair of DNA. Examples of DNA repair inhibitors include: RPA inhibitors, APE1 inhibitors, DNA ligase inhibitors, DNA polymerase inhibitors, Parp inhibitors etc.

The term "DNA damage response inhibitor" refers to any agent that targets components/processes involved in detecting DNA lesions, signaling the presence of DNA damage, and/or promote the repair of DNA damage. Examples of DNA damage response inhibitors include checkpoint inhibitors, ATM and ATR inhibitors, DNA-PK inhibitors, etc.

The term "DNA damaging agent" refers to any agent that directly or indirectly damages DNA for which homologous recombination could repair the damage. The DNA damaging agents is selected from the group consisting of: exposure to a DNA damaging chemical; exposure to a chemotherapeutic agent; exposure to a radiochemotherapy, and exposure to ionizing or ultraviolet radiation. Specific examples of DNA-damaging chemotherapeutic agents include alkylating agents, nitrosoureas, anti-metabolites, plant alkaloids, plant extracts and radioisotopes. Specific examples of the chemotherapeutic agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or .alpha.-, .beta.-, or .gamma.-radiation, as well as environmental shock, e.g., hyperthermia.

"Immunomodulatory agent" means an agent that modulates an immune response to an antigen but is not the antigen or derived from the antigen. "Modulate", as used herein, refers to inducing, enhancing, suppressing, directing, or redirecting an immune response. Such agents include immunostimulatory agents, such as adjuvants, that stimulate (or boost) an immune response to an antigen but is not an antigen or derived from an antigen. There are several distinct types of immunomodulatory agents, which include, but are not limited to, Toll-like Receptor (TLR) agonists and Toll-like Receptor (TLR) antagonists. Such agents also include immunosuppressants. The immunomodulatory agent is selected from the group consisting of immune checkpoint modulators, Toll-like receptor (TLR) agonists, cell-based therapies, cytokines and cancer vaccines.

In certain embodiments, the subject is determined to have an increased level and/or activity of a DNA damage process or DNA editing enzyme. In one aspect of this embodiment, the DNA editing enzyme is selected from the group consisting of activation induced cytidine deaminase (AID or AICDA), APOBEC2, APOBEC3A, APOBEC3C, APOBEC3D, APOBEC3F, APOBEC3G, APOBEC3H, APOBEC4, a Type 1 Topoisomerase, a Type 2 Topoisomerase, Recombination Activating Gene 1 (RAG 1), and Recombination Activating Gene 2 (RAG2).

In certain embodiments, blood cells obtained from the subject have been determined to have a detectable level of activation-induced cytidine deaminase (AID).

In certain embodiments, B cells obtained from the subject have been determined to have a detectable level of activation-induced cytidine deaminase (AID).

In certain embodiments, the detectable level of activation-induced cytidine deaminase (AID) is statistically significantly higher than the level of AID expressed in unactivated B-cells or normal non-immune cells from a healthy subject.

Methods of Administration and Dosage Forms

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, the disclosed RAD51 inhibitors can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g., the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a a RAD51 mediated disease using the disclosed RAD51 inhibitors for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

EXEMPLIFICATION

Abbreviations

Ac acetyl
ACN acetonitrile
aq aqueous
Bn benzyl
Boc tert-butoxycarbonyl
br. broad
d doublet (only when used within 1H NMR spectra)
DCM dichloromethane
DIEA(DIPEA) diisopropylethylamine
DMA dimethylacetamide
DMAP 4-dimethylaminopyridine
DMF N,N-dimethylformamide
DMSO dimethylsulfoxide
dppf 1,1'-bis(diphenylphosphino) ferrocene
eq equivalent
EtOAc ethyl acetate
hr hour
HBTU N,N,N,N',-tetramethyl-O-(1H-benzotriazol-1-yl)uronium hexafluorophosphate
HPLC high performance liquid chromatography
LC-MS liquid chromatography coupled to mass spectrometry
m multiplet
MS ESI mass spectra, electrospray ionization
NBS N-bromosuccinimide
NMR nuclear magnetic resonance
prep preparative
Py pyridine
s singlet
sat saturated
SFC supercritical fluid chromatography
t triplet
TEA triethylamine
TFA trifluoroacetic acid
THF tetrahydrofuran
TLC thin layer chromatography
Tol toluene

| General Method | Reaction Name |
|---|---|
| A | Substitution Reaction |
| B | Suzuki Reaction A |
| C | Deprotection of Boc group A (TFA) |
| D | Acylation Reaction |
| E | Urea Formation |
| F | Deprotection of Boc group B (HCl) |
| G | Reduction with Fe |
| H | Carbamate Formation |
| I | Hydrogenation |
| J | Bromination |
| K | Suzuki Reaction B |
| L | Thionation |
| M | Cyclization |
| N | Coupling Reaction |
| O | Hydrolysis Reaction |

Example 1. Synthesis of (S)-(1-methylpyrrolidin-2-yl)methyl(4-(2-(4-((benzylcarbamoyl)oxy)piperidin-1-yl)thiazol-5-yl)-3-(N-(tert-butyl)sulfamoyl)phenyl) carbamate Scheme 1

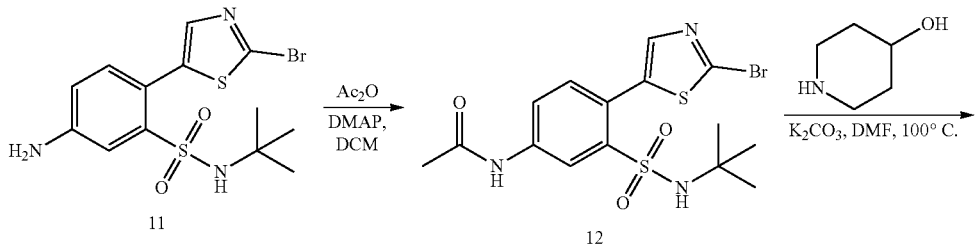

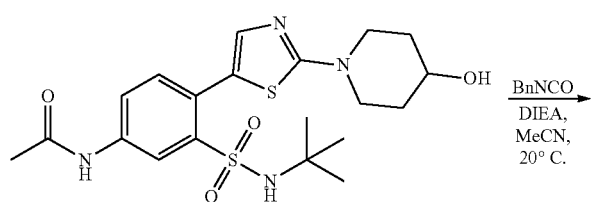

-continued
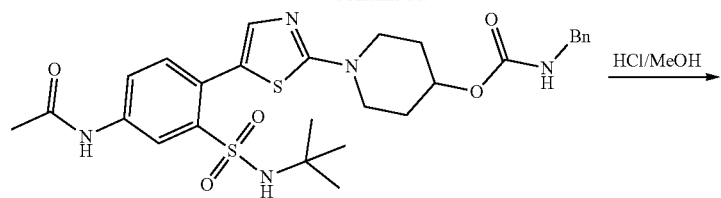
14
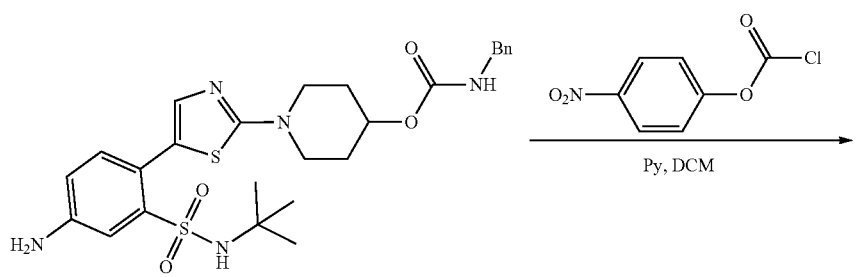
15
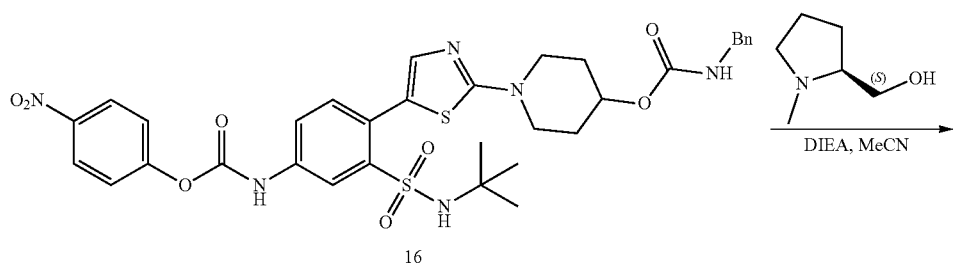
16
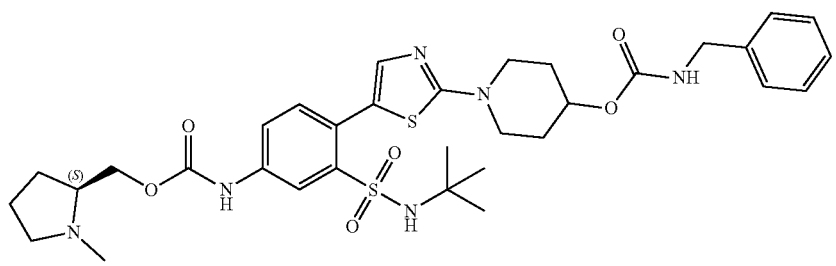
Ex. 1

General Method D for Preparation of Sulfonamide Compound 12.

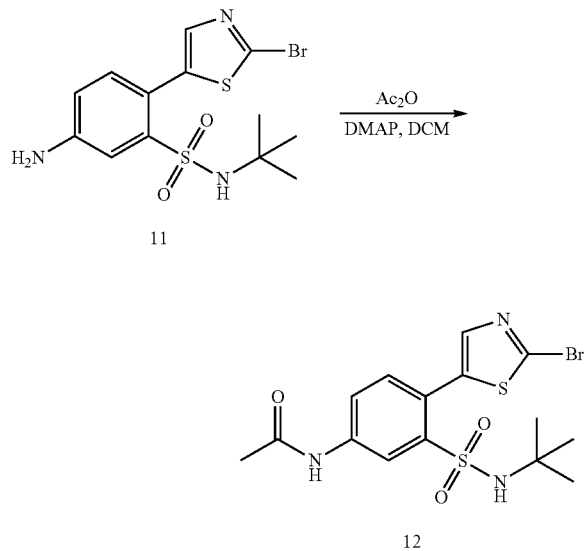

To a solution of N-[4-(2-bromothiazol-5-yl)-3-(tert-butylsulfamoyl)phenyl]acetamide (700 mg, 1.6 mmol, 1 eq.) in DMF (20 mL) were added $K_2CO_3$ (448 mg, 3.3 mmol, 2 eq.) and piperidin-4-ol (246 mg, 2.4 mmol, 1.5 eq.). The mixture was stirred at 100° C. for 12 hrs and then poured into $H_2O$ (100 mL). The aqueous phase was extracted with EtOAc (50 mL×3), the combined organic layers were washed with brine (100 mL), dried over $Na_2SO_4$, filtered and concentrated. The residue was purified by column chromatography ($SiO_2$, Petroleum ether:Ethyl acetate=1:2) to give N-[3-(tert-butylsulfamoyl)-4-[2-(4-hydroxy-1-piperidyl)thiazol-5-yl]phenyl]acetamide (550 mg, 1.2 mmol, 13.2% yield) as a yellow solid. $^1$H NMR (400 MHz, CHLOROFORM-d) δ=8.26 (dd, J=2.2, 8.6 Hz, 2H), 7.93 (d, J=2.4 Hz, 1H), 7.37 (d, J=8.4 Hz, 1H), 7.31 (s, 1H), 4.02-3.94 (m, 1H), 3.88-3.80 (m, 2H), 3.30 (ddd, J=3.5, 9.2, 13.1 Hz, 2H), 2.21 (s, 3H), 2.03-1.95 (m, 2H), 1.67 (dtd, J=4.0, 8.7, 13.0 Hz, 2H), 1.09 (s, 9H). ESI [M+H]=453.1

General Method F for Preparation of Sulfonamide Compound 15.

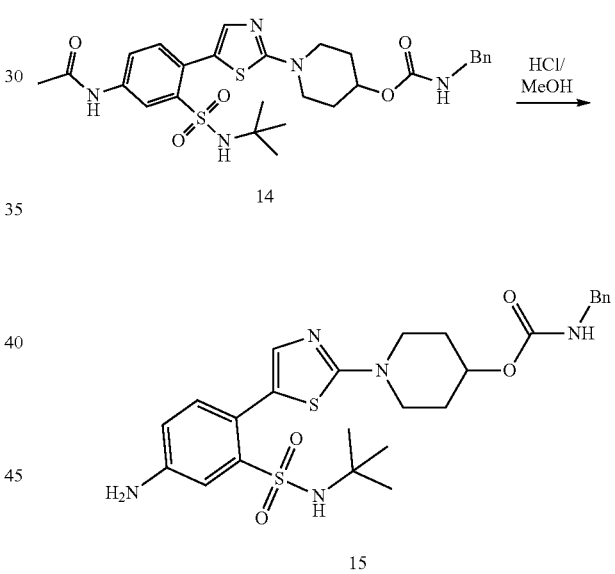

To a solution of 5-amino-2-(2-bromothiazol-5-yl)-N-tert-butyl-benzenesulfonamide (5 g, 12.8 mmol, 1 eq.) in DCM (30 mL) were added DMAP (156 mg, 1.3 mmol, 0.1 eq.) and $Ac_2O$ (1.96 g, 19.2 mmol, 1.5 eq.). The mixture was stirred at 20° C. for 1 hr, and then washed with 1M HCl (50 mL) and sat.aq.$Na_2CO_3$ (50 mL). The organic layer was dried over $Na_2SO_4$, filtered and concentrated. The residue was purified by column chromatography ($SiO_2$, Petroleum ether:Ethyl acetate=5:1 to 2:1) to give N-[4-(2-bromothiazol-5-yl)-3-(tert-butylsulfamoyl)phenyl]acetamide (1.5 g, 3.5 mmol, 27% yield) as a yellow solid. ESI [M+H]=433.9/431.9

General Method A for Preparation of Sulfonamide Compound 13.

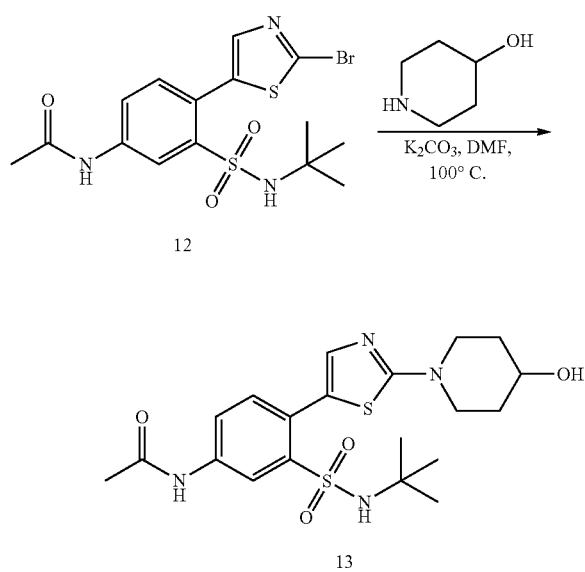

[1-[5-[4-acetamido-2-(tert-butylsulfamoyl)phenyl]thiazol-2-yl]-4-piperidyl]N-benzylcarbamate (380 mg, 649 umol, 1 eq.) was dissolved into HCl/MeOH (4 M, 20 mL) and the mixture was stirred at 20° C. for 1 hr. The mixture was concentrated, diluted with sat.aq.$Na_2CO_3$ (20 mL) and extracted with EtOAc (20 mL×3). The combined organic layers were washed with brine (20 mL), dried over $Na_2SO_4$, filtered and concentrated. The residue was purified by column chromatography ($SiO_2$, Petroleum ether:Ethyl acetate=10:1 to 1:1) to give [1-[5-[4-amino-2-(tert-butylsulfamoyl)phenyl]thiazol-2-yl]-4-piperidyl]N-benzylcarbamate (300 mg, 552 umol, 85% yield) as a yellow solid. ESI [M+H]=544.2 General method H for preparation of Example 1.

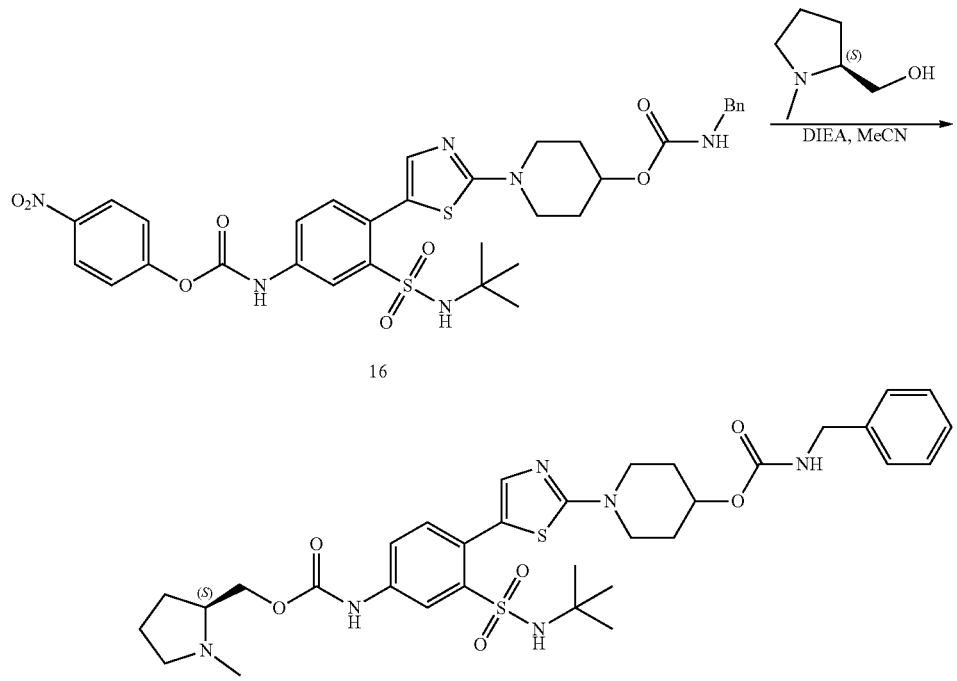

16

To a solution of [(2S)-1-methylpyrrolidin-2-yl]methanol (42 mg, 367 umol, 2 eq.) and DIEA (71.11 mg, 550 umol, 3 eq.) in MeCN (5 mL) was added a solution of [1-[5-[2-(tert-butylsulfamoyl)-4-[(4-nitrophenoxy)carbonylamino]phenyl]thiazol-2-yl]-4-piperidyl]N-benzylcarbamate (130 mg, 184 umol, 1 eq.) in DCM (2 mL) and the mixture was refluxed for 1 hr. The mixture was concentrated and the residue was purified by prep-HPLC to give (S)-(1-methylpyrrolidin-2-yl)methyl(4-(2-(4-((benzylcarbamoyl)oxy)piperidin-1-yl)thiazol-5-yl)-3-(N-(tert-butyl)sulfamoyl)phenyl)carbamate (19.87 mg, 28.8 umol, 15.7% yield, 99.3% purity) as a pale yellow solid. $^1$H NMR (400 MHz, DMSO-d6) δ=10.06 (s, 1H), 8.26 (d, J=2.0 Hz, 1H), 7.71 (t, J=6.2 Hz, 1H), 7.60 (dd, J=2.3, 8.5 Hz, 1H), 7.37-7.14 (m, 7H), 6.94 (s, 1H), 4.81-4.71 (m, 1H), 4.16 (br d, J=6.2 Hz, 2H), 4.10-4.03 (m, 1H), 4.02-3.96 (m, 1H), 3.73-3.63 (m, 2H), 3.28 (br s, 2H), 2.94-2.87 (m, 1H), 2.44-2.37 (m, 1H), 2.30 (s, 3H), 2.18-2.05 (m, 1H), 1.99-1.82 (m, 3H), 1.68-1.52 (m, 5H), 1.12-1.03 (m, 9H). ESI [M+H]=685.2

Example 2. Synthesis of [1-[5-[2-(tert-butylsulfamoyl)-4-[[(2R)-1-methylpyrrolidin-2-yl]methoxycarbonylamino]phenyl]thiazol-2-yl]-4-piperidyl]N-benzylcarbamate The Following Compound was Synthesized Via Same Method by the Key Intermediate 16.

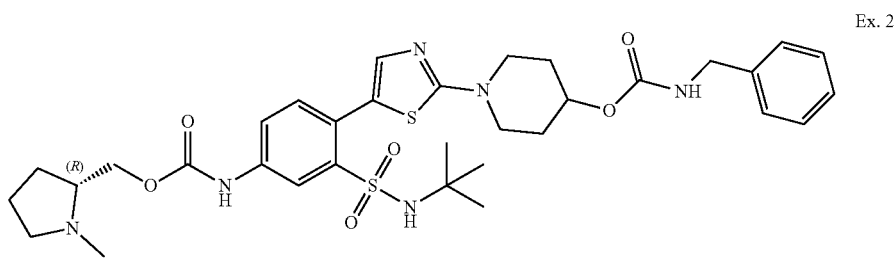

Ex. 2

[1-[5-[2-(tert-butylsulfamoyl)-4-[[(2R)-1-methylpyrrolidin-2-yl]methoxycarbonylamino]phenyl]thiazol-2-yl]-4-piperidyl]N-benzylcarbamate. $^1$H NMR (400 MHz, DMSO-d6) δ=10.07 (s, 1H), 8.29 (d, J=2.2 Hz, 1H), 7.73 (t, J=6.2 Hz, 1H), 7.63 (dd, J=2.3, 8.5 Hz, 1H), 7.39-7.19 (m, 7H), 6.94 (s, 1H), 4.80 (td, J=4.1, 8.0 Hz, 1H), 4.20 (br d, J=6.1 Hz, 2H), 4.14-4.07 (m, 1H), 4.06-3.99 (m, 1H), 3.72 (br d, J=13.6 Hz, 2H), 3.29-3.22 (m, 2H), 2.98-2.92 (m, 1H), 2.45-2.41 (m, 1H), 2.33 (s, 3H), 2.22-2.13 (m, 1H), 2.02-1.79 (m, 3H), 1.72-1.56 (m, 5H), 1.20-1.03 (m, 9H). ESI [M+H]=685.2

Example 3. Synthesis of [1-[5-[4-(benzylcarbamoylamino)-2-(tert-butylsulfamoyl)phenyl]thiazol-2-yl]-4-piperidyl]N-isopropylcarbamate Scheme 2

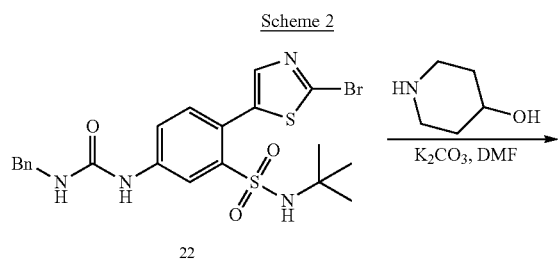

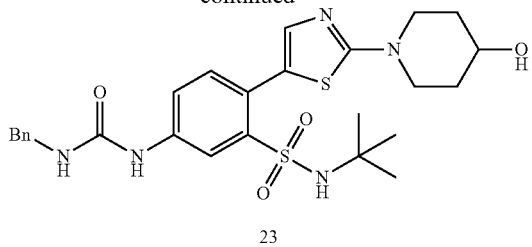

General method A, 1-benzyl-3-[3-(tert-butylsulfamoyl)-4-[2-(4-hydroxy-1-piperidyl) thiazol-5-yl]phenyl]urea. ESI [M+H]=544.1

Preparation of Ex 3.

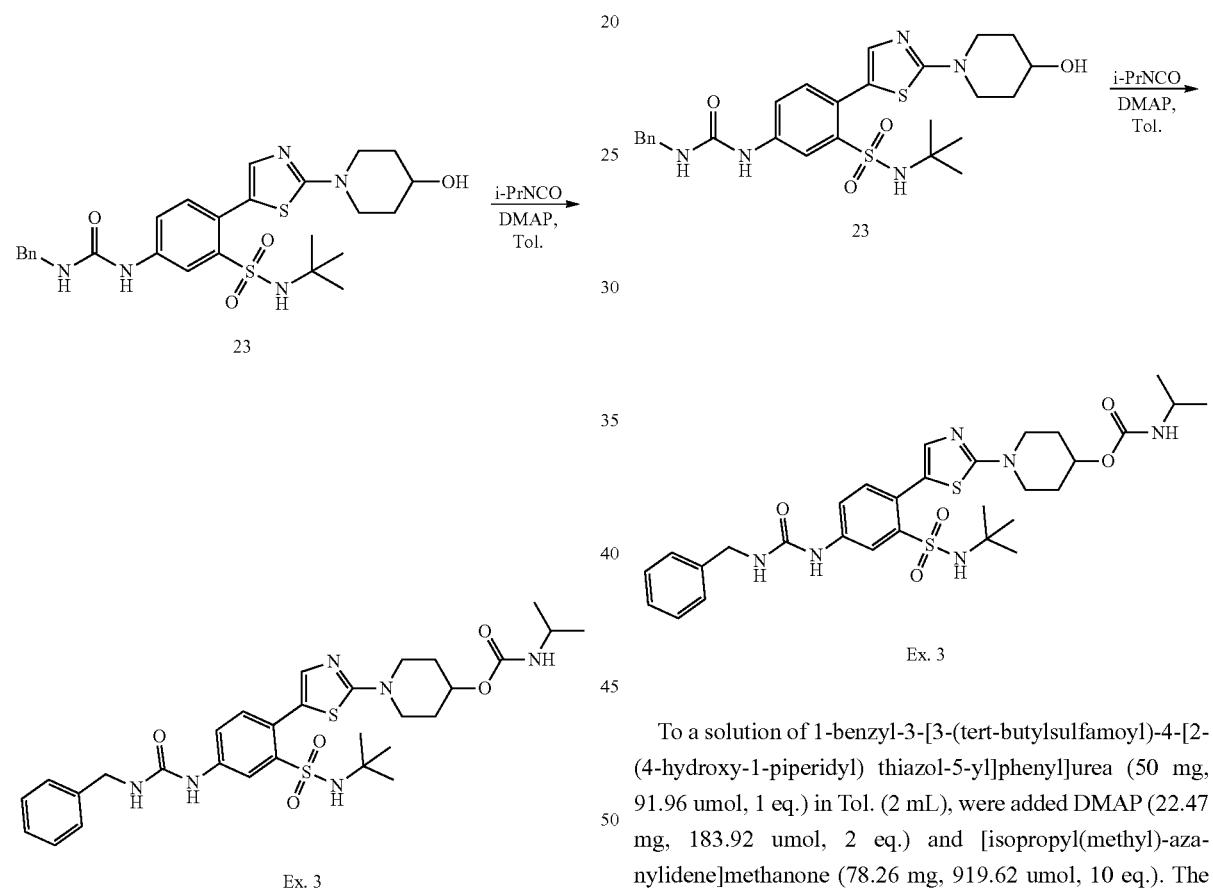

Preparation of Compound 23.

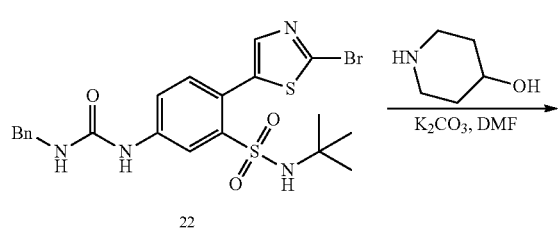

To a solution of 1-benzyl-3-[3-(tert-butylsulfamoyl)-4-[2-(4-hydroxy-1-piperidyl) thiazol-5-yl]phenyl]urea (50 mg, 91.96 umol, 1 eq.) in Tol. (2 mL), were added DMAP (22.47 mg, 183.92 umol, 2 eq.) and [isopropyl(methyl)-azanylidene]methanone (78.26 mg, 919.62 umol, 10 eq.). The mixture was stirred at 100° C. for 4 hrs and then concentrated. The residue was purified by prep-TLC (Petroleum ether/EtOAc=1:3) and then acidic prep-HPLC to give [1-[5-[4-(benzylcarbamoylamino)-2-(tert-butylsulfamoyl)phenyl]thiazol-2-yl]-4-piperidyl]N-isopropylcarbamate (28.31 mg, 99.2% purity) as a yellow solid. $^1$H NMR (400 MHz, METHANOL-d4) δ=8.29 (d, J=2.0 Hz, 1H), 7.71 (dd, J=2.0, 8.3 Hz, 1H), 7.43 (d, J=8.8 Hz, 1H), 7.35 (d, J=3.9 Hz, 5H), 7.27 (dt, J=2.7, 5.7 Hz, 1H), 4.98-4.93 (m, 1H), 4.43 (s, 2H), 3.90-3.59 (m, 5H), 2.19-2.07 (m, 2H), 1.99-1.86 (m, 2H), 1.22 (s, 9H), 1.16 (d, J=6.8 Hz, 6H). ESI [M+H]=629.1

Example 4. Synthesis of isopropyl 4-[5-[2-(tert-butylsulfamoyl)-4-(2-pyridylmethyl carbamoylamino)phenyl]thiazol-2-yl]piperidine-1-carboxylate
Scheme 3
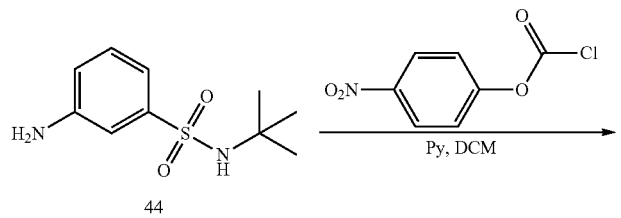
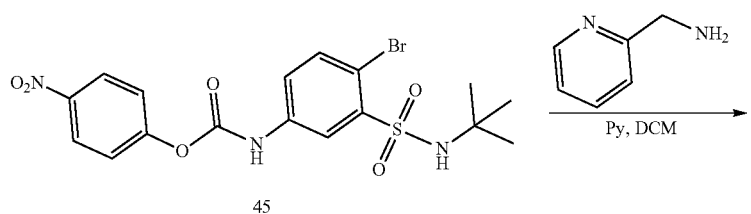
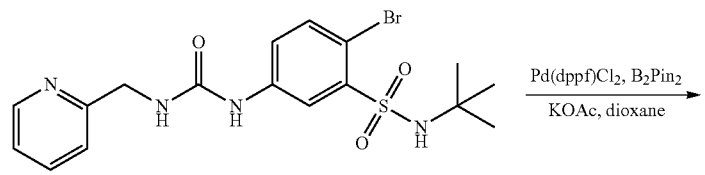
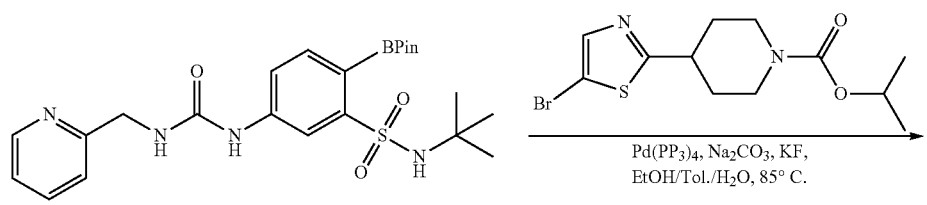
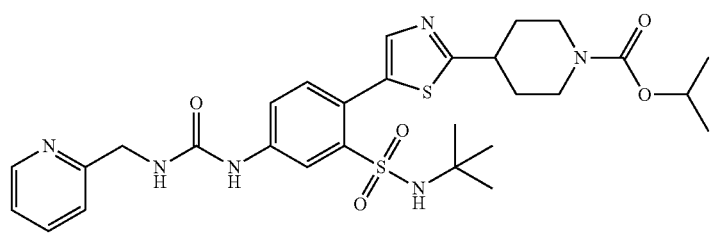
Ex. 4

Preparation of Compound 45

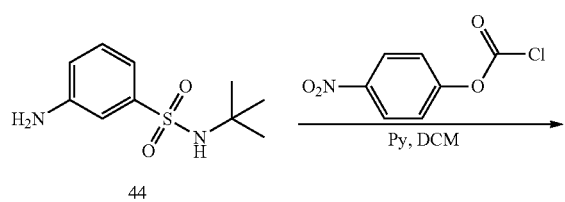

General method D, 4-nitrophenyl(4-bromo-3-(N-(tert-butyl)sulfamoyl)phenyl) carbamate. ESI [M+H]=474.1

General Method E for Preparation of Sulfonamide Compound 46.

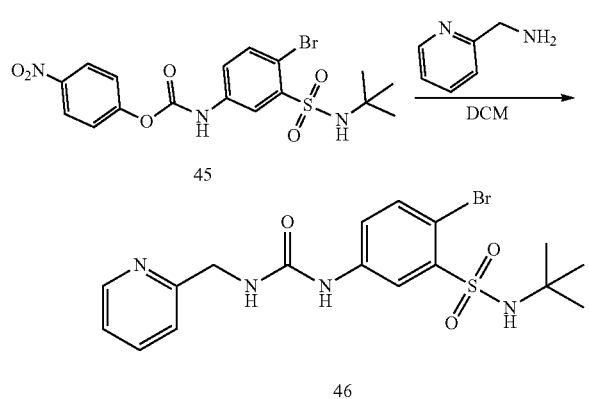

To a solution of 2-pyridylmethanamine (352 mg, 3.3 mmol, 5 eq.) and DIEA (84 mg, 650 umol, 1 eq.) in DCM (3 mL) was added the solution of (4-nitrophenyl)N-[4-bromo-3-(tert-butylsulfamoyl)phenyl]carbamate (307 mg, 650 umol, 1 eq.) in DCM (3 mL). The mixture was stirred at 25° C. for 1 hr, then diluted with DCM (30 mL) and washed with $H_2O$ (20 mL×2). The organic layer was concentrated and the residue was purified by prep-TLC ($SiO_2$, Petroleum ether:Ethyl acetate=0:1) to give 1-[4-bromo-3-(tert-butylsulfamoyl)phenyl]-3-(2-pyridylmethyl)urea (180 mg, crude) as a yellow solid. ESI [M+H]=441.2/443.2

Preparation of compound 47

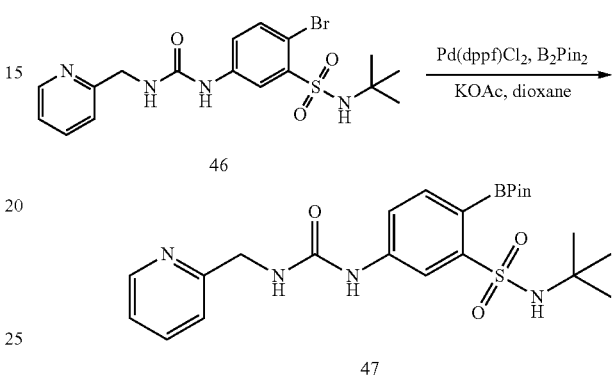

A mixture of 1-[4-bromo-3-(tert-butylsulfamoyl)phenyl]-3-(2-pyridylmethyl)urea (140 mg, 317.21 umol, 1 eq.), 4,4,5,5-tetramethyl-2-(4,4,5,5-tetramethyl-1,3,2-dioxaborolan-2-yl)-1,3,2-dioxaborolane (322.21 mg, 1.27 mmol, 4 eq.), Pd(dppf)Cl$_2$ (116.05 mg, 158.61 umol, 0.5 eq.) and KOAc (93.39 mg, 951.64 umol, 3 eq.) in dioxane (4 mL) was degassed and purged with $N_2$ for 3 times, and then the mixture was stirred at 80° C. for 12 hrs under $N_2$ atmosphere. The mixture was concentrated and the residue was purified by column chromatography ($SiO_2$, Petroleum ether/Ethyl acetate=1/0 to 1:1) to give 1-[3-(tert-butylsulfamoyl)-4-(4,4,5,5-tetramethyl-1,3,2-dioxaborolan-2-yl)phenyl]-3-(2-pyridylmethyl)urea (50 mg, 89.37 umol, 28.17% yield, 87.3% purity). ESI [M+H]=489.4

General Method K for Preparation of Compound Ex. 4

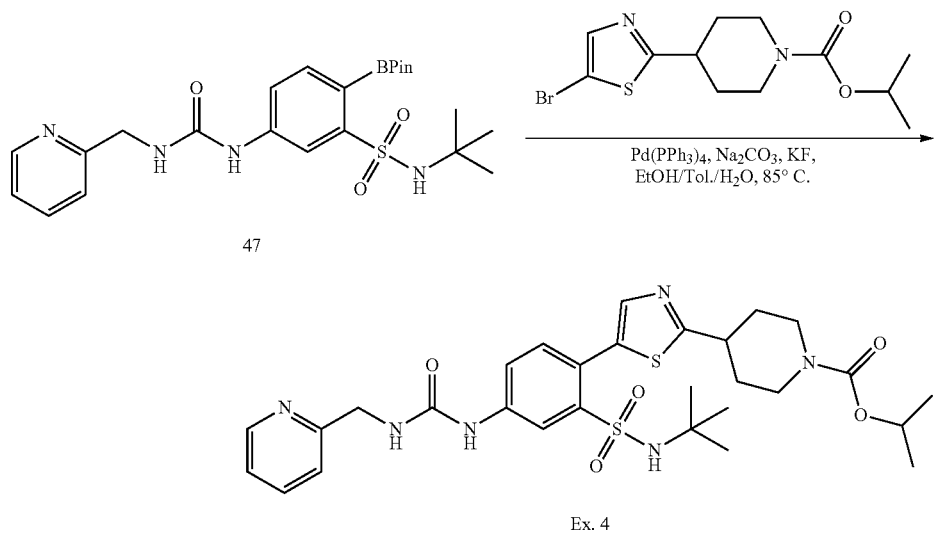

A mixture of 1-[3-(tert-butylsulfamoyl)-4-(4,4,5,5-tetramethyl-,3,2-dioxaborolan-2-yl)phenyl]-3-(2-pyridylmethyl)urea (26.38 mg, 54.01 umol, 1.2 eq.), isopropyl 4-(5-bromothiazol-2-yl)piperidine-1-carboxylate (15 mg, 45.01 umol, 1 eq.), Na$_2$CO$_3$ (9.54 mg, 90.02 umol, 2 eq.), KF (7.85 mg, 135.04 umol, 3 eq.) and Pd(PPh$_3$)$_4$ (5.20 mg, 4.50 umol, 0.1 eq.) in H$_2$O (0.1 mL)/EtOH (0.3 mL)/Tol. (0.3 mL) was degassed and purged with N$_2$ for 3 times, and then the mixture was stirred at 85° C. for 12 hrs under N$_2$ atmosphere. The reaction mixture was filtered and concentrated. The residue was purified by prep-TLC (SiO$_2$, Petroleum ether/Ethyl acetate=1/2) and then prep-HPLC (TFA condition) to give isopropyl 4-[5-[2-(tert-butylsulfamoyl)-4-(2-pyridylmethylcarbamoylamino)phenyl]thiazol-2-yl]piperidine-1-carboxylate (6.36 mg, 8.21 umol, 18.24% yield, 94.07% purity, TFA) as a pale yellow solid. $^1$H NMR (400 MHz, METHANOL-d4) δ=8.75 (br d, J=5.6 Hz, 1H), 8.53 (br t, J=7.9 Hz, 1H), 8.34 (d, J=2.0 Hz, 1H), 8.04 (br d, J=8.1 Hz, 1H), 7.92 (br t, J=6.5 Hz, 1H), 7.75 (s, 1H), 7.69 (dd, J=2.3, 8.4 Hz, 1H), 7.39 (d, J=8.3 Hz, 1H), 4.94-4.92 (m, 1H), 4.77 (s, 2H), 4.24 (br d, J=13.4 Hz, 2H), 3.31-3.25 (m, 1H), 3.02 (br s, 2H), 2.15 (br d, J=11.5 Hz, 2H), 1.76 (dq, J=4.2, 12.3 Hz, 2H), 1.28 (d, J=6.2 Hz, 6H), 1.11 (s, 9H). ESI [M+H]=615.2

Example 5. Synthesis of Isopropyl 4-[5-[2-(tert-butylsulfamoyl)-4-(isopropoxycarbonyl amino)phenyl]thiazol-2-yl]piperazine-1-carboxylate Scheme 4

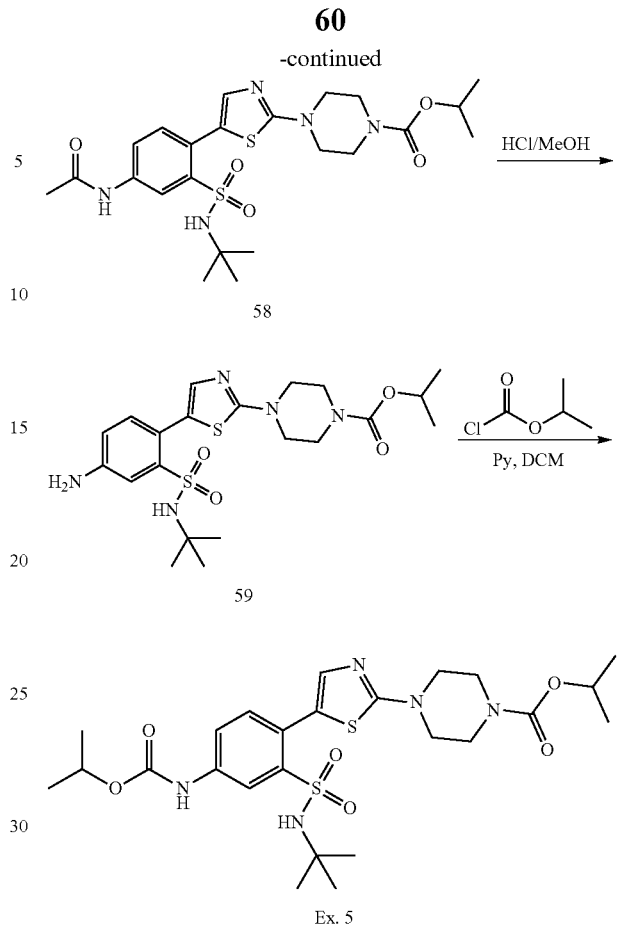

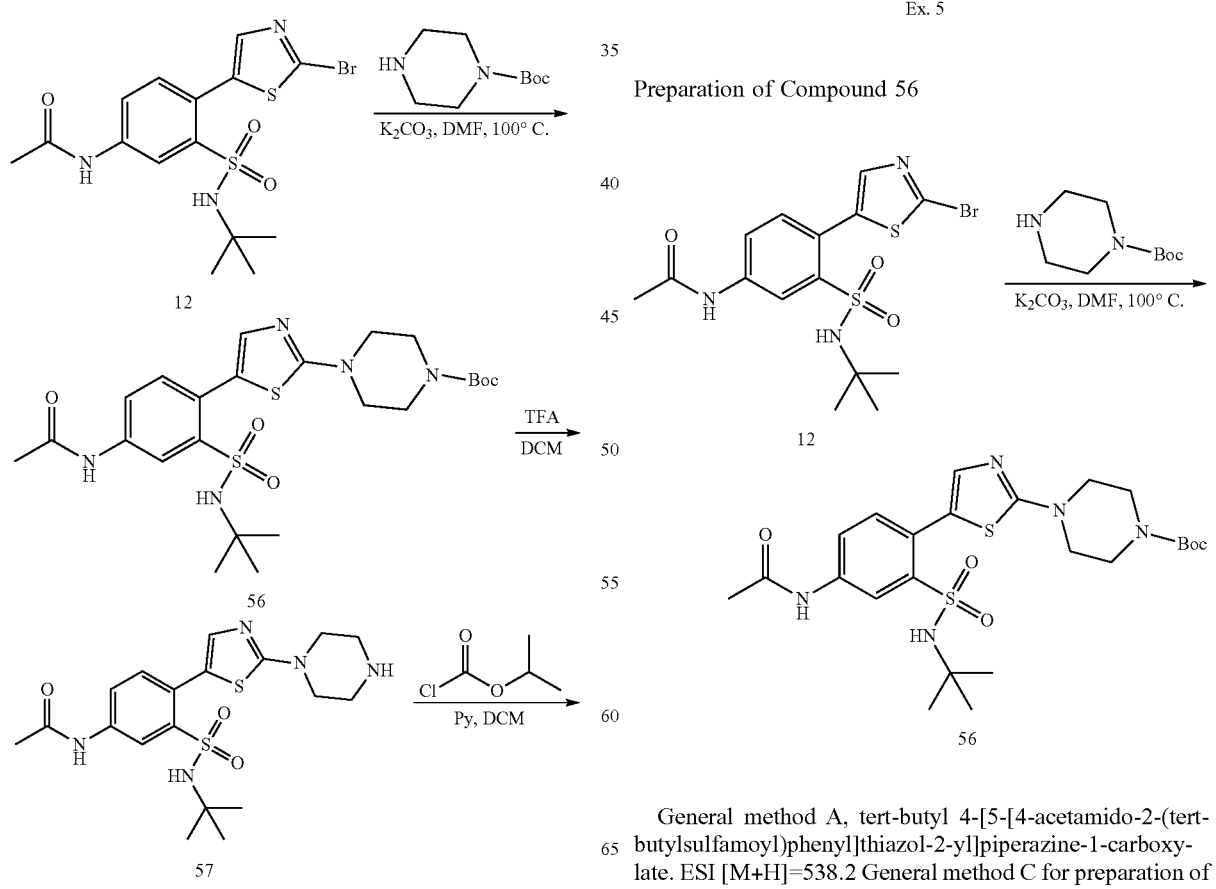

Preparation of Compound 56

General method A, tert-butyl 4-[5-[4-acetamido-2-(tert-butylsulfamoyl)phenyl]thiazol-2-yl]piperazine-1-carboxylate. ESI [M+H]=538.2 General method C for preparation of sulfonamide compound 57.

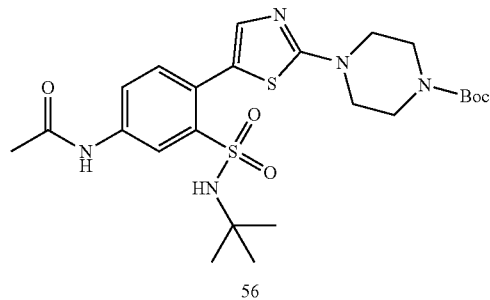

56

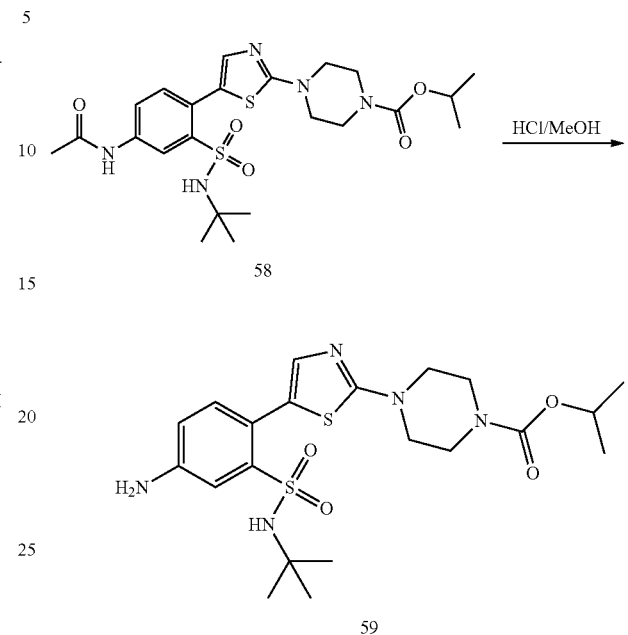

General method D, isopropyl 4-[5-[4-acetamido-2-(tert-butylsulfamoyl)phenyl]thiazol-2-yl]piperazine-1-carboxylate. ESI [M+H]=524.1 Preparation of compound 59

To a solution of tert-butyl 4-[5-[4-acetamido-2-(tert-butylsulfamoyl)phenyl]thiazol-2-yl]piperazine-1-carboxylate (110 mg, 205 umol, 1 eq.) in DCM (2 mL) was added TFA (1 mL) and the mixture was stirred at 25° C. for 30 mins. The mixture was concentrated to give N-[3-(tert-butylsulfamoyl)-4-(2-piperazin-1-ylthiazol-5-yl)phenyl]acetamide (80 mg, 183 umol, 89.4% yield) as a yellow solid. ESI [M+H]=438.2

Preparation of Compound 58

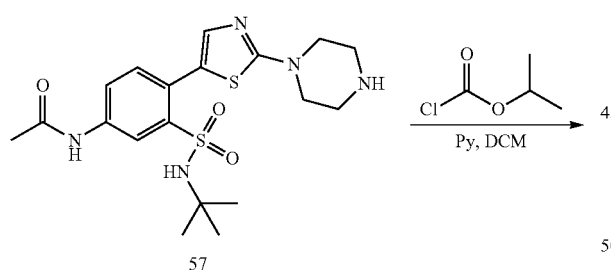

General method F, isopropyl 4-[5-[4-amino-2-(tert-butylsulfamoyl)phenyl]thiazol-2-yl]piperazine-1-carboxylate. ESI [M+H]=482.1

Preparation of Compound Ex. 5

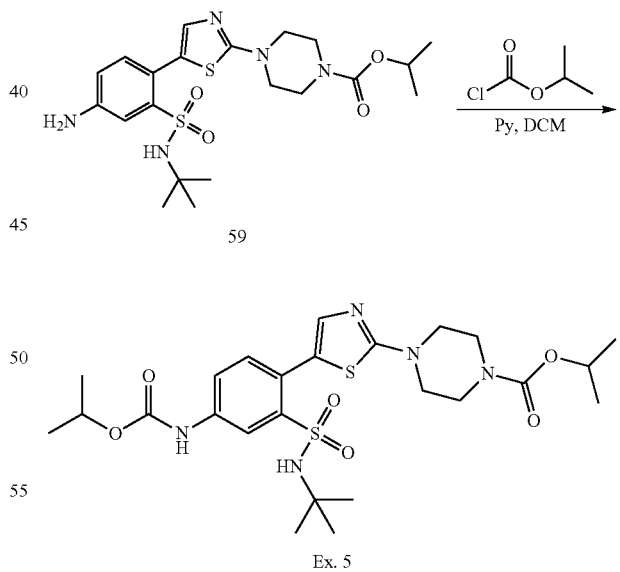

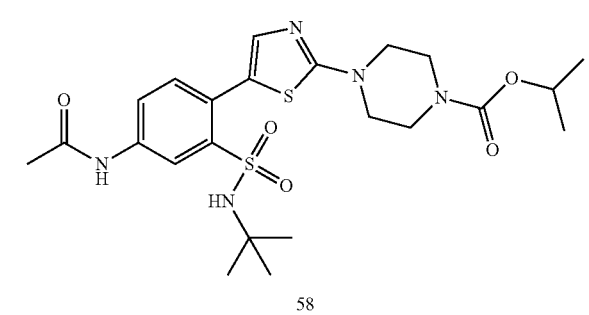

General method D, isopropyl 4-[5-[2-(tert-butylsulfamoyl)-4-(isopropoxycarbonyl amino)phenyl]thiazol-2-yl]piperazine-1-carboxylate. $^1$H NMR (400 MHz, METHANOL-d4) δ=8.22 (d, J=2.1 Hz, 1H), 7.56 (dd, J=2.2, 8.3 Hz, 1H), 7.30 (d, J=8.3 Hz, 1H), 7.20 (s, 1H), 4.94-4.81 (m, 2H), 3.61-3.43 (m, 8H), 1.20 (dd, J=6.2, 14.5 Hz, 12H), 1.07 (s, 9H). ESI [M+H]=568.3

Example 6. Synthesis of Isopropyl 4-[5-[4-(benzyloxycarbonylamino)-2-(tert-butylsulfamoyl)phenyl]thiazol-2-yl]piperazine-1-carboxylate Scheme 5:

Preparation of Compound Ex. 6

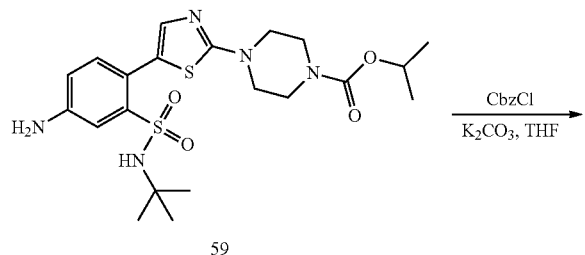

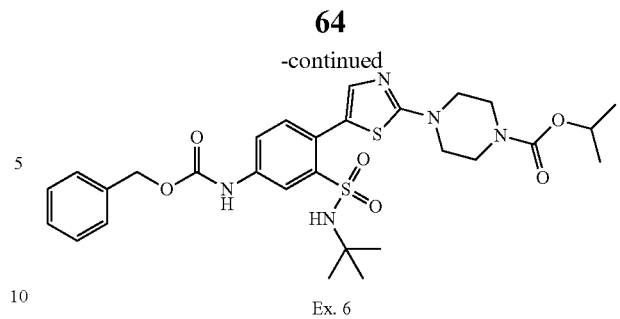

General method D, isopropyl 4-[5-[4-(benzyloxycarbonylamino)-2-(tert-butylsulfamoyl)phenyl]thiazol-2-yl]piperazine-1-carboxylate. $^1$H NMR (400 MHz, METHANOL-d4) δ=8.33 (d, J=2.0 Hz, 1H), 7.68 (dd, J=2.2, 8.4 Hz, 1H), 7.45-7.27 (m, 7H), 5.21 (s, 2H), 4.94-4.88 (m, 1H), 3.68-3.51 (m, 8H), 1.27 (d, J=6.4 Hz, 6H), 1.19-1.11 (m, 9H). ESI [M+H]=616.3

Example 7. Synthesis of trans-isopropyl N-[3-(tert-butylsulfamoyl)-4-[2-[4-(cyclopentoxycarbonylamino)cyclohexyl]thiazol-5-yl]phenyl]carbamate Scheme 6

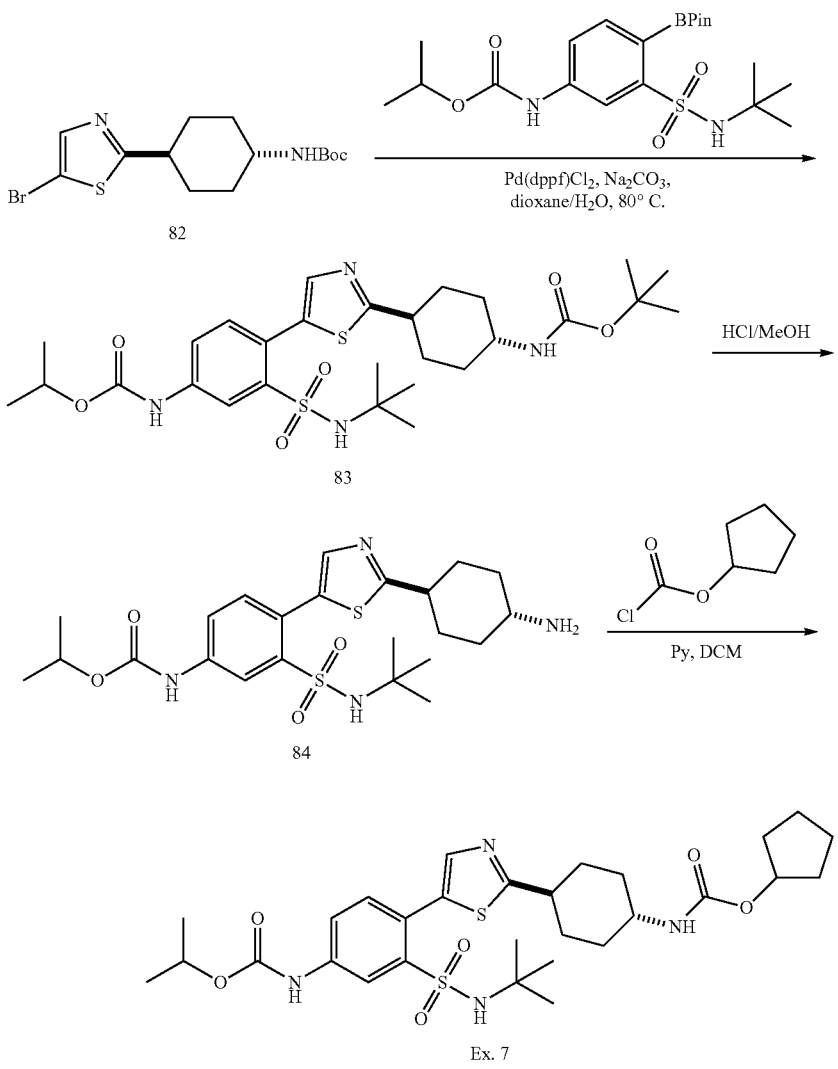

General Method B for Preparation of Sulfonamide Compound 83.

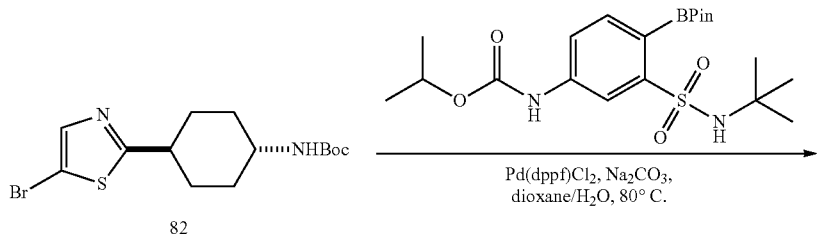

To a mixture of tert-butyl(trans-4-(5-bromothiazol-2-yl)cyclohexyl)carbamate (1.3 g, 3.6 mmol, 2 eq.) and isopropyl N-[3-(tert-butylsulfamoyl)-4-(4,4,5,5-tetramethyl-1,3,2-dioxaborolan-2-yl)phenyl]carbamate (800 mg, 1.8 mmol, 1 eq.) in dioxane (12 mL) and H$_2$O (2 mL) were added Na$_2$CO$_3$ (579 mg, 5.5 mmol, 3 eq.) and Pd(dppf)Cl$_2$ (133 mg, 182 umol, 0.1 eq.). The mixture was stirred at 80° C. for 12 hrs under N$_2$ atmosphere and then concentrated. The residue was diluted with H$_2$O (5 mL) and extracted with ethyl acetate (5 mL×3), dried over Na$_2$SO$_4$, filtered and concentrated. The residue was purified by column chromatography (SiO$_2$, Petroleum ether:Ethyl acetate=1:0 to 3:1) to give trans-isopropyl-N-[4-[2-[4-(tert-butoxycarbonylamino)cyclohexyl]thiazol-5-yl]-3-(tert-butylsulfamoyl)phenyl]carbamate (660 mg, crude), in which 60 mg was purified by prep-HPLC (column: Agela Durashell C18 150×25 5u; mobile phase: [water (0.04% NH3H2O)-ACN]; B %: 60%-90%,10 min) to give pure compound 83 (40.92 mg, 99.64% purity) as a white solid for delivery. $^1$H NMR (400 MHz, DMSO-d6) δ=10.06 (s, 1H), 8.32 (d, J=2.1 Hz, 1H), 7.70-7.60 (m, 2H), 7.38 (d, J=8.4 Hz, 1H), 6.96 (s, 1H), 6.81 (br d, J=7.9 Hz, 1H), 4.99-4.87 (m, 1H), 3.27 (br s, 1H), 2.94-2.84 (m, 1H), 2.13 (br d, J=11.7 Hz, 2H), 1.90 (br d, J=11.1 Hz, 2H), 1.63-1.49 (m, 2H), 1.39 (s, 9H), 1.33 (br d, J=14.4 Hz, 2H), 1.28 (d, J=6.4 Hz, 6H), 1.07 (s, 9H). ESI [M+H]=595.3

Preparation of Compound 84

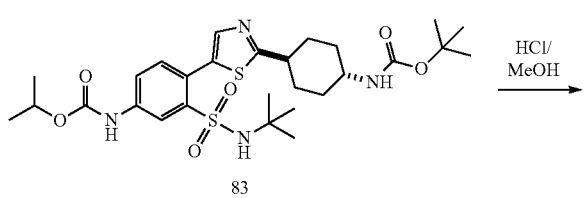

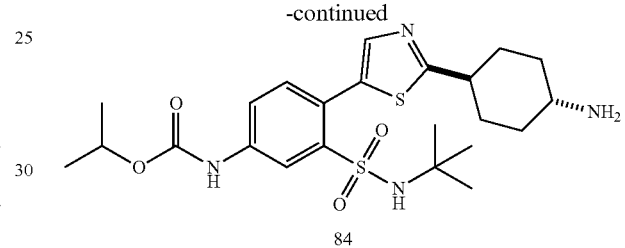

General method F, trans-isopropyl N-[4-[2-(4-aminocyclohexyl)thiazol-5-yl]-3-(tert-butylsulfamoyl)phenyl]carbamate. ESI [M+H]=495.2

Preparation of Ex 7

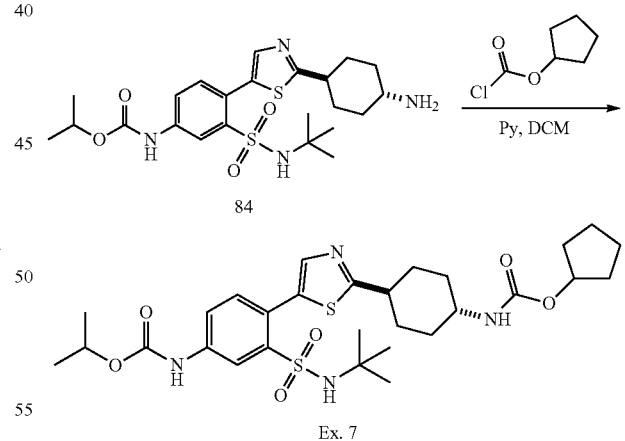

General method D, trans-isopropyl N-[3-(tert-butylsulfamoyl)-4-[2-[4-(cyclopentoxycarbonylamino)cyclohexyl]thiazol-5-yl]phenyl]carbamate. $^1$H NMR (400 MHz, DMSO-d6) δ=10.04 (s, 1H), 8.29 (d, J=2.2 Hz, 1H), 7.61-7.59 (m, 2H), 7.35 (d, J=8.8 Hz, 1H), 7.00 (br d, J=7.9 Hz, 1H), 6.96-6.93 (m, 1H), 4.96-4.87 (m, 2H), 3.29-3.22 (m, 1H), 2.87 (br t, J=11.8 Hz, 1H), 2.10 (br d, J=12.7 Hz, 2H), 1.88 (br d, J=12.7 Hz, 2H), 1.75 (br s, 2H), 1.61-1.48 (m, 8H), 1.36-1.27 (m, 2H), 1.25 (d, J=6.1 Hz, 6H), 1.04 (s, 9H). ESI [M+Na]=629.3

Example 8. Synthesis of [(2R)-1-methylpyrrolidin-2-yl]methyl N-[4-[5-[2-(tert-butylsulfamoyl)-4-(isopropoxycarbonylamino)phenyl]thiazol-2-yl]cyclohexyl]carbamate
Scheme 7
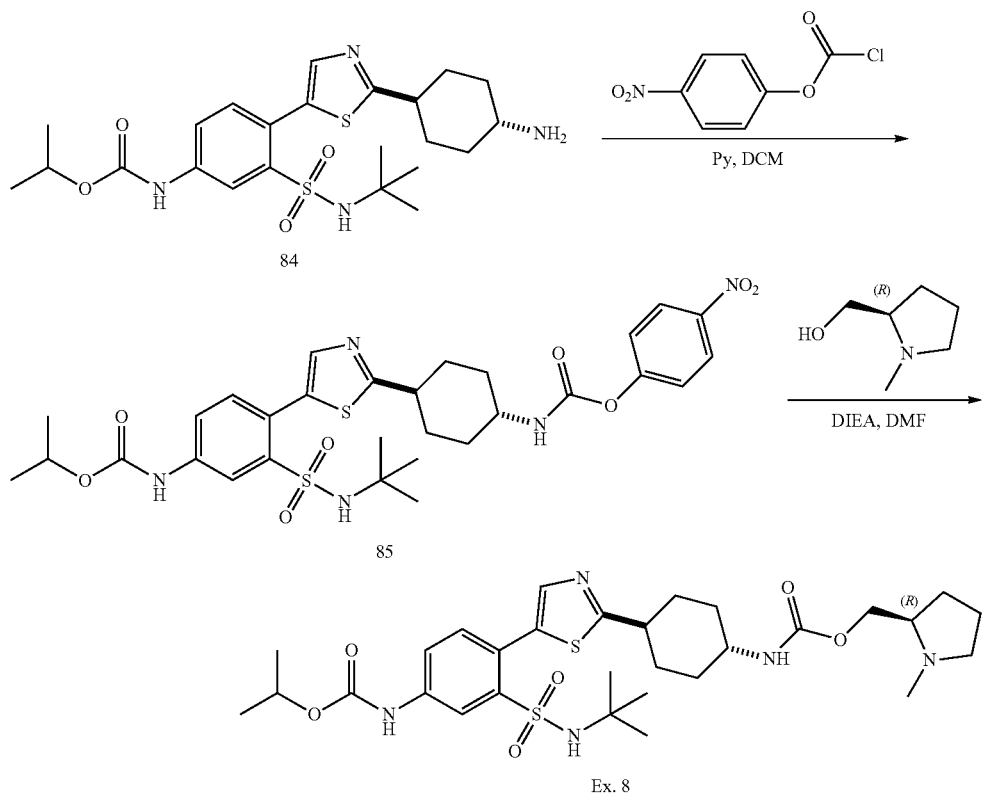
Preparation of Compound 85
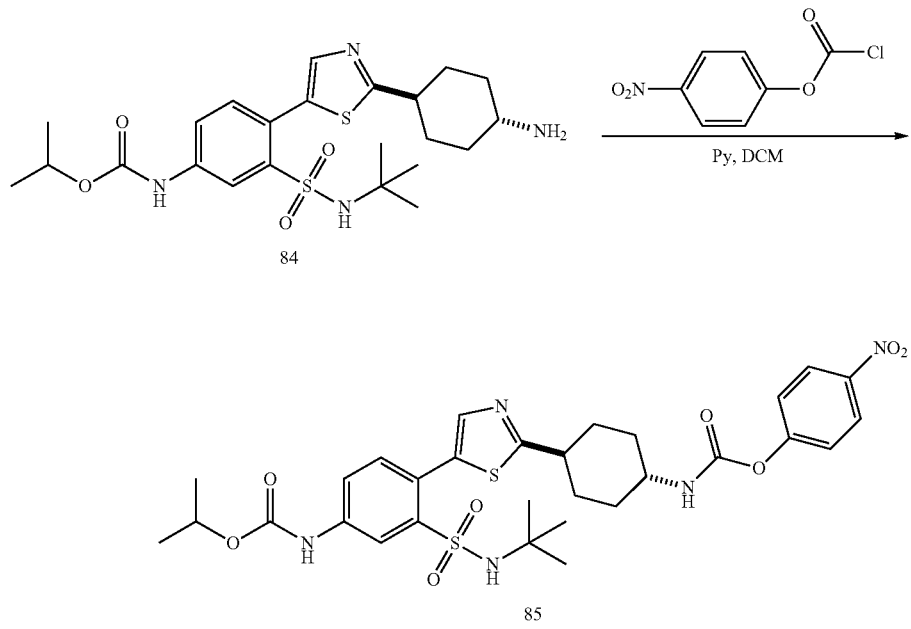

General method D, trans-(4-nitrophenyl)N-[4-[5-[2-(tert-butylsulfamoyl)-4-(isopropoxycarbonylamino)phenyl]thiazol-2-yl]cyclohexyl]carbamate. ESI [M+H]=660.2

Preparation of Compound Ex. 8

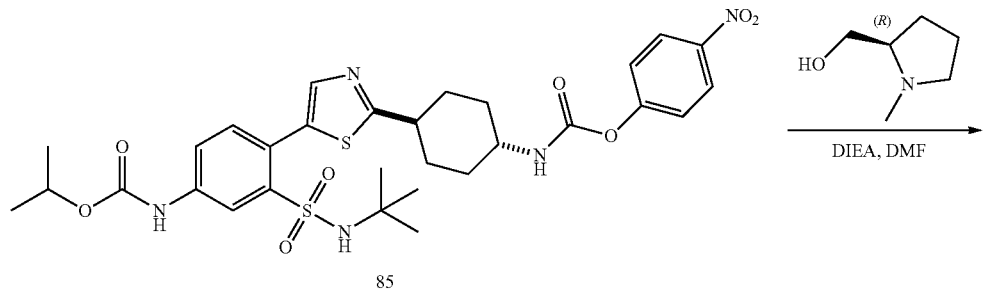

85

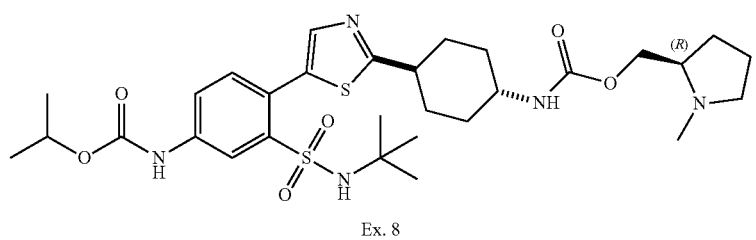

Ex. 8

General method H, [(2R)-1-methylpyrrolidin-2-yl]methyl N-[4-[5-[2-(tert-butylsulfamoyl)-4-(isopropoxycarbonylamino)phenyl]thiazol-2-yl]cyclohexyl]carbamate. $^1$H NMR (400 MHz, METHANOL-d4) δ=8.38 (s, 1H), 7.80-7.73 (m, 1H), 7.69 (dd, J=2.2, 8.4 Hz, 1H), 7.40 (d, J=8.3 Hz, 1H), 5.05-5.00 (m, 1H), 4.48 (br dd, J=3.0, 12.8 Hz, 1H), 4.21 (br dd, J=7.2, 12.6 Hz, 1H), 3.78-3.66 (m, 2H), 3.57-3.46 (m, 1H), 3.22 (td, J=8.3, 11.2 Hz, 1H), 3.07-3.01 (m, 3H), 2.43-1.99 (m, 8H), 1.98-1.88 (m, 1H), 1.80-1.66 (m, 2H), 1.47 (q, J=12.5 Hz, 2H), 1.34 (d, J=6.2 Hz, 6H), 1.20-1.12 (m, 9H). ESI [M+H]=636.2

Example 9. Synthesis of isopropyl(3-(N-(tert-butyl)sulfamoyl)-4-(2-((1S,4r)-4-(((((S)-1-methylpyrrolidin-2-yl)methoxy)carbonyl)amino)cyclohexyl)thiazol-5-yl)phenyl)carbamate The Following Compound was Synthesized Via Same Method by the Key Intermediate 85.

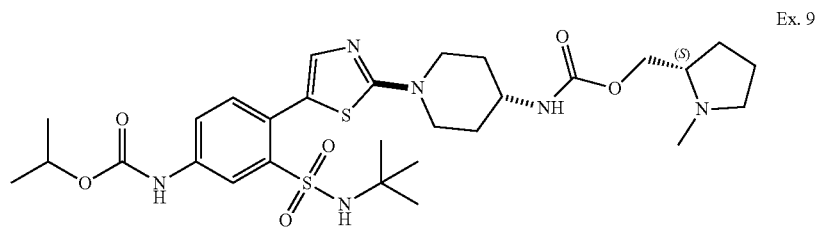

Ex. 9

¹H NMR (METHANOL-d4, 400 MHz): δ=8.34 (d, J=2.2 Hz, 1H), 7.71 (s, 1H), 7.66 (dd, J=8.5, 2.1 Hz, 1H), 7.36 (d, J=8.4 Hz, 1H), 4.93-5.04 (m, 1H), 4.46 (dd, J=13.0, 2.9 Hz, 1H), 4.18 (dd, J=13.0, 7.1 Hz, 1H), 3.64-3.75 (m, 2H), 3.42-3.58 (m, 1H), 3.12-3.25 (m, 1H), 3.00-3.06 (m, 3H), 1.97-2.39 (m, 8H), 1.84-1.96 (m, 1H), 1.64-1.77 (m, 2H), 1.44 (q, J=12.6 Hz, 2H), 1.31 (d, J=6.2 Hz, 6H), 1.13 (s, 9H). ESI [M+H]=636.3

Example 10. Synthesis of trans-tert-butyl N-[4-[5-[4-(benzylcarbamoylamino)-2-(tert-butylsulfamoyl)phenyl]thiazol-2-yl]cyclohexyl]carbamate

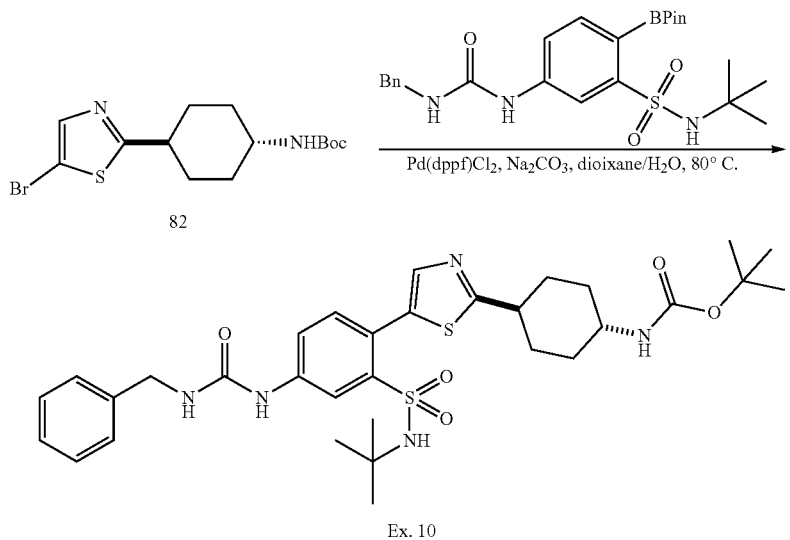

General method B, trans-tert-butyl N-[4-[5-[4-(benzylcarbamoylamino)-2-(tert-butylsulfamoyl)phenyl]thiazol-2-yl]cyclohexyl]carbamate. ¹H NMR (400 MHz, METHANOL-d4) δ=8.24 (d, J=2.4 Hz, 1H), 7.72-7.66 (m, 2H), 7.37-7.29 (m, 5H), 7.28-7.21 (m, 1H), 4.40 (s, 2H), 3.39 (br t, J=11.6 Hz, 1H), 2.98 (tt, J=3.4, 12.1 Hz, 1H), 2.25-2.17 (m, 2H), 2.04 (br d, J=11.5 Hz, 2H), 1.67 (dq, J=2.9, 12.9 Hz, 2H), 1.44 (s, 9H), 1.41-1.32 (m, 2H), 1.10 (s, 9H). ESI [M+H]=642.3

Example 11. Synthesis of [(2R)-1-methylpyrrolidin-2-yl]methyl N-[4-[5-[4-(benzylcarbamoylamino)-2-(tert-butylsulfamoyl)phenyl]thiazol-2-yl]cyclohexyl]carbamate

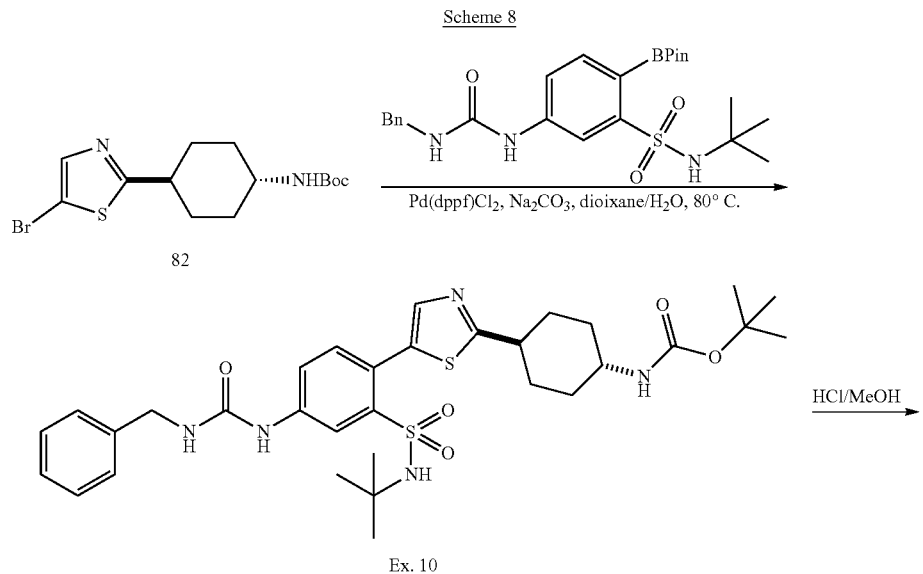

Scheme 8

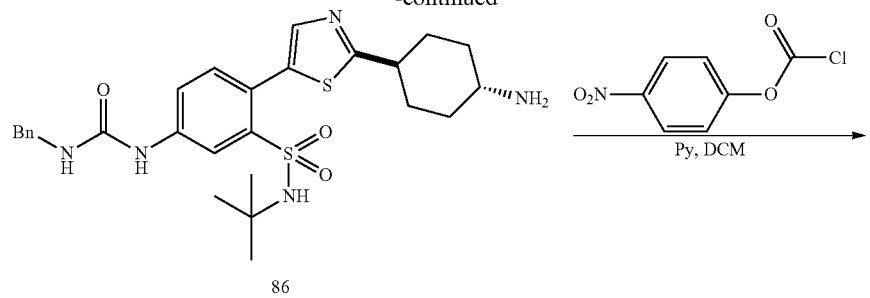
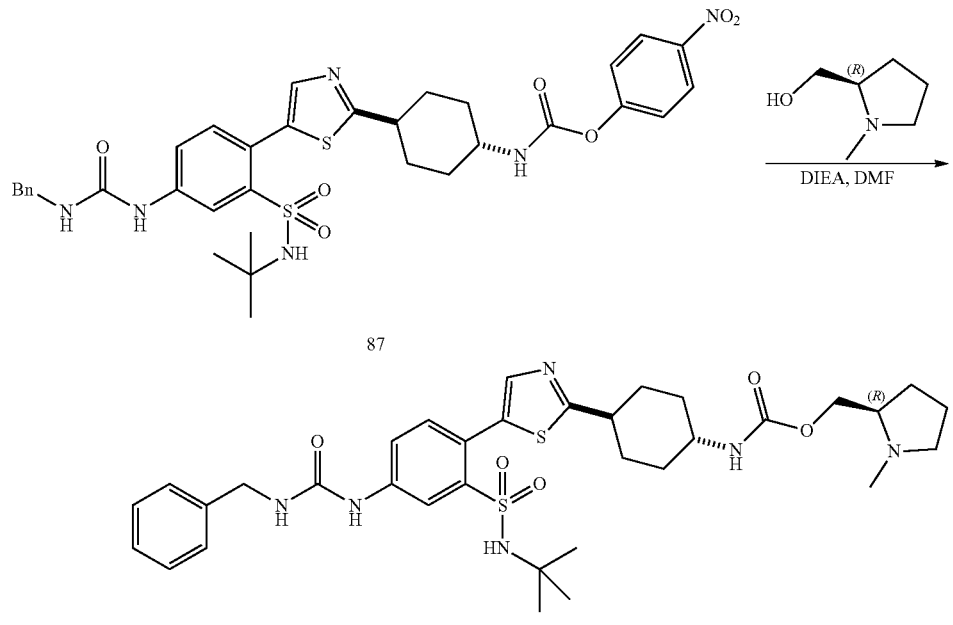
Preparation of Compound 86
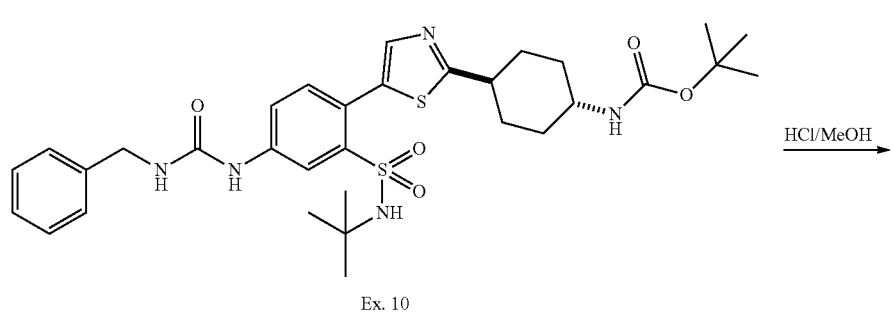
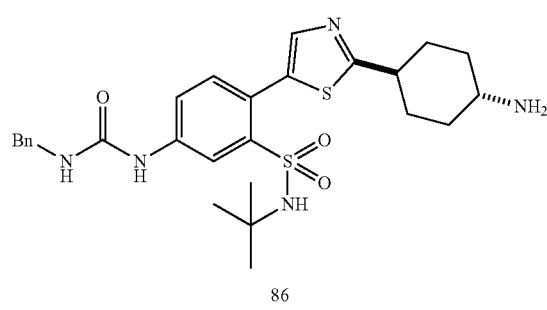

General method F, trans-1-[4-[2-(4-aminocyclohexyl)thiazol-5-yl]-3-(tert-butylsulfamoyl)phenyl]-3-benzyl-urea.
ESI [M+H]=542.3
Preparation of Compound 87

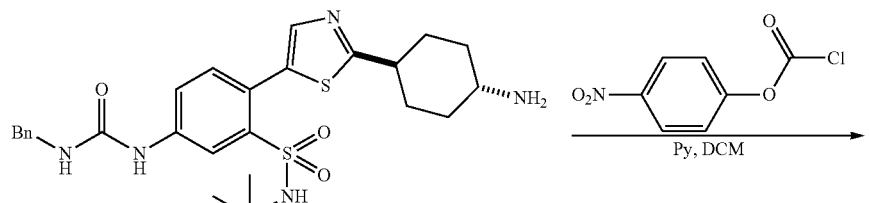

86

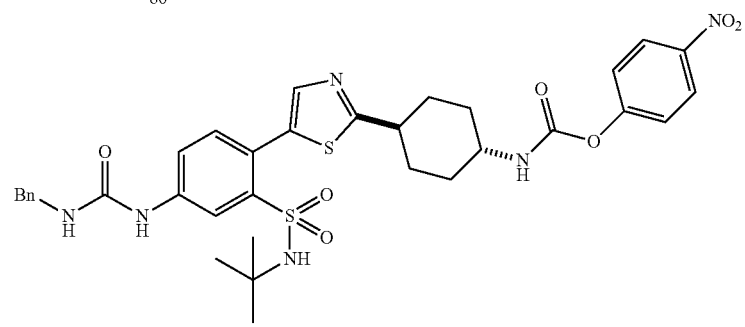

87

General method D, trans-(4-nitrophenyl)N-[4-[5-[4-(benzylcarbamoylamino)-2-(tert-butylsulfamoyl)phenyl]thiazol-2-yl]cyclohexyl]carbamate.
Preparation of Ex. 11

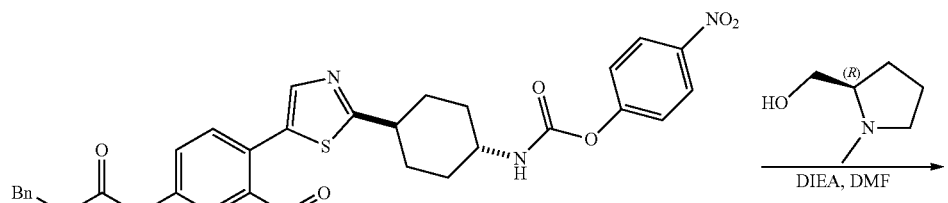

87

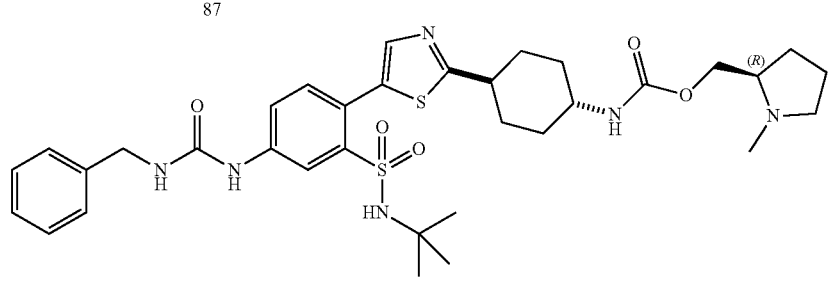

Ex. 11

General method H, [(2R)-1-methylpyrrolidin-2-yl]methyl N-[4-[5-[4-(benzylcarbamoylamino)-2-(tert-butylsulfamoyl)phenyl]thiazol-2-yl]cyclohexyl]carbamate. $^1$H NMR (400 MHz, METHANOL-d4) δ=8.30 (d, J=2.2 Hz, 1H), 7.79 (s, 1H), 7.70 (dd, J=2.3, 8.4 Hz, 1H), 7.42-7.31 (m, 5H), 7.27 (dt, J=2.6, 5.7 Hz, 1H), 4.54-4.41 (m, 3H), 4.21 (dd, J=7.1, 12.7 Hz, 1H), 3.79-3.66 (m, 2H), 3.52 (br t, J=11.6 Hz, 1H), 3.26-3.17 (m, 1H), 3.04 (s, 3H), 2.42-1.98 (m, 8H), 1.97-1.87 (m, 1H), 1.80-1.65 (m, 2H), 1.54-1.40 (m, 2H), 1.15 (s, 9H). ESI [M+H]=683.3

Example 12. Synthesis of ((S)-1-methylpyrrolidin-2-yl)methyl((1r,4S)-4-(5-(4-(3-benzylureido)-2-(N-(tert-butyl)sulfamoyl)phenyl)thiazol-2-yl)cyclohexyl)carbamate The Following Compound was Synthesized Via Same Method by the Key Intermediate 87.

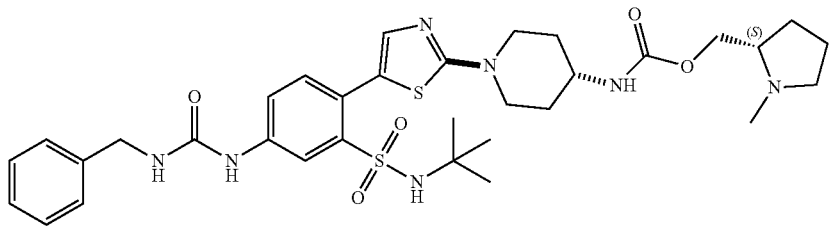

Ex. 12

1H NMR (400 MHz, METHANOL-d4) δ=8.29 (d, J=2.3 Hz, 1H), 7.83-7.74 (m, 1H), 7.73-7.65 (m, 1H), 7.43-7.31 (m, 5H), 7.30-7.22 (m, 1H), 4.55-4.35 (m, 3H), 4.21 (br dd, J=7.1, 12.7 Hz, 1H), 3.79-3.61 (m, 2H), 3.58-3.42 (m, 1H), 3.23 (br s, 1H), 3.08-3.02 (m, 3H), 2.43-1.98 (m, 8H), 1.97-1.86 (m, 1H), 1.80-1.65 (m, 2H), 1.54-1.39 (m, 2H), 1.19-1.07 (m, 9H). ESI [M+H]=683.3

Example 13. Synthesis of isopropyl(S)-(4-(5-(2-(N-(tert-butyl)sulfamoyl)-4-(3-(1-phenylethyl)ureido)phenyl)thiazol-2-yl)bicyclo[2.2.2]octan-1-yl)carbamate Scheme 9

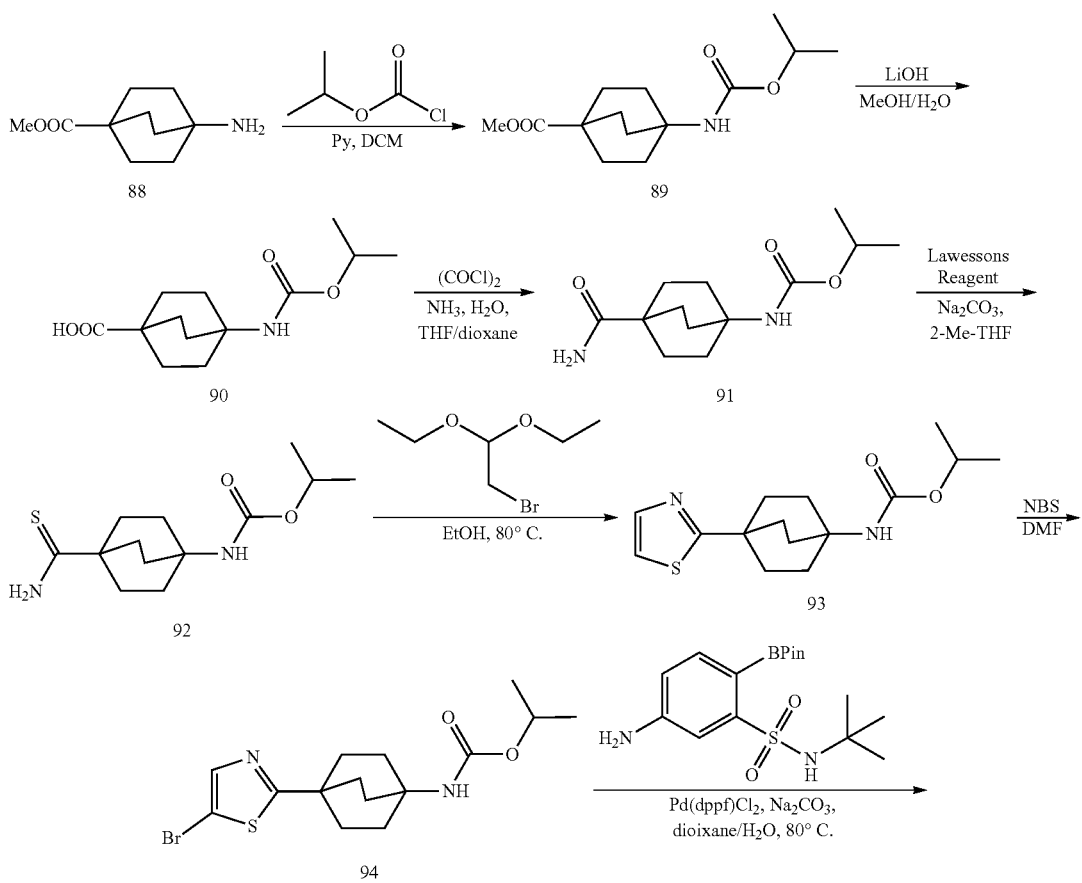

-continued
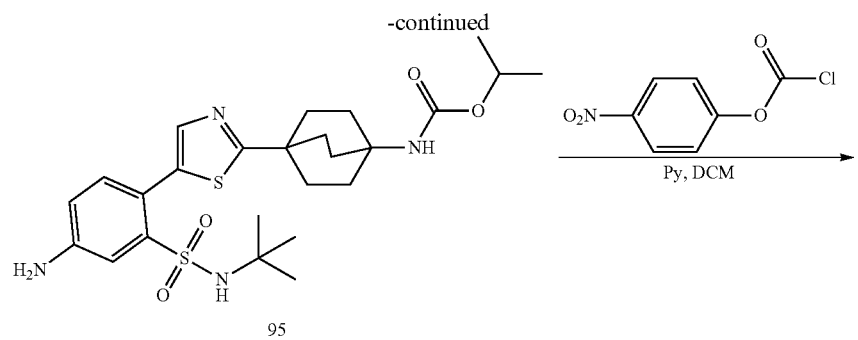
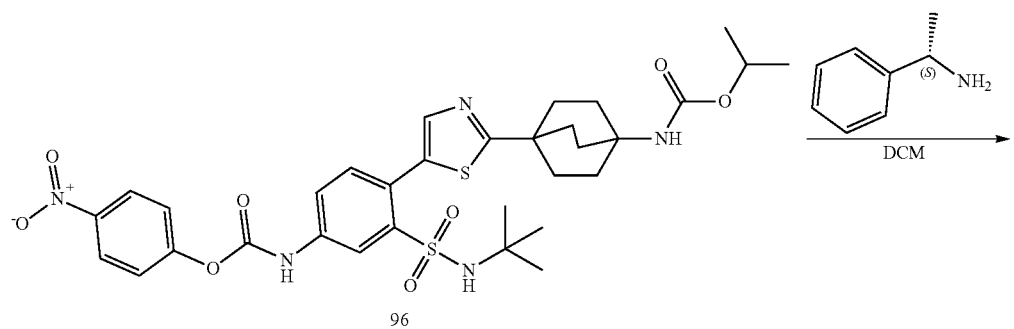
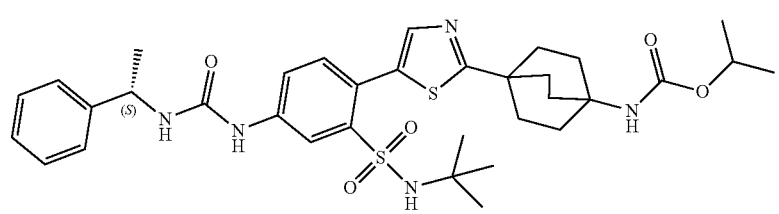
Ex. 13

Preparation of Compound 89

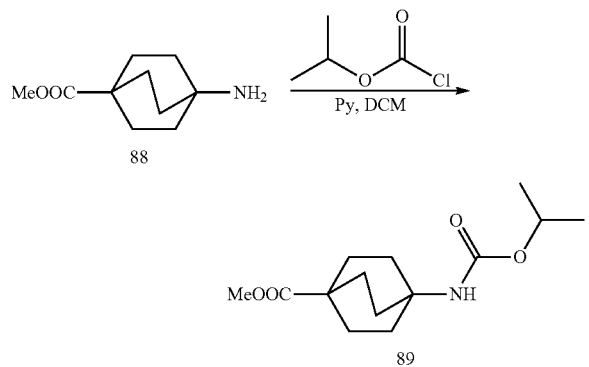

General method D, 4-(isopropoxycarbonylamino)bicyclo[2.2.2]octane-1-carboxylate.

General Method O for Preparation of Compound 90

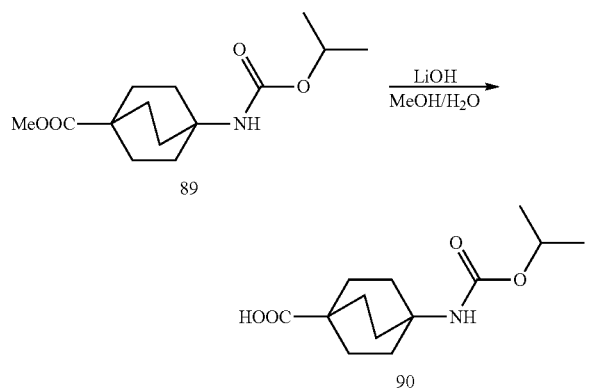

To a solution of methyl 4-(isopropoxycarbonylamino)bicyclo[2.2.2]octane-1-carboxylate (400 mg, 1.49 mmol, 1 eq.) in MeOH (5 mL), was added LiOH (106.70 mg, 4.46 mmol, 3 eq.) in H$_2$O (5 mL) and the mixture was stirred at 50° C. for 1 hr. The mixture was concentrated to remove MeOH and then extracted with MTBE (10 mL*2). The pH of aqueous phase was adjusted to 1-2 by adding 4 N HCl solution and then extracted with EtOAc (10 mL*3). The combined organic phase was dried over Na$_2$SO$_4$, filtered and concentrated to give 4-(isopropoxycarbonylamino)bicyclo[2.2.2]octane-1-carboxylic acid (270 mg, crude) as a yellow solid. $^1$H NMR (400 MHz, CHLOROFORM-d) δ=4.86 (br d, J=6.4 Hz, 1H), 4.46 (br s, 1H), 2.00-1.80 (m, 12H), 1.23 (br d, J=5.9 Hz, 6H).

General Method N for Preparation of Compound 91

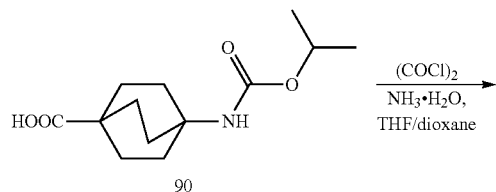

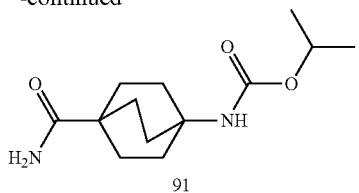

To a solution of 4-(isopropoxycarbonylamino)bicyclo[2.2.2]octane-1-carboxylic acid (270 mg, 1.06 mmol, 1 eq.) in DCM (5 mL), were added DMF (7.73 mg, 105.75 umol, 0.1 eq.) and (COCl)$_2$ (201.34 mg, 1.59 mmol, 1.5 eq.). The mixture was stirred at 26° C. for 0.2 hr and then concentrated. The residue was dissolved into THF (5 mL) and was added into NH$_3$.H$_2$O (741.24 mg, 5.29 mmol, 5 eq.) in dioxane (5 mL) dropwise. Then the mixture was stirred at 26° C. for 0.3 hr. The mixture was concentrated and diluted with EtOAc (20 mL) and washed with H$_2$O (10 mL). The organic phase was dried over Na$_2$SO$_4$, filtered and concentrated to give isopropyl N-(1-carbamoyl-4-bicyclo[2.2.2]octanyl)carbamate as a yellow solid. $^1$H NMR (400 MHz, CHLOROFORM-d) δ=5.43 (br s, 1H), 5.17 (br s, 1H), 4.85-4.71 (m, 1H), 4.35 (br s, 1H), 1.82 (s, 12H), 1.13 (d, J=6.2 Hz, 6H). ESI[M+H]=255.2

General Method L for Preparation of Compound 92

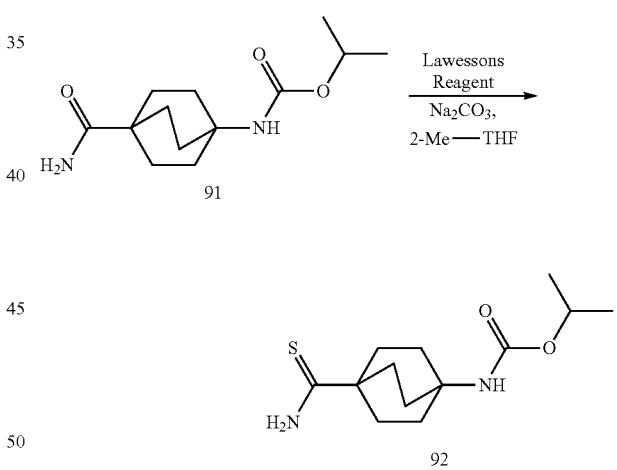

To a solution of isopropyl N-(1-carbamoyl-4-bicyclo[2.2.2]octanyl)carbamate (60 mg, 235.92 umol, 1 eq.) in 2-Me-THF (2 mL), was added 2,4-bis(4-methoxyphenyl)-2,4-dithioxo-1,3,2,4dithiadiphosphetane (95.42 mg, 235.92 umol, 1 eq.) and the mixture was stirred at 80° C. for 0.5 hr. The mixture was poured into sat.aq.Na$_2$CO$_3$ (10 mL) and extracted with EtOAc (10 mL*3). The combined organic phase was dried over Na$_2$SO$_4$, filtered and concentrated. The residue was purified by prep-TLC (Petroleum ether/Ethyl acetate=2:3) to give isopropyl N-(1-carbamothioyl-4-bicyclo[2.2.2]octanyl)carbamate (30 mg, crude) as a yellow solid. ESI [M+H]=271.1

General Method M for Preparation of Compound 93

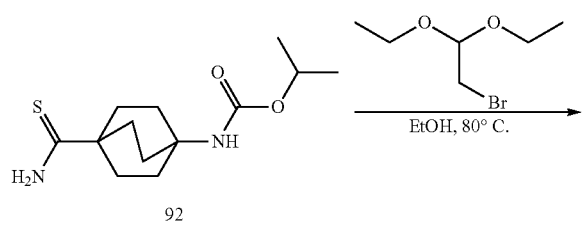

92

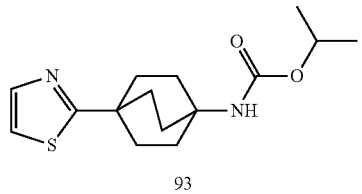

93

To a solution of isopropyl N-(1-carbamothioyl-4-bicyclo[2.2.2]octanyl)carbamate (85 mg, 314.36 umol, 1 eq.) in EtOH (2 mL), were added TsOH.H₂O (119.59 mg, 628.72 umol, 2 eq.) and 2-bromo-1,1-diethoxy-ethane (123.90 mg, 628.72 umol, 2 eq.). The mixture was stirred at 80° C. for 1 hr and then concentrated and diluted with EtOAc (30 mL). The mixture was washed with sat.aq.Na₂CO₃ (10 mL*2) and the combined organic phase was dried over Na₂SO₄, filtered and concentrated. The residue was purified by prep-TLC (Petroleum ether/Ethyl acetate=3:1) to give isopropyl N-(1-thiazol-2-yl-4-bicyclo[2.2.2]octanyl)carbamate (80 mg, crude) as a yellow solid. ESI [M+H]=295.3

Preparation of Compound 94

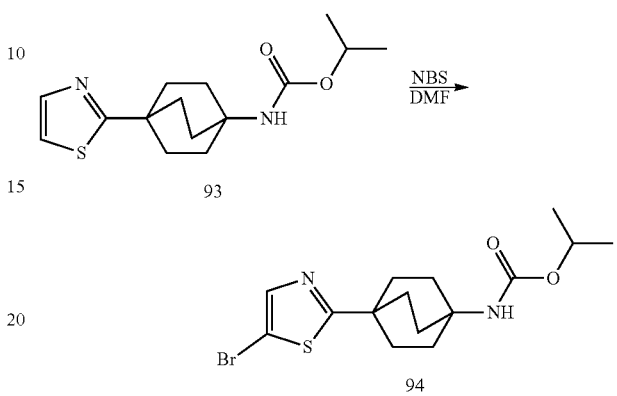

General method J, isopropyl N-[1-(5-bromothiazol-2-yl)-4-bicyclo[2.2.2]octanyl]carbamate. ESI[M+H]=375.2/373.2

Preparation of Compound 95

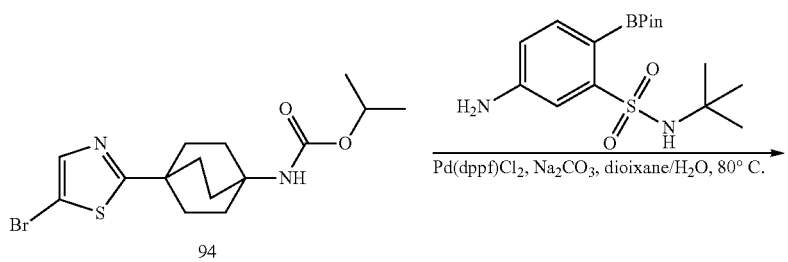

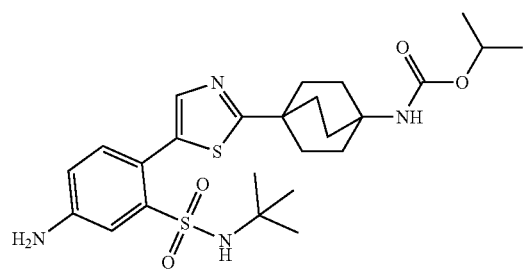

95

General method B, isopropyl N-[1-[5-[4-amino-2-(tert-butylsulfamoyl)phenyl]thiazol-2-yl]-4-bicyclo[2.2.2]octanyl]carbamate. ESI [M+H]=521.2
Preparation of Compound 96
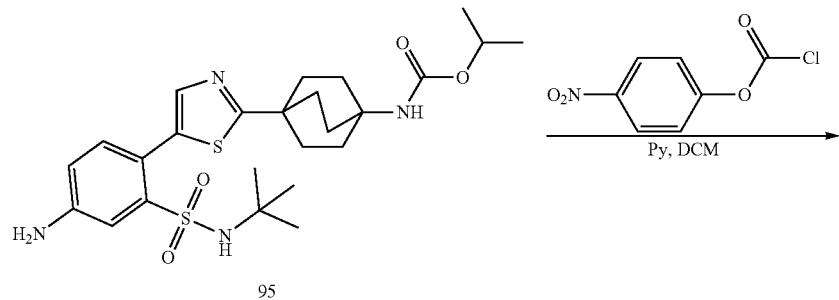
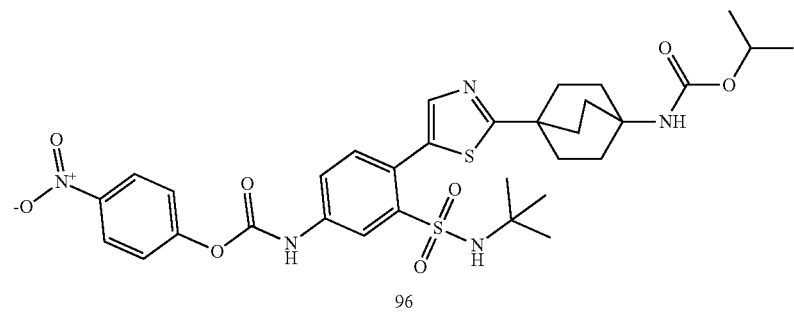
General method D, (4-nitrophenyl)N-[3-(tert-butylsulfamoyl)-4-[2-[4-(isopropoxycarbonylamino)-1-bicyclo[2.2.2]octanyl]thiazol-5-yl]phenyl]carbamate. ESI [M+H]=686.4
Preparation of Ex 13
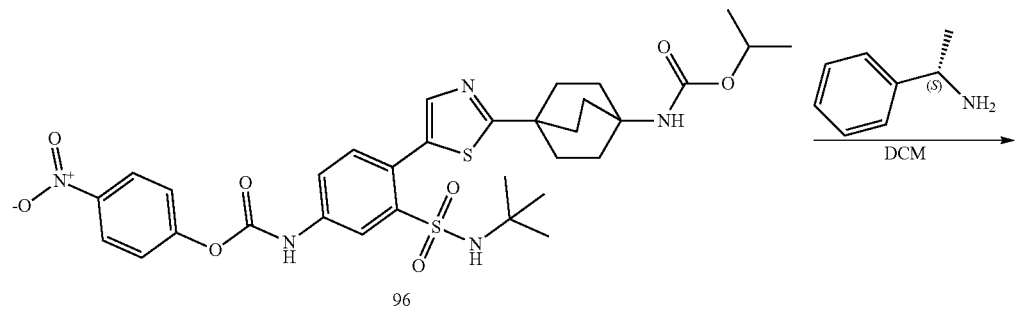
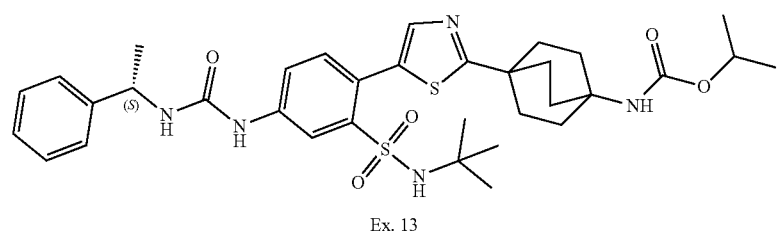

General method E, isopropyl N-[1-[5-[2-(tert-butylsulfamoyl)-4-[[(1S)-1-phenylethyl]carbamoylamino]phenyl]thiazol-2-yl]-4-bicyclo[2.2.2]octanyl]carbamate. $^1$H NMR (400 MHz, METHANOL-d4) δ=8.21 (d, J=2.3 Hz, 1H), 7.75 (s, 1H), 7.67 (dd, J=2.3, 8.3 Hz, 1H), 7.41-7.32 (m, 5H), 7.29-7.23 (m, 1H), 4.99-4.93 (m, 1H), 4.83-4.76 (m, 1H), 2.17-2.08 (m, 6H), 2.07-1.99 (m, 6H), 1.51 (d, J=7.0 Hz, 3H), 1.22 (br d, J=6.0 Hz, 6H), 1.12 (s, 9H). ESI [M+H]=668.3

Example 14. Synthesis of isopropyl(R)-(4-(5-(2-(N-(tert-butyl)sulfamoyl)-4-(3-(1-phenylethyl)ureido)phenyl)thiazol-2-yl)bicyclo[2.2.2]octan-1-yl)carbamate The Following Compound was Synthesized Via Same Method by the Key Intermediate 96.

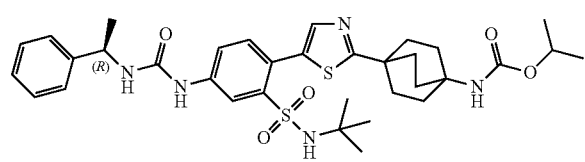
Ex. 14

$^1$H NMR (400 MHz, METHANOL-d4) δ=8.18 (d, J=2.6 Hz, 1H), 7.74-7.69 (m, 1H), 7.64 (dd, J=2.2, 8.3 Hz, 1H), 7.38-7.29 (m, 5H), 7.26-7.19 (m, 1H), 4.92 (q, J=7.0 Hz, 1H), 4.82-4.71 (m, 1H), 2.15-2.05 (m, 6H), 2.04-1.95 (m, 6H), 1.48 (d, J=7.0 Hz, 3H), 1.20 (br d, J=6.1 Hz, 6H), 1.09 (s, 9H). ESI [M+H]=668.3

Example 15. Synthesis of isopropyl(S)-(4-(5-(2-(N-(tert-butyl)sulfamoyl)-4-(3-(1-(pyridin-2-yl)ethyl)ureido)phenyl)thiazol-2-yl)bicyclo[2.2.2]octan-1-yl)carbamate The Following Compound was Synthesized Via Same Method by the Key Intermediate 96.

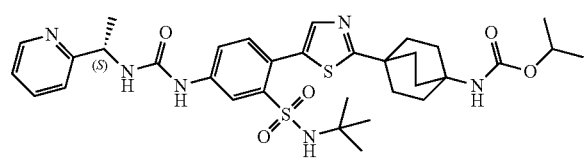
Ex. 15

$^1$H NMR (400 MHz, METHANOL-d4) δ=8.72 (d, J=5.6 Hz, 1H), 8.46 (t, J=7.9 Hz, 1H), 8.28 (d, J=2.3 Hz, 1H), 8.02 (d, J=7.9 Hz, 1H), 7.85 (t, J=6.6 Hz, 1H), 7.72 (s, 1H), 7.63 (dd, J=2.3, 8.4 Hz, 1H), 7.35 (d, J=8.4 Hz, 1H), 5.13 (q, J=7.1 Hz, 1H), 4.84-4.74 (m, 1H), 2.15-2.07 (m, 6H), 2.07-1.98 (m, 6H), 1.65 (d, J=7.1 Hz, 3H), 1.22 (br d, J=6.1 Hz, 6H), 1.09 (s, 9H). ESI [M+H]=669.2

Example 16. Synthesis of isopropyl(R)-(4-(5-(2-(N-(tert-butyl)sulfamoyl)-4-(3-(1-(pyridin-2-yl)ethyl)ureido)phenyl)thiazol-2-yl)bicyclo[2.2.2]octan-1-yl)carbamate The Following Compound was Synthesized Via Same Method by the Key Intermediate 96.

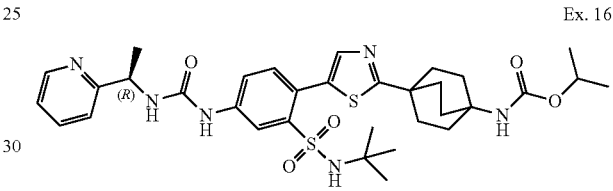
Ex. 16

$^1$H NMR (400 MHz, METHANOL-d4) δ=8.75 (d, J=5.1 Hz, 1H), 8.57 (dt, J=1.5, 7.9 Hz, 1H), 8.29 (d, J=2.2 Hz, 1H), 8.11 (d, J=8.1 Hz, 1H), 7.98-7.90 (m, 1H), 7.75 (s, 1H), 7.62 (dd, J=2.3, 8.3 Hz, 1H), 7.36 (d, J=8.4 Hz, 1H), 5.15 (q, J=7.1 Hz, 1H), 4.84-4.75 (m, 1H), 2.16-2.07 (m, 6H), 2.06-1.97 (m, 6H), 1.67 (d, J=7.2 Hz, 3H), 1.22 (br d, J=6.1 Hz, 6H), 1.09 (s, 9H). ESI [M+H]=669.2

Example 17. Synthesis of isopropyl N-[3-(tert-butylsulfamoyl)-4-[2-[4-(isopropoxycarbonyl amino)-1-bicyclo[2.2.2]octanyl]thiazol-5-yl]phenyl]carbamate Scheme 10:
Preparation of Compound Ex. 17

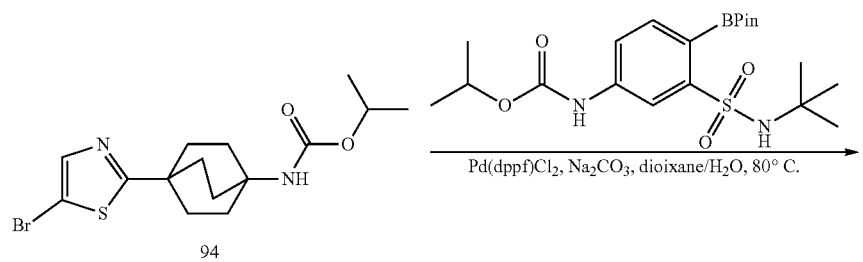
94

-continued

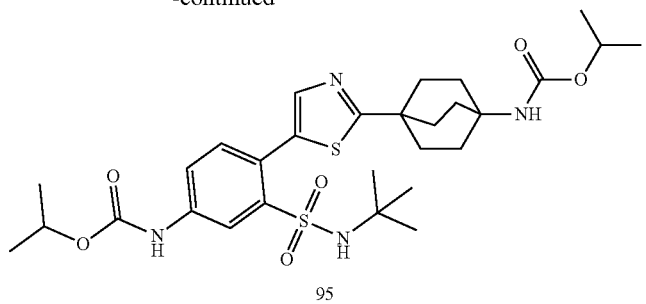

95

General method B, isopropyl N-[3-(tert-butylsulfamoyl)-4-[2-[4-(isopropoxycarbonyl amino)-1-bicyclo[2.2.2]octanyl]thiazol-5-yl]phenyl]carbamate. ¹H NMR (400 MHz, METHANOL-d4) δ=8.33 (d, J=2.0 Hz, 1H), 7.74 (s, 1H), 7.66 (dd, J=2.2, 8.4 Hz, 1H), 7.36 (d, J=8.4 Hz, 1H), 5.03-4.91 (m, 1H), 4.78 (br d, J=6.4 Hz, 1H), 2.16-2.05 (m, 6H), 2.04-1.95 (m, 6H), 1.31 (d, J=6.4 Hz, 6H), 1.20 (br d, J=6.0 Hz, 6H), 1.11 (s, 9H). ESI [M+H]=607.3

Example 18. Synthesis of isopropyl(4-(5-(4-(3-benzylureido)-2-(N-(tert-butyl)sulfamoyl)phenyl)thiazol-2-yl)bicyclo[2.2.2]octan-1-yl)carbamate The Following Compound was Synthesized Via Same Method by the Key Intermediate 94.

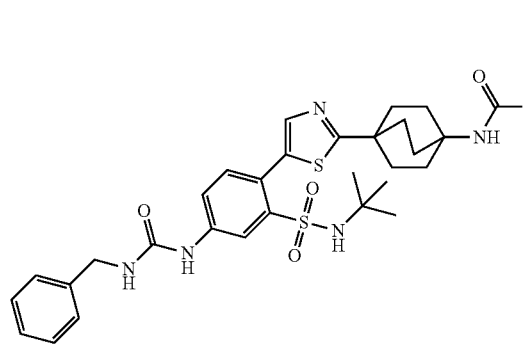

Ex. 18

¹H NMR (400 MHz, METHANOL-d4) δ=8.26 (d, J=2.2 Hz, 1H), 7.77 (s, 1H), 7.72 (dd, J=2.4, 8.4 Hz, 1H), 7.38-7.33 (m, 5H), 7.27 (td, J=2.6, 8.6 Hz, 1H), 4.80 (br d, J=5.7 Hz, 1H), 4.43 (s, 2H), 2.17-2.10 (m, 6H), 2.06-2.00 (m, 6H), 1.25-1.20 (m, 6H), 1.13 (s, 9H). ESI [M+H]=654.1

Example 19. Synthesis of isopropyl(4-(5-(2-(N-(tert-butyl)sulfamoyl)-4-(3-(pyridin-2-ylmethyl)ureido)phenyl)thiazol-2-yl)bicyclo[2.2.2]octan-1-yl)carbamate The Following Compound was Synthesized Via Same Method by the Key Intermediate 94.

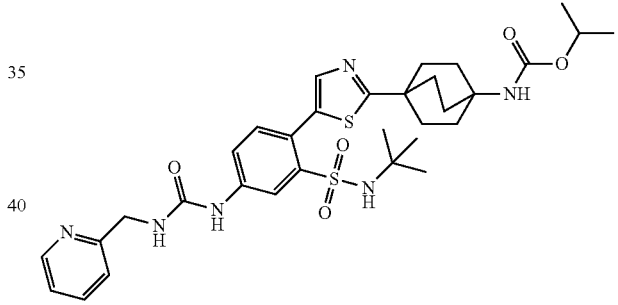

Ex. 19

¹H NMR (400 MHz, METHANOL-d4) δ=8.73 (d, J=5.7 Hz, 1H), 8.51 (dt, J=1.3, 7.9 Hz, 1H), 8.31 (d, J=2.2 Hz, 1H), 8.02 (d, J=8.3 Hz, 1H), 7.90 (t, J=6.8 Hz, 1H), 7.72 (s, 1H), 7.66 (dd, J=2.2, 8.3 Hz, 1H), 7.35 (d, J=8.3 Hz, 1H), 4.75 (s, 3H), 2.15-1.93 (m, 12H), 1.20 (br d, J=6.1 Hz, 6H), 1.07 (s, 9H). ESI [M+H]=655.3

Example 20. Synthesis of trans-isopropyl N-[3-(tert-butylsulfamoyl)-4-[2-[4-(isopropylcarbamoyloxy)cyclohexyl]thiazol-5-yl]phenyl]carbamate Scheme 11

-continued

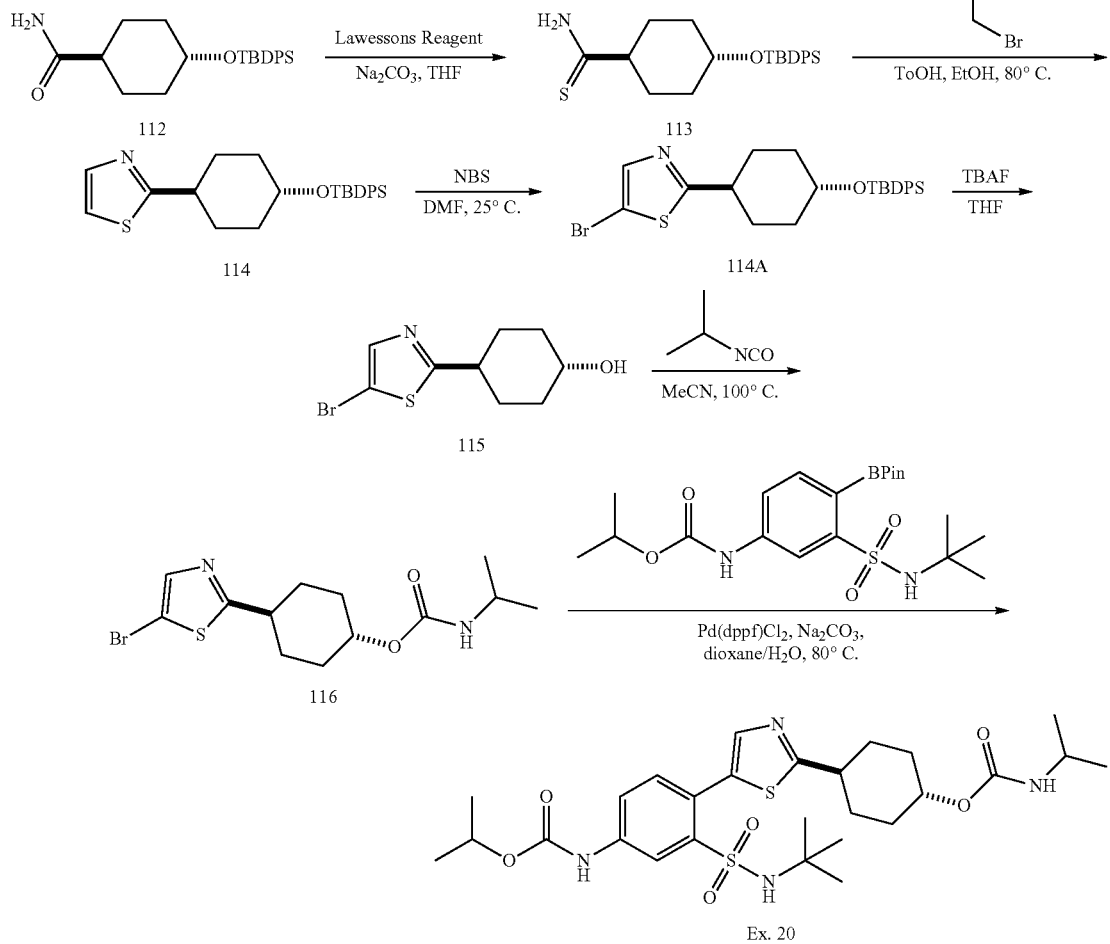

Preparation of Compound 111.

Preparation of Compound 112.

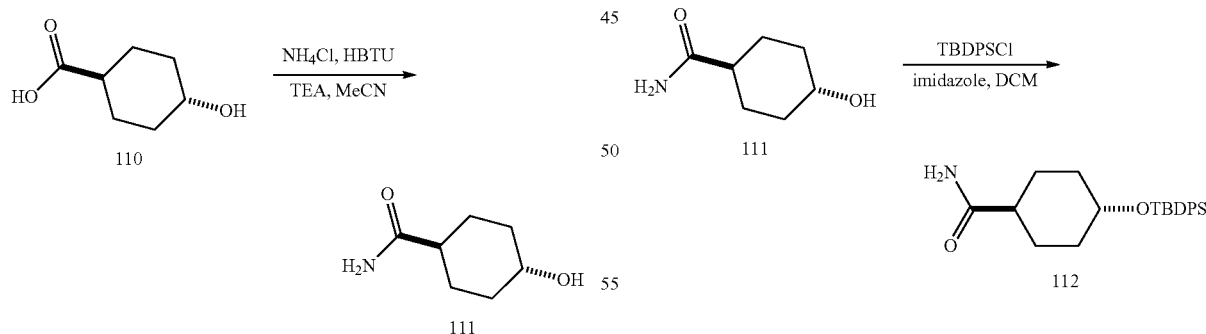

To a solution of trans-4-hydroxycyclohexanecarboxylic acid (1 g, 6.94 mmol, 1 eq.) in MeCN (10 mL), were added HBTU (2.89 g, 7.63 mmol, 1.1 eq.) and TEA (2.11 g, 20.81 mmol, 2.90 mL, 3 eq.) followed by addition of NH$_4$Cl (742.07 mg, 13.87 mmol, 2 eq.) and the mixture was stirred at 26° C. for 1 hr. The mixture was then filtered and dried to give trans-4-hydroxycyclohexanecarboxamide (1 g, crude) as a white solid which can be used without any purification.

To a solution of trans-4-hydroxycyclohexanecarboxamide (12 g, 83.81 mmol, 1 eq.) in DCM (150 mL), were added IMIDAZOLE (11.41 g, 167.62 mmol, 2 eq.) and tert-butyl-chloro-diphenyl-silane (27.64 g, 100.57 mmol, 25.83 mL, 1.2 eq.). The mixture was stirred at 26° C. for 12 hrs and then poured into 1N HCl (200 mL) and the organic phase was washed with sat.aq.Na$_2$CO$_3$ (100 mL). The organic phase was dried over Na$_2$SO$_4$, filtered and concentrated. The residue was washed with a solution (petroleum ether:E-tOAc=10:1, 100 mL) and then filtered. The filter cake was dried to give trans4-[tert-butyl(diphenyl)silyl]oxycyclohexanecarboxamide (31.5 g, crude). ¹H NMR (400 MHz, METHANOL-d4) δ=7.72-7.64 (m, 4H), 7.49-7.36 (m, 6H), 3.69-3.55 (m, 1H), 2.21-2.08 (m, 1H), 1.96-1.83 (m, 2H), 1.82-1.69 (m, 2H), 1.50-1.23 (m, 4H), 1.12-0.98 (m, 9H).

Preparation of Compound 113.

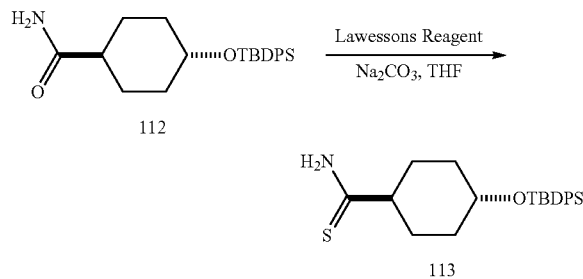

General method L, trans-4-[tert-butyl(diphenyl)silyl]oxy-cyclohexanecarbothioamide. ¹H NMR (400 MHz, METHANOL-d4) δ=7.73-7.64 (m, 4H), 7.52-7.36 (m, 6H), 3.73-3.59 (m, 1H), 2.59-2.44 (m, 1H), 1.91 (br d, J=8.3 Hz, 2H), 1.80-1.66 (m, 2H), 1.57-1.35 (m, 4H), 1.08-1.04 (m, 9H). ESI [M+H]=398.1

Preparation of compound 114.

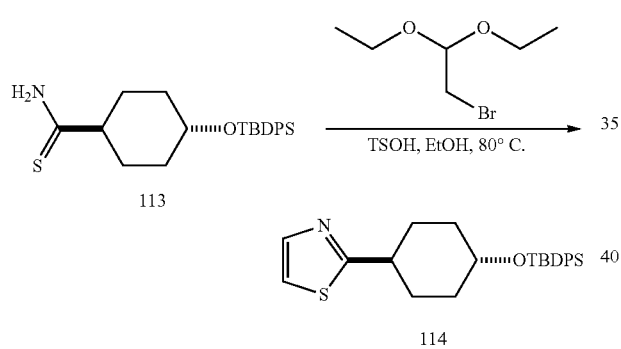

General method M, trans-tert-butyl-diphenyl-(4-thiazol-2-ylcyclohexoxy)silane. ¹H NMR (400 MHz, METHANOL-d4) δ=7.63-7.55 (m, 5H), 7.42-7.25 (m, 7H), 4.05-3.96 (m, 1H), 2.97 (tt, J=3.7, 11.7 Hz, 1H), 2.05 (dq, J=3.2, 12.5 Hz, 2H), 1.84-1.62 (m, 4H), 1.44 (tt, J=2.9, 13.5 Hz, 2H), 1.01-0.98 (m, 9H). ESI [M+H]=422.2

Preparation of Compound 114A.

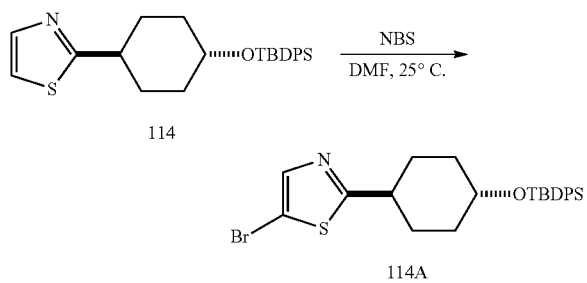

General method J, trans-[4-(5-bromothiazol-2-yl)cyclohexoxy]-tert-butyl-diphenyl-silane (1.8 g, crude). ESI [M+H]=502.0 Preparation of compound 115.

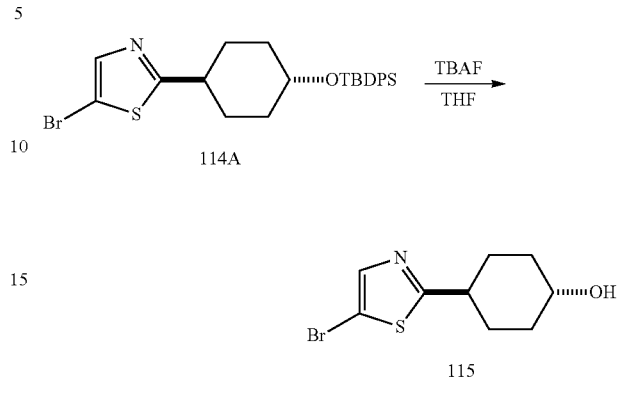

To a solution of trans-[4-(5-bromothiazol-2-yl)cyclohexoxy]-tert-butyl-diphenyl-silane (1.5 g, 3.00 mmol, 1 eq.) in THF (10 mL), was added TBAF (1 M, 4.49 mL, 1.5 eq.) and the mixture was stirred at 26° C. for 12 hrs and then concentrated. The residue was purified by silica gel chromatography (Petroleum ether/Ethyl acetate=20:1-1:1) to afford trans-4-(5-bromothiazol-2-yl)cyclohexanol (500 mg, 1.91 mmol, 63.64% yield) as a yellow solid.

Preparation of Compound 116.

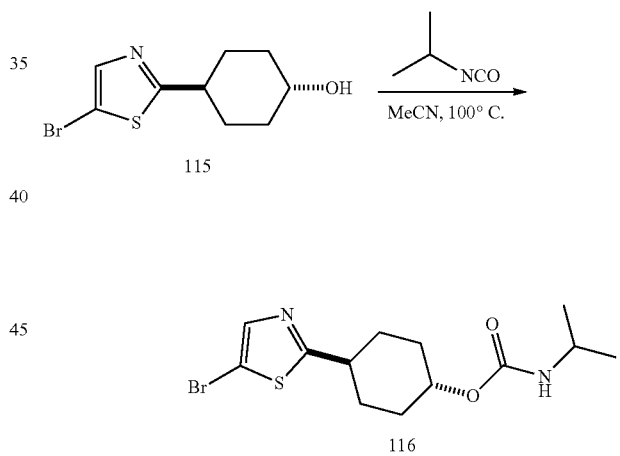

To a solution of trans-4-(5-bromothiazol-2-yl)cyclohexanol (500 mg, 1.91 mmol, 1 eq.) in DMF (5 mL), were added 2-isocyanatopropane (486.93 mg, 5.72 mmol, 3 eq.) and DIEA (739.47 mg, 5.72 mmol, 3 eq.). The mixture was stirred at 100° C. for 40 hrs and then poured into H₂O (50 mL) and extracted with EtOAc (10 mL*3). The combined organic phase was dried over Na₂SO₄, filtered and concentrated. The residue was purified by silica gel chromatography (Petroleum ether/Ethyl acetate=10:1-1:1) to afford trans-[4-(5-bromothiazol-2-yl)cyclohexyl]N-isopropylcarbamate (180 mg, 518.33 umol, 27.18% yield) as a yellow solid. ¹H NMR (400 MHz, METHANOL-d4) δ=7.61 (s, 1H), 3.85-3.64 (m, 2H), 3.15-2.99 (m, 1H), 1.98-1.83 (m, 6H), 1.73 (br d, J=13.5 Hz, 2H), 1.14-1.12 (m, 6H). ESI [M+H]=347.1/349.1

Preparation of Ex 20.

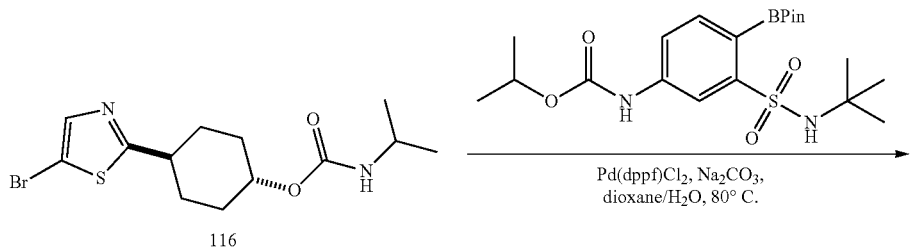

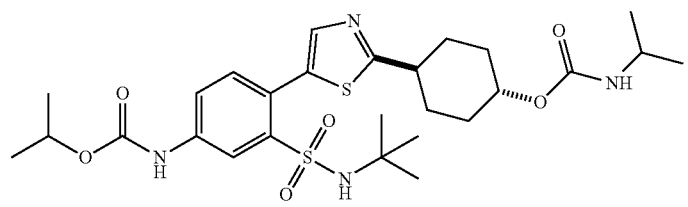

Ex. 20

General method B, trans-isopropyl N-[3-(tert-butylsulfamoyl)-4-[2-[4-(isopropylcarbamoyloxy)cyclohexyl]thiazol-5-yl]phenyl]carbamate. ¹H NMR (400 MHz, METHANOL-d4) δ=8.34 (d, J=2.0 Hz, 1H), 7.75 (s, 1H), 7.67 (dd, J=2.0, 8.4 Hz, 1H), 7.37 (d, J=8.4 Hz, 1H), 5.05-4.93 (m, 1H), 4.89 (br s, 1H), 3.83-3.64 (m, 1H), 3.15 (br s, 1H), 2.12-1.88 (m, 6H), 1.84-1.64 (m, 2H), 1.31 (d, J=6.2 Hz, 6H), 1.19-1.04 (m, 15H). ESI [M+H]=581.4

Example 21. Synthesis of (1r,4r)-4-(5-(4-(3-benzylureido)-2-(N-(tert-butyl)sulfamoyl)phenyl)thiazol-2-yl)cyclohexyl isopropylcarbamate The Following Compound was Synthesized Via Same Method by the Key Intermediate 116.

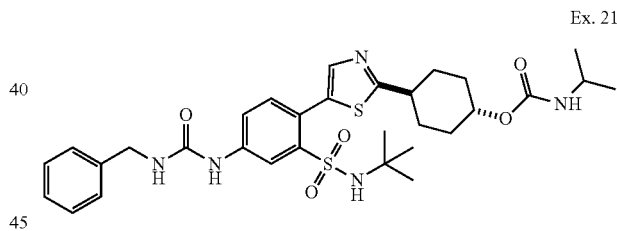

Ex. 21

¹H NMR (400 MHz, METHANOL-d4) δ=8.24 (d, J=2.2 Hz, 1H), 7.74 (s, 1H), 7.69 (dd, J=2.4, 8.4 Hz, 1H), 7.40-7.28 (m, 5H), 7.28-7.17 (m, 1H), 4.89 (br s, 1H), 4.41 (s, 2H), 3.79-3.64 (m, 1H), 3.14 (br s, 1H), 2.04-1.94 (m, 6H), 1.84-1.65 (m, 2H), 1.16-1.08 (m, 15H). ESI [M+H]=628.4

Example 22. Synthesis of trans-isopropyl N-[4-[5-[2-(tert-butylsulfamoyl)-4-(4-pyridylmethylcarbamoylamino)phenyl]thiazol-2-yl]cyclohexyl]carbamate Scheme 12

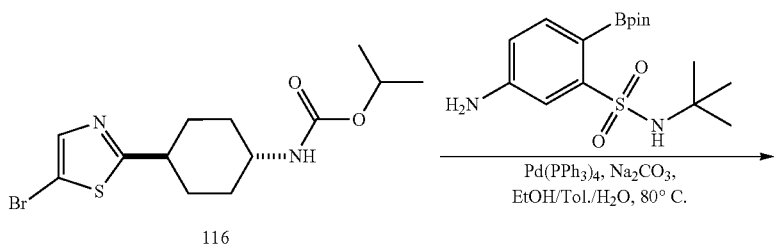

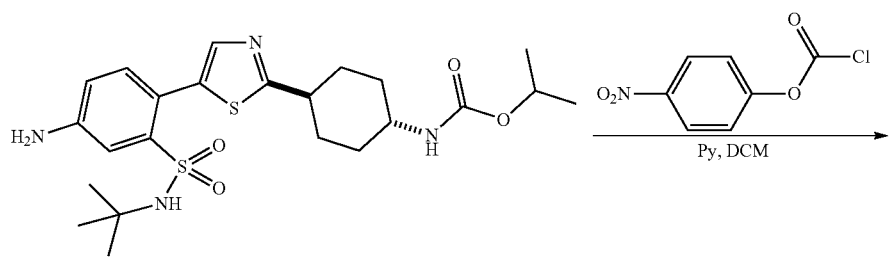
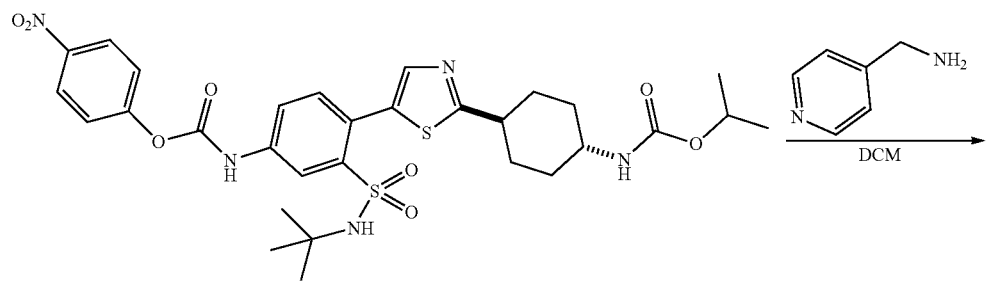
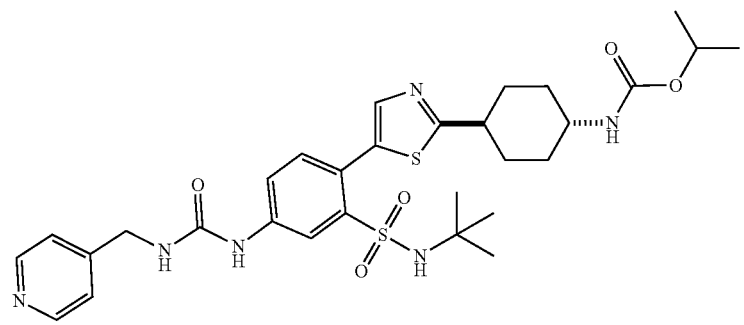
Ex. 22

Preparation of Compound 117.
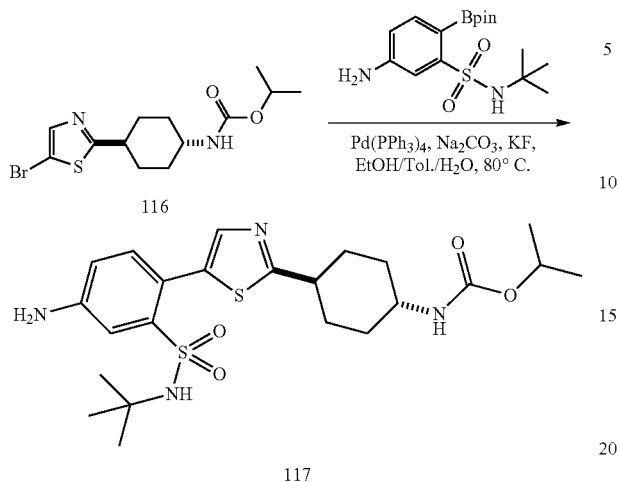
General method K, trans-isopropyl N-[4-[5-[4-amino-2-(tert-butylsulfamoyl)phenyl]thiazol-2-yl]cyclohexyl]carbamate. 1H NMR (400 MHz, METHANOL-d4) δ=7.68-7.57 (s, 1H), 7.43 (d, J=2.4 Hz, 1H), 7.13 (d, J=8.2 Hz, 1H), 6.82 (dd, J=2.4, 8.2 Hz, 1H), 4.84-4.77 (m, 1H), 3.44 (tt, J=3.9, 11.5 Hz, 1H), 2.97 (tt, J=3.6, 12.1 Hz, 1H), 2.26-2.13 (m, 2H), 2.11-2.02 (m, 2H), 1.67 (dq, J=3.0, 12.9 Hz, 2H), 1.49-1.32 (m, 2H), 1.22 (dd, J=2.5, 6.7 Hz, 6H), 1.09 (s, 9H). ESI [M+H]=495.2
Preparation of Compound 118.
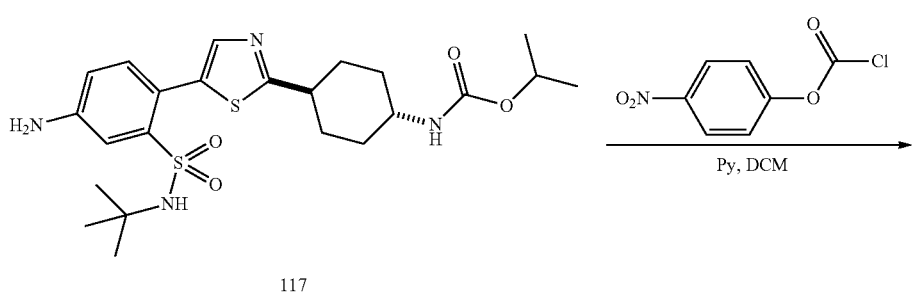
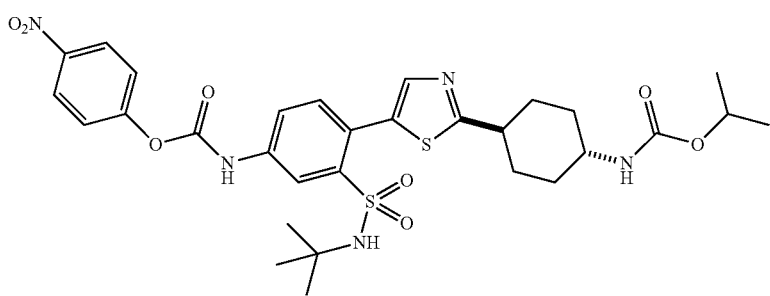

General method D, trans-(4-nitrophenyl)N-[3-(tert-butylsulfamoyl)-4-[2-[4-(isopropoxycarbonylamino)cyclohexyl]thiazol-5-yl]phenyl]carbamate. ESI [M+H]=660.1 Preparation of Ex 22.

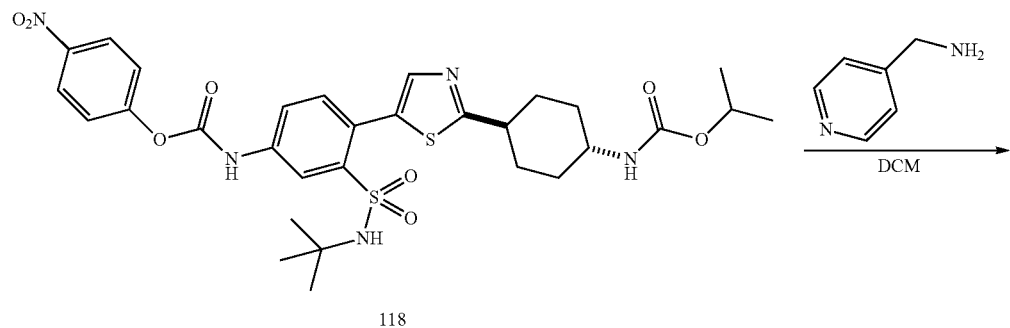

118

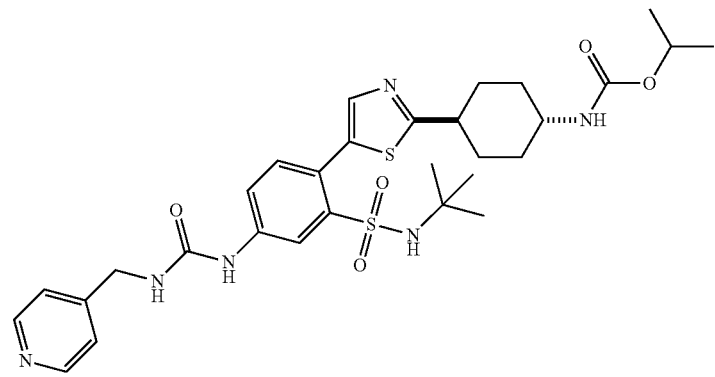

Ex. 22

General method E, trans-isopropyl N-[4-[5-[2-(tert-butylsulfamoyl)-4-(4-pyridylmethylcarbamoylamino)phenyl]thiazol-2-yl]cyclohexyl]carbamate. $^1$H NMR (400 MHz, METHANOL-d4) δ=8.79 (d, J=6.7 Hz, 2H), 8.34 (d, J=2.3 Hz, 1H), 8.07 (d, J=6.6 Hz, 2H), 7.76 (s, 1H), 7.69 (dd, J=2.3, 8.4 Hz, 1H), 7.39 (d, J=8.3 Hz, 1H), 4.85-4.83 (m, 1H), 4.73 (s, 2H), 3.47 (tt, J=3.6, 11.5 Hz, 1H), 3.04 (tt, J=3.4, 12.0 Hz, 1H), 2.30-2.19 (m, 2H), 2.09 (br d, J=10.1 Hz, 2H), 1.71 (dq, J=3.0, 12.9 Hz, 2H), 1.43 (dq, J=3.3, 12.6 Hz, 2H), 1.24 (br d, J=6.1 Hz, 6H), 1.12 (s, 9H). ESI [M+H]=629.2

Example 23. Synthesis of isopropyl((1r,4r)-4-(5-(2-(N-(tert-butyl)sulfamoyl)-4-(3-(4-fluorobenzyl)ureido)phenyl)thiazol-2-yl)cyclohexyl)carbamate The Following Compound was Synthesized Via Same Method by the Key Intermediate 118.

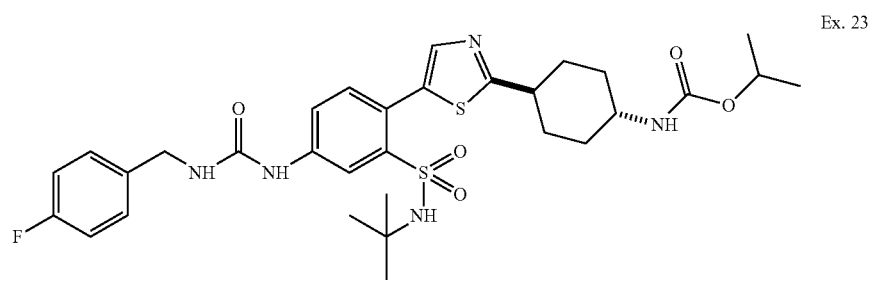 [SMILES: CC(C)OC(=O)N[C@H]1CC[C@H](c2ncc(-c3ccc(NC(=O)NCc4ccc(F)cc4)cc3S(=O)(=O)NC(C)(C)C)s2)CC1]

Ex. 23

¹H NMR (400 MHz, METHANOL-d4) δ=8.27 (d, J=2.3 Hz, 1H), 7.77 (s, 1H), 7.71 (dd, J=2.4, 8.4 Hz, 1H), 7.38 (td, J=2.7, 8.6 Hz, 3H), 7.12-7.04 (m, 2H), 5.00-4.92 (m, 1H), 4.41 (s, 2H), 3.54-3.41 (m, 1H), 3.05 (tt, J=3.5, 12.0 Hz, 1H), 2.13-2.05 (m, 2H), 2.05-2.04 (m, 2H), 1.72 (dq, J=3.0, 12.8 Hz, 2H), 1.43 (dq, J=3.2, 12.5 Hz, 2H), 1.24 (br d, J=6.1 Hz, 6H), 1.14 (s, 9H). ESI [M+H]=646.2

Example 24. Synthesis of isopropyl((1R,4r)-4-(5-(2-(N-isopropylsulfamoyl)-4-(3-((R)-1-phenylethyl)ureido)phenyl)thiazol-2-yl)cyclohexyl)carbamate The Following Compound was Synthesized Via Same Method by the Key Intermediate 118.

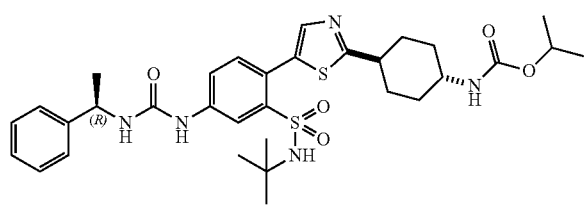

Ex. 24

¹H NMR (400 MHz, METHANOL-d4) δ=8.20 (d, J=2.2 Hz, 1H), 7.73 (s, 1H), 7.64 (dd, J=2.4, 8.4 Hz, 1H), 7.38-7.29 (m, 5H), 7.26-7.19 (m, 1H), 4.94-4.89 (m, 1H), 4.81 (br d, J=6.2 Hz, 1H), 3.44 (tt, J=3.9, 11.6 Hz, 1H), 3.01 (tt, J=3.5, 12.0 Hz, 1H), 2.26-2.17 (m, 2H), 2.10-2.01 (m, 2H), 1.68 (dq, J=2.9, 12.8 Hz, 2H), 1.48 (d, J=7.1 Hz, 3H), 1.43-1.33 (m, 2H), 1.21 (br d, J=6.2 Hz, 6H), 1.10 (s, 9H). ESI [M+H]=642.3

Example 25. Synthesis of isopropyl((1r,4r)-4-(5-(2-(N-(tert-butyl)sulfamoyl)-4-(3-(pyridin-3-ylmethyl)ureido)phenyl)thiazol-2-yl)cyclohexyl)carbamate The Following Compound was Synthesized Via Same Method by the Key Intermediate 118.

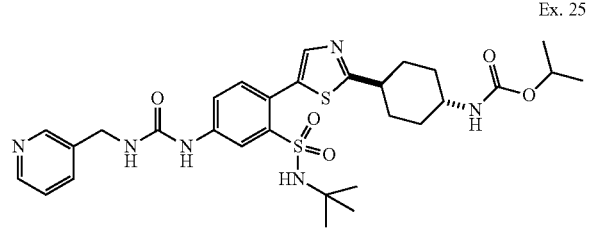 [SMILES: CC(C)OC(=O)N[C@H]1CC[C@H](c2ncc(-c3ccc(NC(=O)NCc4cccnc4)cc3S(=O)(=O)NC(C)(C)C)s2)CC1]

Ex. 25

¹H NMR (400 MHz, METHANOL-d4) δ=8.84 (s, 1H), 8.74 (d, J=5.7 Hz, 1H), 8.60 (d, J=8.2 Hz, 1H), 8.30 (d, J=2.2 Hz, 1H), 8.04 (dd, J=5.8, 7.8 Hz, 1H), 7.72 (s, 1H), 7.65 (dd, J=2.4, 8.4 Hz, 1H), 7.36 (d, J=8.4 Hz, 1H), 4.85-4.77 (m, 1H), 4.60 (s, 2H), 3.44 (tt, J=3.9, 11.5 Hz, 1H), 3.10-2.93 (m, 1H), 2.28-2.17 (m, 2H), 2.13-2.01 (m, 2H), 1.69 (dq, J=3.0, 12.8 Hz, 2H), 1.50-1.33 (m, 2H), 1.22 (br d, J=6.2 Hz, 6H), 1.09 (s, 9H). ESI [M+H]=629.3

Example 26. Synthesis of isopropyl((1S,4r)-4-(5-(2-(N-(tert-butyl)sulfamoyl)-4-(3-((S)-1-phenylethyl)ureido)phenyl)thiazol-2-yl)cyclohexyl)carbamate The Following Compound was Synthesized Via Same Method by the Key Intermediate 118.

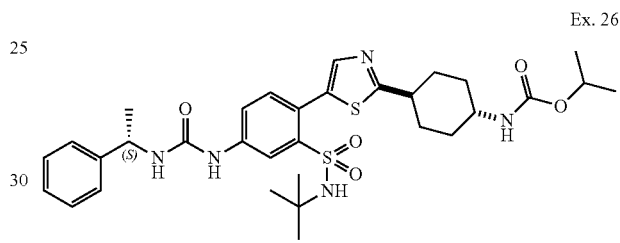

Ex. 26

¹H NMR (400 MHz, METHANOL-d4) δ=8.19 (d, J=2.4 Hz, 1H), 7.70 (s, 1H), 7.65 (dd, J=2.4, 8.4 Hz, 1H), 7.39-7.30 (m, 5H), 7.26-7.21 (m, 1H), 4.93 (q, J=6.5 Hz, 1H), 4.83-4.81 (m, 1H), 3.49-3.40 (m, 1H), 3.05-2.96 (m, 1H), 2.22 (br d, J=11.7 Hz, 2H), 2.06 (br d, J=11.5 Hz, 2H), 1.73-1.62 (m, 2H), 1.49 (d, J=6.8 Hz, 3H), 1.43-1.36 (m, 2H), 1.22 (br d, J=6.0 Hz, 6H), 1.10 (s, 9H). ESI[M+H]=642.3

Example 27. Synthesis of isopropyl((1r,4r)-4-(5-(2-(N-(tert-butyl)sulfamoyl)-4-(3-(3-fluorobenzyl)ureido)phenyl)thiazol-2-yl)cyclohexyl)carbamate The Following Compound was Synthesized Via Same Method by the Key Intermediate 118.

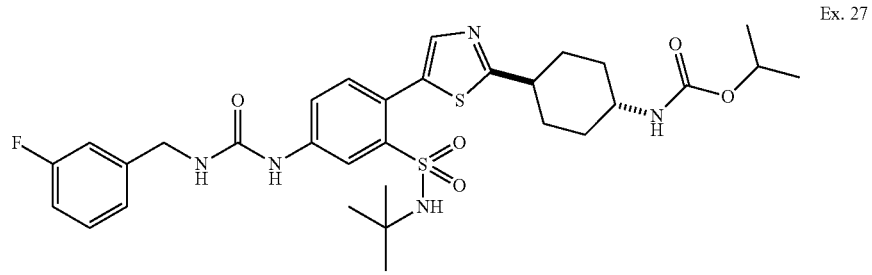 [SMILES: CC(C)OC(=O)N[C@H]1CC[C@H](c2ncc(-c3ccc(NC(=O)NCc4cccc(F)c4)cc3S(=O)(=O)NC(C)(C)C)s2)CC1]

Ex. 27

¹H NMR (400 MHz, METHANOL-d4) δ=8.27 (d, J=2.2 Hz, 1H), 7.74 (s, 1H), 7.71 (dd, J=2.3, 8.3 Hz, 1H), 7.40-7.32 (m, 2H), 7.18 (d, J=7.7 Hz, 1H), 7.10 (br d, J=9.9 Hz, 1H), 6.99 (dt, J=2.2, 8.5 Hz, 1H), 4.87 (br s, 1H), 4.44 (s, 2H), 3.47 (tt, J=3.8, 11.6 Hz, 1H), 3.02 (tt, J=3.5, 12.0 Hz, 1H), 2.24 (br d, J=12.2 Hz, 2H), 2.14-2.04 (m, 2H), 1.71 (dq, J=3.0, 12.9 Hz, 2H), 1.50-1.36 (m, 2H), 1.24 (br d, J=6.1 Hz, 6H), 1.14 (s, 9H). ESI [M+H]=646.2

Example 28. Synthesis of isopropyl((1r,4r)-4-(5-(2-(N-(tert-butyl)sulfamoyl)-4-(3-(2-fluorobenzyl)ureido)phenyl)thiazol-2-yl)cyclohexyl)carbamate The Following Compound was Synthesized Via Same Method by the Key Intermediate 118.

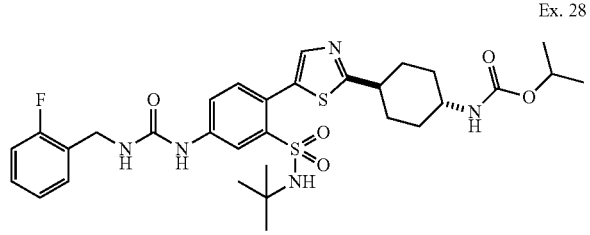 [SMILES: CC(C)OC(=O)N[C@H]1CC[C@H](c2ncc(-c3ccc(NC(=O)NCc4ccccc4F)cc3S(=O)(=O)NC(C)(C)C)s2)CC1]

Ex. 28

¹H NMR (400 MHz, METHANOL-d4) δ=8.23 (d, J=2.2 Hz, 1H), 7.71 (s, 1H), 7.68 (dd, J=2.4, 8.4 Hz, 1H), 7.41 (dt, J=1.5, 7.6 Hz, 1H), 7.35 (d, J=8.4 Hz, 1H), 7.29 (ddt, J=1.8, 5.5, 7.7 Hz, 1H), 7.15 (dt, J=1.0, 7.6 Hz, 1H), 7.11-7.05 (m, 1H), 4.81 (br s, 1H), 4.46 (s, 2H), 3.45 (tt, J=3.7, 11.6 Hz, 1H), 3.00 (tt, J=3.5, 12.0 Hz, 1H), 2.27-2.18 (m, 2H), 2.06 (br d, J=10.1 Hz, 2H), 1.69 (dq, J=3.1, 12.9 Hz, 2H), 1.46-1.34 (m, 2H), 1.22 (br d, J=6.2 Hz, 6H), 1.11 (s, 9H). ESI [M+H]=646.2

Example 29. Synthesis of isopropyl((1r,4r)-4-(5-(2-(N-(tert-butyl)sulfamoyl)-4-(3-(pyridin-2-ylmethyl)ureido)phenyl)thiazol-2-yl)cyclohexyl)carbamate The Following Compound was Synthesized Via Same Method by the Key Intermediate 118.

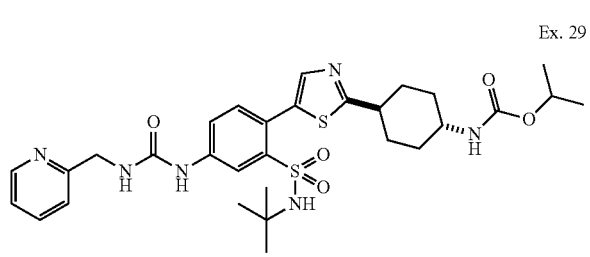 [SMILES: CC(C)OC(=O)N[C@H]1CC[C@H](c2ncc(-c3ccc(NC(=O)NCc4ccccn4)cc3S(=O)(=O)NC(C)(C)C)s2)CC1]

Ex. 29

¹H NMR (400 MHz, METHANOL-d4) δ=8.79-8.73 (m, 1H), 8.56 (dt, J=1.5, 7.9 Hz, 1H), 8.35 (d, J=2.2 Hz, 1H), 8.06 (d, J=8.1 Hz, 1H), 7.94 (t, J=6.4 Hz, 1H), 7.77 (s, 1H), 7.69 (dd, J=2.3, 8.4 Hz, 1H), 7.39 (d, J=8.3 Hz, 1H), 4.86-4.83 (m, 1H), 4.79 (s, 2H), 3.47 (tt, J=3.9, 11.6 Hz, 1H), 3.05 (tt, J=3.5, 12.0 Hz, 1H), 2.29-2.21 (m, 2H), 2.09 (br d, J=10.1 Hz, 2H), 1.71 (dq, J=2.9, 12.8 Hz, 2H), 1.43 (dq, J=3.3, 12.6 Hz, 2H), 1.24 (br d, J=6.2 Hz, 6H), 1.11 (s, 9H). ESI [M+H]=629.3

Example 30. Synthesis of isopropyl((1R,4r)-4-(5-(2-(N-(tert-butyl)sulfamoyl)-4-(3-((R)-1-(pyridin-2-yl)ethyl)ureido)phenyl)thiazol-2-yl)cyclohexyl)carbamate The Following Compound was Synthesized Via Same Method by the Key Intermediate 118.

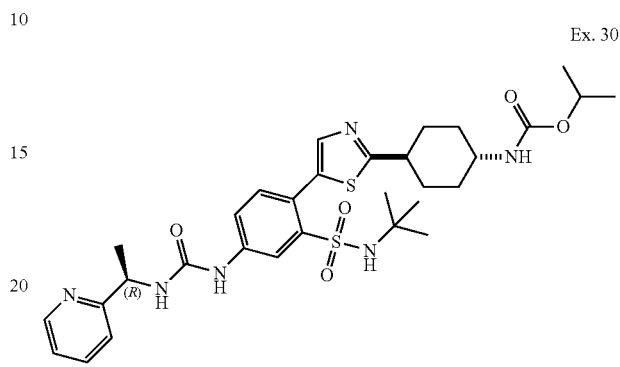

Ex. 30

¹H NMR (400 MHz, METHANOL-d4) δ=8.73 (d, J=5.7 Hz, 1H), 8.53 (dt, J=1.8, 7.9 Hz, 1H), 8.28 (d, J=2.2 Hz, 1H), 8.08 (d, J=8.3 Hz, 1H), 7.94-7.85 (m, 1H), 7.80-7.68 (m, 1H), 7.61 (dd, J=2.2, 8.3 Hz, 1H), 7.35 (d, J=8.3 Hz, 1H), 5.13 (q, J=7.0 Hz, 1H), 4.85-4.78 (m, 1H), 3.49-3.39 (m, 1H), 3.08-2.96 (m, 1H), 2.22 (br d, J=12.3 Hz, 2H), 2.06 (br d, J=10.1 Hz, 2H), 1.76-1.61 (m, 5H), 1.49-1.34 (m, 2H), 1.22 (br d, J=6.1 Hz, 6H), 1.14-1.02 (m, 9H). ESI [M+H]=643.3

Example 31. Synthesis of isopropyl((1r,4r)-4-(5-(2-(N-(tert-butyl)sulfamoyl)-4-(3-((3-fluoropyridin-2-yl)methyl)ureido)phenyl)thiazol-2-yl)cyclohexyl)carbamate The Following Compound was Synthesized Via Same Method by the Key Intermediate 118.

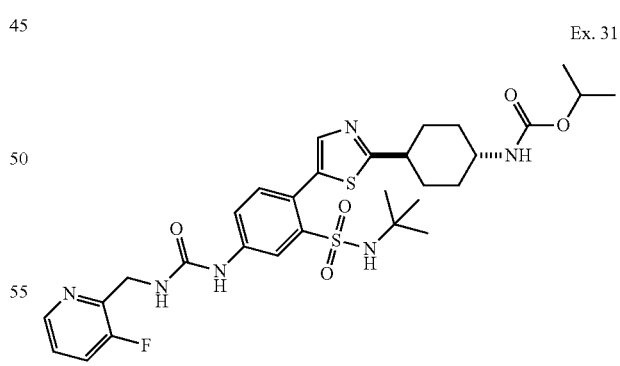

Ex. 31

¹H NMR (400 MHz, METHANOL-d4) δ=8.42 (d, J=4.8 Hz, 1H), 8.28 (d, J=2.2 Hz, 1H), 7.78-7.62 (m, 3H), 7.44 (td, J=4.4, 8.5 Hz, 1H), 7.38 (d, J=8.4 Hz, 1H), 4.86-4.81 (m, 1H), 4.65 (s, 2H), 3.47 (ddd, J=4.0, 7.7, 11.4 Hz, 1H), 3.10-3.00 (m, 1H), 2.25 (br d, J=12.1 Hz, 2H), 2.09 (br d, J=10.5 Hz, 2H), 1.72 (dq, J=3.0, 12.9 Hz, 2H), 1.43 (dq, J=3.2, 12.6 Hz, 2H), 1.24 (br d, J=6.1 Hz, 6H), 1.14 (s, 9H). ESI [M+H]=647.2

Example 32. Synthesis of isopropyl((1S,4r)-4-(5-(2-(N-(tert-butyl)sulfamoyl)-4-(3-((S)-1-(pyridin-2-yl)ethyl)ureido)phenyl)thiazol-2-yl)cyclohexyl)carbamate The Following Compound was Synthesized Via Same Method by the Key Intermediate 118.

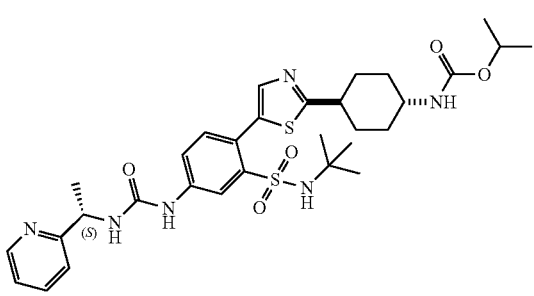

Ex. 32

¹H NMR (400 MHz, METHANOL-d4) δ=8.72 (d, J=5.3 Hz, 1H), 8.50 (dt, J=1.8, 7.9 Hz, 1H), 8.27 (d, J=2.2 Hz, 1H), 8.05 (d, J=8.3 Hz, 1H), 7.88 (t, J=6.6 Hz, 1H), 7.72 (s, 1H), 7.61 (dd, J=2.6, 8.3 Hz, 1H), 7.34 (d, J=8.8 Hz, 1H), 5.12 (q, J=7.0 Hz, 1H), 4.87-4.68 (m, 1H), 3.51-3.38 (m, 1H), 3.01 (tt, J=3.3, 12.0 Hz, 1H), 2.21 (br d, J=11.8 Hz, 2H), 2.10-1.97 (m, 2H), 1.76-1.57 (m, 5H), 1.48-1.33 (m, 2H), 1.22 (d, J=6.1 Hz, 6H), 1.13-1.00 (m, 9H). ESI [M+H]= 643.3

Example 33. Synthesis of trans-4-piperidylmethyl N-[3-(tert-butylsulfamoyl)-4-[2-[4-(isopropoxycarbonylamino)cyclohexyl]thiazol-5-yl]phenyl]carbamate Scheme 13

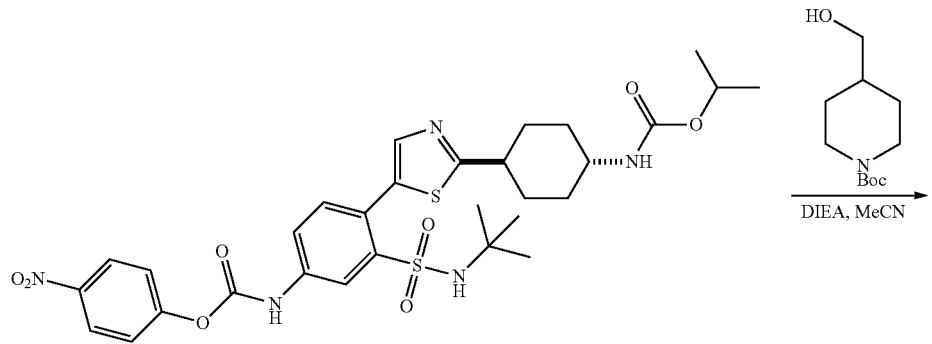

118

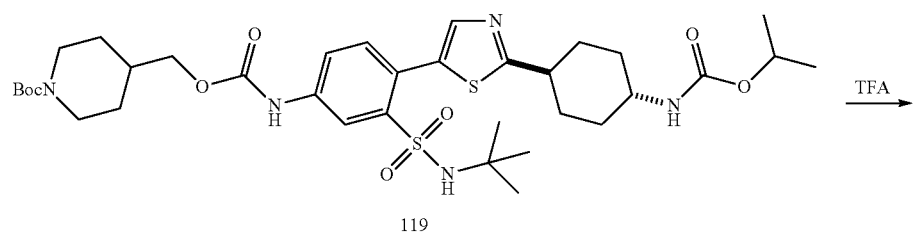

119

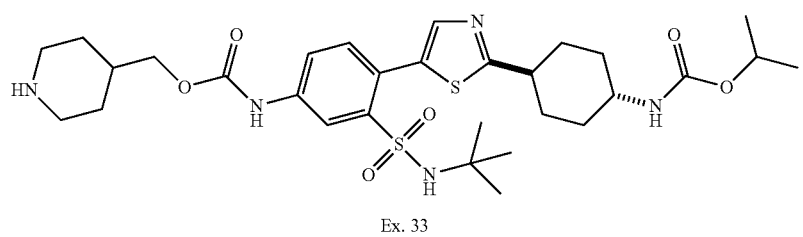

Ex. 33

Preparation of Compound 119.
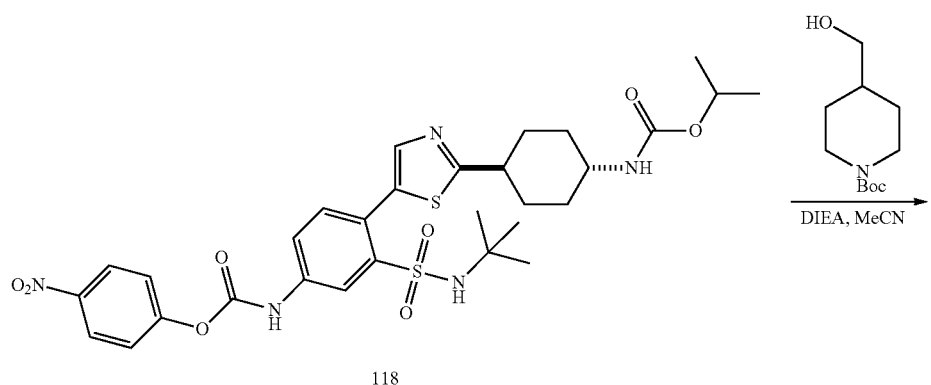
118
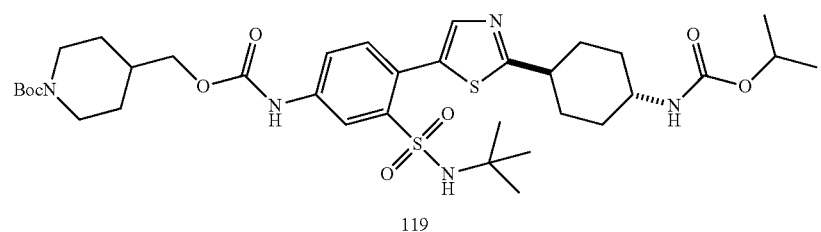
119
General method H, trans-tert-butyl 4-[[3-(tert-butylsulfamoyl)-4-[2-[4-(isopropoxycarbonylamino)cyclohexyl]thiazol-5-yl]phenyl]carbamoyloxymethyl]piperidine-1-carboxylate. ESI [M+H]=736.5
Preparation of Ex 33.
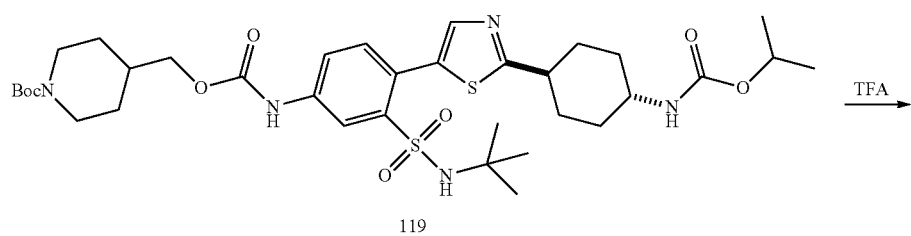
119
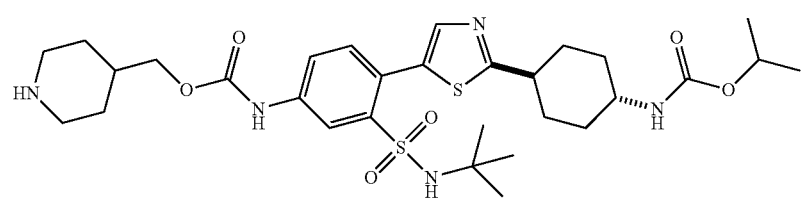
Ex. 33

General method C, trans-4-piperidylmethyl N-[3-(tert-butylsulfamoyl)-4-[2-[4-(isopropoxycarbonylamino)cyclohexyl]thiazol-5-yl]phenyl]carbamate. ¹H NMR (400 MHz, METHANOL-d4) δ=8.37 (d, J=2.2 Hz, 1H), 7.78 (s, 1H), 7.68 (br d, J=7.9 Hz, 1H), 7.40 (d, J=8.4 Hz, 1H), 4.86-4.78 (m, 1H), 4.11 (d, J=6.2 Hz, 2H), 3.50-3.39 (m, 3H), 3.11-2.96 (m, 3H), 2.23 (br d, J=12.3 Hz, 2H), 2.13-1.98 (m, 5H), 1.70 (dq, J=2.8, 12.8 Hz, 2H), 1.60-1.34 (m, 4H), 1.22 (br d, J=6.2 Hz, 6H), 1.11 (s, 9H). ESI [M/2+H]=318.6

Example 34. Synthesis of isopropyl((1R,4r)-4-(5-(2-(N-(tert-butyl)sulfamoyl)-4-(((((R)-1-methylpyrrolidin-2-yl)methoxy)carbonyl)amino)phenyl)thiazol-2-yl)cyclohexyl)carbamate The Following Compound was Synthesized Via Same Method by the Key Intermediate 118.

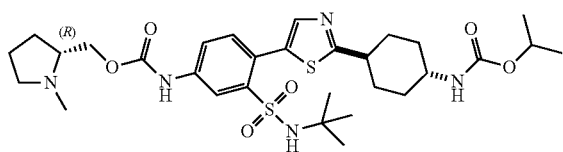

Ex. 34

¹H NMR (400 MHz, METHANOL-d4) δ=8.41 (d, J=2.2 Hz, 1H), 7.80-7.73 (m, 2H), 7.45 (d, J=8.4 Hz, 1H), 4.86-4.81 (m, 1H), 4.67 (dd, J=3.2, 12.8 Hz, 1H), 4.35 (dd, J=7.1, 12.8 Hz, 1H), 3.85-3.71 (m, 2H), 3.47 (tt, J=3.9, 11.6 Hz, 1H), 3.26 (td, J=8.1, 11.5 Hz, 1H), 3.10 (s, 3H), 3.08-2.98 (m, 1H), 2.46-2.35 (m, 1H), 2.30-2.18 (m, 3H), 2.15-1.95 (m, 4H), 1.72 (dq, J=3.1, 12.9 Hz, 2H), 1.43 (dq, J=3.3, 12.6 Hz, 2H), 1.25 (br d, J=6.2 Hz, 6H), 1.13 (s, 9H). ESI [M+H]=636.3

Example 35. Synthesis of isopropyl((1S,4r)-4-(5-(2-(N-(tert-butyl)sulfamoyl)-4-(((((S)-1-methylpyrrolidin-2-yl)methoxy)carbonyl)amino)phenyl)thiazol-2-yl)cyclohexyl)carbamate The Following Compound was Synthesized Via Same Method by the Key Intermediate 118.

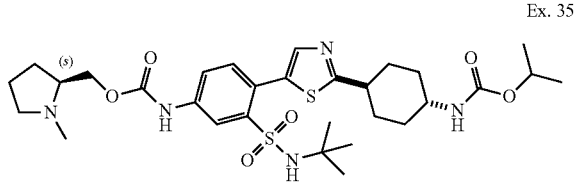

Ex. 35

¹H NMR (400 MHz, METHANOL-d4) δ=8.41 (d, J=2.0 Hz, 1H), 7.80-7.71 (m, 2H), 7.44 (d, J=8.3 Hz, 1H), 4.86-4.79 (m, 1H), 4.67 (dd, J=3.2, 13.0 Hz, 1H), 4.40-4.31 (m, 1H), 3.87-3.66 (m, 2H), 3.47 (tt, J=3.8, 11.6 Hz, 1H), 3.26 (td, J=8.3, 11.4 Hz, 1H), 3.10 (s, 3H), 3.04 (tt, J=3.4, 12.0 Hz, 1H), 2.48-2.33 (m, 1H), 2.30-2.16 (m, 3H), 2.15-1.92 (m, 4H), 1.72 (dq, J=2.7, 12.8 Hz, 2H), 1.51-1.36 (m, 2H), 1.25 (br d, J=6.4 Hz, 6H), 1.13 (s, 9H). ESI [M/2+H]=318.6

Example 36. Synthesis of isopropyl((1R,4r)-4-(5-(2-(N-(tert-butyl)sulfamoyl)-4-(((((R)-pyrrolidin-2-yl)methoxy)carbonyl)amino)phenyl)thiazol-2-yl)cylohexyl)carbamate The Following Compound was Synthesized Via Same Method by the Key Intermediate 118.

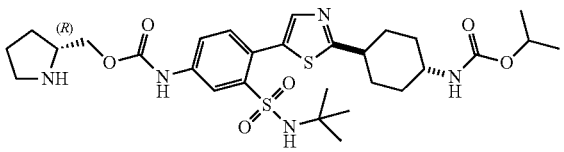

Ex. 36

¹H NMR (400 MHz, METHANOL-d4) δ=8.38 (br d, J=2.2 Hz, 1H), 7.75-7.66 (m, 2H), 7.41 (d, J=8.4 Hz, 1H), 4.81 (br s, 1H), 4.48 (br dd, J=3.4, 12.5 Hz, 1H), 4.33 (dd, J=7.8, 12.5 Hz, 1H), 3.93 (dq, J=3.6, 8.0 Hz, 1H), 3.49-3.33 (m, 3H), 3.00 (ddd, J=3.5, 8.5, 12.0 Hz, 1H), 2.30-2.18 (m, 3H), 2.10-2.00 (m, 3H), 1.85 (qd, J=8.5, 12.9 Hz, 2H), 1.74-1.61 (m, 2H), 1.46-1.34 (m, 2H), 1.22 (br d, J=6.2 Hz, 6H), 1.09 (s, 9H). ESI [M/2+H]=311.6

Example 37. Synthesis of isopropyl((1S,4r)-4-(5-(2-(N-(tert-butyl)sulfamoyl)-4-(((((S)-pyrrolidin-2-yl)methoxy)carbonyl)amino)phenyl)thiazol-2-yl)cyclohexyl)carbamate The Following Compound was Synthesized Via Same Method by the Key Intermediate 118.

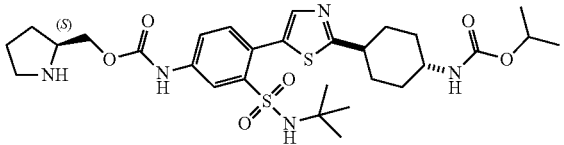

Ex. 37

¹H NMR (400 MHz, METHANOL-d4) δ=8.38 (d, J=1.8 Hz, 1H), 7.79-7.68 (m, 2H), 7.41 (d, J=8.2 Hz, 1H), 4.85-4.78 (m, 1H), 4.49 (dd, J=3.4, 12.5 Hz, 1H), 4.33 (dd, J=7.9, 12.3 Hz, 1H), 3.94 (dq, J=3.4, 8.0 Hz, 1H), 3.49-3.40 (m, 1H), 3.40-3.33 (m, 2H), 3.08-2.97 (m, 1H), 2.31-2.19 (m, 3H), 2.17-2.00 (m, 4H), 1.85 (qd, J=8.5, 13.0 Hz, 1H), 1.75-1.62 (m, 2H), 1.46-1.35 (m, 2H), 1.22 (br d, J=6.2 Hz, 6H), 1.10 (s, 9H). ESI [M/2+H]=311.6

Example 38. Synthesis of isopropyl((1r,4r)-4-(5-(2-(N-(tert-butyl)sulfamoyl)-4-(((oxetan-3-yloxy)carbonyl)amino)phenyl)thiazol-2-yl)cyclohexyl)carbamate The Following Compound was Synthesized Via Same Method by the Key Intermediate 118.

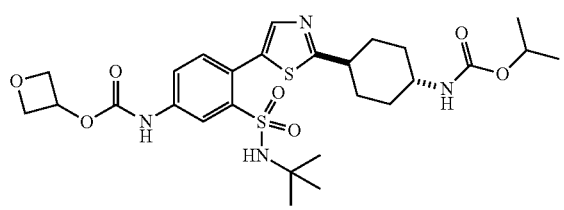

Ex. 38

¹H NMR (METHANOL-d4, 400 MHz): δ=8.33 (s, 1H), 7.63-7.72 (m, 2H), 7.38 (d, J=8.4 Hz, 1H), 5.50 (br t, J=5.5 Hz, 1H), 4.92 (t, J=6.9 Hz, 2H), 4.81-4.83 (m, 1H), 4.64-4.73 (m, 2H), 3.44 (br t, J=11.7 Hz, 1H), 2.99 (br t, J=11.8 Hz, 1H), 2.21 (br d, J=12.3 Hz, 2H), 2.06 (br d, J=11.7 Hz, 2H), 1.59-1.75 (m, 2H), 1.30-1.47 (m, 2H), 1.21 (br d, J=6.0 Hz, 6H), 1.10 ppm (s, 9H). ESI [M+H]=595.1

Example 39. Synthesis of benzyl(3-(N-(tert-butyl)sulfamoyl)-4-(2-((1r,4r)-4-((isopropoxycarbonyl)amino)cyclohexyl)thiazol-5-yl)phenyl)carbamate The Following Compound was Synthesized Via Same Method by the Key Intermediate 118.

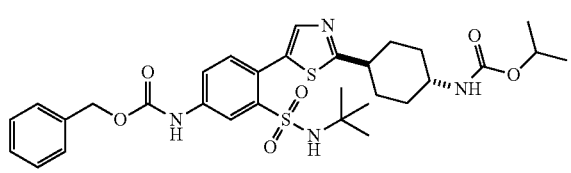

Ex. 39

¹H NMR (400 MHz, METHANOL-d4) δ=8.36 (s, 1H), 7.75-7.67 (m, 2H), 7.46-7.28 (m, 6H), 5.28-5.14 (m, 2H), 4.85-4.76 (m, 1H), 3.47 (br d, J=11.8 Hz, 1H), 3.01 (br s, 1H), 2.23 (br d, J=12.7 Hz, 2H), 2.07 (br d, J=14.5 Hz, 2H), 1.70 (br d, J=11.0 Hz, 2H), 1.40 (br d, J=12.7 Hz, 2H), 1.22 (br d, J=6.1 Hz, 6H), 1.12 (s, 9H). ESI [M+H]=629.2

Example 40. Synthesis of 2-fluorobenzyl(3-(N-(tert-butyl)sulfamoyl)-4-(2-((1r,4r)-4-((isopropoxycarbonyl)amino)cyclohexyl)thiazol-5-yl)phenyl)carbamate The Following Compound was Synthesized Via Same Method by the Key Intermediate 118.

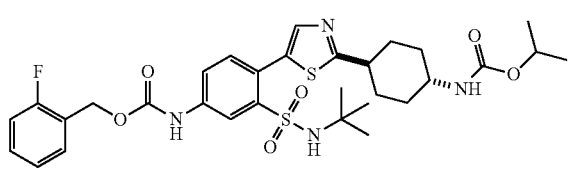

Ex. 40

1H NMR (400 MHz, METHANOL-d4) δ=8.36 (s, 1H), 7.77-7.63 (m, 2H), 7.52 (t, J=7.0 Hz, 1H), 7.44-7.31 (m, 2H), 7.23-7.08 (m, 2H), 5.29 (s, 2H), 4.83 (br s, 1H), 3.46 (br d, J=11.8 Hz, 1H), 3.00 (br t, J=11.8 Hz, 1H), 2.22 (br d, J=12.7 Hz, 2H), 2.07 (br d, J=11.4 Hz, 2H), 1.76-1.62 (m, 2H), 1.47-1.35 (m, 2H), 1.22 (br d, J=6.1 Hz, 6H), 1.12 (s, 9H). ESI [M+H]=647.2

Example 41. Synthesis of (S)-1-phenylethyl(3-(N-(tert-butyl)sulfamoyl)-4-(2-((1r,4S)-4-((isopropoxycarbonyl)amino)cyclohexyl)thiazol-5-yl)phenyl)carbamate The Following Compound was Synthesized Via Same Method by the Key Intermediate 118.

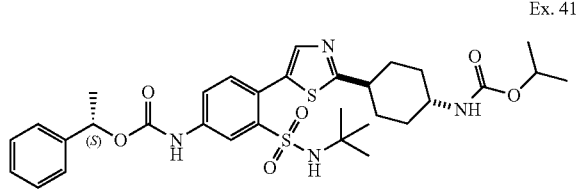

Ex. 41

¹H NMR (400 MHz, METHANOL-d4) δ=8.35 (br s, 1H), 7.81-7.65 (m, 2H), 7.48-7.36 (m, 5H), 7.31 (br d, J=6.8 Hz, 1H), 5.89 (br d, J=6.2 Hz, 1H), 4.85 (br d, J=5.5 Hz, 1H), 3.47 (br s, 1H), 3.03 (br s, 1H), 2.24 (br d, J=11.2 Hz, 2H), 2.08 (br d, J=11.0 Hz, 2H), 1.71 (q, J=11.9 Hz, 2H), 1.61 (br d, J=6.4 Hz, 3H), 1.49-1.37 (m, 2H), 1.24 (br d, J=5.4 Hz, 6H), 1.13 (s, 9H). ESI [M+H]=643.2

Example 42. Synthesis of pyridin-2-ylmethyl(3-(N-(tert-butyl)sulfamoyl)-4-(2-((1r,4r)-4-((isopropoxycarbonyl)amino)cyclohexyl)thiazol-5-yl)phenyl) carbamate The Following Compound was Synthesized Via Same Method by the Key Intermediate 118.

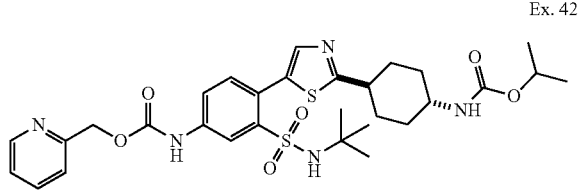 [SMILES: CC(C)OC(=O)N[C@H]1CC[C@H](c2ncc(-c3ccc(NC(=O)OCc4ccccn4)cc3S(=O)(=O)NC(C)(C)C)s2)CC1]

Ex. 42

¹H NMR (400 MHz, METHANOL-d4) δ=8.56 (br d, J=4.5 Hz, 1H), 8.38 (d, J=1.8 Hz, 1H), 7.94-7.87 (m, 1H), 7.78-7.72 (m, 2H), 7.59 (br d, J=7.8 Hz, 1H), 7.44-7.38 (m, 2H), 5.32 (s, 2H), 4.85 (td, J=5.9, 12.0 Hz, 1H), 3.47 (br t, J=11.8 Hz, 1H), 3.07-2.96 (m, 1H), 2.24 (br d, J=12.3 Hz, 2H), 2.13-2.04 (m, 2H), 1.77-1.65 (m, 2H), 1.48-1.37 (m, 2H), 1.24 (br d, J=6.1 Hz, 6H), 1.14 (s, 9H). ESI [M+H]=630.2

Example 43. Synthesis of (R)-1-phenylethyl(3-(N-(tert-butyl)sulfamoyl)-4-(2-((1r,4R)-4-((isopropoxycarbonyl)amino)cyclohexyl)thiazol-5-yl)phenyl) carbamate The Following Compound was Synthesized Via Same Method by the Key Intermediate 118.

Ex. 43

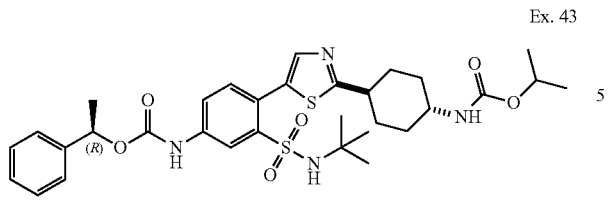

¹H NMR (400 MHz, DMSO-d6) δ=8.28 (d, J=2.2 Hz, 1H), 7.70-7.57 (m, 2H), 7.47-7.24 (m, 7H), 7.05-6.84 (m, 2H), 5.82 (q, J=6.6 Hz, 1H), 4.79-4.65 (m, 1H), 3.35-3.24 (m, 1H), 2.88 (tt, J=3.4, 11.9 Hz, 1H), 2.11 (br d, J=11.7 Hz, 2H), 1.89 (br d, J=9.9 Hz, 2H), 1.54 (d, J=6.6 Hz, 5H), 1.30 (br s, 2H), 1.14 (d, J=6.2 Hz, 6H), 1.08-0.99 (m, 9H). ESI [M+H]=643.3

Example 44. Synthesis of trans-isopropyl N-[4-[2-[4-(tert-butoxycarbonylamino)cyclohexyl]thiazol-5-yl]-3-(tert-butylsulfamoyl)phenyl]carbamate Ex. 45

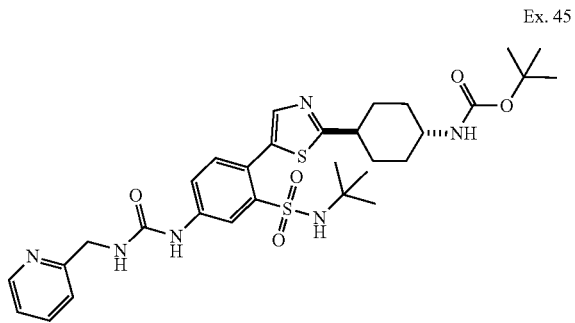 [SMILES: CC(C)(C)NS(=O)(=O)c1cc(NC(=O)NCc2ccccn2)ccc1-c1cnc([C@H]2CC[C@H](NC(=O)OC(C)(C)C)CC2)s1]

¹H NMR (400 MHz, METHANOL-d4) δ=8.17 (d, J=2.2 Hz, 1H), 7.75-7.59 (m, 2H), 7.43-7.22 (m, 3H), 7.21-7.03 (m, 2H), 4.53 (m, 2H), 3.43 (br t, J=11.8 Hz, 1H), 2.99 (br t, J=12.1 Hz, 1H), 2.22 (br d, J=12.7 Hz, 2H), 2.06 (br d, J=10.5 Hz, 2H), 1.77-1.60 (m, 2H), 1.58-1.34 (m, 11H), 1.09 (s, 9H). ESI [M+H]=643.3

Scheme 14

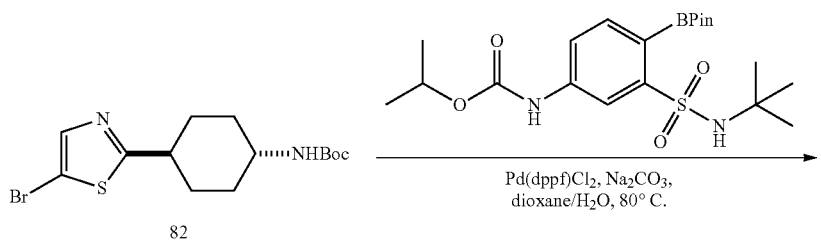

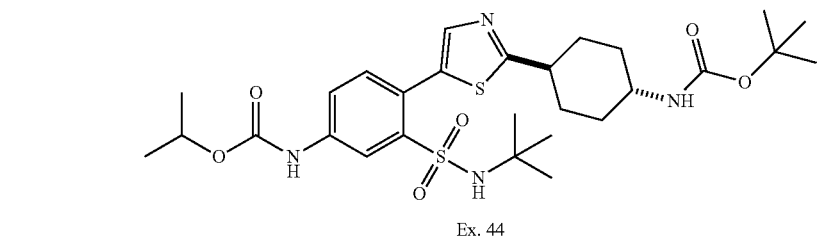

Ex. 44

General method B, trans-isopropyl N-[4-[2-[4-(tert-butoxycarbonylamino)cyclohexyl]thiazol-5-yl]-3-(tert-butylsulfamoyl)phenyl]carbamate. ¹H NMR (400 MHz, DMSO-d6) δ=10.06 (s, 1H), 8.32 (d, J=2.1 Hz, 1H), 7.70-7.60 (m, 2H), 7.38 (d, J=8.4 Hz, 1H), 6.96 (s, 1H), 6.81 (br d, J=7.9 Hz, 1H), 4.99-4.87 (m, 1H), 3.27 (br s, 1H), 2.94-2.84 (m, 1H), 2.13 (br d, J=11.7 Hz, 2H), 1.90 (br d, J=11.1 Hz, 2H), 1.63-1.49 (m, 2H), 1.39 (s, 9H), 1.33 (br d, J=14.4 Hz, 2H), 1.28 (d, J=6.4 Hz, 6H), 1.07 (s, 9H). ESI [M+H]=595.1

Example 45. Synthesis of tert-butyl((1r,4r)-4-(5-(2-(N-(tert-butyl)sulfamoyl)-4-(3-(pyridin-2-ylmethyl)ureido)phenyl)thiazol-2-yl)cyclohexyl)carbamate The Following Compound was Synthesized Via Same Method by the Key Intermediate 82.

Example 46. Synthesis of isopropyl N-[3-(tert-butylsulfamoyl)-4-[2-[3-(isopropoxycarbonyl amino) azetidin-1-yl]thiazol-5-yl]phenyl]carbamate Scheme 15

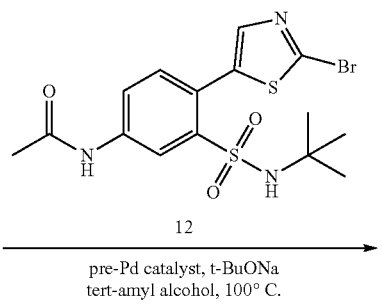

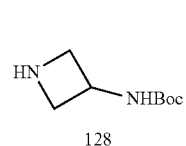

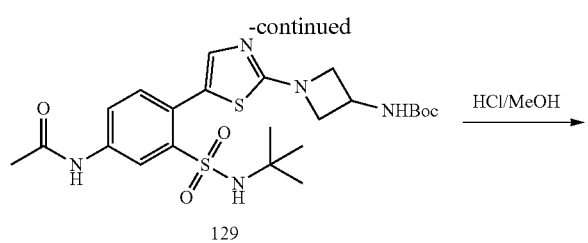

Preparation of Compound 129.

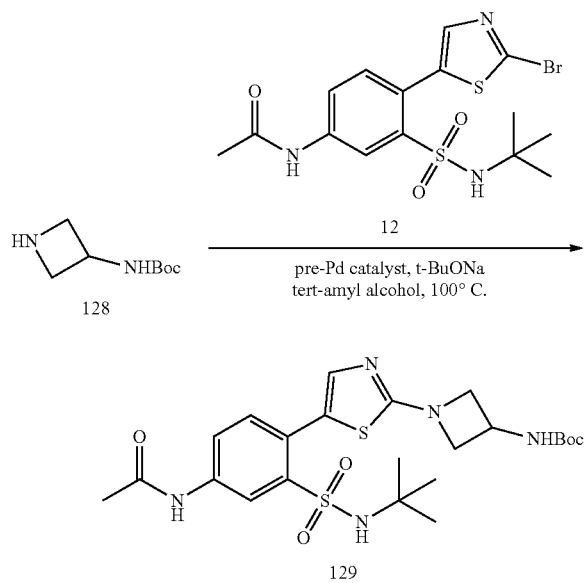

A mixture of tert-butyl N-(azetidin-3-yl)carbamate; hydrochloride (72.40 mg, 346.94 umol, 1.50 eq.), N-[4-(2-bromothiazol-5-yl)-3-(tert-butylsulfamoyl)phenyl]acetamide (100 mg, 231.29 umol, 1 eq.), t-BuONa (66.68 mg, 693.87 umol, 3 eq.), [2-(2-aminoethyl)phenyl]-chloro-palladium; ditert-butyl-[2-(2,4,6-triisopropylphenyl)phenyl]phosphane (15.88 mg, 23.13 umol, 0.1 eq.) in tert-amyl alcohol (2 mL) was degassed and purged with $N_2$ for 3 times, and then the mixture was stirred at 100° C. for 12 hrs under $N_2$ atmosphere and then concentrated. The residue was diluted with Ethyl acetate (20 mL) and washed with $H_2O$ (20 mL). The organic layer was dried and concentrated and the residue was purified by prep-TLC (EtOAc) to give tert-butyl N-[1-[5-[4-acetamido-2-(tert-butylsulfamoyl)phenyl]thiazol-2-yl]azetidin-3-yl]carbamate (46 mg, crude) as a yellow solid. ESI [M+H]=524.3 Preparation of compound 130.

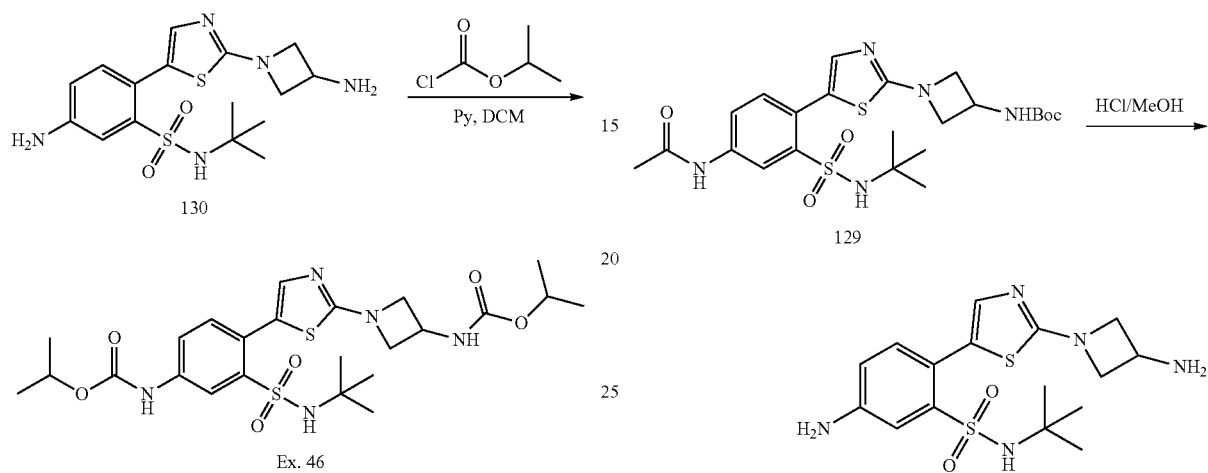

General method F, 5-amino-2-[2-(3-aminoazetidin-1-yl)thiazol-5-yl]-N-tert-butyl-benzenesulfonamide. ESI[M+H]=382.0

Preparation of Example 46

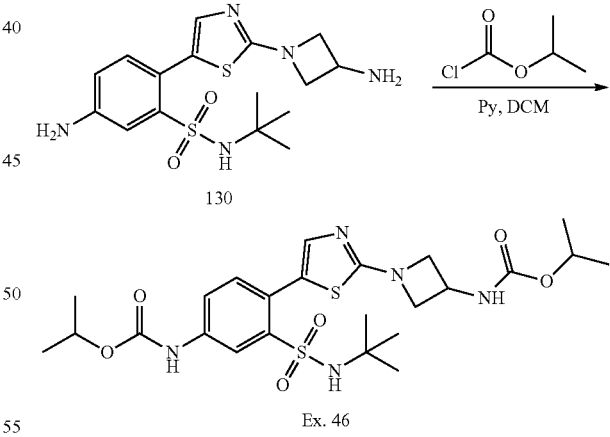

General method D, isopropyl N-[3-(tert-butylsulfamoyl)-4-[2-[3-(isopropoxycarbonyl amino)azetidin-1-yl]thiazol-5-yl]phenyl]carbamate. $^1$H NMR (400 MHz, METHANOL-d4) δ=8.35 (d, J=2.0 Hz, 1H), 7.67 (dd, J=2.2, 8.4 Hz, 1H), 7.45-7.32 (m, 2H), 5.04-4.94 (m, 1H), 4.92-4.88 (m, 1H), 4.73-4.63 (m, 1H), 4.56 (br t, J=8.5 Hz, 2H), 4.27 (br s, 2H), 1.31 (d, b=6.2 Hz, 6H), 1.27-1.19 (m, 15H). ESI [M+H]=554.2

Example 47. Synthesis of trans-oxetan-3-yl N-[4-[5-[4-(benzylcarbamoylamino)-2-(tert-butylsulfamoyl)phenyl]thiazol-2-yl]cyclohexyl]carbamate Scheme 16

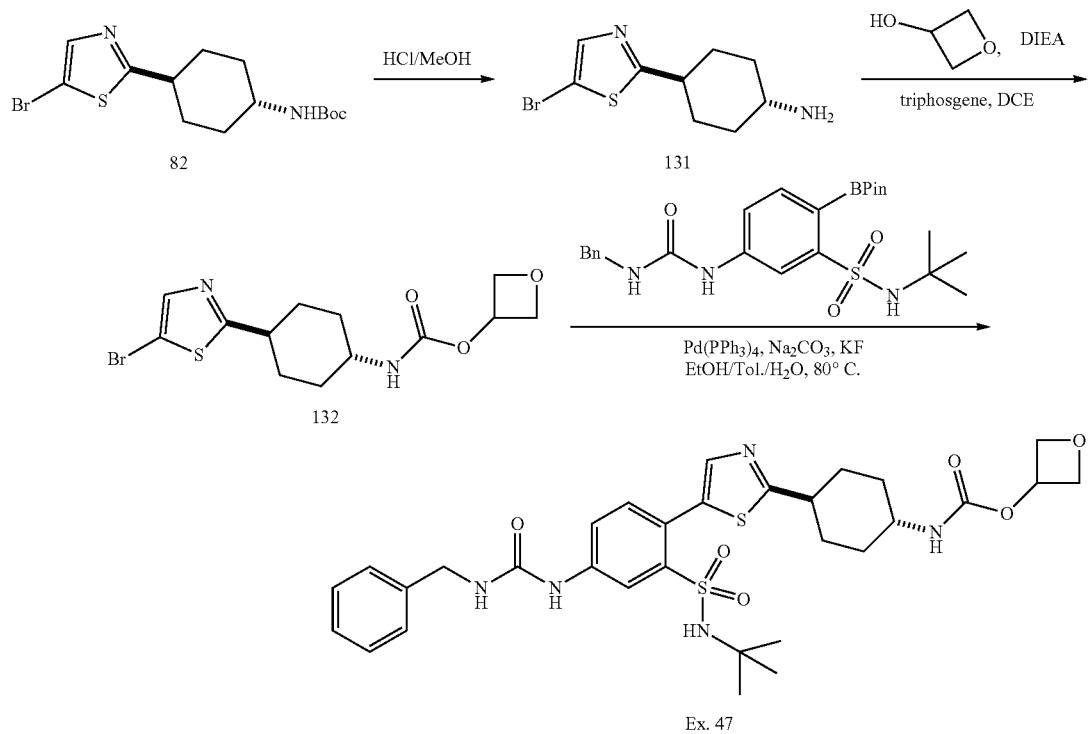

Preparation of Compound 131.

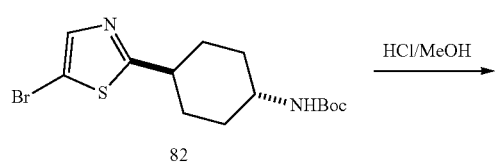

Preparation of Compound 132.

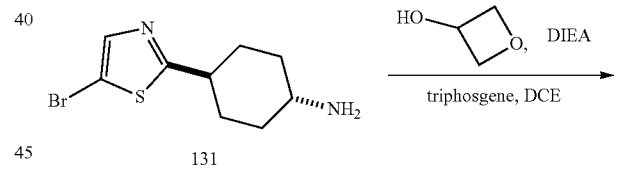

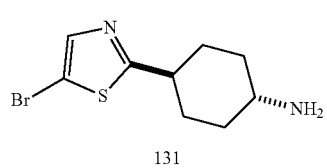

General method F, trans-4-(5-bromothiazol-2-yl)cyclohexanamine. ESI [M+H]=260.9/262.9

To a solution of oxetan-3-ol (1.15 g, 15.51 mmol, 3 eq.) in DCE (10 mL) were added DIEA (3.34 g, 25.84 mmol, 4.50 mL, 5 eq.) and TRIPHOSGENE (1.53 g, 5.17 mmol, 1 eq.). The mixture was stirred at 25-50° C. for 1 hr and then added a solution of trans-4-(5-bromothiazol-2-yl)cyclohexanamine (1.35 g, 5.17 mmol, 1 eq.), DIEA (3.34 g, 25.84 mmol, 4.50 mL, 5 eq.) in DCE (10 mL). The mixture was stirred at 25° C. for 0.5 hr. The mixture was concentrated and the residue was purified by column chromatography (SiO$_2$, Petroleum ether/Ethyl acetate=30/1 to 5:1) to give trans-oxetan-3-yl N-[4-(5-bromothiazol-2-yl)cyclohexyl]carbamate (1.5 g, crude) as a white solid. ESI [M+H]=363.1/361.1

Preparation of Ex 47

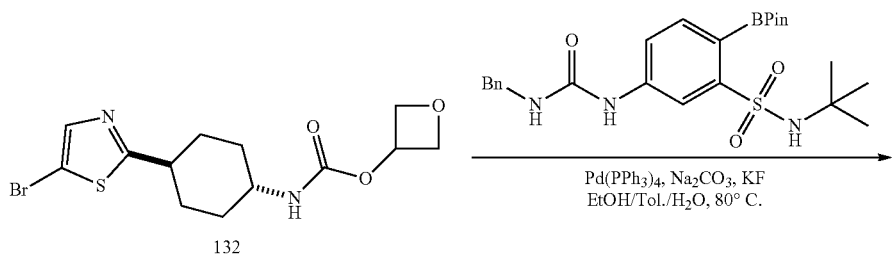

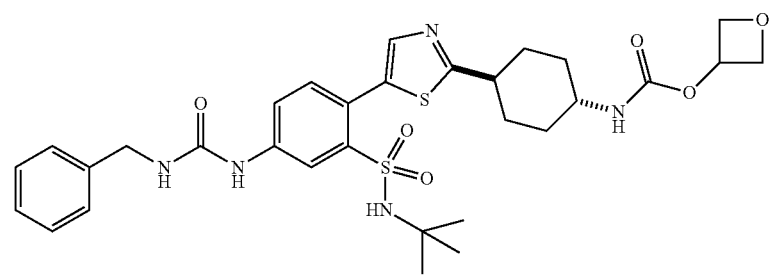

Ex. 47

General method K, trans-oxetan-3-yl N-[4-[5-[4-(benzyl-carbamoylamino)-2-(tert-butylsulfamoyl)phenyl]thiazol-2-yl]cyclohexyl]carbamate. ¹H NMR (400 MHz, METHANOL-d4) δ=8.23 (d, J=2.2 Hz, 1H), 7.71-7.66 (m, 2H), 7.37-7.29 (m, 5H), 7.24 (br s, 1H), 5.40-5.27 (m, 2H), 4.66-4.55 (m, 3H), 4.40 (s, 2H), 3.45 (br d, J=11.0 Hz, 1H), 3.00 (br t, J=11.8 Hz, 1H), 2.22 (br d, J=13.0 Hz, 2H), 2.07 (br d, J=11.2 Hz, 2H), 1.74-1.63 (m, 2H), 1.47-1.37 (m, 2H), 1.10 (s, 9H). ESI [M+H]=642.3

Example 48. Synthesis of oxetan-3-yl((1r,4r)-4-(5-(2-(N-(tert-butyl)sulfamoyl)-4-((isopropoxycarbonyl)amino)phenyl)thiazol-2-yl)cyclohexyl)carbamate The Following Compound was Synthesized Via Same Method by the Key Intermediate 132.

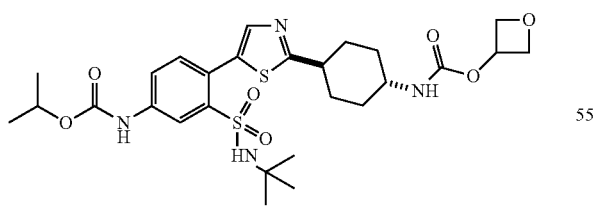

Ex. 48

¹H NMR (400 MHz, METHANOL-d4) δ=8.33 (d, J=2.0 Hz, 1H), 7.71-7.64 (m, 2H), 7.36 (d, J=8.4 Hz, 1H), 5.41-5.27 (m, 2H), 4.98 (td, J=6.4, 12.6 Hz, 1H), 4.87 (br s, 1H), 4.63-4.56 (m, 2H), 3.45 (br d, J=12.3 Hz, 1H), 3.00 (br t, J=12.0 Hz, 1H), 2.22 (br d, J=13.0 Hz, 2H), 2.11-2.02 (m, 2H), 1.74-1.63 (m, 2H), 1.42 (q, J=12.7 Hz, 2H), 1.31 (d, J=6.2 Hz, 6H), 1.11 (s, 9H). ESI [M+H]=595.3

Example 49. Synthesis of trans-oxetan-3-yl N-[3-(tert-butylsulfamoyl)-4-[2-[4-(oxetan-3-yloxycarbonylamino)cyclohexyl]thiazol-5-yl]phenyl]carbamate
Scheme 17
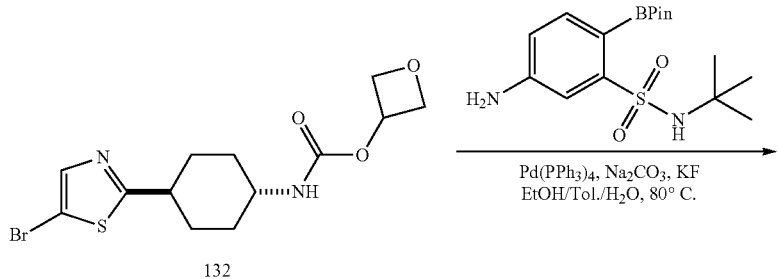
132
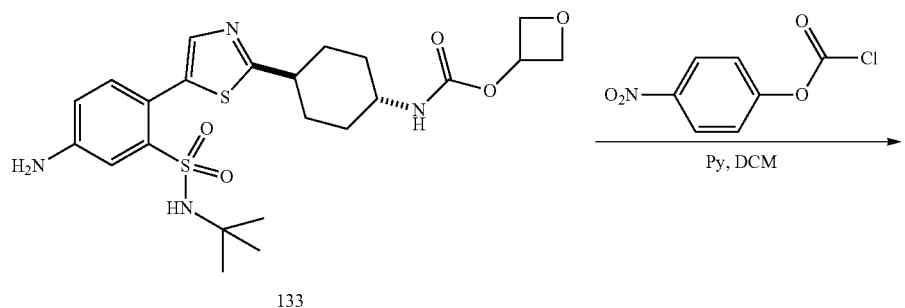
133
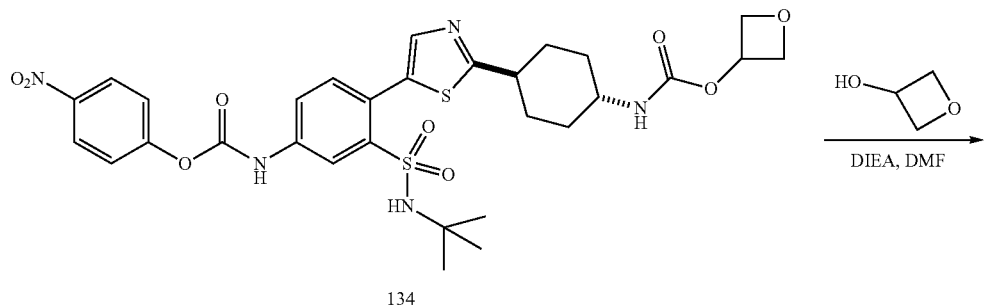
134
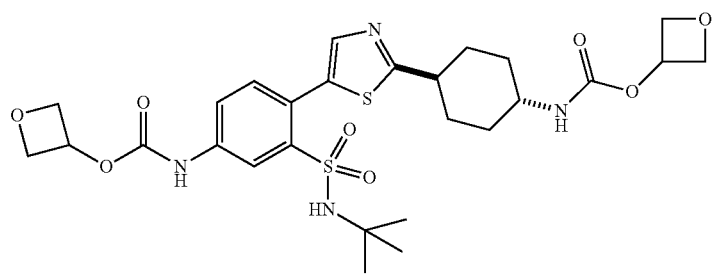
Ex. 49

Preparation of Compound 133.
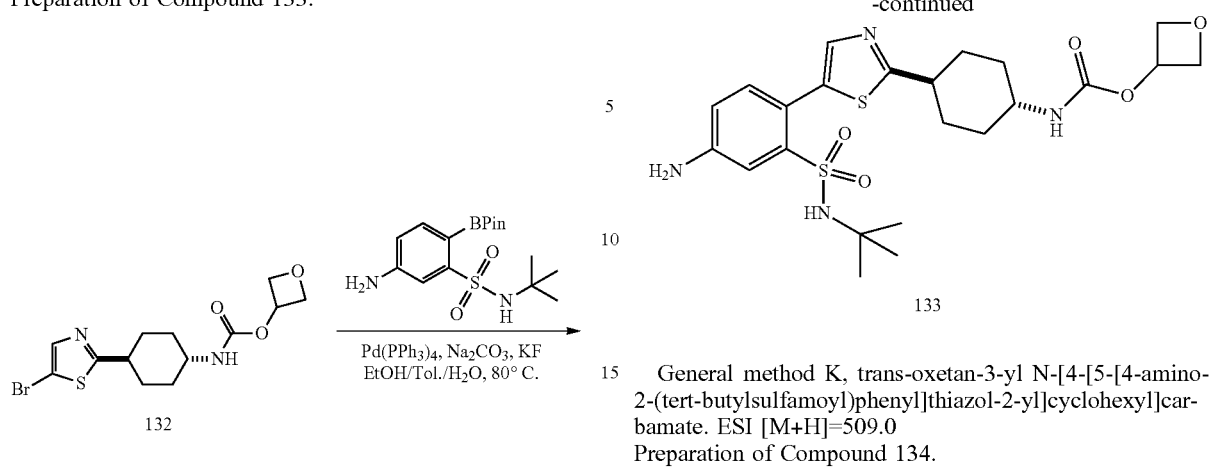
General method K, trans-oxetan-3-yl N-[4-[5-[4-amino-2-(tert-butylsulfamoyl)phenyl]thiazol-2-yl]cyclohexyl]carbamate. ESI [M+H]=509.0
Preparation of Compound 134.
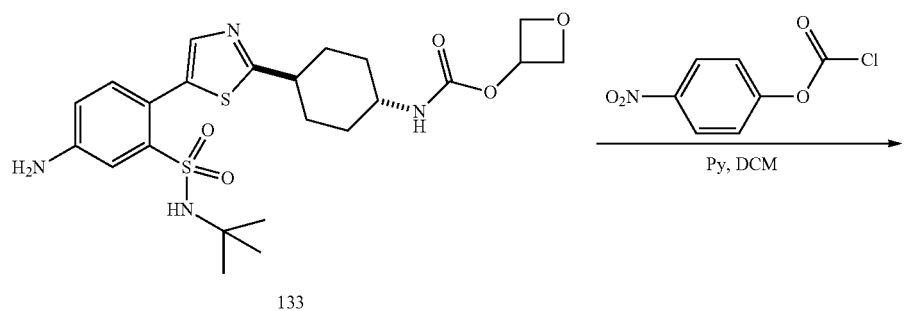
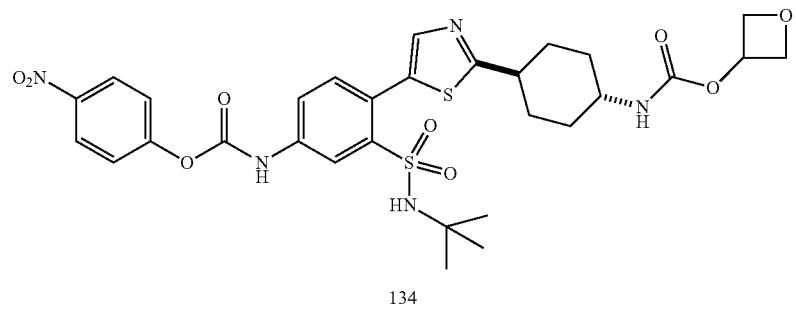

General method D, trans-oxetan-3-yl N-[4-[5-[2-(tert-butylsulfamoyl)-4-[(4-nitrophenoxy)carbonylamino]phenyl]thiazol-2-yl]cyclohexyl]carbamate. ESI [M+H]=674.2

Preparation of Example 49

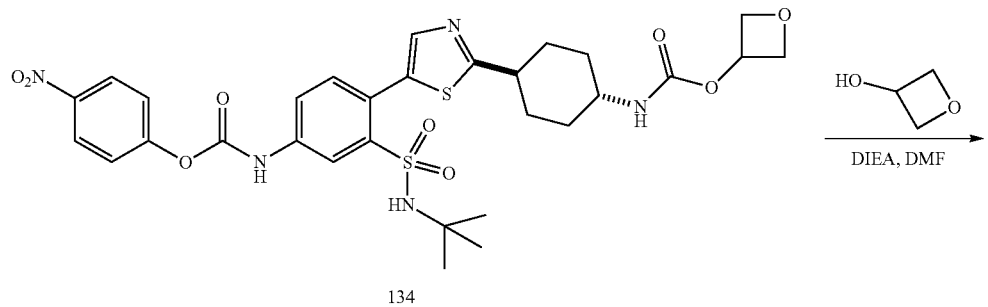

134

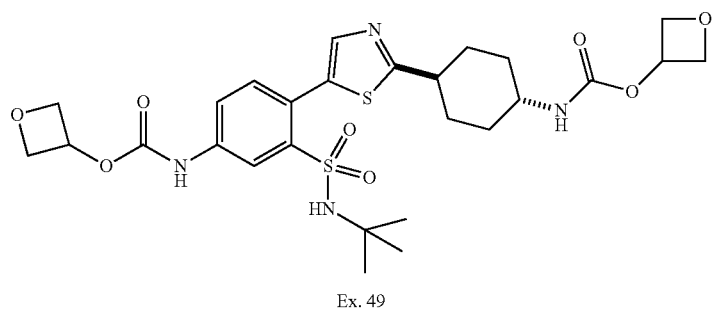

Ex. 49

General method H, trans-oxetan-3-yl N-[3-(tert-butylsulfamoyl)-4-[2-[4-(oxetan-3-yloxycarbonylamino)cyclohexyl]thiazol-5-yl]phenyl]carbamate. $^1$H NMR (400 MHz, DMSO-d6) δ=10.39 (s, 1H), 8.28 (d, J=2.2 Hz, 1H), 7.71-7.58 (m, 2H), 7.48-7.34 (m, 2H), 6.97 (s, 1H), 5.50-5.39 (m, 1H), 5.32-5.20 (m, 1H), 4.87-4.68 (m, 4H), 4.61-4.36 (m, 4H), 3.30-3.23 (m, 1H), 3.01-2.82 (m, 1H), 2.12 (br d, J=11.7 Hz, 2H), 1.90 (br d, J=10.4 Hz, 2H), 1.66-1.47 (m, 2H), 1.43-1.26 (m, 2H), 1.04 (s, 9H). ESI [M+H]=609.2

Example 50. Synthesis of oxetan-3-yl((1r,4r)-4-(5-(2-(N-(tert-butyl)sulfamoyl)-4-(3-(pyridin-2-ylmethyl)ureido)phenyl)thiazol-2-yl)cyclohexyl)carbamate The Following Compound was Synthesized Via Same Method by the Key Intermediate 134.

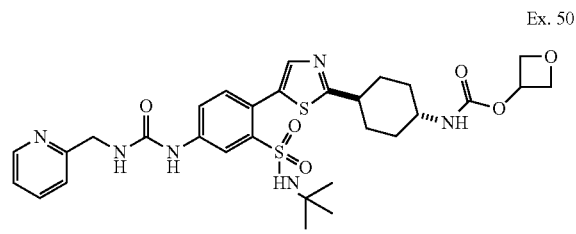 [SMILES: CC(C)(C)NS(=O)(=O)c1cc(NC(=O)NCc2ccccn2)ccc1-c1cnc([C@H]2CC[C@H](NC(=O)OC3COC3)CC2)s1]

Ex. 50

$^1$H NMR (400 MHz, METHANOL-d4) δ=8.49 (d, J=4.8 Hz, 1H), 8.25 (d, J=2.2 Hz, 1H), 7.82 (dt, J=1.8, 7.7 Hz, 1H), 7.73-7.63 (m, 2H), 7.45 (d, J=7.9 Hz, 1H), 7.38-7.26 (m, 2H), 5.39-5.28 (m, 1H), 4.84 (br s, 1H), 4.70-4.56 (m, 3H), 4.53 (s, 2H), 3.44 (br t, J=12.1 Hz, 1H), 3.06-2.92 (m, 1H), 2.22 (br d, J=13.2 Hz, 2H), 2.07 (br d, J=11.0 Hz, 2H), 1.79-1.60 (m, 2H), 1.50-1.35 (m, 2H), 1.10 (s, 9H). ESI [M+H]=643.2

Example 51. Synthesis of oxetan-3-yl((1S,4r)-4-(5-(2-(N-(tert-butyl)sulfamoyl)-4-(3-((S)-1-phenylethyl)ureido)phenyl)thiazol-2-yl)cyclohexyl)carbamate The Following Compound was Synthesized Via Same Method by the Key Intermediate 134.

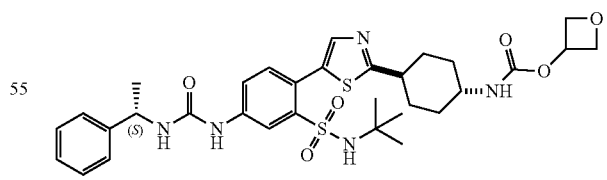

Ex. 51

$^1$H NMR (400 MHz, METHANOL-d4) δ=8.19 (d, J=2.2 Hz, 1H), 7.70-7.63 (m, 2H), 7.39-7.30 (m, 5H), 7.27-7.20 (m, 1H), 5.35 (t, J=5.7 Hz, 1H), 4.92 (q, J=6.8 Hz, 2H), 4.84 (br s, 1H), 4.60 (t, J=6.4 Hz, 2H), 3.49-3.38 (m, 1H), 3.05-2.95 (m, 1H), 2.22 (br d, J=12.3 Hz, 2H), 2.10-2.02 (m, 2H), 1.74-1.61 (m, 2H), 1.49 (d, J=7.1 Hz, 3H), 1.45-1.34 (m, 2H), 1.09 (s, 9H). ESI [M+H]=656.3

Example 52. Synthesis of oxetan-3-yl((1R,4r)-4-(5-(2-(N-(tert-butyl)sulfamoyl)-4-(3-((R)-1-phenyl-ethyl)ureido)phenyl)thiazol-2-yl)cyclohexyl)carbamate The Following Compound was Synthesized Via Same Method by the Key Intermediate 134.

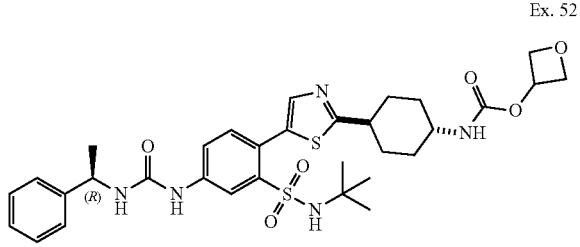
Ex. 52

¹HNMR (400 MHz, METHANOL-d4) δ=8.19 (d, J=2.2 Hz, 1H), 7.75-7.61 (m, 2H), 7.42-7.18 (m, 6H), 5.35 (quin, J=5.7 Hz, 1H), 5.01-4.87 (m, 3H), 4.70-4.52 (m, 2H), 3.51-3.38 (m, 1H), 3.06-2.92 (m, 1H), 2.22 (br d, J=11.9 Hz, 2H), 2.07 (br d, J=11.7 Hz, 2H), 1.77-1.62 (m, 2H), 1.54-1.35 (m, 5H), 1.10 (s, 9H). ESI [M+H]=656.2

Example 53. Synthesis of oxetan-3-yl((1r,4r)-4-(5-(2-(N-(tert-butyl)sulfamoyl)-4-(3-(2-fluorobenzyl)ureido)phenyl)thiazol-2-yl)cyclohexyl)carbamate The Following Compound was Synthesized Via Same Method by the Key Intermediate 134.

Ex. 53

¹HNMR (400 MHz, METHANOL-d4) δ=8.23 (d, J=2.4 Hz, 1H), 7.75-7.63 (m, 2H), 7.46-7.24 (m, 3H), 7.20-7.03 (m, 2H), 5.43-5.28 (m, 1H), 4.85 (br s, 2H), 4.67-4.56 (m, 2H), 4.47 (s, 2H), 3.53-3.37 (m, 1H), 3.08-2.93 (m, 1H), 2.29-1.99 (m, 4H), 1.78-1.61 (m, 2H), 1.53-1.35 (m, 2H), 1.11 (s, 9H). ESI [M+H]=660.2

Example 54. Synthesis of oxetan-3-yl((1R,4r)-4-(5-(2-(N-(tert-butyl)sulfamoyl)-4-(3-((R)-1-(2-fluorophenyl)ethyl)ureido)phenyl)thiazol-2-yl)cyclohexyl)carbamate The Following Compound was Synthesized Via Same Method by the Key Intermediate 134.

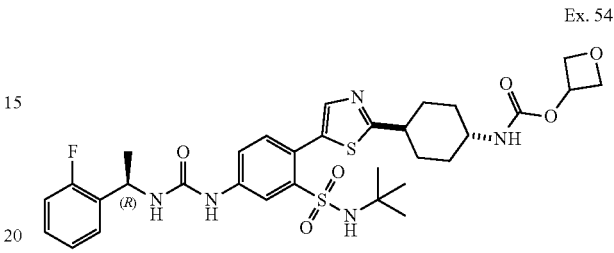
Ex. 54

¹H NMR (400 MHz, METHANOL-d4) δ=8.20 (d, J=2.3 Hz, 1H), 7.73-7.65 (m, 2H), 7.45-7.39 (m, 1H), 7.38-7.26 (m, 2H), 7.21-7.04 (m, 2H), 5.37 (quin, J=5.7 Hz, 1H), 5.20 (q, J=7.0 Hz, 1H), 4.89-4.86 (m, 2H), 4.65-4.59 (m, 2H), 3.52-3.41 (m, 1H), 3.08-2.96 (m, 1H), 2.24 (br d, J=12.2 Hz, 2H), 2.13-2.05 (m, 2H), 1.76-1.64 (m, 1H), 1.52 (d, J=7.0 Hz, 3H), 1.47-1.39 (m, 2H), 1.12 (s, 9H). ESI [M+H]=674.2

Example 55. Synthesis of oxetan-3-yl((1S,4r)-4-(5-(2-(N-(tert-butyl)sulfamoyl)-4-(3-((S)-1-(2-fluorophenyl)ethyl)ureido)phenyl)thiazol-2-yl)cyclohexyl)carbamate The Following Compound was Synthesized Via Same Method by the Key Intermediate 134.

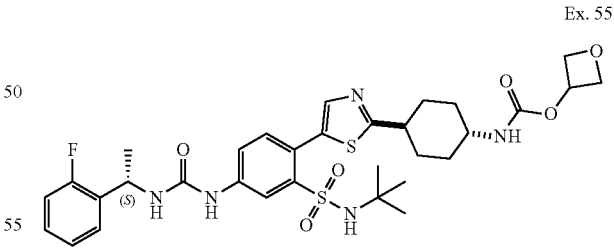
Ex. 55

¹HNMR (400 MHz, METHANOL-d4) δ=8.17 (d, J=2.2 Hz, 1H), 7.75-7.59 (m, 2H), 7.43-7.22 (m, 3H), 7.21-7.03 (m, 2H), 5.39-5.28 (m, 1H), 5.17 (q, J=7.0 Hz, 1H), 4.90-4.87 (m, 1H), 4.84 (s, 1H), 4.66-4.54 (m, 2H), 3.43 (br t, J=11.8 Hz, 1H), 2.99 (br t, J=12.1 Hz, 1H), 2.22 (br d, J=12.7 Hz, 2H), 2.06 (br d, J=10.5 Hz, 2H), 1.77-1.60 (m, 2H), 1.58-1.34 (m, 5H), 1.09 (s, 9H). ESI [M+H]=674.2

Example 56. Synthesis of 4-piperidylmethyl N-[3-(tert-butylsulfamoyl)-4-[2-[5-(isopropoxycarbonylamino)-3-methoxy-2-pyridyl]thiazol-5-yl]phenyl] carbamate
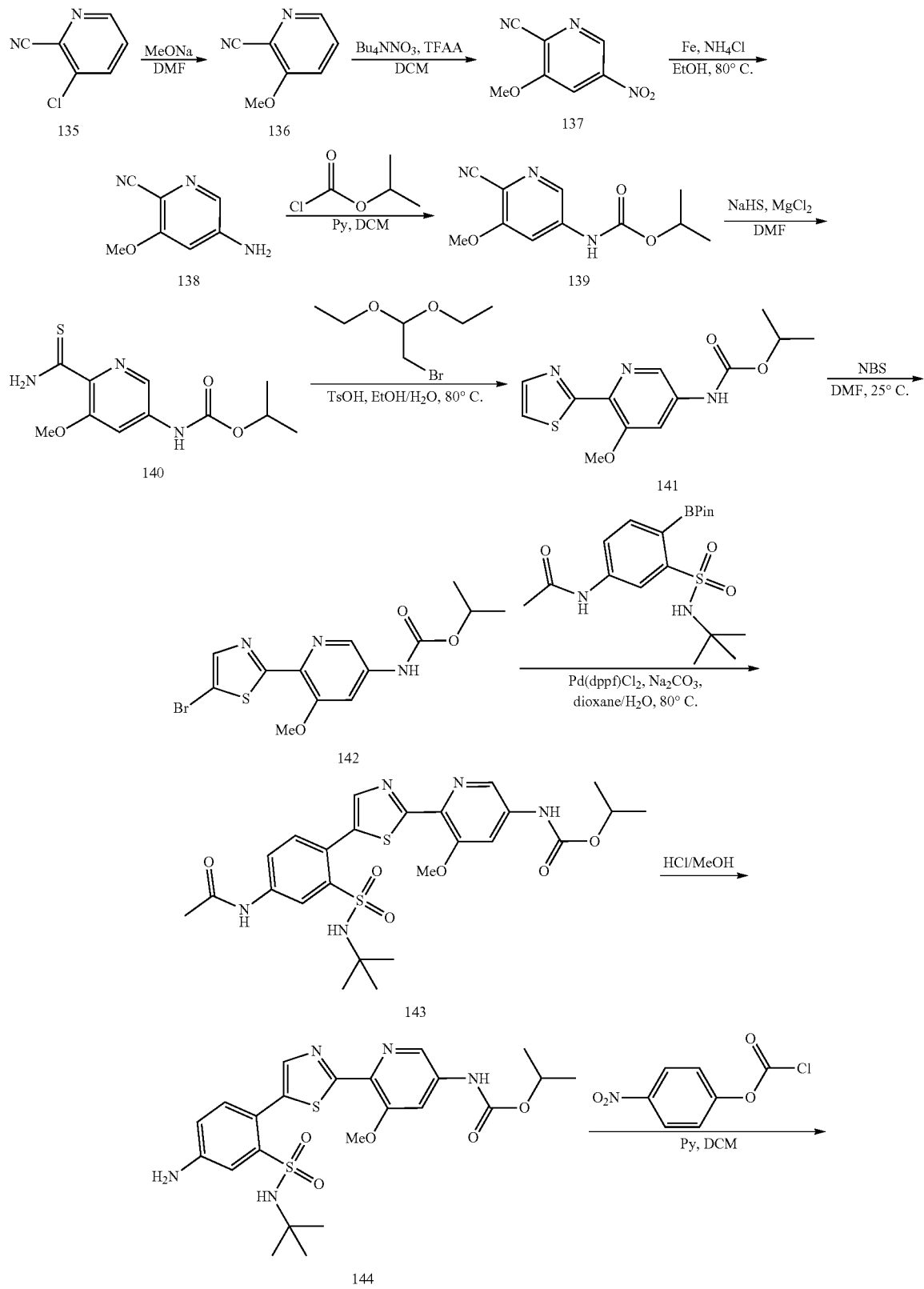

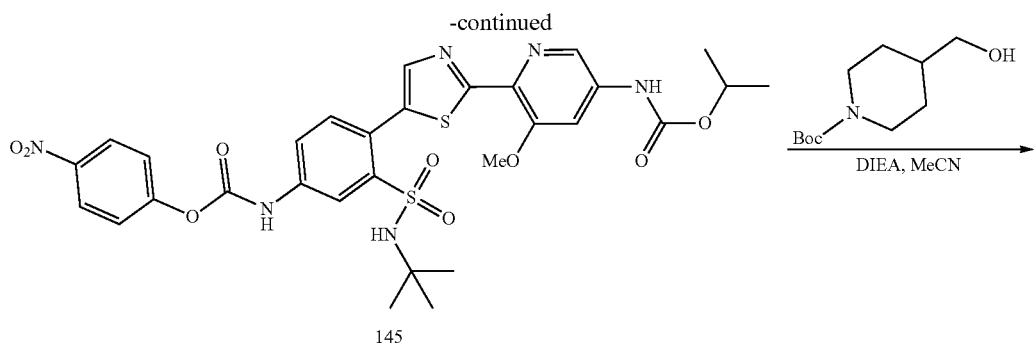

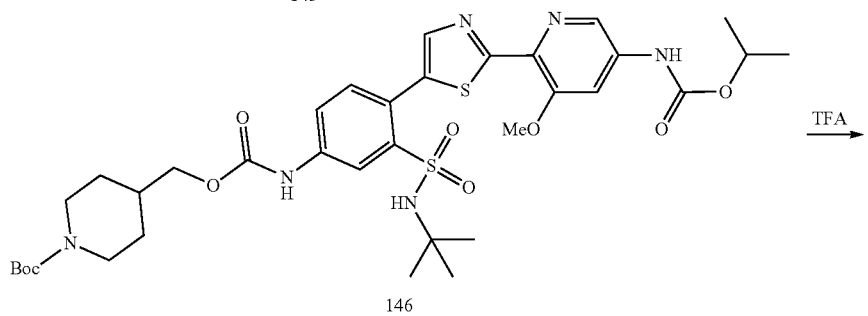

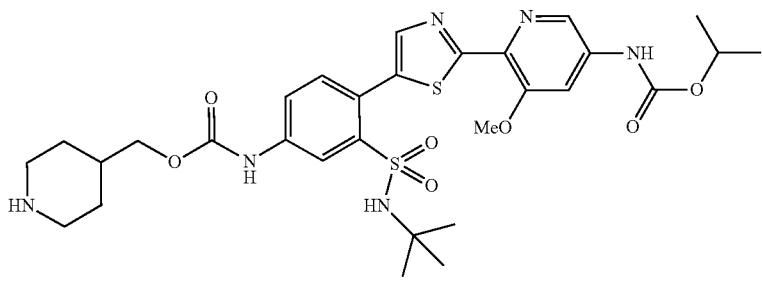

Preparation of Compound 136.

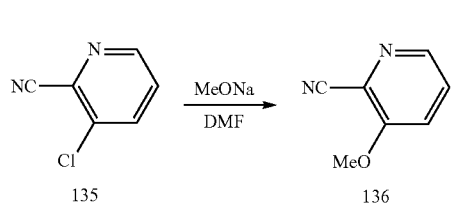

Na (8.75 g, 380.60 mmol, 9.02 mL, 1.51 eq.) was added into MeOH (300 mL) portionwise and after Na was dissolved, the mixture was concentrated to dryness. The resulting gray solid (NaOMe) was added into DMF (300 mL) and 3-chloropyridine-2-carbonitrile (35 g, 252.61 mmol, 1 eq.) was added at 0° C. The reaction mixture was stirred at 20° C. for 12 hrs and then diluted with H₂O (800 mL) and filtered. The cake dried to give 3-methoxypyridine-2-carbonitrile (25 g, crude) as a white solid. ESI [M+H]=135.1

Preparation of Compound 137

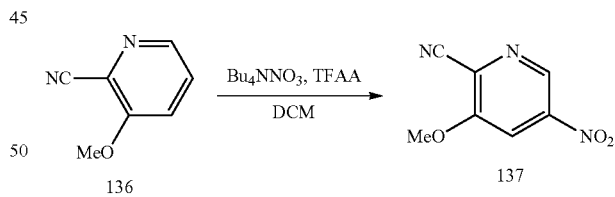

To a solution of 3-methoxypyridine-2-carbonitrile (24.5 g, 182.65 mmol, 1 eq.) in DCM (450 mL) was added a mixture of Bu₄NNO₃ (83.30 g, 273.59 mmol, 1.5 eq.) and TFAA (57.54 g, 273.98 mmol, 38.11 mL, 1.5 eq.) in DCM (150 mL) dropwise at 0° C. The mixture was stirred at 20° C. for 12 hrs and then poured into sat.aq.NaHCO₃ (300 mL) at 0° C. and the organic layer was dried over Na₂SO₄, filtered and concentrated. The residue was purified by column chromatography (SiO₂, Petroleum ether/Ethyl acetate=20/1 to 10:1) to give 3-methoxy-5-nitro-pyridine-2-carbonitrile (27 g, crude) as a white solid. ¹H NMR (400 MHz, CHLOROFORM-d) δ=9.06 (d, J=2.2 Hz, 1H), 8.13 (d, J=2.2 Hz, 1H), 4.16-4.08 (m, 3H). ESI [M+H]=180.1

General Method G for Preparation of Compound 138.

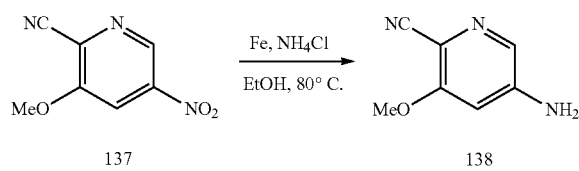 [SMILES: COc1cc([N+](=O)[O-])cnc1C#N ; COc1cc(N)cnc1C#N]

To a solution of 3-methoxy-5-nitro-pyridine-2-carbonitrile (27 g, 151 mmol, 1 eq.) in THF (100 mL)/EtOH (500 mL) were added Fe (4 g, 754 mmol, 5 eq.) and a solution of NH$_4$Cl (24.2 g, 452 mmol, 3 eq.) in H$_2$O (50 mL). The mixture was stirred at 80° C. for 30 mins, then diluted with THF (500 mL) and filtered. The filtrate was concentrated, diluted with H$_2$O (500 mL) and then extracted with DCM (400 mL×3). The combined organic layers were dried over Na$_2$SO$_4$, filtered and concentrated to give 5-amino-3-methoxy-pyridine-2-carbonitrile (14.5 g, crude) as a pale yellow solid. ESI [M+H]=150.1

Preparation of Compound 139.

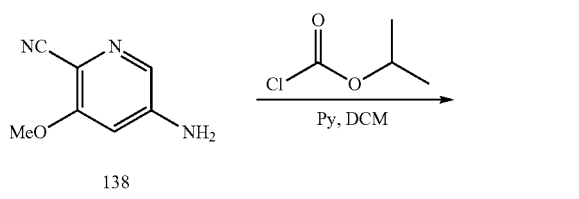

General method D, isopropyl N-(6-cyano-5-methoxy-3-pyridyl)carbamate. $^1$H NMR (400 MHz, METHANOL-d4) δ=8.13 (d, J=2.2 Hz, 1H), 7.95 (d, J=1.8 Hz, 1H), 5.04-4.95 (m, 1H), 3.96 (s, 3H), 1.31 (d, J=6.2 Hz, 6H). ESI [M+H]=236.1

Preparation of Compound 140.

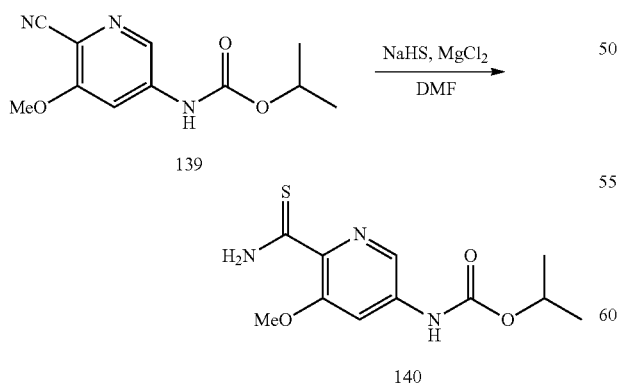

To a solution of isopropyl N-(6-cyano-5-methoxy-3-pyridyl)carbamate (16 g, 68.02 mmol, 1 eq.) in DMF (200 mL) were added NaHS (19.06 g, 340.08 mmol, 5 eq.) and then MgCl$_2$ (19.43 g, 204.05 mmol, 8.37 mL, 3 eq.). The mixture was stirred at 25° C. for 12 hrs and then poured into H$_2$O (500 ml) and extracted with DCM (40 mL*3). The combined organic layers were dried over Na$_2$SO$_4$, filtered and concentrated. The residue was washed with a solution (Petroleum ether:EtOAc=8:1), filtered and the filter cake was dried to give isopropyl N-(6-carbamothioyl-5-methoxy-3-pyridyl)carbamate (21 g, crude) as a yellow solid. $^1$H NMR (400 MHz, DMSO-d6) δ=9.92-9.84 (m, 2H), 9.38 (br s, 1H), 8.08 (d, J=1.8 Hz, 1H), 7.66 (s, 1H), 4.89 (spt, J=6.3 Hz, 1H), 3.74 (s, 3H), 1.24 (d, J=6.1 Hz, 6H). ESI [M+H]=270.0

Preparation of Compound 141.

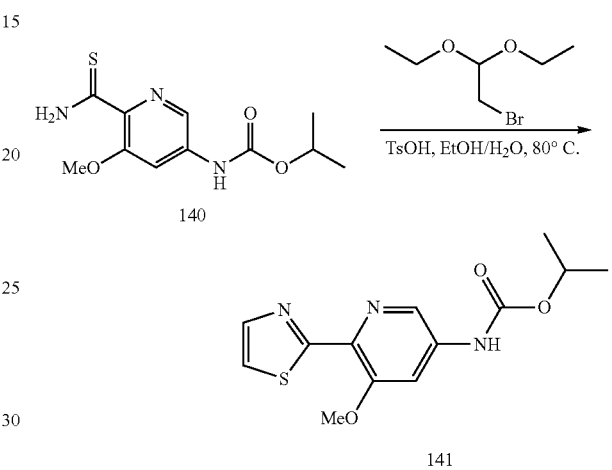

General method M, isopropyl N-(5-methoxy-6-thiazol-2-yl-3-pyridyl)carbamate $^1$H NMR (400 MHz, DMSO-d6) δ=10.07 (s, 1H), 8.26 (d, J=2.0 Hz, 1H), 7.88 (d, J=3.1 Hz, 1H), 7.85 (d, J=1.3 Hz, 1H), 7.71 (d, J=3.3 Hz, 1H), 4.91 (spt, J=6.2 Hz, 1H), 3.88 (s, 3H), 1.26 (d, J=6.4 Hz, 6H). ESI [M+H]=294.1

Preparation of Compound 142.

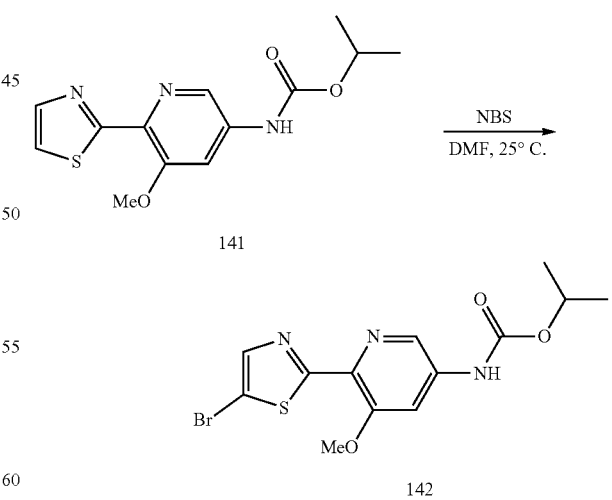

General method J, isopropyl N-[6-(5-bromothiazol-2-yl)-5-methoxy-3-pyridyl]carbamate. $^1$H NMR (400 MHz, DMSO-d6) δ=10.17 (s, 1H), 8.28 (d, J=1.8 Hz, 1H), 8.08-7.86 (m, 2H), 4.99 (br s, 1H), 3.93 (s, 3H), 1.29 (d, J=6.4 Hz, 6H). ESI [M+H]=371.8/373.8

Preparation of Compound 143.
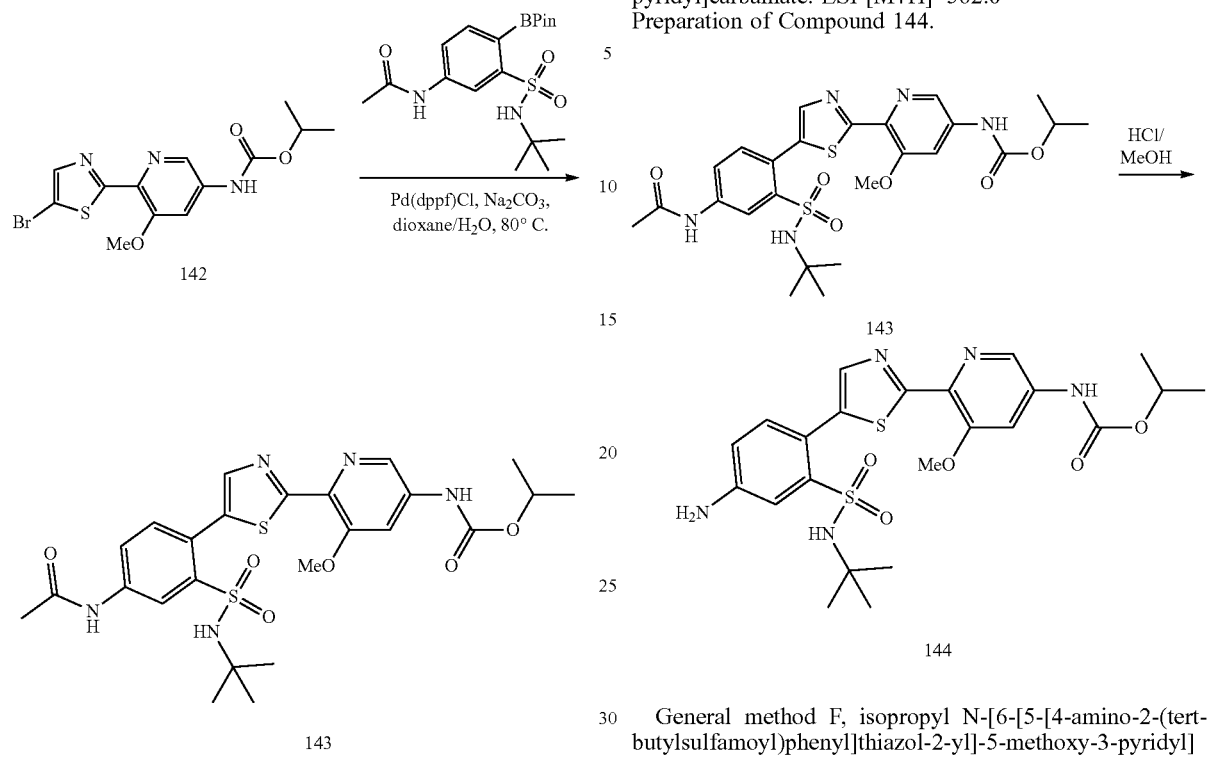
General method B, isopropyl N-[6-[5-[4-acetamido-2-(tert-butylsulfamoyl)phenyl]thiazol-2-yl]-5-methoxy-3-pyridyl]carbamate. ESI [M+H]=562.0
Preparation of Compound 144.
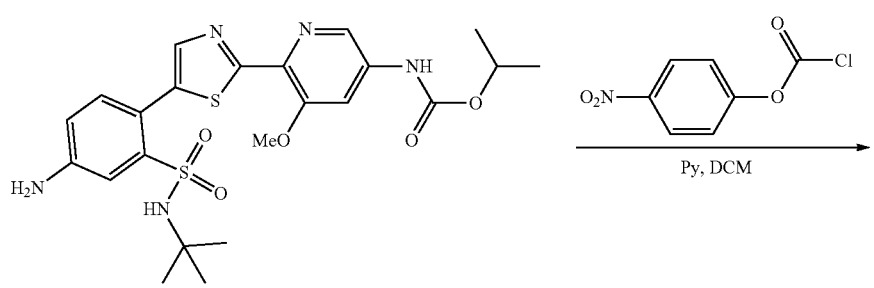
General method F, isopropyl N-[6-[5-[4-amino-2-(tert-butylsulfamoyl)phenyl]thiazol-2-yl]-5-methoxy-3-pyridyl]carbamate. ESI [M+H]=520.2
Preparation of Compound 145.
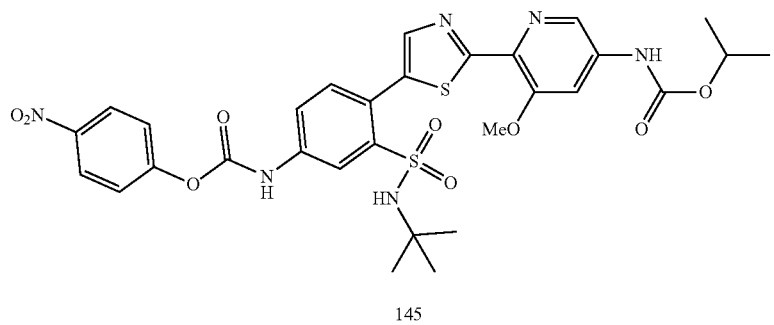

General method D, (4-nitrophenyl)N-[3-(tert-butylsulfamoyl)-4-[2-[5-(isopropoxycarbonylamino)-3-methoxy-2-pyridyl]thiazol-5-yl]phenyl]carbamate. ESI [M+H]=685.1
Preparation of Compound 146.

General method C, 4-piperidylmethyl N-[3-(tert-butylsulfamoyl)-4-[2-[5-(isopropoxycarbonylamino)-3-methoxy-2-pyridyl]thiazol-5-yl]phenyl]carbamate. ¹H NMR (400 MHz, DMSO-d6) δ=10.19-10.10 (m, 2H), 8.35 (d, J=2.1 Hz, 1H),

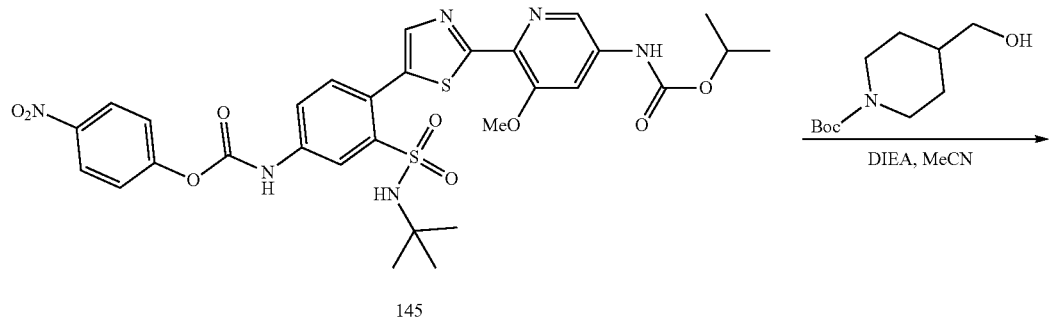

145

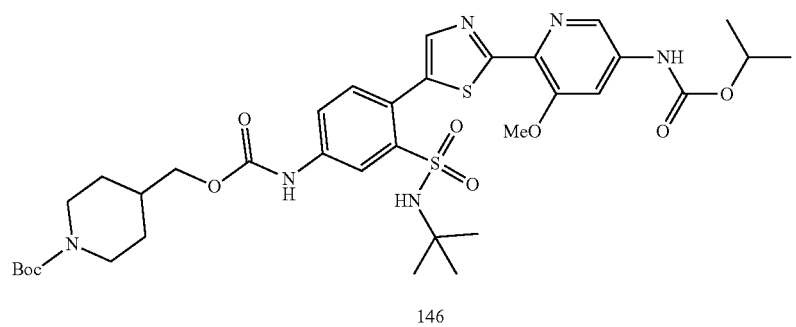

146

General method H, tert-butyl 4-[[3-(tert-butylsulfamoyl)-4-[2-[5-(isopropoxycarbonylamino)-3-methoxy-2-pyridyl]thiazol-5-yl]phenyl]carbamoyloxymethyl]piperidine-1-carboxylate. ESI [M+H]=761.4
Preparation of Ex 56

8.30 (d, J=1.8 Hz, 1H), 7.89 (s, 2H), 7.68 (dd, J=2.0, 8.4 Hz, 1H), 7.46 (d, J=8.4 Hz, 1H), 7.12 (br s, 1H), 4.95 (td, J=6.2, 12.5 Hz, 1H), 3.98 (d, J=6.5 Hz, 2H), 3.93 (s, 3H), 3.00 (br d, J=12.1 Hz, 2H), 2.70-2.56 (m, 2H), 1.77 (br d, J=4.0 Hz, 1H), 1.67 (br d, J=12.1 Hz, 2H), 1.30 (d, J=6.2 Hz, 6H), 1.16 (br dd, J=3.4, 12.0 Hz, 2H), 1.09 (s, 9H). ESI [M+H]=661.3

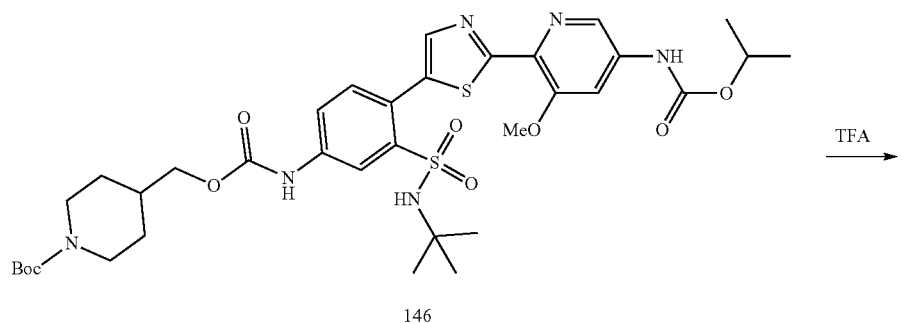

146

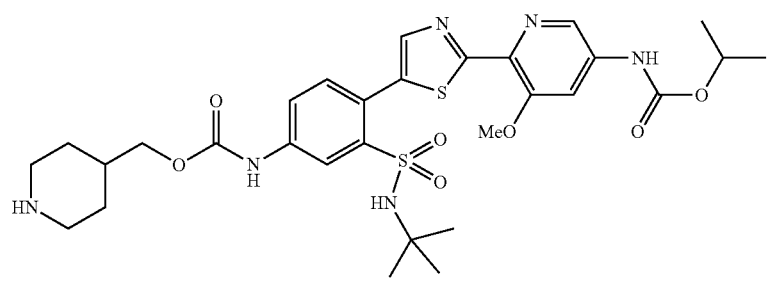

Ex. 56

Example 57 Synthesis of trans-isopropyl N-[4-[5-[4-(benzylcarbamoylamino)-2-(tert-butylsulfamoyl)phenyl]-4-fluoro-thiazol-2-yl]cyclohexyl]carbamate

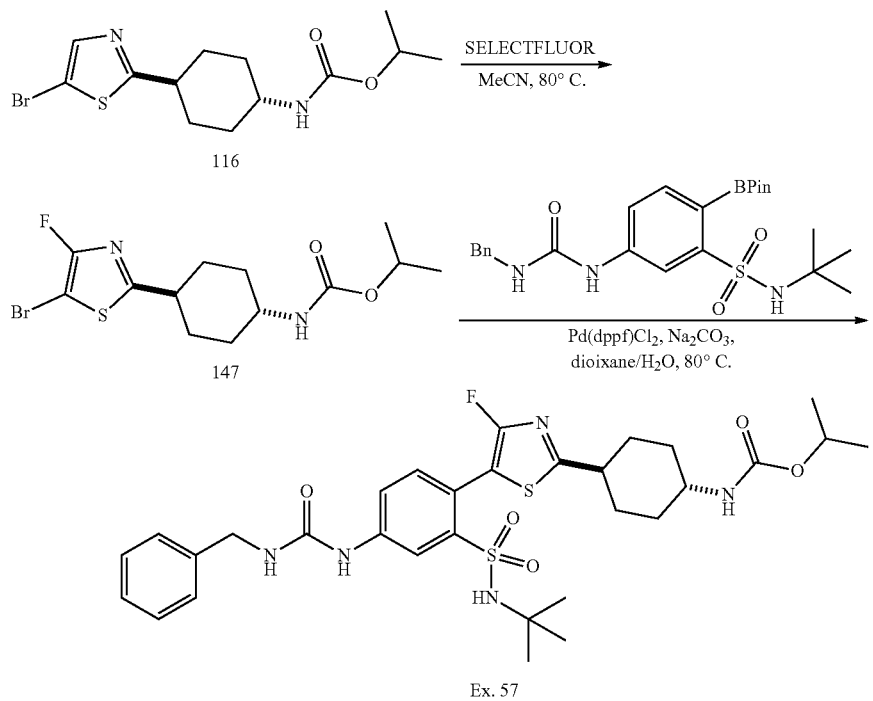

Preparation of Compound 147

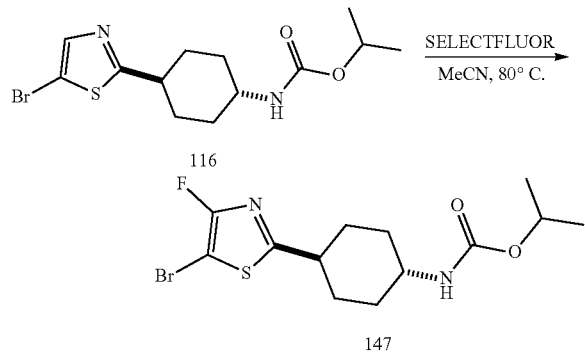

To a solution of trans-isopropyl N-[4-(5-bromothiazol-2-yl)cyclohexyl]carbamate (1.50 g, 4.32 mmol, 1 eq.) in ACN (20 mL) was added 1-(chloromethyl)-4-fluoro-1,4-diazoniabicyclo[2.2.2]octane; ditetrafluoroborate (3.06 g, 8.64 mmol, 2 eq.) and the mixture was stirred at 80° C. for 12 hrs. The mixture was then concentrated and the residue was purified by column chromatography ($SiO_2$, Petroleum ether/Ethyl acetate=3/1 to 3:1) to give trans-isopropyl N-[4-(5-bromo-4-fluoro-thiazol-2-yl)cyclohexyl]carbamate (0.2 g, 547.55 umol, 12.68% yield) as yellow gum. ESI [M+H]= 365.1/367.1

Preparation of Ex 57

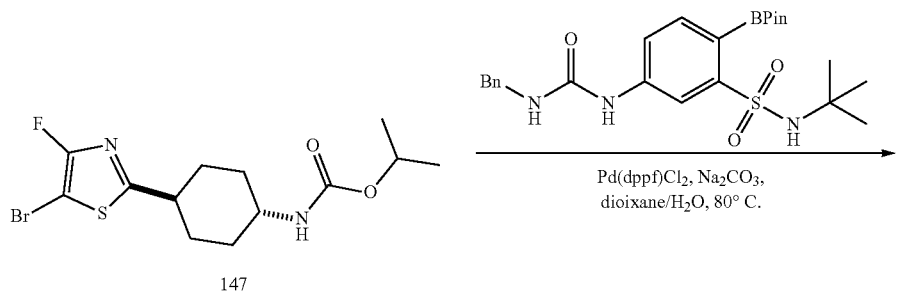

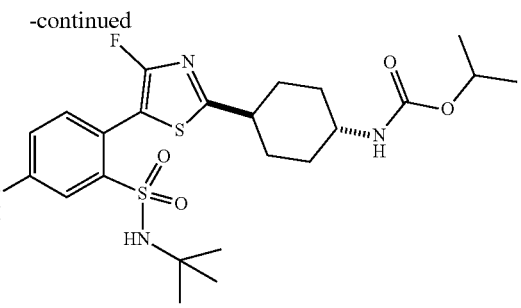

Ex. 57

General method B, trans-isopropyl N-[4-[5-[4-(benzylcarbamoylamino)-2-(tert-butylsulfamoyl)phenyl]-4-fluorothiazol-2-yl]cyclohexyl]carbamate. ¹H NMR (400 MHz, METHANOL-d4) δ=8.24 (d, J=2.0 Hz, 1H), 7.67 (dd, J=2.0, 8.4 Hz, 1H), 7.37-7.29 (m, 5H), 7.24 (br d, J=2.6 Hz, 1H), 4.82-4.77 (m, 1H), 4.40 (s, 2H), 3.42 (br t, J=11.6 Hz, 1H), 2.87 (br t, J=12.0 Hz, 1H), 2.20 (br d, J=12.3 Hz, 2H), 2.05 (br d, J=11.0 Hz, 2H), 1.69-1.57 (m, 2H), 1.43-1.30 (m, 2H), 1.21 (br d, J=5.7 Hz, 6H), 1.15 (s, 9H). ESI [M+H]=646.2

Example 58 Synthesis of isopropyl((1r,4r)-4-(5-(2-(N-(tert-butyl)sulfamoyl)-4-((isopropoxycarbonyl)amino)phenyl)-4-fluorothiazol-2-yl)cyclohexyl)carbamate The Following Compound was Synthesized Via Same Method by the Key Intermediate 147.

Ex. 58

¹H NMR (400 MHz, METHANOL-d4) δ=8.35 (s, 1H), 7.69 (br d, J=8.1 Hz, 1H), 7.37 (d, J=8.3 Hz, 1H), 5.01 (td, J=6.1, 12.4 Hz, 1H), 4.83 (br s, 1H), 3.53-3.39 (m, 1H), 2.96-2.85 (m, 1H), 2.23 (br d, J=12.3 Hz, 2H), 2.08 (br d, J=10.5 Hz, 2H), 1.75-1.60 (m, 2H), 1.47-1.38 (m, 2H), 1.34 (d, J=6.2 Hz, 6H), 1.24 (br d, J=6.0 Hz, 6H), 1.18 (s, 9H). ESI [M+H]=599.2

Example 59 Synthesis of trans-isopropyl N-[6-[5-[4-(benzylcarbamoylamino)-2-(tert-butylsulfamoyl)phenyl]thiazol-2-yl]tetrahydropyran-3-yl]carbamate Scheme 20

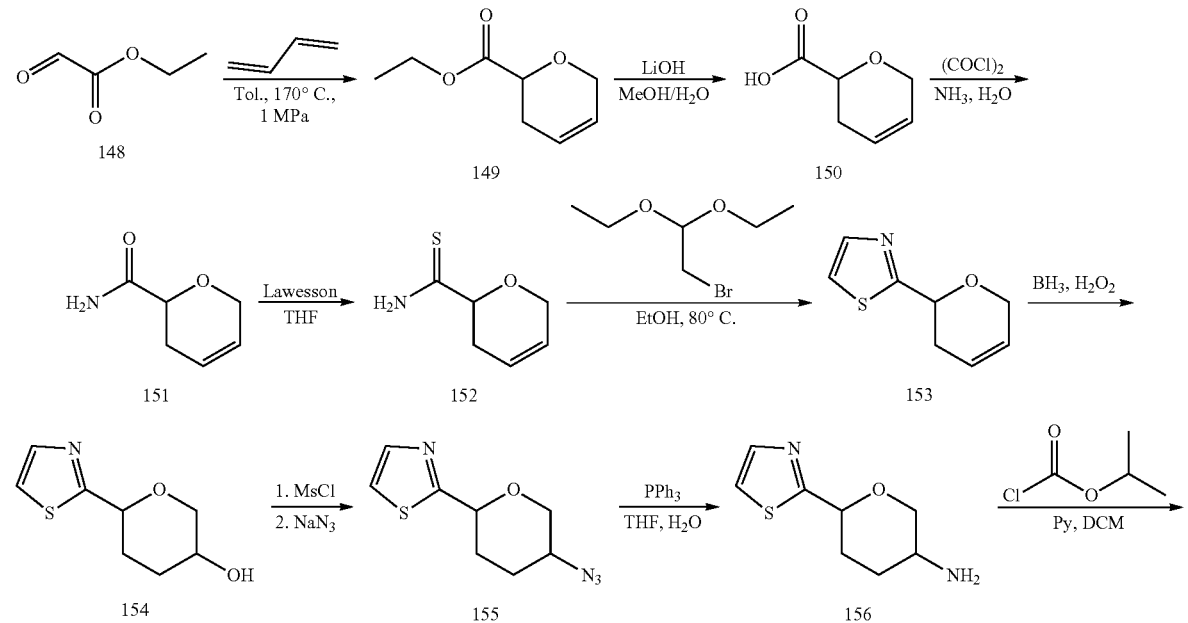

-continued

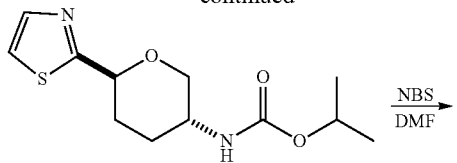

157

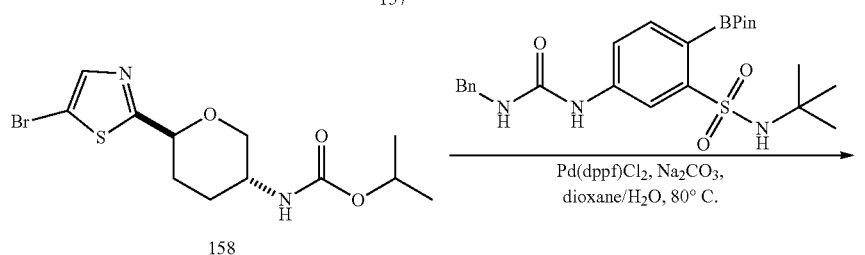

158

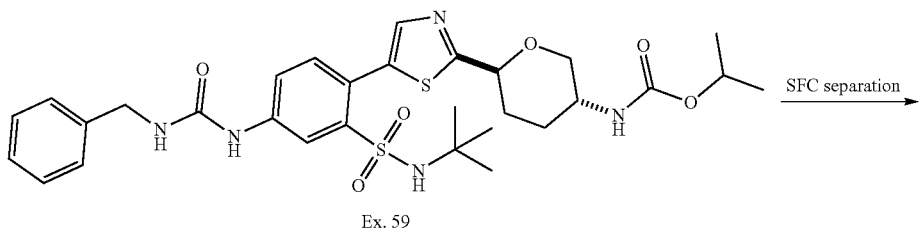

Ex. 59

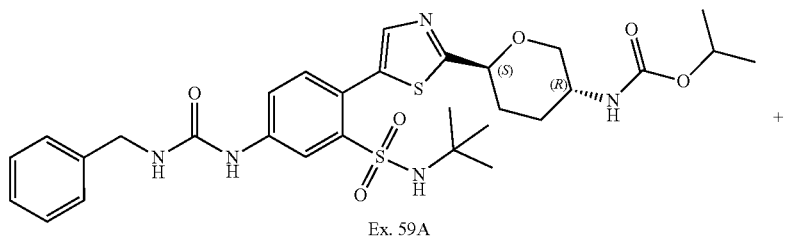

Ex. 59A

+

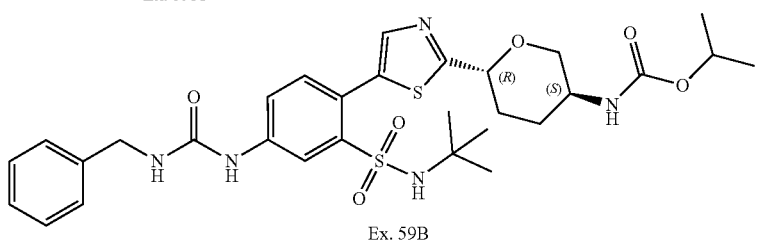

Ex. 59B

Preparation of Compound 149

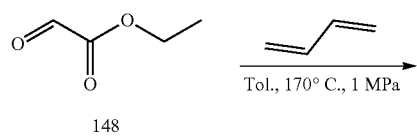

148

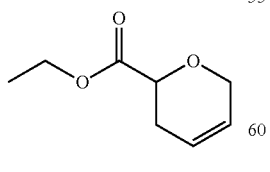

149

To a solution of ethyl 2-oxoacetate (250 g, 1.22 mol, 1 eq.) in Tol. (1.5 L), were added buta-1,3-diene (92.72 g, 1.71 mol, 149.55 mL, 1.4 eq.) and 2,6-ditert-butyl-4-methyl- phenol (5.40 g, 24.49 mmol, 0.02 eq.). The mixture was stirred at 170° C. for 8 hrs in high pressure tube under 1 MPa and then concentrated. The residue was purified by silica gel chromatography (Petroleum ether/Ethyl acetate=100:1-10:1) to afford ethyl 3,6-dihydro-2H-pyran-2-carboxylate (26 g, 166.48 mmol, 13.60% yield) as yellow oil. $^1$H NMR (400 MHz, CHLOROFORM-d) δ=5.82-5.74 (m, 1H), 5.71-5.64 (m, 1H), 4.36-4.27 (m, 1H), 4.23-4.12 (m, 4H), 2.39-2.23 (m, 2H), 1.24 (t, J=7.1 Hz, 3H).

Preparation of Compound 150

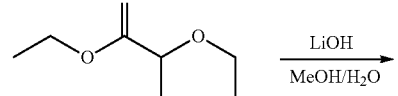

149

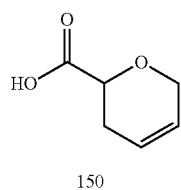

150

General method O, 3,6-dihydro-2H-pyran-2-carboxylic acid. ¹H NMR (400 MHz, CHLOROFORM-d) δ=5.88 (qdd, J=2.3, 5.1, 10.2 Hz, 1H), 5.80-5.71 (m, 1H), 4.43-4.19 (m, 3H), 2.53-2.31 (m, 2H)

Preparation of Compound 151

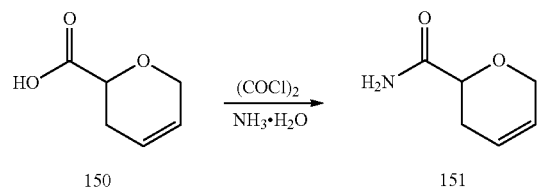

General method N, 3,6-dihydro-2H-pyran-2-carboxamide. ¹H NMR (400 MHz, CHLOROFORM-d) δ=6.50 (br s, 1H), 5.89-5.76 (m, 1H), 5.67 (br d, J=9.8 Hz, 1H), 5.50 (br s, 1H), 4.22 (br s, 2H), 3.97 (dd, J=3.9, 10.8 Hz, 1H), 2.49-2.35 (m, 1H), 2.28-2.09 (m, 1H) Preparation of compound 152

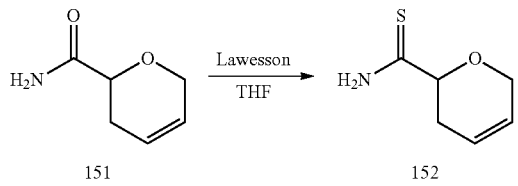 [SMILES: NC(=O)C1CC=CCO1 ; NC(=S)C1CC=CCO1 ; "THF"]

General method L, 3,6-dihydro-2H-pyran-2-carbothioamide. ESI [M+H]=144.1

Preparation of Compound 153

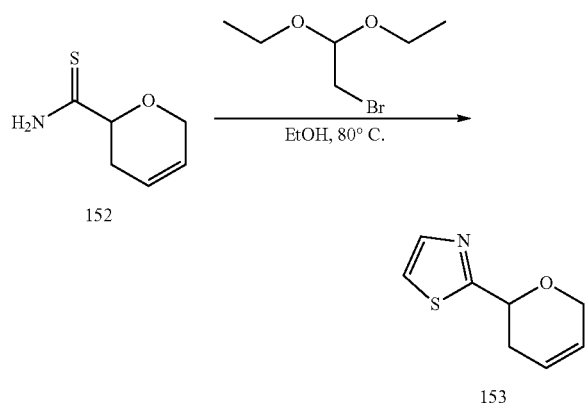

General method M, 2-(3,6-dihydro-2H-pyran-2-yl)thiazole. ¹H NMR (400 MHz, CHLOROFORM-d) δ=7.69 (d, J=2.9 Hz, 1H), 7.26 (d, J=2.9 Hz, 1H), 5.93-5.83 (m, 1H), 5.70-5.63 (m, 1H), 4.86 (dd, J=3.9, 9.8 Hz, 1H), 4.33 (br s, 2H), 2.61-2.37 (m, 2H). ESI [M+H]=168.1

Preparation of Compound 154

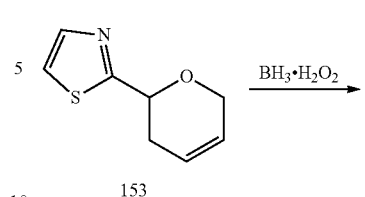

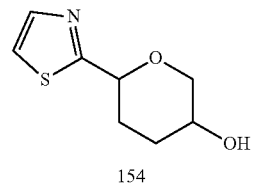

To a solution of 2-(3,6-dihydro-2H-pyran-2-yl)thiazole (13 g, 77.74 mmol, 1 eq.) in THF (150 mL), was added BH₃-Me₂S (10 M, 15.55 mL, 2 eq.) at 0° C. dropwise and the mixture was stirred at 26° C. for 2 hrs. Then the mixture was quenched by NaOH (62.19 g, 1.55 mol, 20 eq.) in H₂O (150 mL) slowly at 0° C. followed by addition of H₂O₂ (264.42 g, 2.33 mol, 224.09 mL, 30% purity, 30 eq.). The mixture was stirred at 26° C. for another 12 hrs. The mixture was quenched by sat.aq.Na₂SO₃ solution (1 L) and extracted with EtOAc (1 L*2). The combined organic phased was dried over Na₂SO₄, filtered and concentrated. The residue was purified by column (Petroleum ether:EtOAc=5:1-1:1) to afford 6-thiazol-2-yltetrahydropyran-3-ol (7 g, crude) as a yellow solid. ESI [M+H]=186.2 Preparation of compound 155

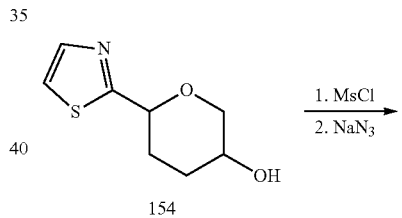

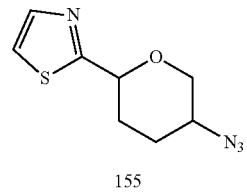

To a solution of 6-thiazol-2-yltetrahydropyran-3-ol (7 g, 37.79 mmol, 1 eq.) in DCM (100 mL), were added TEA (7.65 g, 75.58 mmol, 10.52 mL, 2 eq.) and methanesulfonyl chloride (6.49 g, 56.68 mmol, 4.39 mL, 1.5 eq.) dropwise at 0° C. and the mixture was stirred at 26° C. for 2 hrs. The mixture was diluted with DCM (100 mL) and washed with water (200 mL). The organic phase was dried over Na₂SO₄, filtered and concentrated to give crude (6-thiazol-2-yltetrahydropyran-3-yl) methanesulfonate (7 g, crude) as yellow oil which can be used directly.

To a solution of (6-thiazol-2-yltetrahydropyran-3-yl) methanesulfonate (7 g, 26.58 mmol, 1 eq.) in DMF (60 mL), was added azidosodium (8.64 g, 132.91 mmol, 5 eq.) and the mixture was stirred at 80° C. for 12 hrs and then poured into sat.aq.Na₂CO₃ (500 mL) and extracted with EtOAc (200 mL*3). The combined organic phase was washed with brine (200 mL) and dried over Na$_2$SO$_4$, filtered and concentrated to give crude 2-(5-azidotetrahydropyran-2-yl)thiazole (5 g, crude) as yellow oil which can be used without any purification.

Preparation of Compound 156

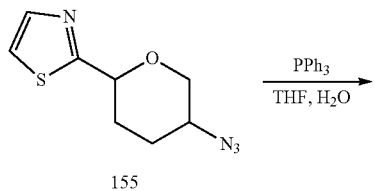

To a solution of 2-(5-azidotetrahydropyran-2-yl)thiazole (5 g, 23.78 mmol, 1 eq.) in THF (80 mL) and H$_2$O (40 mL), was added PPh$_3$ (9.36 g, 35.67 mmol, 1.5 eq.). The mixture was stirred at 50° C. for 12 hrs and then poured into 4N HCl solution (100 mL) and extracted with EtOAc (50 mL*2). Then the aqueous phase was bacified by sat.aq.Na$_2$CO$_3$ until pH>12 and extracted with a solution (DCM/MeOH=5:1) (100 mL*3). The combined organic phase was dried over Na$_2$SO$_4$, filtered and concentrated to give crude 6-thiazol-2-yltetrahydropyran-3-amine (3 g, crude) as yellow oil. ESI [M+H]=185.2

Preparation of Compound 157

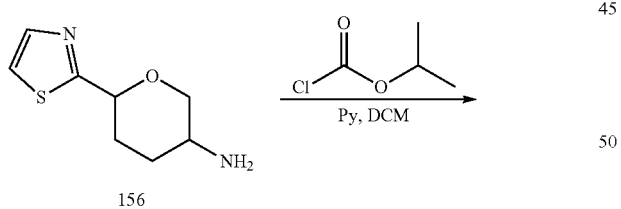

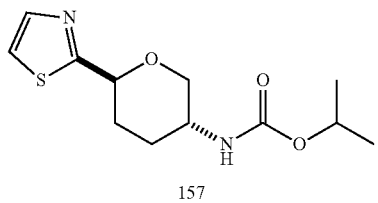

General method D, trans-isopropyl N-(6-thiazol-2-yltetrahydropyran-3-yl)carbamate. $^1$H NMR (400 MHz, METHANOL-d4) δ=7.74 (d, J=3.3 Hz, 1H), 7.55 (d, J=3.3 Hz, 1H), 4.86-4.77 (m, 2H), 4.64 (dd, J=2.4, 10.8 Hz, 1H), 4.12 (ddd, J=2.0, 4.6, 10.8 Hz, 1H), 3.75-3.55 (m, 1H), 2.32-2.20 (m, 1H), 2.16-2.03 (m, 1H), 1.81-1.54 (m, 2H), 1.22 (br d, J=6.2 Hz, 6H). ESI [M+H]=271.2 Note: Cpd. 157 was purified by prep-TLC and then prep-HPLC to separate out other isomers.

Preparation of Compound 158

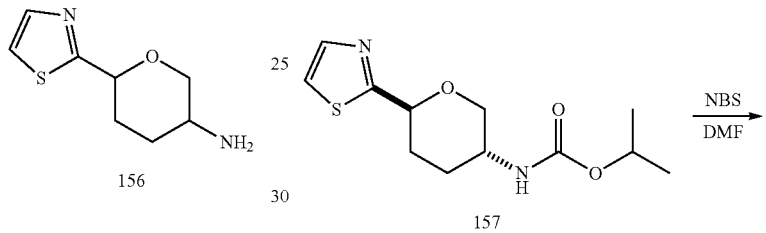

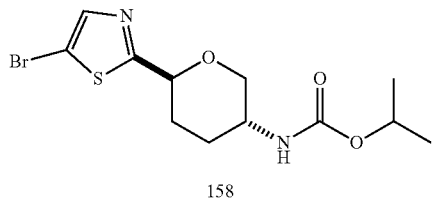

General method J, trans-isopropyl N-[6-(5-bromothiazol-2-yl)tetrahydropyran-3-yl]carbamate. ESI [M+H]=351.1/349.1

Preparation of Compound Ex. 59

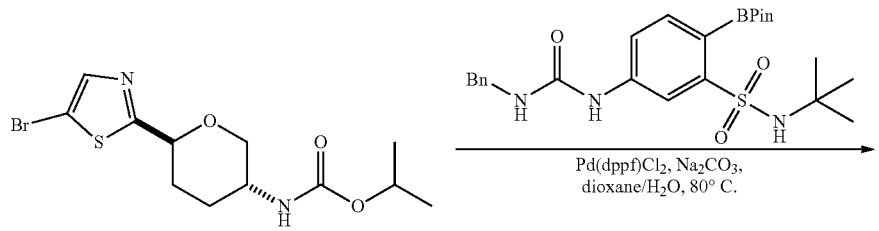

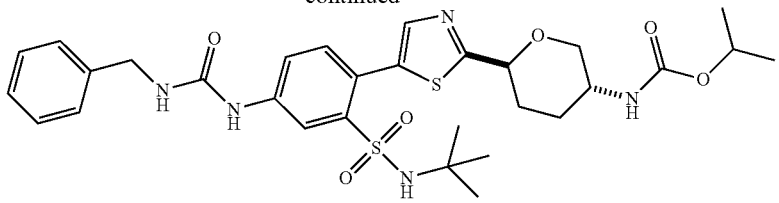
Ex. 59
General method B, trans-isopropyl N-[6-[5-[4-(benzylcarbamoylamino)-2-(tert-butylsulfamoyl)phenyl]thiazol-2-yl]tetrahydropyran-3-yl]carbamate. $^1$H NMR (400 MHz, METHANOL-d4) δ=8.24 (d, J=2.2 Hz, 1H), 7.74 (s, 1H), 7.68 (dd, J=2.2, 8.4 Hz, 1H), 7.37-7.29 (m, 5H), 7.27-7.19 (m, 1H), 4.84-4.78 (m, 2H), 4.64 (dd, J=2.0, 11.0 Hz, 1H), 4.40 (s, 2H), 4.12 (br dd, J=3.2, 10.7 Hz, 1H), 3.69-3.58 (m, 1H), 2.33-2.26 (m, 1H), 2.13 (br d, J=10.4 Hz, 1H), 1.82-1.71 (m, 1H), 1.69-1.57 (m, 1H), 1.26-1.19 (m, 6H), 1.10 (s, 9H). ESI [M+H]=630.3
Preparation of Compound Ex. 59A and Ex 59B
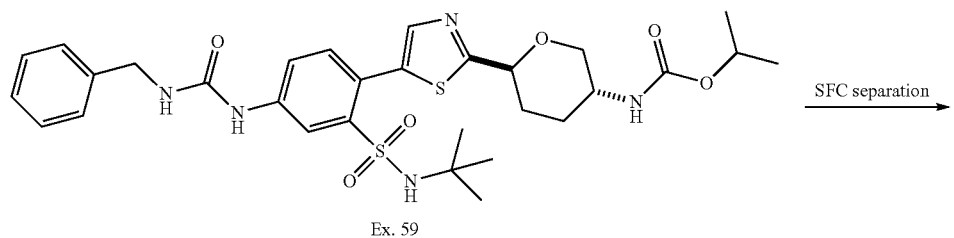
Ex. 59
→ SFC separation
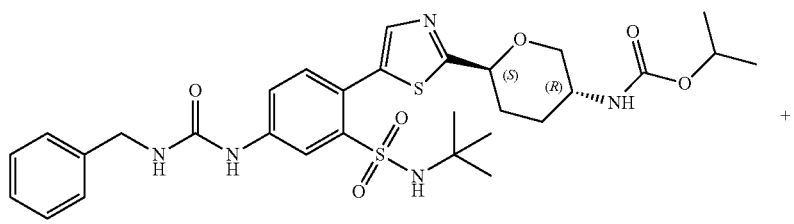
Ex. 59A
+
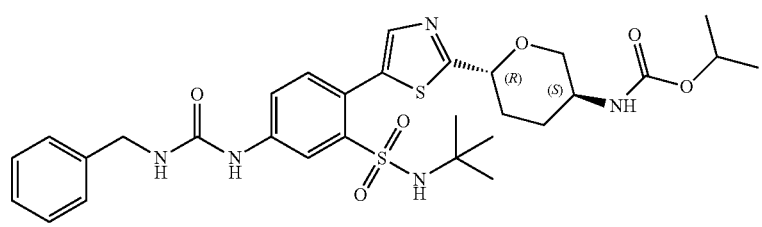
Ex. 59B Ex. 59 was further separated by SFC (condition: Instrument: Thar SFC80 preparative SFC; Column: Chiralpak IC-H 250*30 mm i.d. 5u; Mobile phase: A for CO$_2$ and B for MeOH (0.1% NH$_3$.H$_2$O); Gradient: B %=42%; Flow rate 70 g/min; Wavelength:220 nm; Column temperature: 40° C.; System back pressure: 100 bar to give Ex. 59A. $^1$H NMR (400 MHz, METHANOL-d4) δ=8.27 (d, J=2.2 Hz, 1H), 7.77 (s, 1H), 7.72 (dd, J=2.3, 8.3 Hz, 1H), 7.40-7.33 (m, 5H), 7.30-7.23 (m, 1H), 4.89-4.79 (m, 2H), 4.67 (dd, J=2.3, 11.0 Hz, 1H), 4.43 (s, 2H), 4.16 (br dd, J=3.0, 10.9 Hz, 1H), 3.67 (br t, J=10.9 Hz, 1H), 2.33 (br dd, J=2.6, 13.1 Hz, 1H), 2.16 (br d, J=10.6 Hz, 1H), 1.88-1.58 (m, 2H), 1.31-1.22 (m, 6H), 1.13 (s, 9H). ESI [M+H]=630.2

Ex. 59B: $^1$H NMR (400 MHz, METHANOL-d4) δ=8.25 (d, J=2.2 Hz, 1H), 7.76 (s, 1H), 7.70 (dd, J=2.2, 8.3 Hz, 1H), 7.37 (s, 1H), 7.36-7.31 (m, 4H), 7.28-7.18 (m, 1H), 4.87-4.74 (m, 1H), 4.65 (br d, J=9.2 Hz, 1H), 4.41 (s, 2H), 4.19-4.04 (m, 1H), 3.63 (br d, J=10.5 Hz, 1H), 3.34 (br s, 1H), 2.31 (br d, J=13.2 Hz, 1H), 2.13 (br d, J=10.1 Hz, 1H), 1.84-1.72 (m, 1H), 1.71-1.58 (m, 1H), 1.22 (d, J=6.1 Hz, 6H), 1.11 (s, 9H). ESI [M+H]=630.3

Example 60 Synthesis of trans-isopropyl N-[6-[5-[2-(tert-butylsulfamoyl)-4-(isopropoxycarbonylamino)phenyl]thiazol-2-yl]tetrahydropyran-3-yl] carbamate Scheme 21:

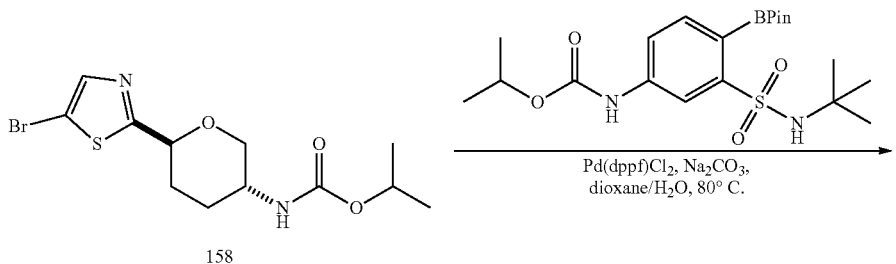

158

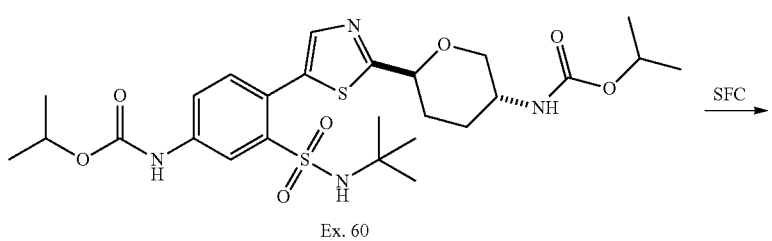

Ex. 60

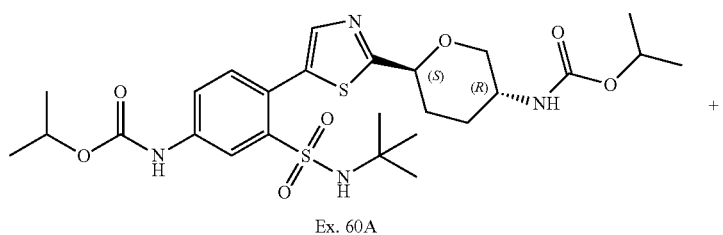

Ex. 60A

+

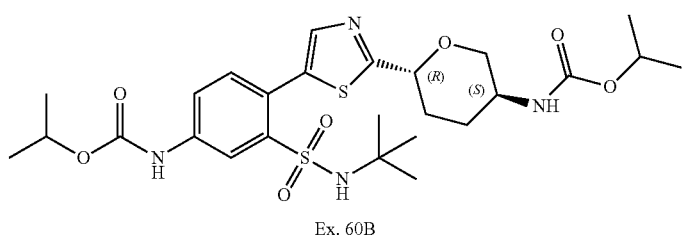

Ex. 60B

Preparation of Ex 60

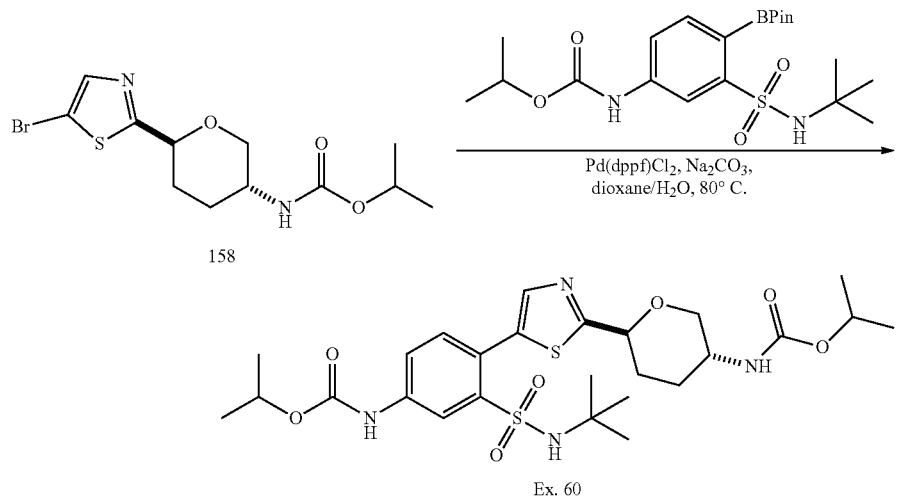

General method B, trans-isopropyl N-[6-[5-[2-(tert-butylsulfamoyl)-4-(isopropoxycarbonylamino)phenyl]thiazol-2-yl]tetrahydropyran-3-yl]carbamate. ¹H NMR (400 MHz, METHANOL-d4) δ=8.37 (d, J=2.0 Hz, 1H), 7.79 (s, 1H), 7.70 (dd, J=2.4, 8.3 Hz, 1H), 7.40 (d, J=8.3 Hz, 1H), 5.01 (spt, J=6.3 Hz, 1H), 4.87-4.79 (m, 1H), 4.68 (dd, J=2.4, 11.2 Hz, 1H), 4.16 (dd, J=2.9, 10.8 Hz, 1H), 3.72-3.60 (m, 1H), 3.38-3.34 (m, 1H), 2.39-2.29 (m, 1H), 2.16 (br d, J=12.2 Hz, 1H), 1.89-1.74 (m, 1H), 1.72-1.59 (m, 1H), 1.39-1.21 (m, 12H), 1.14 (s, 9H). ESI [M+H]=583.3

Preparation of Compound Ex. 60A and Ex 60B

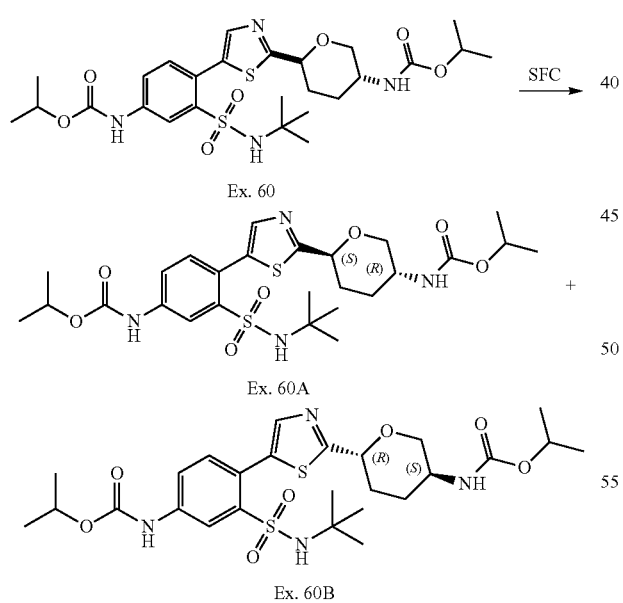

Ex. 60 was further separated by SFC (condition: Instrument: Thar SFC80 preparative SFC; Column: Chiralpak IC-H 250*30 mm i.d. 5u; Mobile phase: A for CO2 and B for MeOH (0.1% NH₃.H₂O); Gradient: B %=38%; Flow rate: 65 g/min; Wavelength:220 nm; Column temperature: 40° C.; System back pressure: 100 bar) to give Ex. 60A: ¹H NMR (400 MHz, METHANOL-d4) δ=8.37 (d, J=2.2 Hz, 1H), 7.78 (s, 1H), 7.70 (dd, J=2.0, 8.4 Hz, 1H), 7.40 (d, J=8.3 Hz, 1H), 5.05-4.95 (m, 1H), 4.90-4.81 (m, 1H), 4.67 (dd, J=2.4, 11.1 Hz, 1H), 4.70-4.64 (m, 1H), 4.16 (br dd, J=2.9, 10.9 Hz, 1H), 3.73-3.62 (m, 1H), 2.33 (br dd, J=2.8, 13.2 Hz, 1H), 2.16 (br d, J=11.9 Hz, 1H), 1.86-1.74 (m, 1H), 1.70-1.61 (m, 1H), 1.34 (d, J=6.2 Hz, 6H), 1.25 (br d, J=6.1 Hz, 6H), 1.14 (s, 9H). ESI [M+H]=583.3

Ex. 60B: ¹H NMR (400 MHz, METHANOL-d4) δ=8.34 (d, J=2.2 Hz, 1H), 7.80-7.72 (m, 1H), 7.67 (dd, J=2.0, 8.6 Hz, 1H), 7.36 (d, J=8.3 Hz, 1H), 4.98 (spt, J=6.2 Hz, 1H), 4.85-4.75 (m, 1H), 4.65 (dd, J=2.4, 11.2 Hz, 1H), 4.13 (br dd, J=3.1, 11.0 Hz, 1H), 3.72-3.56 (m, 1H), 3.33 (s, 1H), 2.30 (br dd, J=2.6, 13.2 Hz, 1H), 2.13 (br d, J=11.4 Hz, 1H), 1.85-1.71 (m, 1H), 1.69-1.57 (m, 1H), 1.31 (d, J=6.1 Hz, 6H), 1.27-1.17 (m, 6H), 1.11 (s, 9H). ESI [M+H]=583.2

Example 61 Synthesis of [1-[5-[4-(benzylcarbamoylamino)-2-(tert-butylsulfamoyl)phenyl]thiazol-2-yl]-4-bicyclo[2.2.2]octanyl]N-isopropylcarbamate Scheme 22:

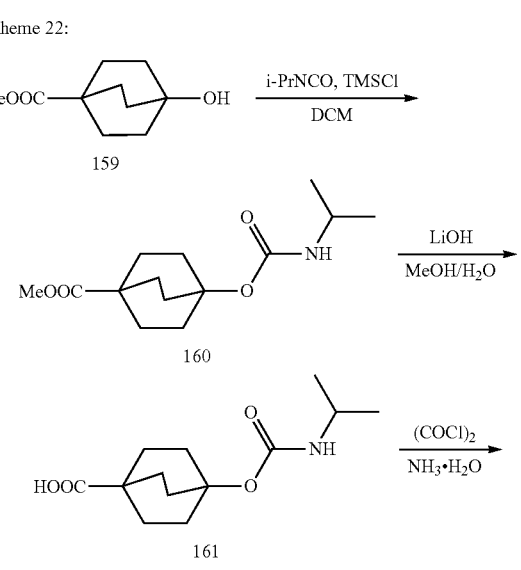

-continued

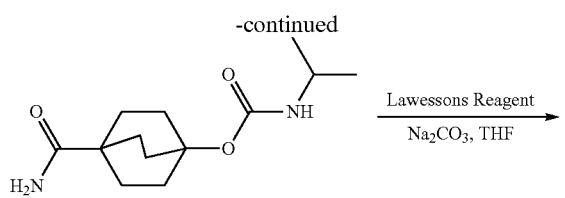

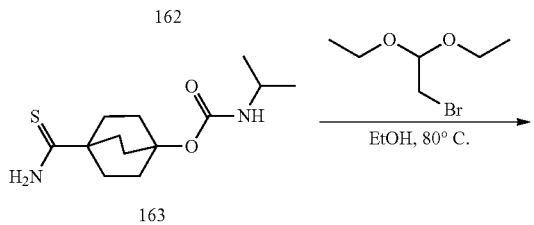

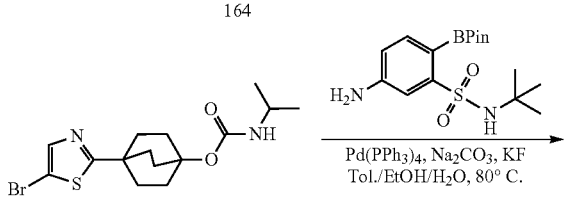

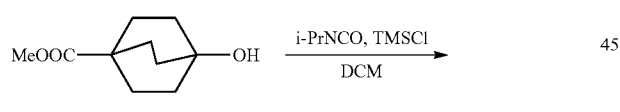

Ex. 61

Preparation of Compound 160.

To a solution of methyl 4-hydroxybicyclo[2.2.2]octane-1-carboxylate (0.4 g, 2.17 mmol, 1 eq.) in DCM (10 mL) were added TMSCl (23.59 mg, 217.12 umol, 0.1 eq.) and 2-isocyanatopropane (554.33 mg, 6.51 mmol, 3 eq.). The mixture was stirred at 25° C. for 12 hrs and then washed with 1 N HCl (20 mL) and sat.aq.Na$_2$CO$_3$ (20 mL). The organic layer was dried over Na$_2$SO$_4$, filtered and concentrated to give methyl 4-(isopropylcarbamoyloxy)bicyclo[2.2.2]octane-1-carboxylate (0.45 g, crude) as a yellow gum. $^1$H NMR (400 MHz, CHLOROFORM-d) δ=4.34 (br s, 1H), 3.72-3.61 (m, 1H), 3.56 (s, 3H), 1.94 (br d, J=7.7 Hz, 6H), 1.90-1.81 (m, 6H), 1.08-1.00 (m, 6H). ESI [M+H]=269.9

Preparation of Compound 161.

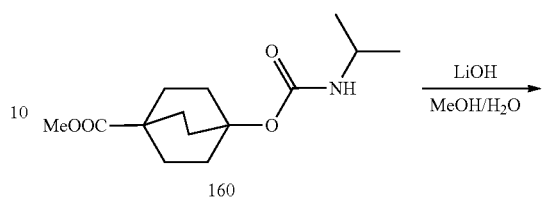

General method O, 4-(isopropylcarbamoyloxy)bicyclo[2.2.2]octane-1-carboxylic acid. $^1$H NMR (400 MHz, CHLOROFORM-d) δ=4.32 (br s, 1H), 3.71-3.60 (m, 1H), 1.93 (br s, 6H), 1.88 (br d, J=9.3 Hz, 6H), 1.05 (d, J=6.5 Hz, 6H). ESI [M+H]=256.0 Preparation of compound 162.

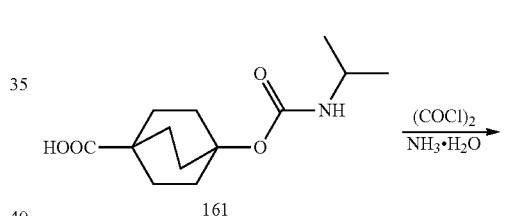

General method N, (1-carbamoyl-4-bicyclo[2.2.2]octanyl)N-isopropylcarbamate. $^1$H NMR (400 MHz, CHLOROFORM-d) δ=5.56-5.31 (m, 2H), 4.34 (br s, 1H), 3.72-3.57 (m, 1H), 1.96 (br s, 6H), 1.97-1.93 (m, 1H), 1.92-1.80 (m, 6H), 1.05 (d, J=6.6 Hz, 6H). ESI [M+H]=255.3

Preparation of Compound 163.

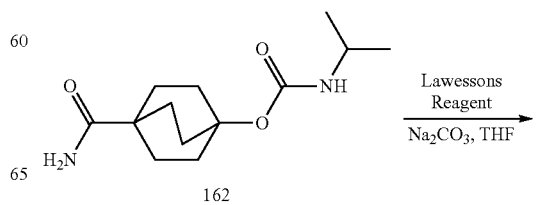

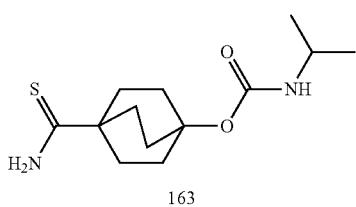

General method L, (1-carbamothioyl-4-bicyclo[2.2.2]oc-tanyl)N-isopropylcarbamate. ESI [M+H]=271.3
Preparation of Compound 164.

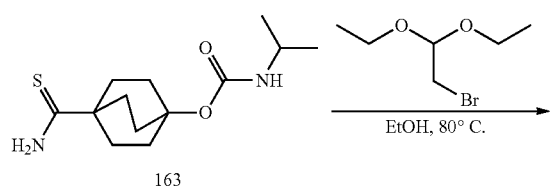

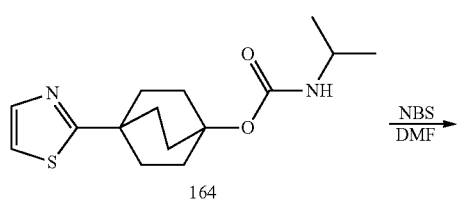

General method M, (1-thiazol-2-yl-4-bicyclo[2.2.2]octa-nyl)N-isopropylcarbamate. ESI [M+H]=295.0
Preparation of Compound 165

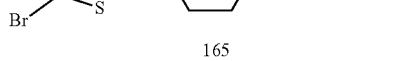

General method J, [1-(5-bromothiazol-2-yl)-4-bicyclo[2.2.2]octanyl]N-isopropylcarbamate. ESI [M+H]=372.8/374.8

Preparation of Ex 61.

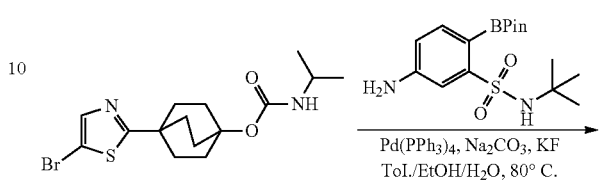

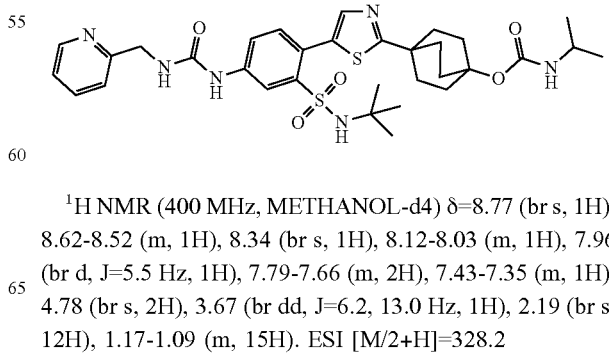

General method K, [1-[5-[4-(benzylcarbamoylamino)-2-(tert-butylsulfamoyl)phenyl]thiazol-2-yl]-4-bicyclo[2.2.2]octanyl]N-isopropylcarbamate. $^1$H NMR (400 MHz, METHANOL-d4) δ=8.26 (d, J=2.2 Hz, 1H), 7.74-7.68 (m, 2H), 7.38-7.32 (m, 4H), 7.30-7.23 (m, 1H), 4.43 (s, 2H), 3.71-3.61 (m, 1H), 2.18 (s, 12H), 1.16-1.09 (m, 15H). ESI [M+H]=654.3

Example 62 Synthesis of 4-(5-(2-(N-(tert-butyl)sulfamoyl)-4-(3-(pyridin-2-ylmethyl)ureido)phenyl)thiazol-2-yl)bicyclo[2.2.2]octan-1-yl isopropylcarbamate The Following Compound was Synthesized Via Same Method by the Key Intermediate 165.

$^1$H NMR (400 MHz, METHANOL-d4) δ=8.77 (br s, 1H), 8.62-8.52 (m, 1H), 8.34 (br s, 1H), 8.12-8.03 (m, 1H), 7.96 (br d, J=5.5 Hz, 1H), 7.79-7.66 (m, 2H), 7.43-7.35 (m, 1H), 4.78 (br s, 2H), 3.67 (br dd, J=6.2, 13.0 Hz, 1H), 2.19 (br s, 12H), 1.17-1.09 (m, 15H). ESI [M/2+H]=328.2

Example 63 Synthesis of trans-isopropyl N-6-[5-[2-(tert-butylsulfamoyl)-4-(isopropoxycarbonylamino)phenyl]thiazol-2-yl-3-piperidyl]carbamate
Scheme 23
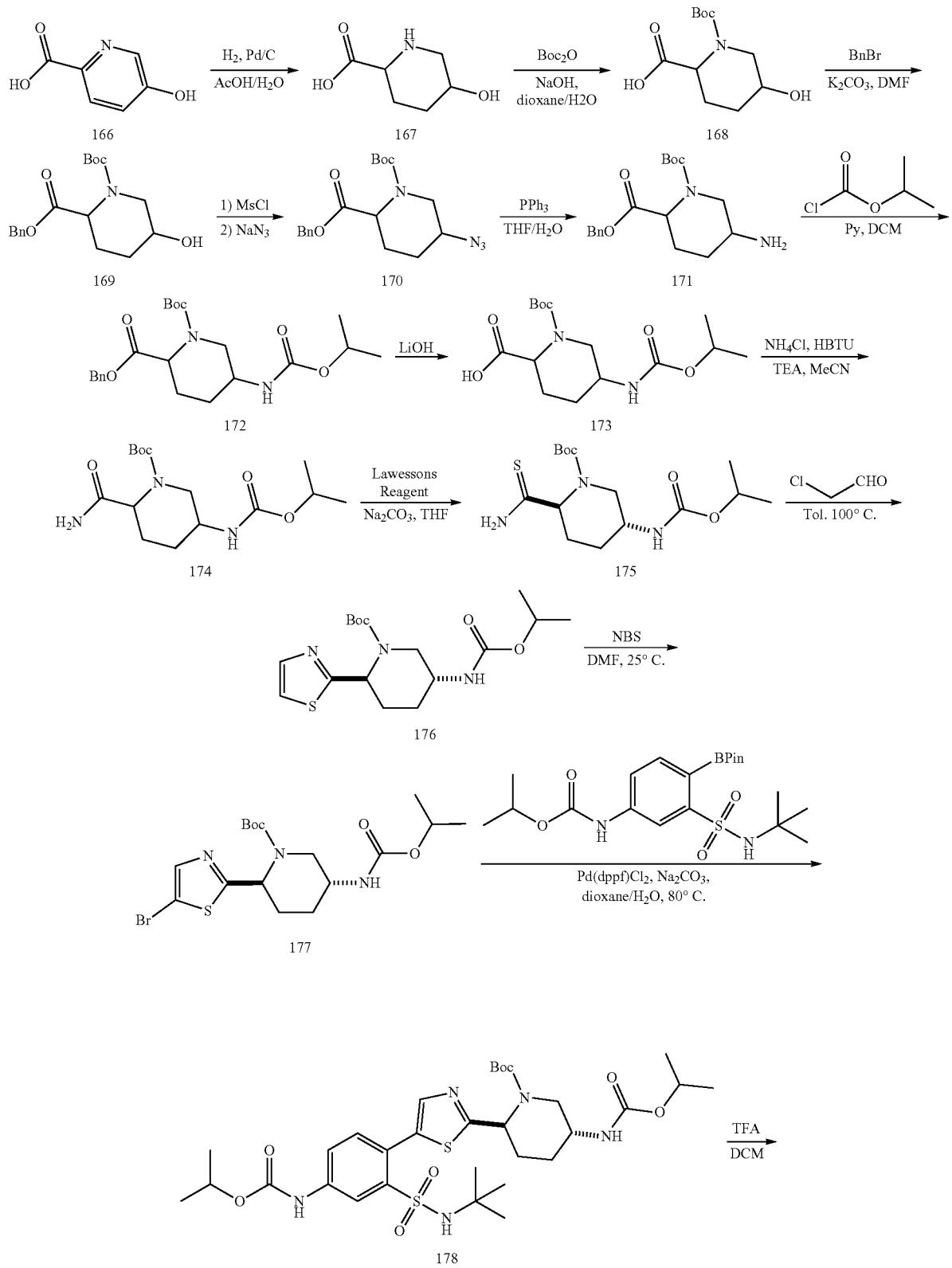

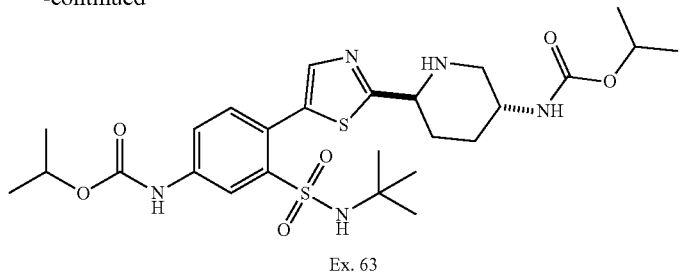

Ex. 63

General Method I for Preparation of Compound 167.

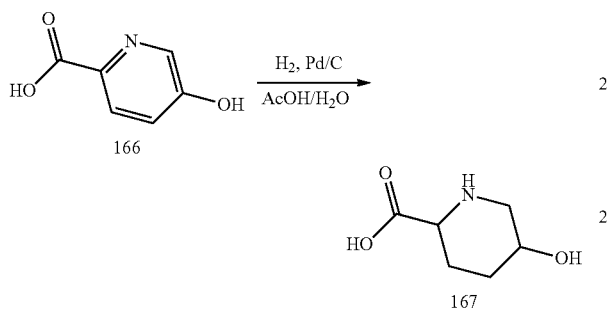

To a solution of 5-hydroxypyridine-2-carboxylic acid (60 g, 431 mmol, 1 eq.) in AcOH (200 mL)/H₂O (600 mL) was added wet Pd/C (2 g, 10% content) under N₂. The suspension was degassed under vacuum and purged with H2 several times. The mixture was stirred under H2 (50 psi) at 50° C. for 12 hrs, then filtered and concentrated to give 5-hydroxypiperidine-2-carboxylic acid (62.61 g, crude) as a yellow oil. ESI [M+H]=146.5

Preparation of Compound 168

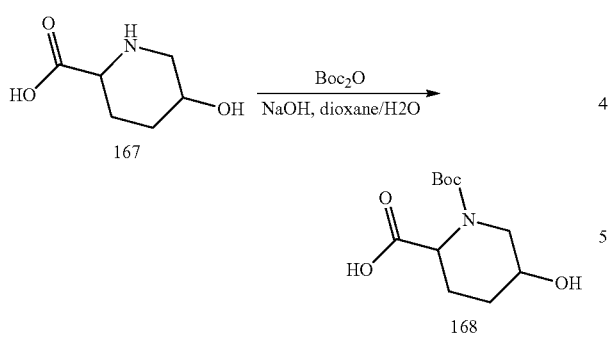

To a mixture of 5-hydroxypiperidine-2-carboxylic acid (62 g, 427.13 mmol, 1 eq.) and Boc₂O (102.54 g, 469.84 mmol, 107.94 mL, 1.1 eq.) in dioxane (500 mL) was added NaOH (34.17 g, 854.25 mmol, 2 eq.) and the mixture was stirred at 25° C. for 18 hrs. The mixture was then concentrated to remove dioxane and the pH was adjusted to 2-3 by addition of 1N HCl solution. The aqueous phase was extracted with 2-Me-THF (500 mL*3). The combined organic layers was dried over Na₂SO₄, filtered and concentrated to give 1-tert-butoxycarbonyl-5-hydroxy-piperidine-2-carboxylic acid (40 g, crude) as yellow oil. ESI [M+Na]= 267.9

Preparation of Compound 169

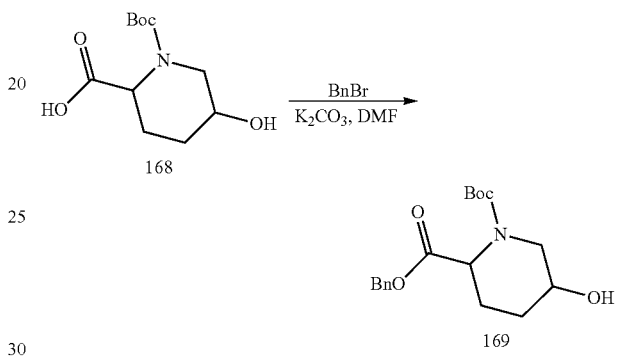

General method A, O₂-benzyl O₁-tert-butyl 5-hydroxypiperidine-1,2-dicarboxylate. ESI [M+Na+]=358.0

Preparation of Compound 170

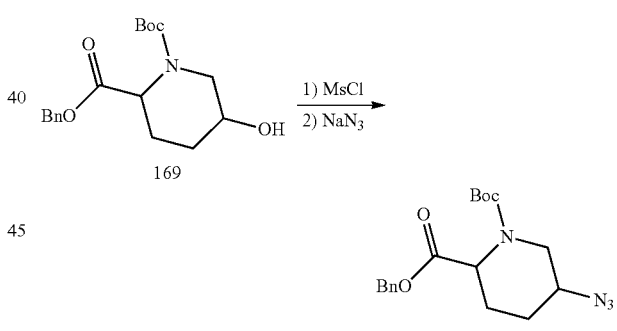

A mixture of O₂-benzyl O1-tert-butyl 5-hydroxypiperidine-1,2-dicarboxylate (10 g, 29.82 mmol, 1 eq.), TEA (3.62 g, 35.78 mmol, 4.98 mL, 1.2 eq.) in DCM (100 mL) was added methanesulfonyl chloride (4.10 g, 35.78 mmol, 2.77 mL, 1.2 eq.) at 0° C. and the mixture was stirred at 25° C. 1 hr. The mixture was then washed with H₂O (50 mL) and the organic layer was dried and concentrated. The residue was purified by column chromatography (SiO₂, Petroleum ether/Ethyl acetate=40/1 to 5:1) to afford O₂-benzyl O1-tert-butyl 5-methylsulfonyloxypiperidine-1,2-dicarboxylate (9.5 g, 18.98 mmol, 63.65% yield, 82.6% purity) as yellow oil.

A mixture of O₂-benzyl O1-tert-butyl 5-methylsulfonyloxypiperidine-1,2-dicarboxylate (9.5 g, 22.98 mmol, 1 eq.), NaN₃ (8.96 g, 137.85 mmol, 6 eq.) in DMF (20 mL) was stirred at 100° C. for 4 hrs. Then the mixture was quenched with sat.aq.Na₂SO₃ (30 mL) and extracted with EtOAc (100 mL*3). The combined organic layers were washed with brine (40 mL*3), dried over Na₂SO₄, filtered and concentrated to give O₂-benzyl O₁-tert-butyl 5-azidopiperidine-1,2-dicarboxylate (8.82 g, crude) as yellow oil.

Preparation of Compound 171

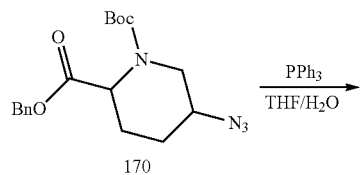

A mixture of O₂-benzyl O1-tert-butyl 5-azidopiperidine-1,2-dicarboxylate (8 g, 22.20 mmol, 1 eq.), triphenylphosphane (8.73 g, 33.30 mmol, 1.5 eq.), in H₂O (50 mL) and THF (50 mL) was stirred at 45° C. for 4 hrs. The mixture was concentrated to remove the THF and pH was adjust to 2-3 by addition of 1N HCl solution. The aqueous phase was extracted with MTBE (30 mL) and then aqueous phase was basified to adjust pH to 9 and extracted with EtOAc (50 mL*3). The combined organic layers were dried over Na₂SO₄ filtered and concentrated to give O₂-benzyl O₁-tert-butyl 5-aminopiperidine-1,2-dicarboxylate (6 g, crude) as yellow oil. ESI [M+H]=335.2

Preparation of Compound 172

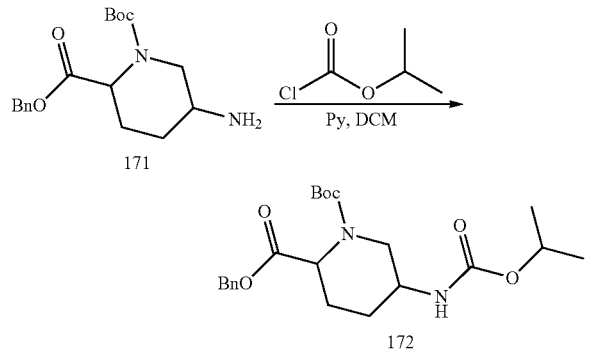

General method D, O₂-benzyl O1-tert-butyl 5-(isopropoxycarbonylamino)piperidine-1,2-dicarboxylate. ESI [M+H]=421.2 Preparation of compound 173

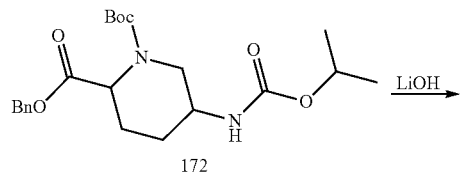

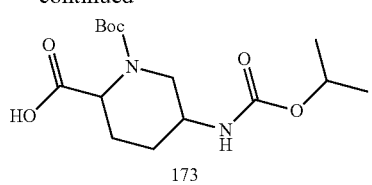

General method O, 1-tert-butoxycarbonyl-5-isopropoxycarbonyloxy-piperidine-2-carboxylic acid. ESI [M+H]= 331.2

Preparation of Compound 174

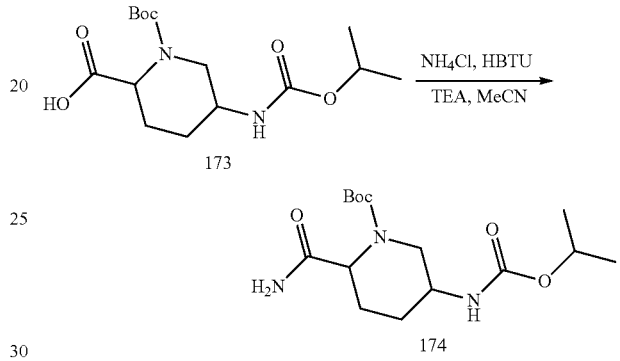

A mixture of 1-tert-butoxycarbonyl-5-(isopropoxycarbonylamino)piperidine-2-carboxylic acid (1.3 g, 3.93 mmol, 1 eq.), NH₄Cl (315.73 mg, 5.90 mmol, 1.5 eq.), TEA (1.19 g, 11.80 mmol, 1.64 mL, 3 eq.) and HBTU (1.64 g, 4.33 mmol, 1.1 eq.) in ACN (10 mL) as stirred at 25° C. for 2 hrs and then concentrated. The mixture was then poured into H₂O (20 mL) and extracted with EtOAc (20 ml*3). The combined organic layers were dried over Na₂SO₄, filtered and concentrated. The mixture was purified by prep-HPLC (column: Phenomenex Gemini C18 250*50 10u; mobile phase: [water (0.05% ammonia hydroxide v/v)-ACN]; B %: 10%-40%,20 min) to give tert-butyl 2-carbamoyl-5-(isopropoxycarbonylamino)piperidine-1-carboxylate (1 g, 3.01 mmol, 76.38% yield, 99% purity) as a white solid. ESI [M+H]=330.2

Preparation of Compound 175

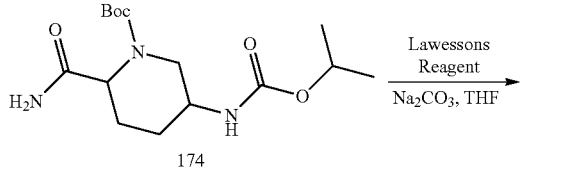

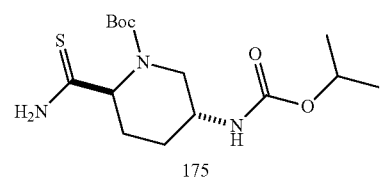

General method L, trans-tert-butyl 2-carbamothioyl-5-(isopropoxycarbonylamino) piperidine-1-carboxylate. ESI [M+H]=346.1

Preparation of Compound 176

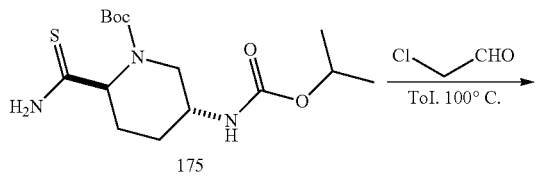

To a solution of trans-tert-butyl 2-carbamothioyl-5-(isopropoxycarbonylamino) piperidine-1-carboxylate (650 mg, 1.88 mmol, 1.0 eq.) in tol. (20 mL) were added BUFFER (784.76 mg, 2.82 mmol, 1.5 eq.) and 2-chloroacetaldehyde (3.69 g, 18.82 mmol, 3.03 mL, 10 eq.).

The mixture was stirred at 100° C. for 1.5 hrs and then poured into water (20 mL) and extracted with EtOAc (10 mL×3). The combined organic phase was dried over Na$_2$SO$_4$, filtered and concentrated. The residue was purified by basic prep-HPLC to give trans-tert-butyl 5-(isopropoxycarbonylamino)-2-thiazol-2-yl-piperidine-1-carboxylate (80 mg, 216.52 umol, 11.51% yield) as a yellow solid. $^1$H NMR (400 MHz, METHANOL-d4) δ=7.75 (d, J=3.4 Hz, 1H), 7.58 (d, J=2.9 Hz, 1H), 5.60 (br s, 1H), 4.95-4.90 (m, 1H), 4.23 (br d, J=14.7 Hz, 1H), 3.68 (br s, 1H), 3.11-2.94 (m, 1H), 2.42-2.31 (m, 1H), 2.30-2.17 (m, 1H), 1.93-1.79 (m, 1H), 1.75-1.64 (m, 1H), 1.50 (s, 9H), 1.30-1.23 (m, 6H)

Preparation of Compound 177

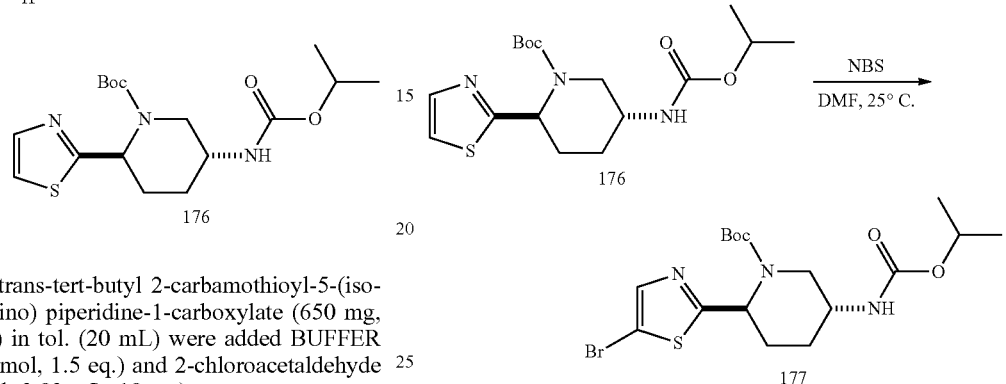

General method J, trans-tert-butyl 2-(5-bromothiazol-2-yl)-5-(isopropoxycarbonyl amino)piperidine-1-carboxylate. ESI [M+H]=450.2/448.2 Preparation of compound 178

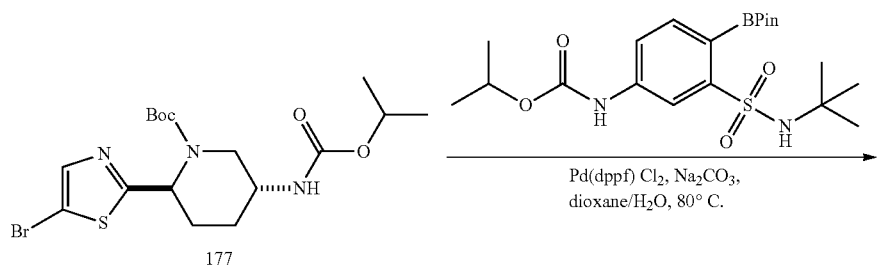

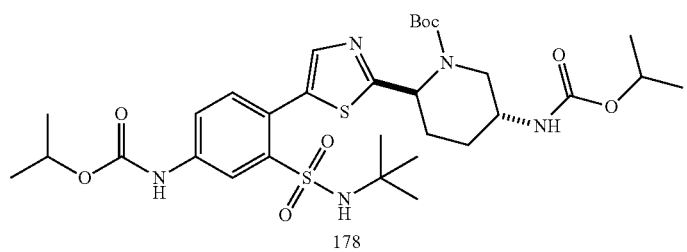

General method B, trans-tert-butyl 2-[5-[2-(tert-butylsulfamoyl)-4-(isopropoxycarbonylamino)phenyl]thiazol-2-yl]-5-(isopropoxycarbonylamino)piperidine-1-carboxylate. ESI [M+H]=682.3

Preparation of Ex 63

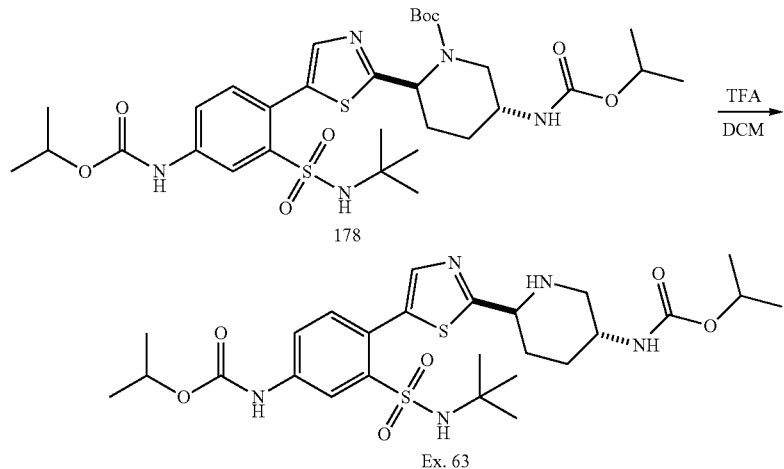

General method C, trans-isopropyl N-[6-[5-[2-(tert-butylsulfamoyl)-4-(isopropoxycarbonylamino)phenyl]thiazol-2-yl]-3-piperidyl]carbamate. $^1$H NMR (400 MHz, METHANOL-d4) δ=8.40 (d, J=2.0 Hz, 1H), 7.86 (s, 1H), 7.65 (dd, J=2.2, 8.4 Hz, 1H), 7.38 (d, J=8.4 Hz, 1H), 5.05-4.94 (m, 1H), 4.85-4.81 (m, 1H), 4.67 (dd, J=2.9, 11.9 Hz, 1H), 3.92-3.82 (m, 1H), 3.60 (br dd, J=3.6, 11.8 Hz, 1H), 2.92 (t, J=11.9 Hz, 1H), 2.48 (br dd, J=3.2, 14.2 Hz, 1H), 2.22-2.03 (m, 2H), 1.82-1.70 (m, 1H), 1.32 (d, J=6.4 Hz, 6H), 1.24 (br d, J=6.2 Hz, 6H), 1.19 (s, 9H). ESI [M+H]=582.2

Example 64 Synthesis of isopropyl((3R,6S)-6-(5-(4-(3-benzylureido)-2-(N-(tert-butyl)sulfamoyl)phenyl)thiazol-2-yl)piperidin-3-yl)carbamate The Following Compound was Synthesized Via Same Method by the Key Intermediate 178.

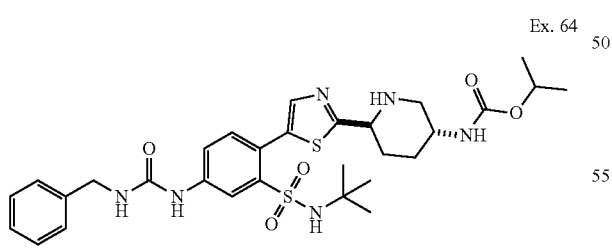

$^1$H NMR (400 MHz, METHANOL-d4) δ=8.30 (d, J=2.2 Hz, 1H), 7.86 (s, 1H), 7.66 (dd, J=2.2, 8.4 Hz, 1H), 7.38-7.20 (m, 6H), 4.85-4.82 (m, 1H), 4.70 (dd, J=3.2, 12.0 Hz, 1H), 4.42 (s, 2H), 3.93-3.82 (m, 1H), 3.62 (br dd, J=3.5, 11.7 Hz, 1H), 3.00-2.90 (m, 1H), 2.52-2.44 (m, 1H), 2.23-2.04 (m, 2H), 1.84-1.70 (m, 1H), 1.26-1.21 (m, 6H), 1.18 (s, 9H). ESI [M+H]=629.2

Example 65 Synthesis of isopropyl N-[3-(tert-butylsulfamoyl)-4-[2-[3-(isopropoxycarbonyl amino)cyclobutyl]thiazol-5-yl]phenyl]carbamate Scheme 24

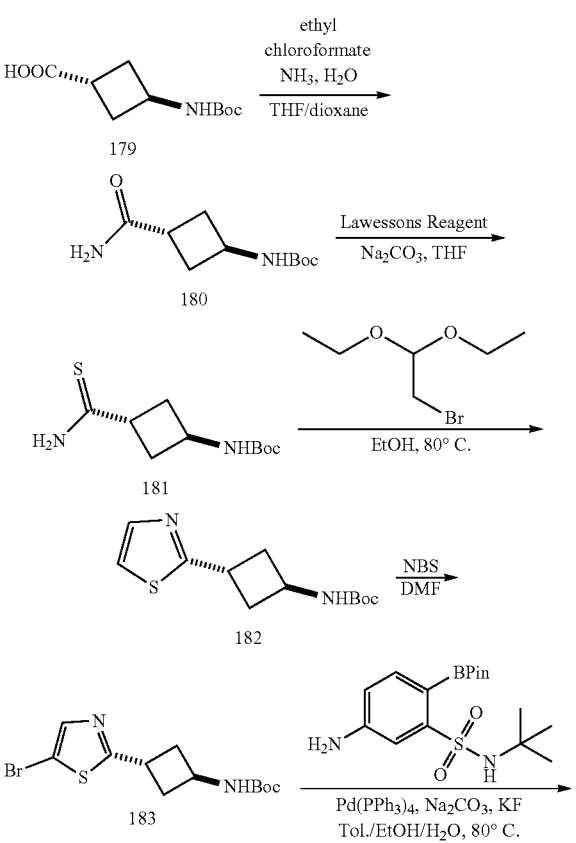

-continued

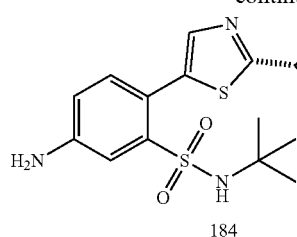

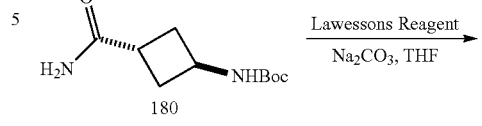

Preparation of Compound 181

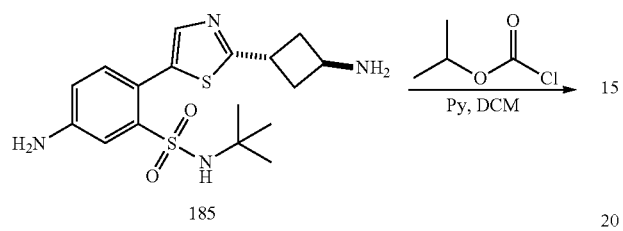

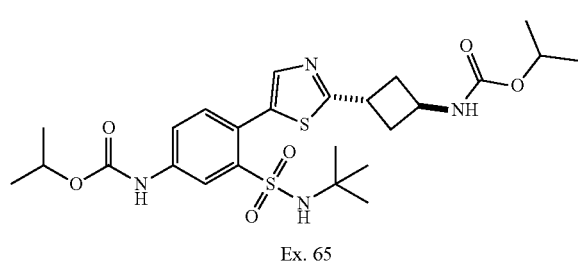

Ex. 65

Preparation of Compound 180

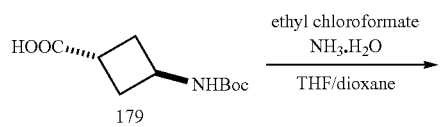

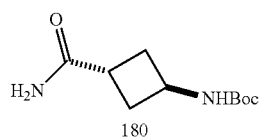

To a solution of trans-3-(tert-butoxycarbonylamino)cyclobutanecarboxylic acid (500 mg, 2.32 mmol, 1 eq.), DIEA (750.54 mg, 5.81 mmol, 1.01 mL, 2.5 eq.) in THF (10 mL) was added ETHYL CHLOROFORMATE (277.29 mg, 2.56 mmol, 1.1 eq.) and the mixture was stirred 0° C. for 1 hr. Then it was added into NH$_3$.H$_2$O (1.30 g, 9.29 mmol, 1.43 mL, 25% purity, 4 eq.) in THF (10 mL) and dioxane (10 mL) and the mixture was stirred at 25° C. for 1 hr. The mixture was washed with 1N HCl (20 mL), sat.aq.Na$_2$CO$_3$ (20 mL) and the organic phase was dried over Na$_2$SO$_4$, filtered and concentrated to give trans-tert-butyl N-(3-carbamoylcyclobutyl) carbamate (0.39 g, crude) as a white solid. $^1$H NMR (400 MHz, DMSO-d6) δ=7.20-7.07 (m, 2H), 6.71 (br s, 1H), 4.09-4.00 (m, 1H), 2.72 (br t, J=9.3 Hz, 1H), 2.23 (br t, J=8.7 Hz, 2H), 2.01 (q, J=9.8 Hz, 2H), 1.34 (s, 9H. ESI [M+Na]=237.1

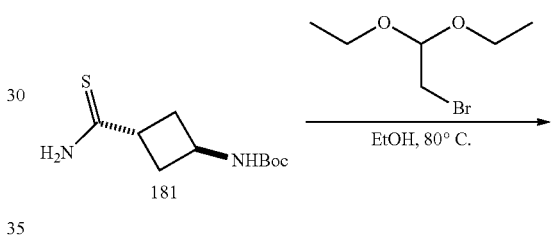

General method L, trans-tert-butyl N-(3-carbamothioyl-cyclobutyl)carbamate. 1H NMR (400 MHz, DMSO-d6) δ=9.33 (br s, 1H), 9.02 (br s, 1H), 7.18 (br d, J=5.5 Hz, 1H), 4.16-4.03 (m, 1H), 3.33 (br s, 1H), 2.45 (br d, J=12.2 Hz, 2H), 2.15 (br d, J=6.5 Hz, 2H), 1.37 (br s, 9H)

Preparation of Compound 182

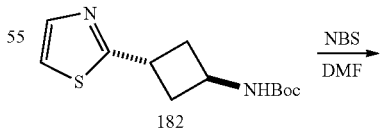

General method M, trans-tert-butyl N-(3-thiazol-2-ylcyclobutyl)carbamate. $^1$H NMR (400 MHz, CHLOROFORM-d) δ=7.62 (d, J=3.2 Hz, 1H), 7.14 (dd, J=3.3, 8.3 Hz, 1H), 4.79 (br s, 1H), 4.34 (br s, 1H), 3.47-3.36 (m, 1H), 2.81 (br d, J=8.8 Hz, 1H), 2.66 (ddd, J=4.5, 7.9, 12.8 Hz, 1H), 2.46-2.34 (m, 1H), 2.17-2.09 (m, 1H), 1.38 (s, 9H). ESI[M+H]=255.3

Preparation of Compound 183

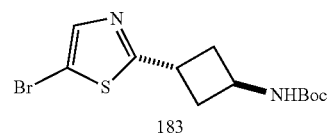

General method J, trans-tert-butyl N-[3-(5-bromothiazol-2-yl)cyclobutyl]carbamate. ESI[M+H]=335.1/333.1

Preparation of Compound 184

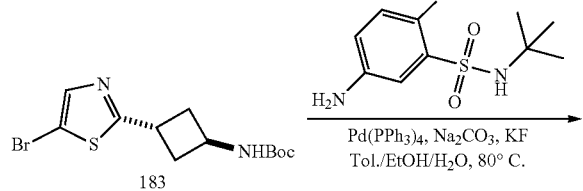

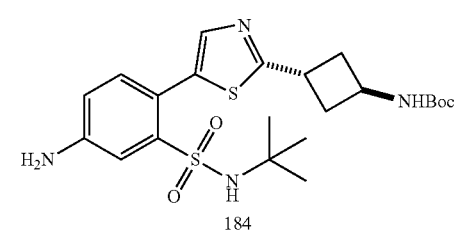

184

General method K, trans-tert-butyl N-[3-[5-[4-amino-2-(tert-butylsulfamoyl)phenyl]thiazol-2-yl]cyclobutyl]carbamate. ESI [M+H]=481.0

Preparation of Compound 185

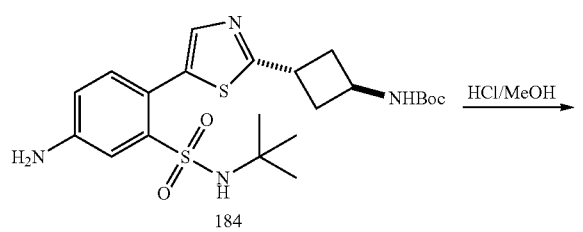

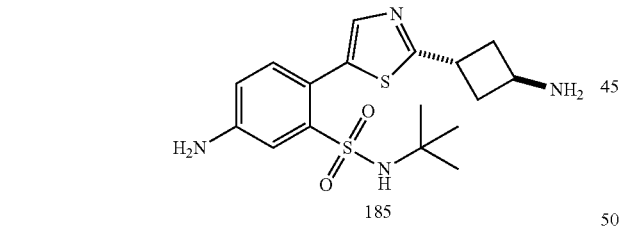

185

General method F, trans-5-amino-2-[2-(3-aminocyclobutyl)thiazol-5-yl]-N-tert-butyl-benzenesulfonamide. ESI [M+H]=381.2

Preparation of Ex 65

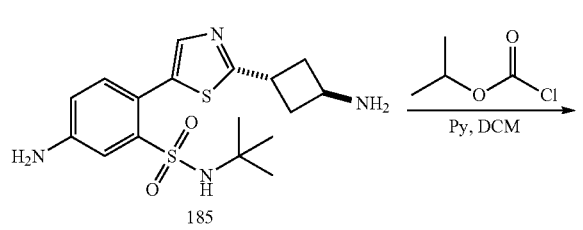

185

-continued

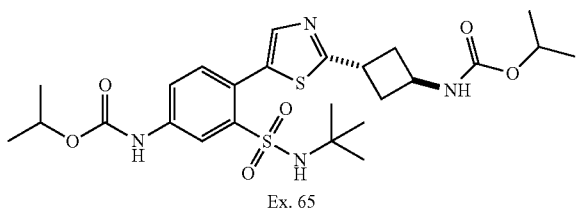

Ex. 65

General method D, isopropyl N-[3-(tert-butylsulfamoyl)-4-[2-[3-(isopropoxycarbonylamino)cyclobutyl]thiazol-5-yl]phenyl]carbamate. $^1$H NMR (400 MHz, METHANOL-d4) δ=8.34 (d, J=1.5 Hz, 1H), 7.76-7.65 (m, 2H), 7.38 (t, J=8.5 Hz, 1H), 5.04-4.94 (m, 1H), 4.82 (br d, J=6.4 Hz, 1H), 4.42-4.32 (m, 0.5H), 4.13 (br t, J=8.0 Hz, 0.5H), 3.87-3.78 (m, 0.5H), 3.58-3.48 (m, 0.5H), 2.82 (dq, J=2.6, 7.9 Hz, 1H), 2.72-2.64 (m, 1H), 2.60-2.50 (m, 1H), 2.34-2.23 (m, 1H), 1.31 (d, J=6.2 Hz, 6H), 1.22 (br d, J=6.0 Hz, 6H), 1.13 (s, 9H). ESI [M+H]=553.4

Examples 66A and 66B

Scheme 25

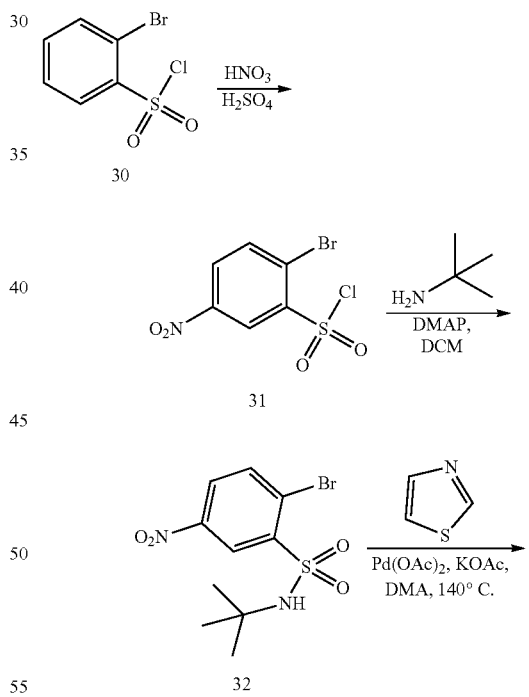

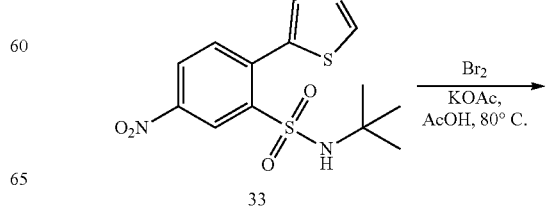

33

-continued

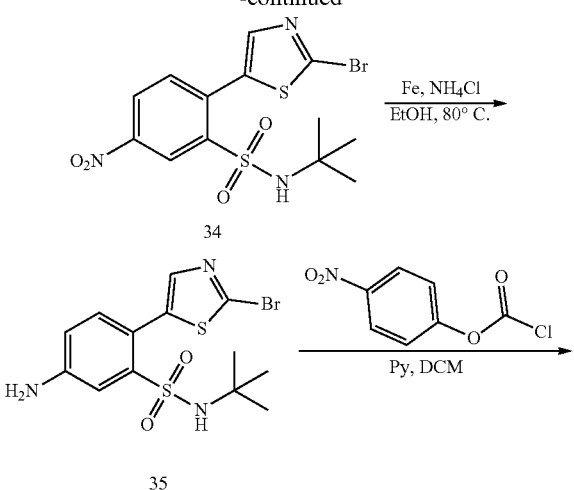

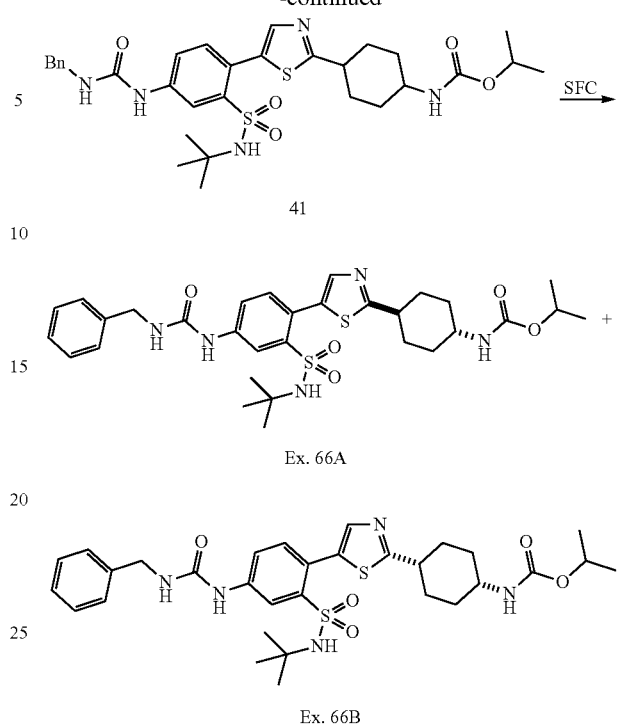

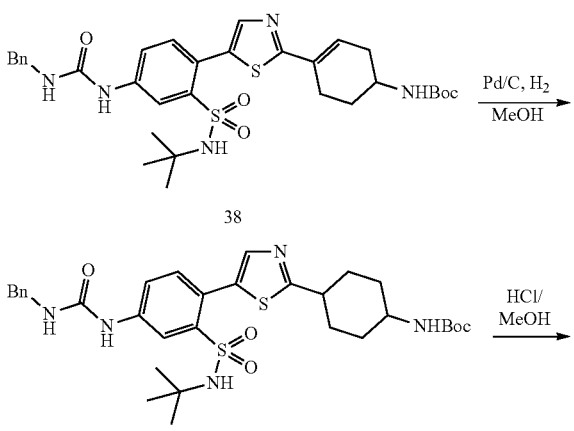

Preparation of compound 31.

To a solution of 2-bromobenzenesulfonyl chloride (100.00 g, 391.36 mmol, 1.00 eq.) in $H_2SO_4$ (1.0 L) was added a solution of $HNO_3$ (79.95 g, 1.21 mol, 57.11 mL, 95% purity, 3.08 eq.) in $H_2SO_4$ (0.50 L) drop-wise at 0° C. The mixture was stirred at 26° C. for 2 hrs. TLC (Petroleum ether:EtOAc=10:1, Rf=0.40) showed the reaction was complete. The mixture was added slowly to ice water (5 L) with vigorous stirring and then filtered. The filter cake was washed with $H_2O$ (1 L×3) and dried to give 2-bromo-5-nitro-benzenesulfonyl chloride (105.00 g, crude) as a yellow solid. $^1H$ NMR (400 MHz, CHLOROFORM-d) δ=8.98 (d, J=2.4 Hz, 1H), 8.37 (dd, J=2.5, 8.7 Hz, 1H), 8.09 (d, J=8.6 Hz, 1H).

Preparation of Compound 32.

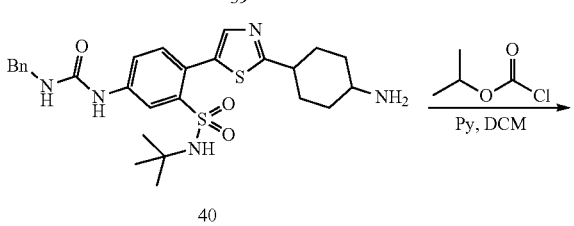

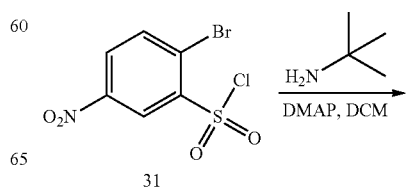

-continued

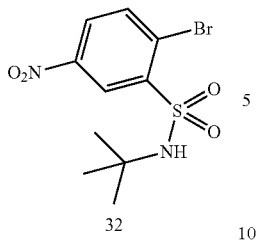

To a mixture of 2-methylpropan-2-amine (200 g, 2.73 mol, 287.36 mL, 3.29 eq.) and DMAP (10 g, 81.85 mmol, 0.1 eq.) in DCM (2 L) was added 2-bromo-5-nitro-benzenesulfonyl chloride (250 g, 831.91 mmol, 1 eq.) portionwise at 0° C. The mixture was warmed to 15° C. and stirred for 1 hr. LCMS showed the reaction was complete. The mixture was washed with HCl (1 N, 2 L), sat.aq. NaHCO$_3$ (500 mL) and brine (500 mL), dried over Na$_2$SO$_4$, filtered and concentrated to give 2-bromo-N-tert-butyl-5-nitro-benzenesulfonamide (240 g, crude) as a gray solid. ESI [M+H]=336.9/338.9.

Preparation of Compound 33.

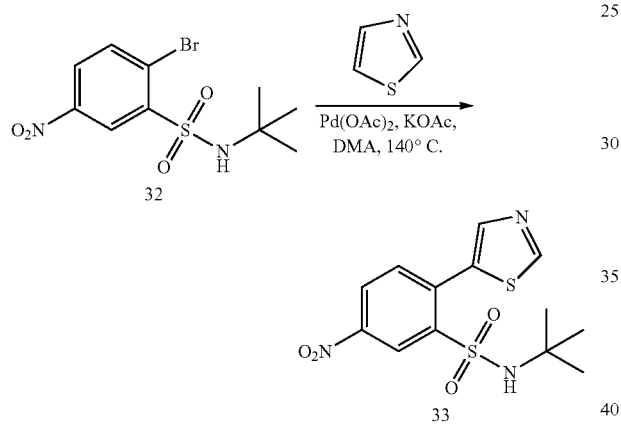

To a solution of 2-bromo-N-tert-butyl-5-nitro-benzenesulfonamide (35 g, 103.80 mmol, 1 eq.) in DMA (300 mL), were added thiazole (26.51 g, 311.40 mmol, 3 eq.), Pd(OAc)$_2$ (2.33 g, 10.38 mmol, 0.1 eq.) and KOAc (30.56 g, 311.40 mmol, 3 eq.). The mixture was stirred at 140° C. for 16 hrs under N$_2$. LCMS showed the reaction was complete, the mixture was poured into water (3 L) and filtered. The filter cake was washed with water (200 mL×3) and then dried to give N-tert-butyl-5-nitro-2-thiazol-5-yl-benzenesulfonamide (25.1 g, crude) as a black brown solid. $^1$H NMR (400 MHz, DMSO-d6) δ=9.30 (s, 1H), 8.81 (d, J=2.4 Hz, 1H), 8.46 (dd, J=2.4, 8.3 Hz, 1H), 8.12 (s, 1H), 7.83 (d, J=8.3 Hz, 1H), 7.60 (s, 1H), 1.07 (s, 9H). ESI [M+H]=342.0.

Preparation of Compound 34.

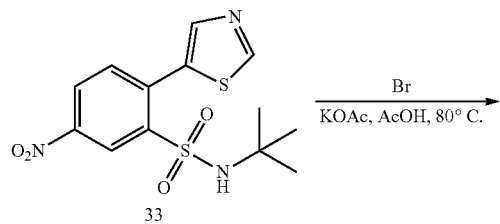

-continued

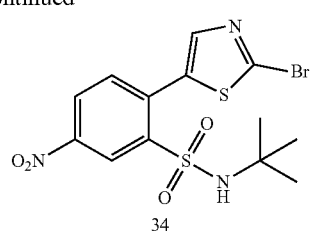

To a solution of N-tert-butyl-5-nitro-2-thiazol-5-yl-benzenesulfonamide (15 g, 43.94 mmol, 1 eq.) in AcOH (200 mL), were added KOAc (21.56 g, 219.68 mmol, 5 eq.) and Br$_2$ (35.11 g, 219.68 mmol, 5 eq.). The mixture was stirred at 80° C. for 3 hrs. LCMS showed the reaction was complete, the mixture was quenched by sat.aq.Na$_2$CO$_3$ (1 L) and extracted with EtOAc (300 mL×3). The combined organic phase was dried over Na$_2$SO$_4$, filtered and concentrated to give 2-(2-bromothiazol-5-yl)-N-tert-butyl-5-nitro-benzenesulfonamide (18 g, crude) as a green solid which was used without any purification.

Preparation of Compound 35.

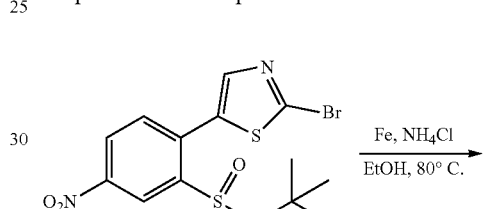

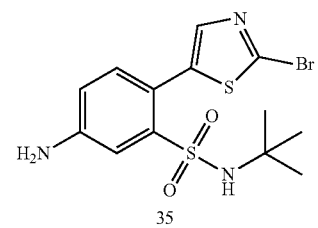

To a solution of 2-(2-bromothiazol-5-yl)-N-tert-butyl-5-nitro-benzenesulfonamide (8.5 g, 20.22 mmol, 1 eq.) in EtOH (70 mL), THF (40 mL) and H$_2$O (20 mL), were added Fe (3.39 g, 60.67 mmol, 3 eq.) and NH$_4$Cl (3.25 g, 60.67 mmol, 2.12 mL, 3 eq.). The mixture was stirred at 90° C. for 1 hr. LCMS showed the reaction was complete. The mixture was filtered, the filtrate was concentrated to remove organic solvent and extracted with DCM (200 mL×2). The organic phase was dried over Na$_2$SO$_4$, filtered and concentrated to afford 5-amino-2-(2-bromothiazol-5-yl)-N-tert-butyl-benzenesulfonamide (6 g, crude) as a yellow solid. $^1$HNMR showed the structure was correct. 1H NMR (400 MHz, DMSO-d6) δ=7.58-7.52 (m, 1H), 7.30 (d, J=2.4 Hz, 1H), 7.11 (d, J=8.3 Hz, 1H), 6.99 (s, 1H), 6.73 (dd, J=2.4, 8.3 Hz, 1H), 5.94 (s, 2H), 1.07 (s, 9H). ESI [M+H]=390.0/392.0.

Preparation of Compound 36.
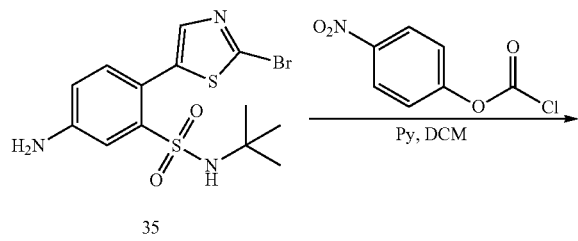
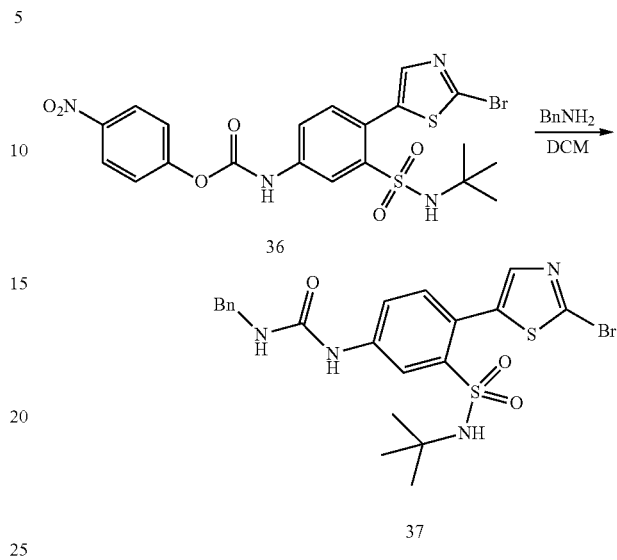
General method D, (4-nitrophenyl)N-[4-(2-bromothiazol-5-yl)-3-(tert-butylsulfamoyl)phenyl]carbamate as DCM solution ESI [M+H]=555.0/557.0
Preparation of Compound 37.
General method H, 1-benzyl-3-[4-(2-bromothiazol-5-yl)-3-(tert-butylsulfamoyl)phenyl]urea. ESI [M+H]=523.0/525.0.
Preparation of Compound 38.
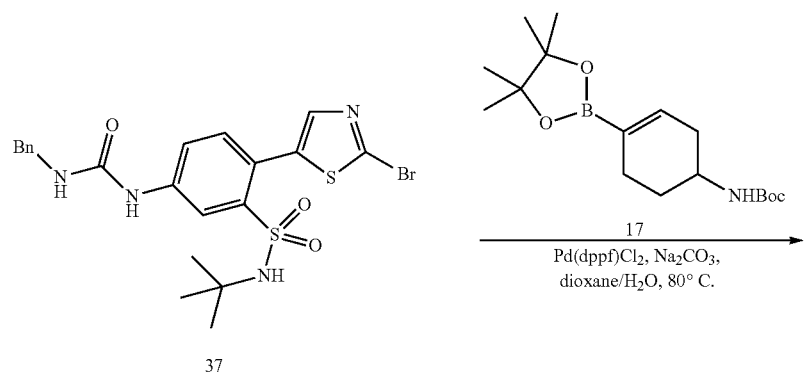
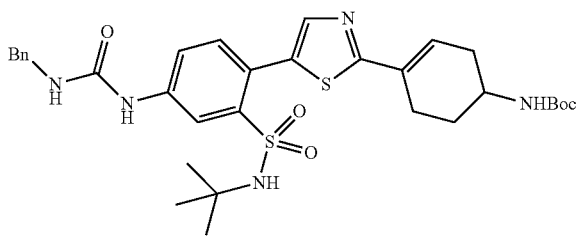

General method B (Suzuki reaction), tert-butyl-N-[4-[5-[4-(benzylcarbamoylamino)-2-(tert-butylsulfamoyl)phenyl]thiazol-2-yl]cyclohex-3-en-1-yl]carbamate (Compound 38). To a solution of Compound 17 (1 eq.) in dioxane and H$_2$O, were added Pd(dppf)Cl$_2$ (0.1 eq.), Compound 37 (0.9 eq.) and Na$_2$CO$_3$ (3 eq.). The mixture was stirred at 80° C. for 12 hrs under N$_2$. LCMS showed the reaction was complete. The mixture was concentrated and the residue was purified by prep-TLC (PE/EtOAc=1:1) to yield product 38. ESI [M+H]= 640.5

Preparation of Compound 39.

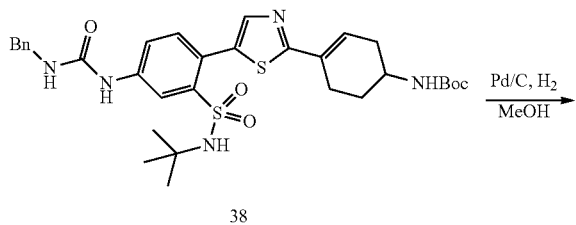

38

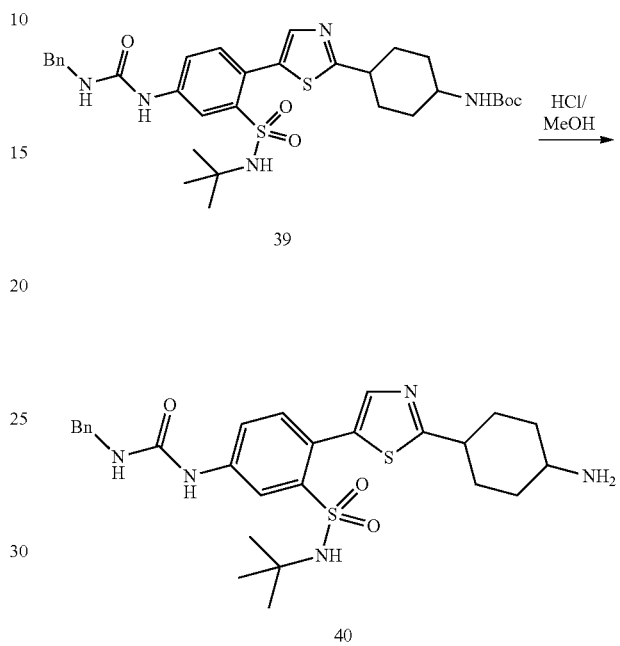

39 tert-butyl N-[4-[5-[4-(benzylcarbamoylamino)-2-(tert-butylsulfamoyl)phenyl]thiazol-2-yl]cyclohexyl]carbamate To a solution of Compound 38 (1 eq.) and AcOH (0.1 eq.) in EtOAc was added Pd/C (10% purity, 1.00 eq.). The mixture was stirred under H$_2$ (15 psi) at 40° C. for 1 hr. LCMS showed the reaction was complete and then the mixture was filtered and concentrated. The residue was purified by column chromatography (SiO$_2$, Petroleum ether/Ethyl acetate=10/1 to 1:1) to give Compound 39. ESI [M+H]=642.5

Preparation of Compound 40.

39

40

General method F, 1-[4-[2-(4-aminocyclohexyl)thiazol-5-yl]-3-(tert-butylsulfamoyl)phenyl]-3-benzyl-urea. ESI [M+H]=542.5.

Preparation of Compound 41

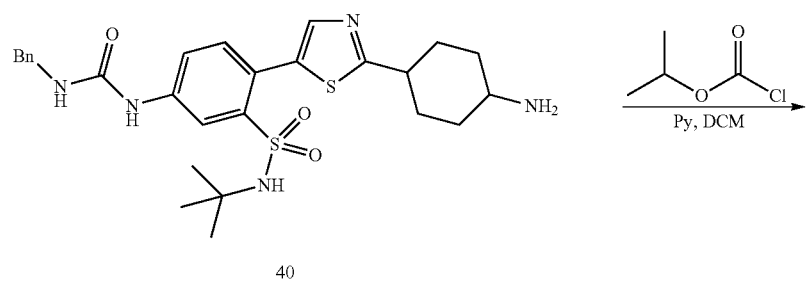

40

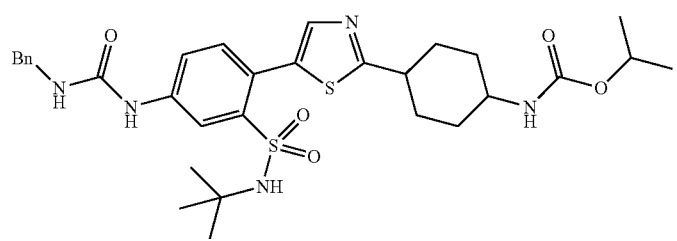

41

General method D, isopropyl N-[4-[5-[4-(benzylcarbamoylamino)-2-(tert-butylsulfamoyl)phenyl]thiazol-2-yl]cyclohexyl]carbamate, ESI [M+H]=628.3.

Preparation of Compound Ex. 66A and Ex 66B.

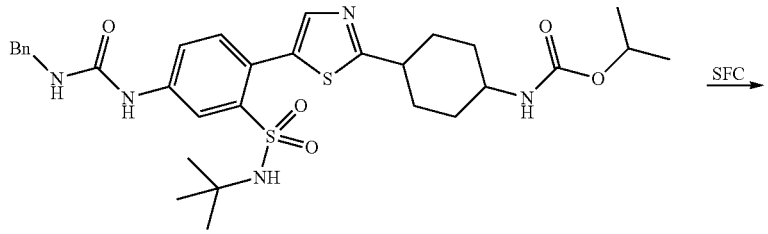

41

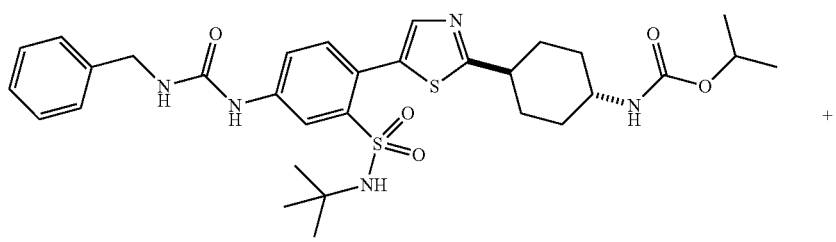

Ex. 66A

+

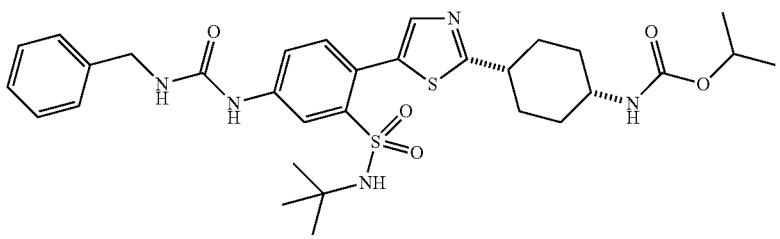

Ex. 66B

Compound 41 was separated by SFC (Instrument: Thar SFC80 preparative SFC; Column: Chiralpak AD-H 250*30 mm i.d. 5u; Mobile phase: A for $CO_2$ and B for IPA (0.1% $NH_3H_2O$); Gradient: B %=42%; Flow rate: 70 g/min; Wavelength: 220 nm; Column temperature: 40° C.; System back pressure: 100 bar; Cycle time: 20 min; Injection amount: 4 mg per injection), and then purified by prep-HPLC (Column: Luna C18 100*30 5u; mobile phase: [water (0.1% TFA)-ACN]; B %: 35%-75%,5 min). trans-isopropyl N-[4-[5-[4-(benzylcarbamoylamino)-2-(tert-butylsulfamoyl)phenyl]thiazol-2-yl]cyclohexyl]carbamate Ex. 66A (11.54 mg, 18.38 umol, 5.53% yield, 100% purity) and cis-isopropyl N-[4-[5-[4-(benzylcarbamoylamino)-2-(tert-butylsulfamoyl)phenyl]thiazol-2-yl]cyclohexyl]carbamate Ex. 66B (9.38 mg, 14.94 umol, 4.50% yield, 100% purity) were obtained.

Trans-isopropyl N-[4-[5-[4-(benzylcarbamoylamino)-2-(tert-butylsulfamoyl)phenyl]thiazol-2-yl]cyclohexyl]carbamate, $^1$H NMR (400 MHz, METHANOL-d4) δ=8.24 (d, J=2.2 Hz, 1H), 7.72 (s, 1H), 7.69 (dd, J=2.6, 8.3 Hz, 1H), 7.37-7.30 (m, 5H), 7.27-7.22 (m, 1H), 4.85-4.78 (m, 1H), 4.41 (s, 2H), 3.50-3.39 (m, 1H), 3.06-2.96 (m, 1H), 2.22 (br d, J=11.8 Hz, 2H), 2.07 (br d, J=10.1 Hz, 2H), 1.76-1.62 (m, 2H), 1.41 (dq, J=3.1, 12.7 Hz, 2H), 1.22 (br d, J=6.1 Hz, 6H), 1.11 (s, 9H). ESI [M+H]=628.2.

Cis-isopropyl N-[4-[5-[4-(benzylcarbamoylamino)-2-(tert-butylsulfamoyl)phenyl]thiazol-2-yl]cyclohexyl]carbamate. $^1$H NMR (400 MHz, METHANOL-d4) δ=8.25 (d, J=2.2 Hz, 1H), 7.74 (s, 1H), 7.70 (dd, J=2.2, 8.3 Hz, 1H), 7.38-7.30 (m, 5H), 7.28-7.22 (m, 1H), 4.82 (br d, J=6.1 Hz, 1H), 4.41 (s, 2H), 3.74 (br s, 1H), 3.20-3.13 (m, 1H), 2.03-1.95 (m, 4H), 1.86-1.72 (m, 4H), 1.23 (d, J=6.1 Hz, 6H), 1.12 (s, 9H). ESI [M+H]=628.2.

Examples 67A and 67B
Scheme 26
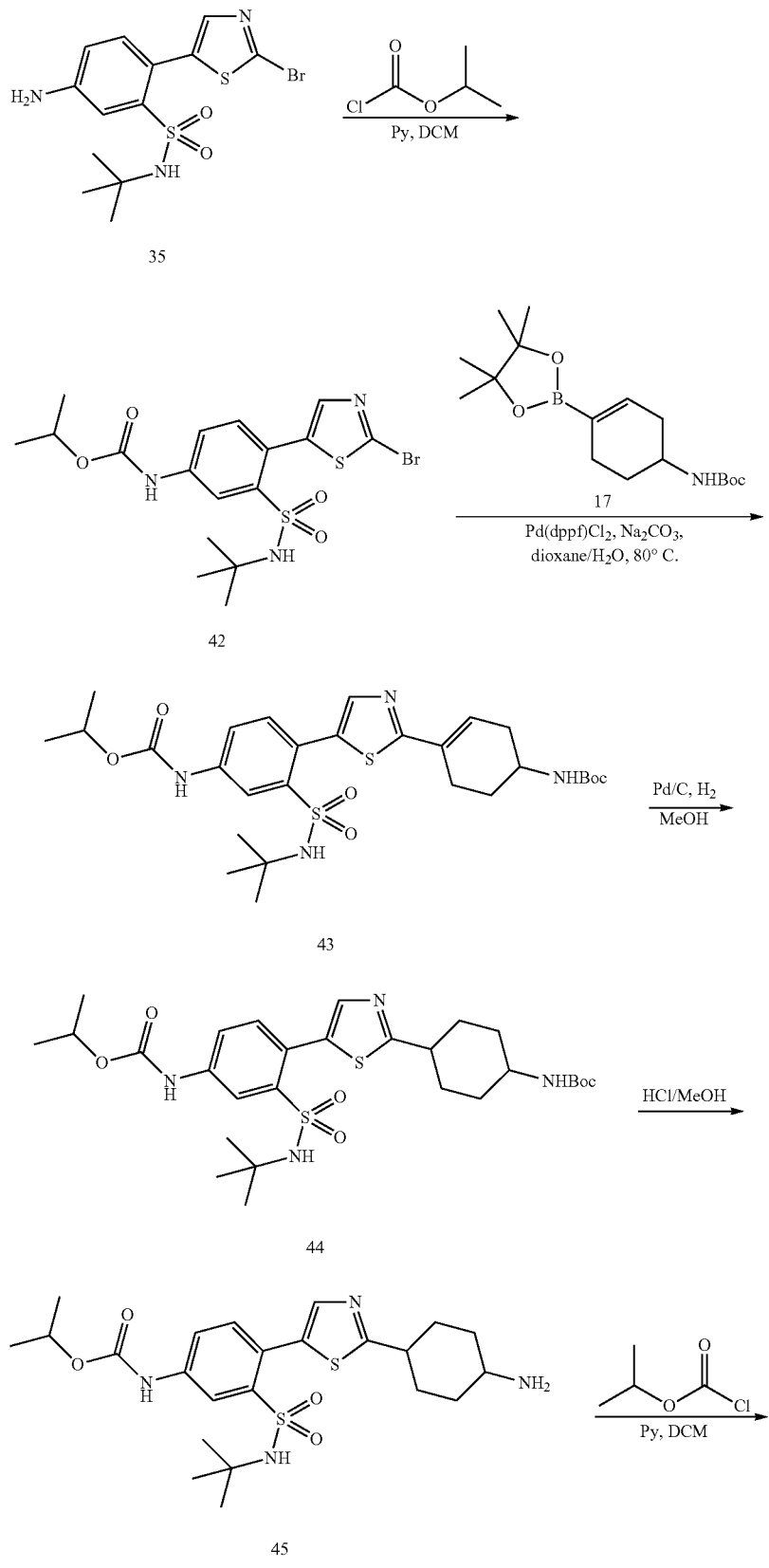

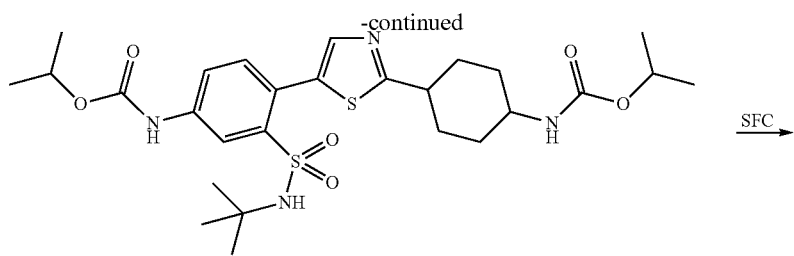
46
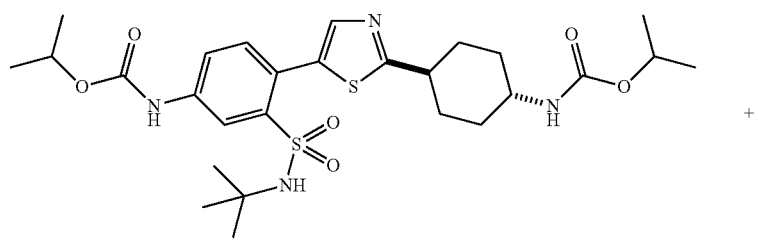
Ex. 67A
+
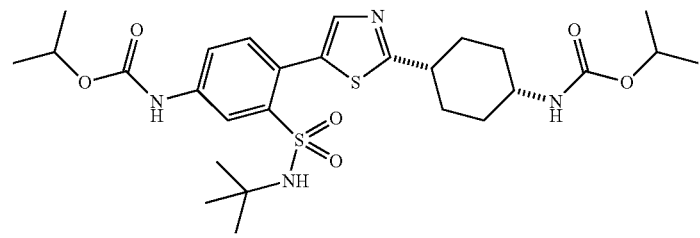
Ex. 67B
Preparation of Compound 42.
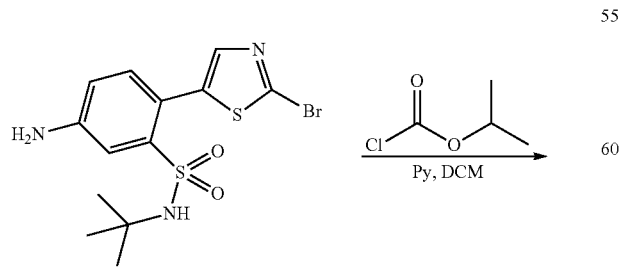
35
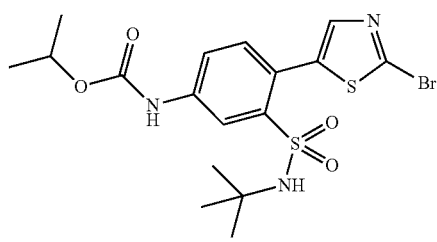
42

General method D, isopropyl N-[4-(2-bromothiazol-5-yl)-3-(tert-butylsulfamoyl)phenyl]carbamate. ESI [M+H]=476.0/478.0.

Preparation of Compound 43

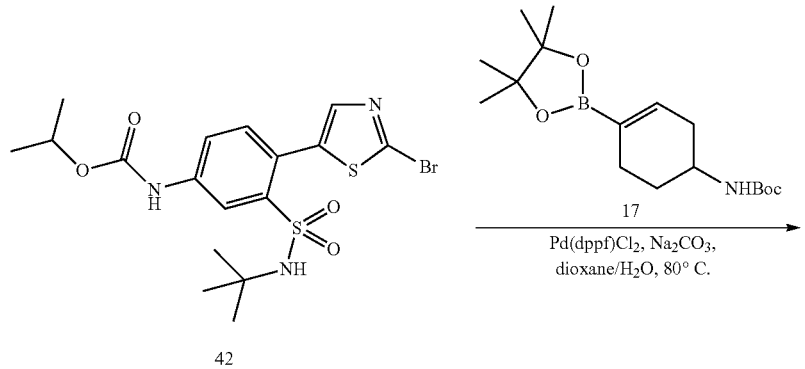

42

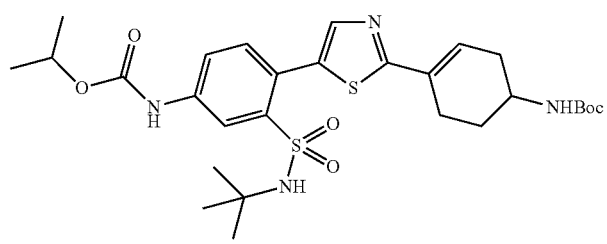

43

General method B, isopropyl N-[4-[2-[4-(tert-butoxycarbonylamino)cyclohexen-1-yl]thiazol-5-yl]-3-(tert-butylsulfamoyl)phenyl]carbamate. ESI [M+H]=593.3.

Preparation of Compound 44.

General method I, isopropyl N-[4-[2-[4-(tert-butoxycarbonylamino)cyclohexyl]thiazol-5-yl]-3-(tert-butylsulfamoyl)phenyl]carbamate. ESI [M+H]=595.3.

Preparation of Compound 45.

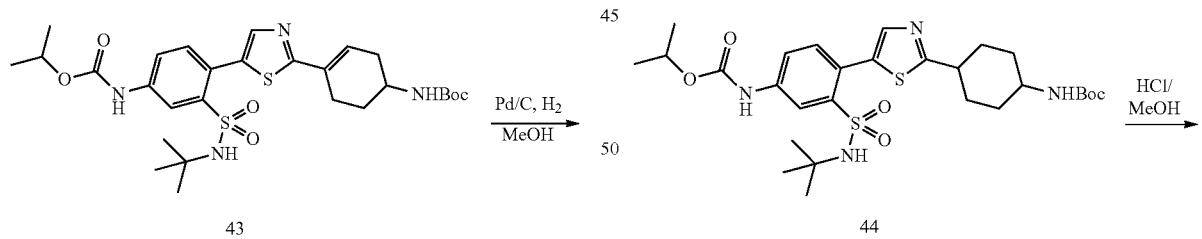

43

44

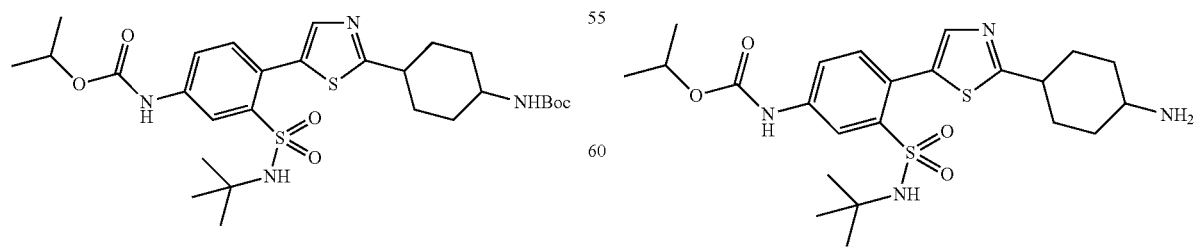

44

45

General method F, isopropyl N-[4-[2-(4-aminocyclohexyl) thiazol-5-yl]-3-(tert-butylsulfamoyl)phenyl]carbamate. ESI [M+H]=495.2.
Preparation of Compound 46.
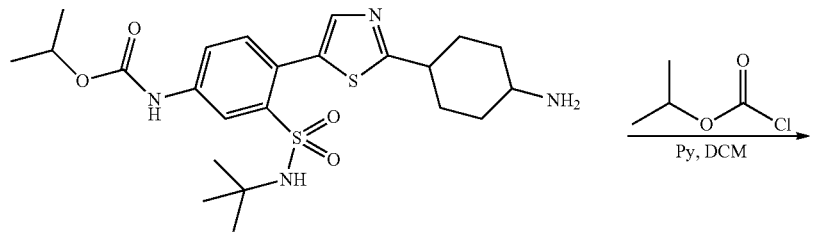
45
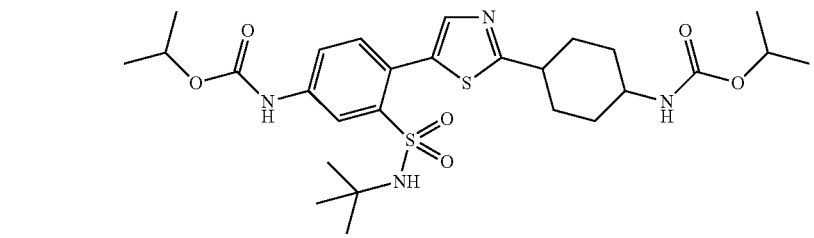
46
General method D, isopropyl N-[3-(tert-butylsulfamoyl)-4-[2-[4-(isopropoxycarbonylamino)cyclohexyl]thiazol-5-yl]phenyl]carbamate. ESI [M+H]=581.2.
Preparation of Ex 67A and Ex. 67B.
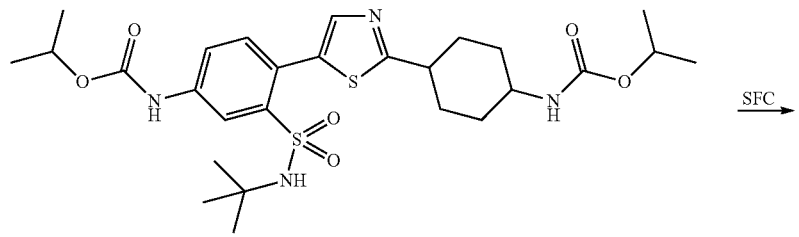
46
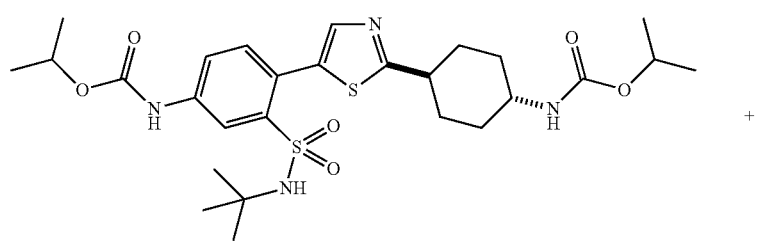
Ex. 67A

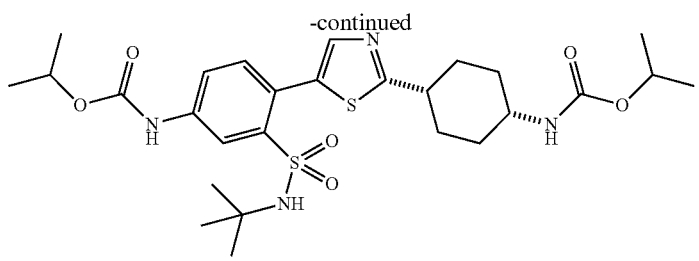

Ex. 67B

Compound 46 was separated by SFC (Instrument: Thar SFC80 preparative SFC; Column: ChiralpakAD-H 250*30 mm i.d. 5u; Mobile phase: A for $CO_2$ and B for IPA (0.1% $NH_3H_2O$); Gradient: B %=30%; Flow rate: 70 g/min; Wavelength: 220 nm; Column temperature: 40° C.; System back pressure: 100 bar; Cycle time: 8 min; Injection amount: 3 mg per injection); and then purified by prep-HPLC (Column: Agela Durashell C18 150*25 5u; mobile phase: [water (0.1% TFA)-ACN]; B %: 55%-85%,12 min), trans-isopropyl N-[3-(tert-butylsulfamoyl)-4-[2-[4-(isopropoxycarbonylamino)cyclohexyl]thiazol-5-yl]phenyl]carbamate Ex. 67A (5.76 mg, 100% purity) and cis-isopropyl N-[3-(tert-butylsulfamoyl)-4-[2-[4-(isopropoxycarbonylamino)cyclohexyl]thiazol-5-yl]phenyl]carbamate Ex. 67B (3.95 mg, 100% purity) were obtained as a pale yellow solid.

Trans-isopropyl N-[3-(tert-butylsulfamoyl)-4-[2-[4-(isopropoxycarbonylamino)cyclohexyl]thiazol-5-yl]phenyl]carbamate (Compound S12). $^1$H NMR (400 MHz, METHANOL-d4) δ=8.37 (d, J=2.3 Hz, 1H), 7.75 (s, 1H), 7.69 (dd, J=2.2, 8.4 Hz, 1H), 7.40 (d, J=8.3 Hz, 1H), 5.01 (td, J=6.3, 12.5 Hz, 1H), 4.86-4.82 (m, 1H), 3.52-3.42 (m, 1H), 3.04 (tt, J=3.5, 12.0 Hz, 1H), 2.35-2.19 (m, 2H), 2.15-1.99 (m, 2H), 1.72 (dq, J=3.0, 12.9 Hz, 2H), 1.43 (dq, J=3.3, 12.6 Hz, 2H), 1.34 (d, J=6.2 Hz, 6H), 1.25 (br d, J=6.1 Hz, 6H), 1.14 (s, 9H). ESI [M+H]=581.2.

Cis-isopropyl N-[3-(tert-butylsulfamoyl)-4-[2-[4-(isopropoxycarbonylamino)cyclohexyl]thiazol-5-yl]phenyl]carbamate (Compound S13). $^1$H NMR (400 MHz, METHANOL-d4) δ=8.37 (d, J=2.2 Hz, 1H), 7.76 (s, 1H), 7.70 (dd, J=2.2, 8.3 Hz, 1H), 7.40 (d, J=8.3 Hz, 1H), 5.01 (td, J=6.3, 12.5 Hz, 1H), 4.84 (br s, 1H), 3.77 (br s, 1H), 3.23-3.15 (m, 1H), 2.05-1.98 (m, 4H), 1.89-1.72 (m, 4H), 1.34 (d, J=6.2 Hz, 6H), 1.25 (d, J=6.1 Hz, 6H), 1.16 (s, 9H). ESI [M+H]=581.2

Example 68 Synthesis of isopropyl N-[1-[5-[4-(benzylcarbamoylamino)-2-(tert-butyl sulfamoyl)phenyl]thiazol-2-yl]-4-piperidyl]carbamate

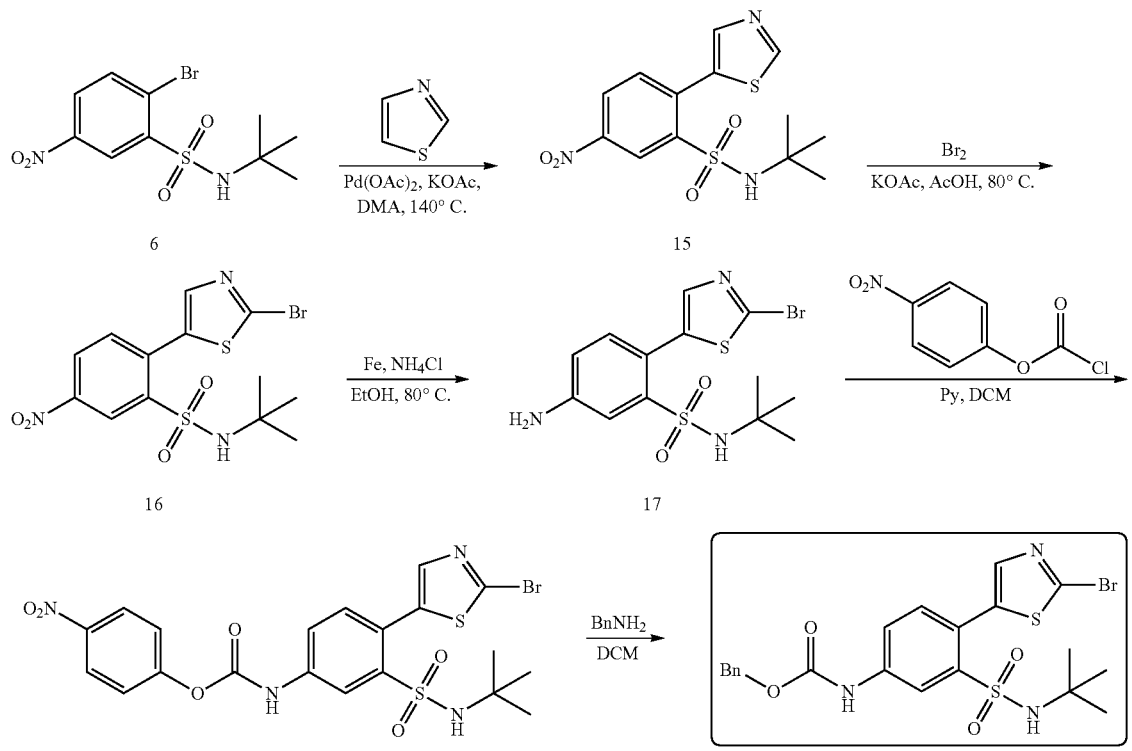

Preparation of Compound 24.

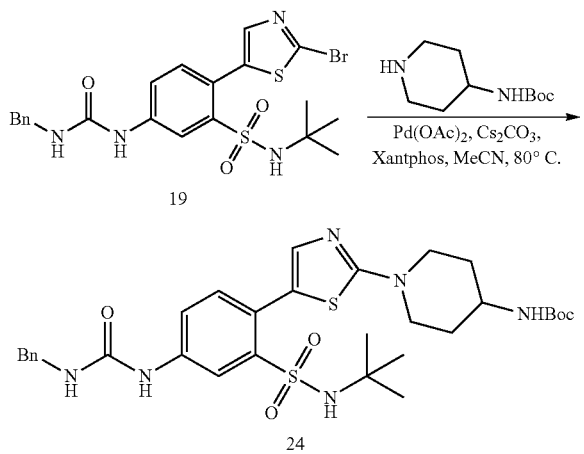

19

24

A mixture of 1-benzyl-3-[4-(2-bromothiazol-5-yl)-3-(tert-butylsulfamoyl)phenyl]urea (0.06 g, 114.62 umol, 1.0 eq.), tert-butyl N-(4-piperidyl)carbamate (40 mg, 199.72 umol, 1.74 eq.), Xantphos (6.63 mg, 11.46 umol, 0.1 eq.), Pd(OAc)$_2$ (2.57 mg, 11.46 umol, 0.1 eq.) and Cs$_2$CO$_3$ (112.04 mg, 343.86 umol, 3.0 eq.) in ACN (3 mL) was heated to 80° C. for 12 hrs under N$_2$. LCMS showed the reaction was complete and the mixture was concentrated. The residue was purified by prep-TLC (Petroleum ether: Ethyl acetate=1:1) to give tert-butyl N-[1-[5-[4-(benzylcarbamoylamino)-2-(tert-butylsulfamoyl)phenyl]thiazol-2-yl]-4-piperidyl]carbamate (0.03 g, crude) as a yellow solid. ESI [M+H]=643.1.

Preparation of Compound 25.

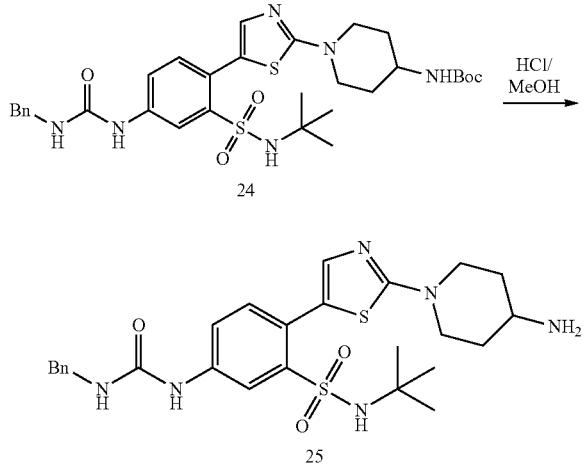 [SMILES: CC(C)(C)NS(=O)(=O)c1cc(NC(=O)NCc2ccccc2)ccc1-c1cnc(N2CCC(NC(=O)OC(C)(C)C)CC2)s1 ; CC(C)(C)NS(=O)(=O)c1cc(NC(=O)NCc2ccccc2)ccc1-c1cnc(N2CCC(N)CC2)s1]

24

25

Tert-butyl N-[1-[5-[4-(benzylcarbamoylamino)-2-(tert-butylsulfamoyl)phenyl]thiazol-2-yl]-4-piperidyl]carbamate (30 mg, 46.67 umol, 1.0 eq.) was dissolved into HCl/MeOH (4M, 1 mL) and the mixture was stirred at 20° C. for 0.5 hr. LCMS showed the reaction was complete and the mixture was concentrated to give 1-[4-[2-(4-amino-1-piperidyl)thiazol-5-yl]-3-(tert-butylsulfamoyl)phenyl]-3-benzyl-urea (27 mg, crude, HCl salt) as a yellow solid. ESI [M+H]=543.2.

Preparation of Ex 68.

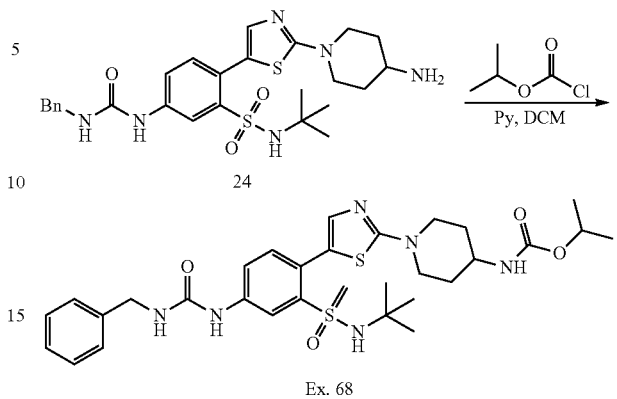

24

Ex. 68

General method D, isopropyl N-[1-[5-[4-(benzylcarbamoylamino)-2-(tert-butyl sulfamoyl)phenyl]thiazol-2-yl]-4-piperidyl]carbamate. $^1$H NMR (400 MHz, METHANOL-d4) δ=8.24 (d, J=2.2 Hz, 1H), 7.69 (dd, J=2.4, 8.4 Hz, 1H), 7.39 (d, J=8.4 Hz, 1H), 7.36-7.19 (m, 6H), 4.82-4.73 (m, 1H), 4.40 (s, 2H), 3.92 (br d, J=13.7 Hz, 2H), 3.75-3.68 (m, 1H), 3.43 (br t, J=11.0 Hz, 2H), 2.10-2.02 (m, 2H), 1.71-1.60 (m, 2H), 1.22 (br d, J=6.2 Hz, 6H), 1.18 (s, 9H). ESI [M+H]=629.2.

Example 69 Synthesis of isopropyl N-[1-[5-[2-(tert-butylsulfamoyl)-4-(isopropoxy carbonylamino)phenyl]thiazol-2-yl]-4-piperidyl]carbamate Scheme 28

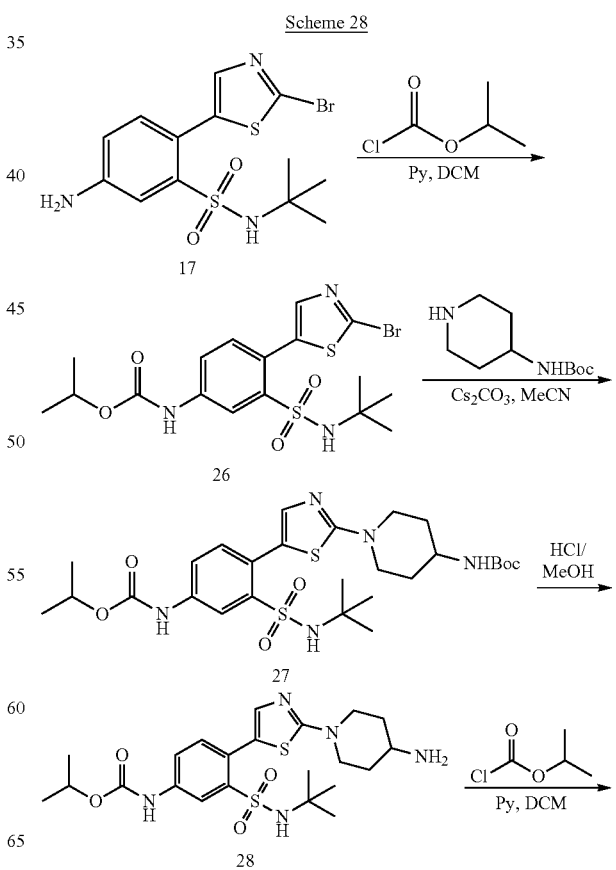

17

26

27

28

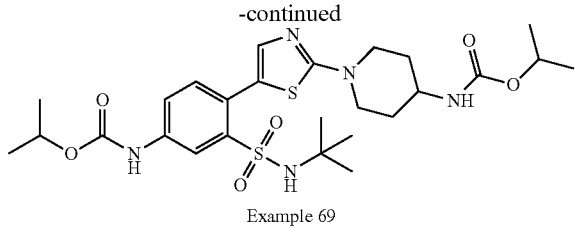

Example 69

Preparation of Compound 26.

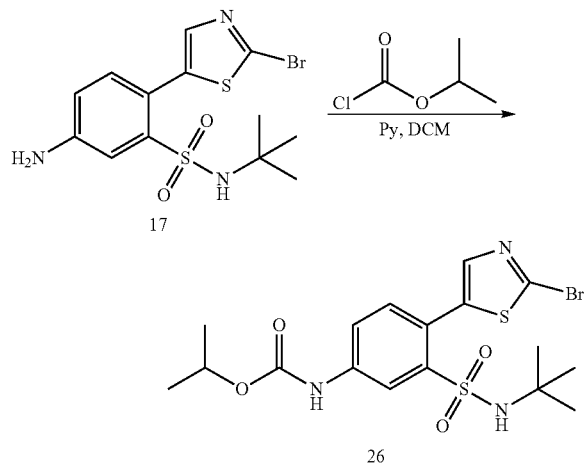

General method D, isopropyl N-[4-(2-bromothiazol-5-yl)-3-(tert-butylsulfamoyl)phenyl]carbamate. ESI [M+H]= 478.0/476.0.

Preparation of Compound 27.

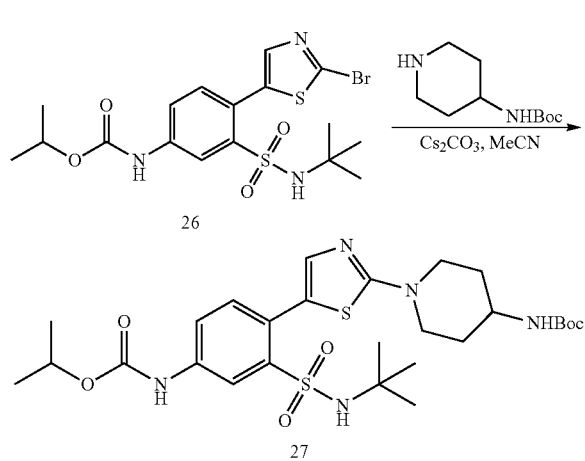

To a solution of isopropyl N-[4-(2-bromothiazol-5-yl)-3-(tert-butylsulfamoyl)phenyl]carbamate (0.05 g, 104.95 umol, 1.0 eq.) in MeCN (2 mL) were added Cs$_2$CO$_3$ (102.59 mg, 314.86 umol, 3.0 eq.), KI (17.42 mg, 104.95 umol, 1.0 eq.) and tert-butyl N-(4-piperidyl)carbamate (105.10 mg, 524.76 umol, 5.0 eq.). The mixture was stirred at 95° C. for 12 hrs and then concentrated. The residue was purified by prep-TLC (SiO$_2$, Petroleum ether:Ethyl acetate=4:3) to give N-4-[2-[4-(tert-butoxycarbonylamino)-1-piperidyl]thiazol-5-yl-3-(tert-butylsulfamoyl)phenyl]carbamate (0.025 g, crude) as a white solid. ESI [M+H]=596.2.

Preparation of Compound 28.

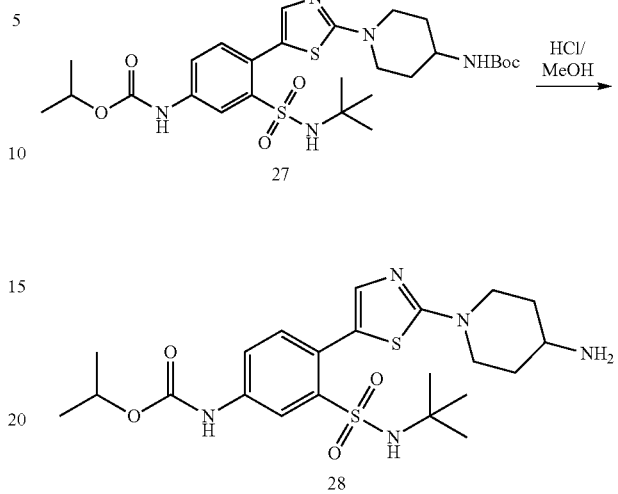

Isopropyl N-[4-[2-[4-(tert-butoxycarbonylamino)-1-piperidyl]thiazol-5-yl]-3-(tert-butylsulfamoyl)phenyl]carbamate (0.025 g, 41.96 umol, 1.0 eq.) was dissolved into HCl/MeOH (4M, 1.5 mL) and the mixture was stirred at 20° C. for 0.5 hr. LCMS showed the reaction was complete and the mixture was concentrated to give the N-4-[2-(4-amino-1-piperidyl)thiazol-5-yl]-3-(tert-butylsulfamoyl)phenyl carbamate (0.02 g, crude, HCl salt) as a white solid. ESI [M+H]=496.2.

Preparation of Ex 69.

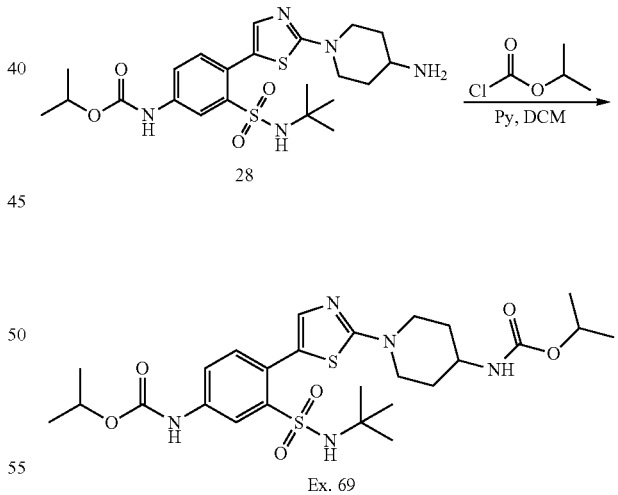

General method D, isopropyl N-[1-[5-[2-(tert-butylsulfamoyl)-4-(isopropoxy carbonylamino)phenyl]thiazol-2-yl]-4-piperidyl]carbamate. $^1$H NMR (400 MHz, METHANOL-d4) δ=8.35 (s, 1H), 7.66 (br d, J=8.4 Hz, 1H), 7.42 (d, J=8.4 Hz, 1H), 7.31 (s, 1H), 4.98 (td, J=6.2, 12.5 Hz, 1H), 4.84-4.77 (m, 1H), 3.93 (br d, J=13.5 Hz, 2H), 3.77-3.67 (m, 1H), 3.44 (br t, J=12.3 Hz, 2H), 2.06 (br dd, J=3.1, 13.2 Hz, 2H), 1.71-1.61 (m, 2H), 1.31 (d, J=6.4 Hz, 6H), 1.23 (br d, J=6.2 Hz, 6H), 1.19 (s, 9H). ESI [M+H]=582.2.

Example 70 Synthesis of trans-isopropyl N-[4-[5-[2-(tert-butylsulfamoyl)-4-[(2-fluorophenyl)methoxy carbonylamino]phenyl]thiazol-2-yl]cyclohexyl]carbamate
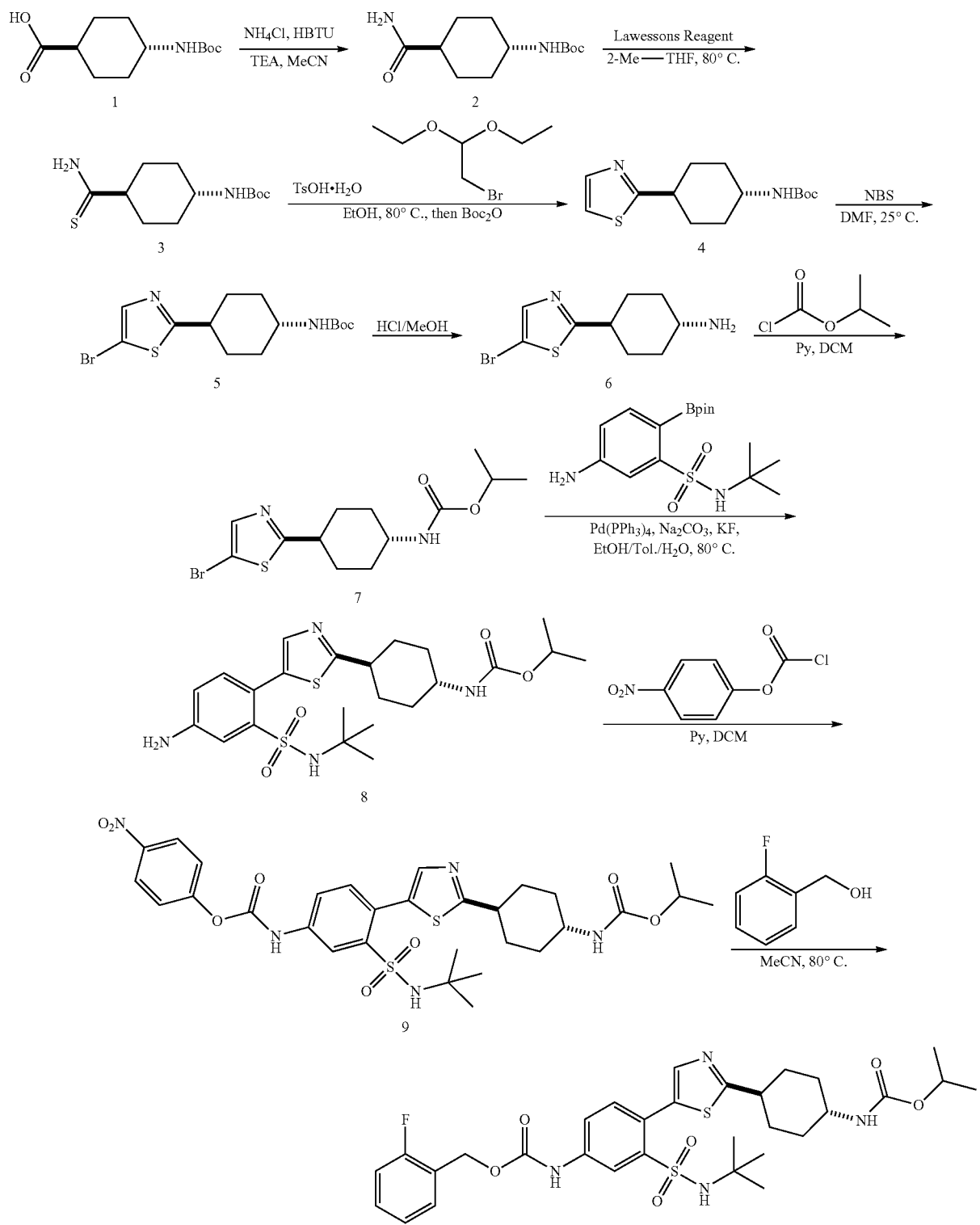
Scheme 29

Preparation of Compound 2.

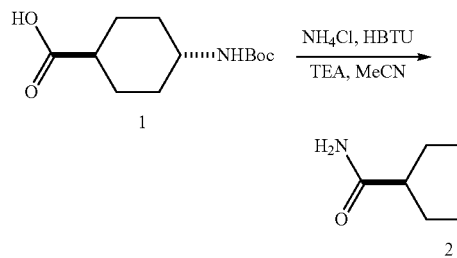

To a mixture of trans-4-(tert-butoxycarbonylamino)cyclohexanecarboxylic acid (65.0 g, 267.2 mmol, 1.0 eq.), NH$_4$Cl (21.4 g, 400.7 mmol, 1.5 eq.) and TEA (801.5 mmol, 111.6 mL, 3 eq.) in MeCN (1.3 L) was added HBTU (111.5 g, 293.9 mmol, 1.1 eq.) and the mixture was stirred at 25° C. for 3 hrs. The mixture was filtered and then the filter cake was washed with petroleum ether (200 mL) and dried to give trans-tert-butyl N-(4-carbamoylcyclohexyl)carbamate (140 g, crude, 2 batches) as a white solid. $^1$H NMR (METHANOL-d4, 400 MHz) δ=3.25-3.34 (m, 1H), 2.14 (tt, J=12.3, 3.5 Hz, 1H), 1.83-1.99 (m, 4H), 1.52 (qd, J=13.1, 2.9 Hz, 2H), 1.42 (s, 9H), 1.21 (qd, J=12.7, 3.5 Hz, 2H)

Preparation of Compound 3.

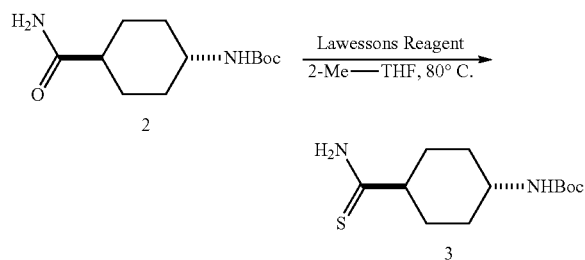

A mixture of trans-tert-butyl N-(4-carbamoylcyclohexyl) carbamate (90.0 g, 371.4 mmol, 1.0 eq.), Na$_2$CO$_3$ (39.4 g, 371.4 mmol, 1.0 eq.) and Lawesson's reagent (82.6 g, 204.3 mmol, 0.55 eq.) in 2-Me-THF (600 mL) was stirred at 80° C. for 2 hrs and then the reaction mixture was poured into H$_2$O (200 mL). The aqueous phase was extracted with EtOAc (500 mL×2).

The combined organic layers were dried over Na$_2$SO$_4$, filtered and concentrated to give trans-tert-butyl N-(4-carbamothioylcyclohexyl)carbamate (180 g, crude, 2 batches) as a white solid. $^1$H NMR (METHANOL-d4, 400 MHz) δ=3.35-3.46 (m, 1H), 2.87-3.00 (m, 1H), 2.09-2.20 (m, 2H), 1.99-2.09 (m, 2H), 1.54-1.68 (m, 2H), 1.26-1.45 (m, 2H), 1.14-1.25 (m, 9H)

Preparation of Compound 4.

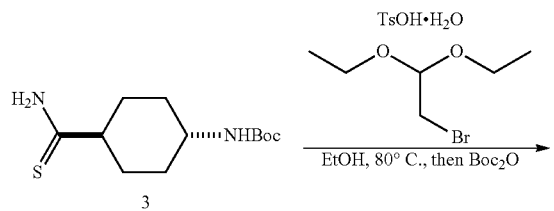

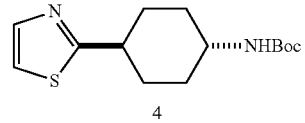

A mixture of trans-tert-butyl N-(4-carbamothioylcyclohexyl)carbamate (180.0 g, 696.7 mmol, 1.0 eq.), 2-bromo-1,1-diethoxy-ethane (137.3 g, 696.7 mmol, 1.0 eq.) and TsOH.H$_2$O (265 g, 1.4 mol, 2 eq.) in EtOH (2.0 L) was stirred at 80° C. for 6 hrs. Then the mixture was cooled to RT and adjusted to PH=9 with aq.sat.Na$_2$CO$_3$ and Boc$_2$O (152 g, 696.7 mmol, 1 eq.) was added. The mixture was stirred at 30° C. for 3 hrs, then concentrated and diluted with H$_2$O (2 L). The mixture was extracted with EtOAc (800 mL×3) and the combined organic layers were dried over Na$_2$SO$_4$, filtered and concentrated. The residue was triturated with petroleum ether (1.5 L) to give trans-tert-butyl N-(4-thiazol-2-ylcyclohexyl) carbamate (70 g, 247.87 mmol, 35.58% yield) as a white solid. $^1$H NMR (METHANOL-d4, 400 MHz) δ=7.67 (d, J=3.1 Hz, 1H), 7.44 (d, J=3.5 Hz, 1H), 3.33-3.44 (m, 1H), 2.93-3.06 (m, 1H), 2.12-2.21 (m, 2H), 2.00-2.09 (m, 2H), 1.57-1.71 (m, 2H), 1.41-1.48 (m, 9H), 1.29-1.38 (m, 1H), 1.13-1.28 (m, 1H).

Preparation of Compound 5.

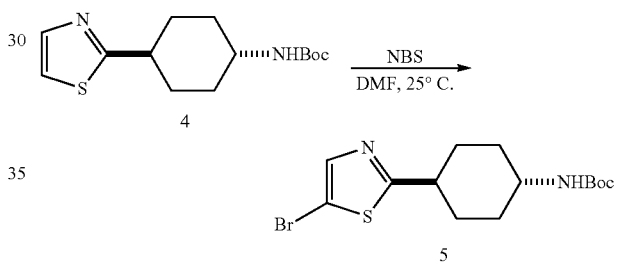

A mixture of trans-tert-butyl N-(4-thiazol-2-ylcyclohexyl)carbamate (68 g, 240.8 mmol, 1 eq.) and NBS (47.1 g, 264.9 mmol, 1.1 eq.) in DMF (500 mL) was stirred at 25° C. for 10 hrs and then poured into H$_2$O (2 L) and extracted with EtOAc (500 mL×3). The combined organic layers were washed with brine (300 mL×5), dried over Na$_2$SO$_4$, filtered and concentrated. The residue was purified by column chromatography (SiO$_2$, Petroleum ether:Ethyl acetate=20:1 to 10:1) to give trans-tert-butyl N-[4-(5-bromothiazol-2-yl)cyclohexyl]carbamate (78 g, crude) as a yellow solid. ESI [M+H]=363.0/361.0

Preparation of Compound 6.

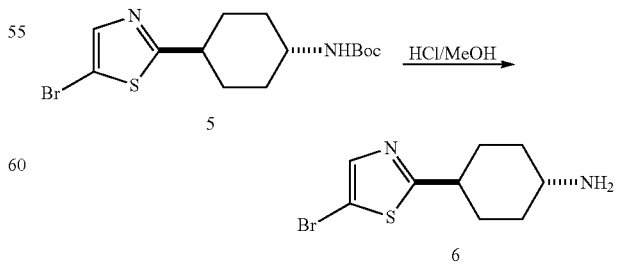

A mixture of trans-tert-butyl N-[4-(5-bromothiazol-2-yl)cyclohexyl]carbamate (50 g, 138.4 mmol, 1 eq.) in HCl/

MeOH (4 M, 700 mL) was stirred at 25° C. for 0.5 hr and then concentrated to give trans-4-(5-bromothiazol-2-yl)cyclohexanamine (45 g, crude, HCl salt) as a yellow solid. ESI [M+H]=263.0/261.0

Preparation of Compound 7.

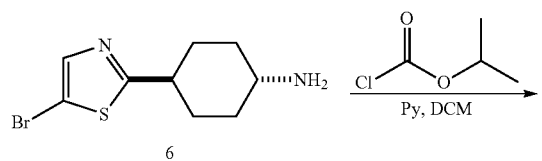

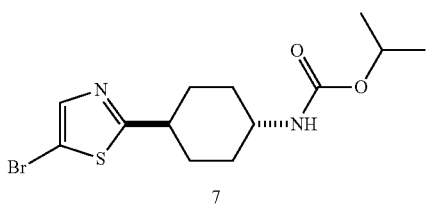

To a solution of trans-4-(5-bromothiazol-2-yl)cyclohexanamine (45 g, HCl salt, 172.3 mmol, 1 eq.), Pyridine (61.5 mmol, 69.5 mL, 5 eq.) and DMAP (4.2 g, 34.5 mmol, 0.2 eq.) in DCM (300 mL) was added isopropyl carbonochloridate (258.5 mmol, 35.9 mL, 1.5 eq.) dropwise at 0° C. The mixture was stirred at 25° C. for 0.5 hr and then washed with HCl (1N, 1 L) and sat.aq.Na$_2$CO$_3$ (1 L). The organic layers were dried over Na$_2$SO$_4$, filtered and concentrated. The residue was purified by column chromatography (SiO$_2$, Petroleum ether:Ethyl acetate=15:1 to 10:1) to give trans-isopropyl N-[4-(5-bromothiazol-2-yl)cyclohexyl]carbamate (37 g, 106.55 mmol, 61.84% yield) as a yellow solid. $^1$H NMR (METHANOL-d4, 400 MHz) δ=7.60 (s, 1H), 4.81 (dt, J=12.2, 6.2 Hz, 1H), 3.41 (tt, J=11.6, 4.0 Hz, 1H), 2.88-3.00 (m, 1H), 2.10-2.20 (m, 2H), 1.98-2.07 (m, 2H), 1.55-1.68 (m, 2H), 1.30-1.43 (m, 2H), 1.21 (br d, J=6.2 Hz, 6H).

Preparation of Compound 8.

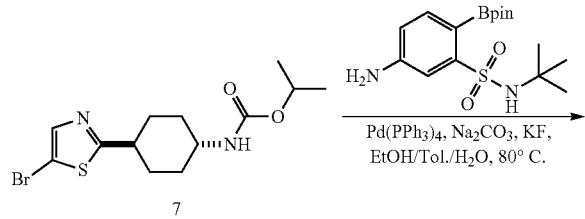

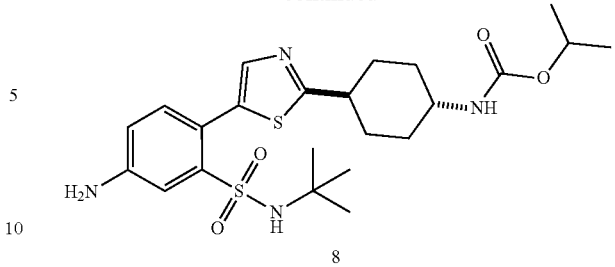

A mixture of trans-isopropyl N-[4-(5-bromothiazol-2-yl)cyclohexyl]carbamate (16.2 g, 46.7 mmol, 1 eq.), 5-amino-N-tert-butyl-2-(4,4,5,5-tetramethyl-1,3,2-dioxaborolan-2-yl)benzenesulfonamide (19.9 g, 56.1 mmol, 1.2 eq.), KF (4.1 g, 70.1 mmol, 1.5 eq.), Na$_2$CO$_3$ (14.9 g, 140.2 mmol, 3 eq.) and Pd(PPh$_3$)$_4$ (1.6 g, 1.4 mmol, 0.03 eq.) in toluene (150 mL), EtOH (150 mL) and H$_2$O (50 mL) stirred at 80° C. for 6 hrs under N$_2$ atmosphere. The reaction mixture was concentrated and the residue was diluted with H$_2$O (100 mL) and extracted with EtOAc (100 mL×2). The combined organic layers were dried over Na$_2$SO$_4$, filtered and concentrated. The residue was purified by column chromatography (SiO$_2$, Petroleum ether:Ethyl acetate=20:1 to 1:1) to give trans-isopropyl N-[4-[5-[4-amino-2-(tert-butylsulfamoyl)phenyl]thiazol-2-yl]cyclohexyl]carbamate (13 g, 26.3 mmol, 56.2% yield) as a white solid. $^1$H NMR (400 MHz, METHANOL-d4) δ=7.65-7.60 (m, 1H), 7.43 (d, J=2.2 Hz, 1H), 7.13 (d, J=8.3 Hz, 1H), 6.83 (dd, J=2.6, 8.3 Hz, 1H), 4.81 (br s, 1H), 3.76-3.71 (m, 1H), 3.05-2.86 (m, 1H), 2.20 (br d, J=12.3 Hz, 2H), 2.06 (br d, J=10.5 Hz, 2H), 1.75-1.60 (m, 2H), 1.47-1.34 (m, 2H), 1.22 (br d, J=6.1 Hz, 6H), 1.09 (s, 9H).

Preparation of Compound 9.

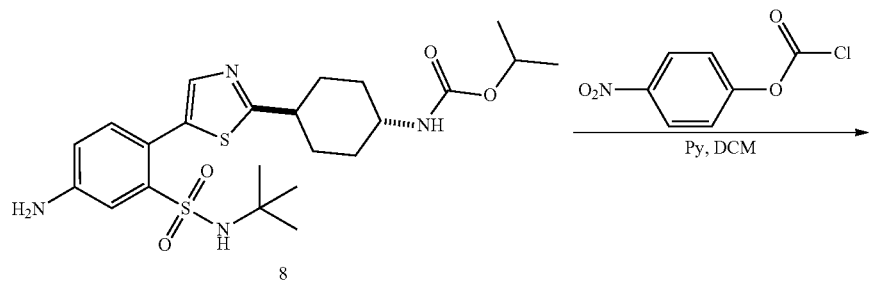

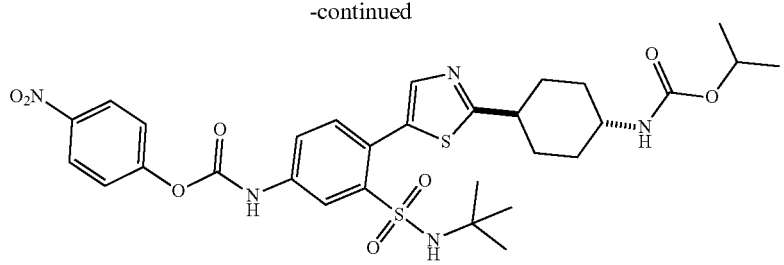
To a solution of trans-isopropyl N-[4-[5-[4-amino-2-(tert-butylsulfamoyl)phenyl]thiazol-2-yl]cyclohexyl]carbamate (250 mg, 505.4 umol, 1 eq.) in DCM (4 mL) were added DMAP (6.2 mg, 50.5 umol, 0.1 eq.), Pyridine (120 mg, 1.5 mmol, 3 eq.) and (4-nitrophenyl) carbonochloridate (153 mg, 758 umol, 1.5 eq.). The mixture was stirred at 25° C. for 0.5 hr and used directly for the next step. ESI [M+H]=660.2
Preparation of Compound Ex. 70.
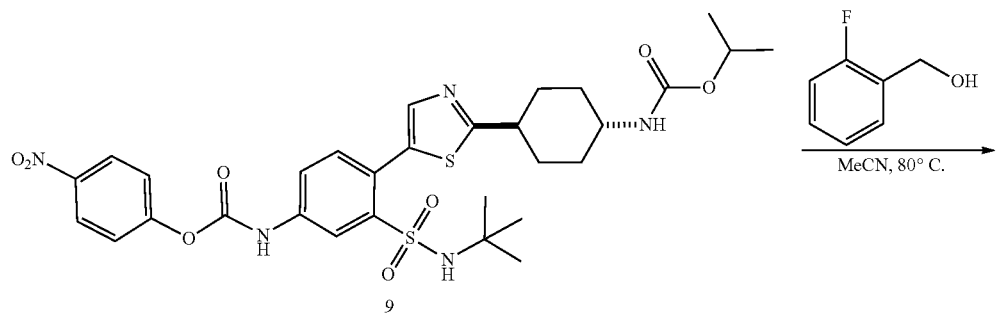
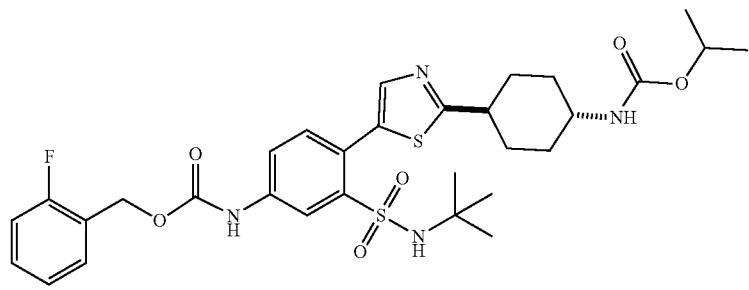
Ex. 70

To a solution of (2-fluorophenyl)methanol (45.9 mg, 363.8 umol, 3 eq.) and DIEA (47 mg, 363.8 umol, 3 eq.) in MeCN (1 mL) was added the aboved solution (1 mL). The mixture was stirred at 80° C. for 1 hr, then concentrated and the residue was purified by prep-HPLC (Column: Waters Xbridge 150*25 5u; Mobile phase: [water (10 mM NH$_4$HCO$_3$)-ACN]; B %: 42%-72%, 12 min) to give trans-isopropyl N-[4-[5-[2-(tert-butylsulfamoyl)-4-[(2-fluorophenyl)methoxy carbonylamino]phenyl]thiazol-2-yl]cyclohexyl]carbamate (16.34 mg, 25.26 umol, 20.83% yield, 100% purity) as a yellow solid. $^1$H NMR (400 MHz, METHANOL-d4) δ=8.36 (s, 1H), 7.77-7.63 (m, 2H), 7.52 (t, J=7.0 Hz, 1H), 7.44-7.31 (m, 2H), 7.23-7.08 (m, 2H), 5.29 (s, 2H), 4.83 (br s, 1H), 3.46 (br d, J=11.8 Hz, 1H), 3.00 (br t, J=11.8 Hz, 1H), 2.22 (br d, J=12.7 Hz, 2H), 2.07 (br d, J=11.4 Hz, 2H), 1.76-1.62 (m, 2H), 1.47-1.35 (m, 2H), 1.22 (br d, J=6.1 Hz, 6H), 1.12 (s, 9H). ESI [M+H]=647.2

Example 71 Synthesis of trans-[(1S)-1-phenylethyl] N-[3-(tert-butylsulfamoyl)-4-[2-[4-(isopropoxycarbonylamino)cyclohexyl]thiazol-5-yl]phenyl]carbamate Scheme 30

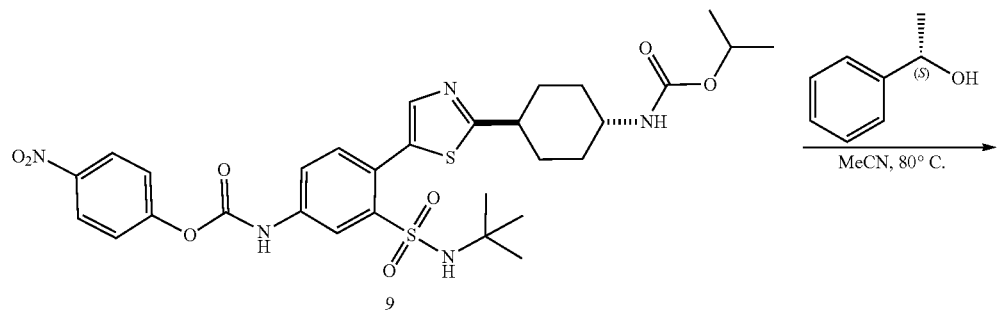

9

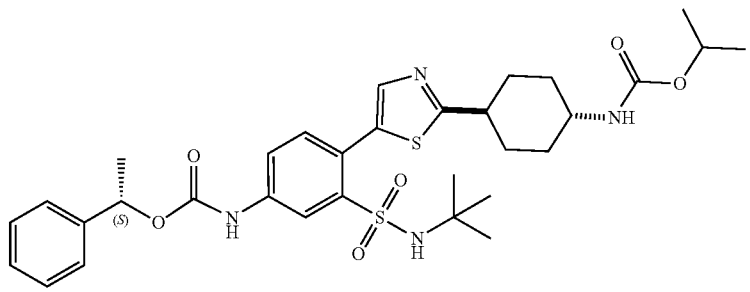

Ex. 71

Preparation of Ex 71.

To a solution of (1S)-1-phenylethanol (29.6 mg, 242.5 umol, 2 eq.) and DIEA (47 mg, 363.8 umol, 3 eq.) in MeCN (2 mL) was added a solution of trans-(4-nitrophenyl)N-[3-(tert-butylsulfamoyl)-4-[2-[4-(isopropoxycarbonylamino) cyclohexyl]thiazol-5-yl]phenyl]carbamate (80 mg, 121.25 umol, 1 eq.) in DCM (1 mL). The mixture was stirred at 80° C. for 1 hr, then concentrated and the residue was purified by prep-HPLC (Column: Nano-Micro UniSil 5-100 C18 ULTRA 100*250 mm 5 um; mobile phase: [water (0.1% TFA)-ACN]; B %: 55%-80%,11 min) to give trans-[(1S)-1-phenylethyl]N-[3-(tert-butylsulfamoyl)-4-[2-[4-(isopropoxycarbonylamino)cyclohexyl]thiazol-5-yl]phenyl]carbamate (12.19 mg, 18.77 umol, 15.48% yield, 99% purity) as a white solid. $^{1}$H NMR (400 MHz, METHANOL-d4) δ=8.35 (br s, 1H), 7.81-7.65 (m, 2H), 7.48-7.36 (m, 5H), 7.31 (br d, J=6.8 Hz, 1H), 5.89 (br d, J=6.2 Hz, 1H), 4.85 (br d, J=5.5 Hz, 1H), 3.47 (br s, 1H), 3.03 (br s, 1H), 2.24 (br d, J=11.2 Hz, 2H), 2.08 (br d, J=11.0 Hz, 2H), 1.71 (q, J=11.9 Hz, 2H), 1.61 (br d, J=6.4 Hz, 3H), 1.49-1.37 (m, 2H), 1.24 (br d, J=5.4 Hz, 6H), 1.13 (s, 9H). ESI [M+H]= 643.2

Example 72 Synthesis of N-[3-(tert-butylsulfamoyl)-4-[2-[4-(isopropoxycarbonylamino)cyclohexyl]thiazol-5-yl]phenyl]carbamate Scheme 31

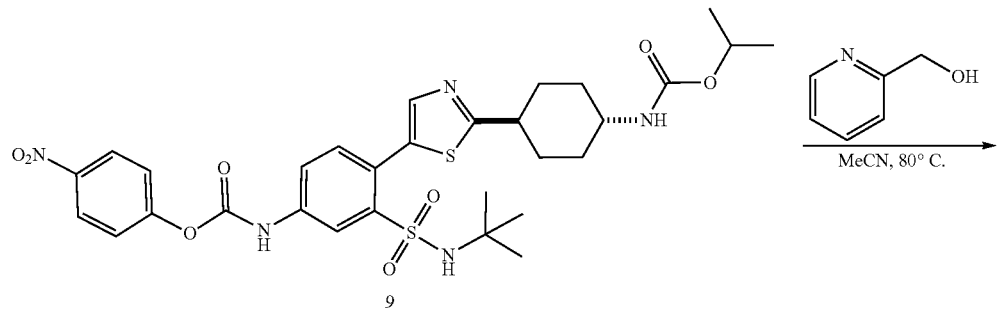

9

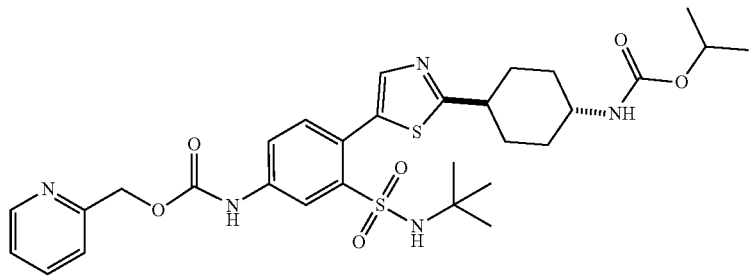

Ex. 72

Preparation of Ex 72.

To a solution of 2-pyridylmethanol (26.5 mg, 242.5 umol, 2 eq.) and DIEA (47 mg, 363.8umol, 3 eq.) in MeCN (2 mL) was added a solution of trans-(4-nitrophenyl)N-[3-(tert-butylsulfamoyl)-4-[2-[4-(isopropoxycarbonylamino)cyclohexyl]thiazol-5-yl]phenyl]carbamate (80 mg, 121.3 umol, 1 eq.) in DCM (1 mL). The mixture was stirred at 80° C. for 1 hr, then concentrated and the residue was purified by prep-HPLC (Column: Waters Xbridge 150*25 5u; Mobile phase: [water (0.04% $NH_3H_2O$+10 mM $NH_4HCO_3$)-ACN]; B %: 35%-65%, 10 min) to give trans-2-pyridylmethyl N-[3-(tert-butylsulfamoyl)-4-[2-[4-(isopropoxycarbonylamino)cyclohexyl]thiazol-5-yl]phenyl]carbamate (18.59 mg, 28.82 umol, 23.77% yield, 97.65% purity) as a pale yellow solid. $^1$H NMR (400 MHz, METHANOL-d4) δ=8.56 (br d, J=4.5 Hz, 1H), 8.38 (d, J=1.8 Hz, 1H), 7.94-7.87 (m, 1H), 7.78-7.72 (m, 2H), 7.59 (br d, J=7.8 Hz, 1H), 7.44-7.38 (m, 2H), 5.32 (s, 2H), 4.85 (td, J=5.9, 12.0 Hz, 1H), 3.47 (br t, J=11.8 Hz, 1H), 3.07-2.96 (m, 1H), 2.24 (br d, J=12.3 Hz, 2H), 2.13-2.04 (m, 2H), 1.77-1.65 (m, 2H), 1.48-1.37 (m, 2H), 1.24 (br d, J=6.1 Hz, 6H), 1.14 (s, 9H). ESI [M+H]= 630.2

Example 73 Synthesis of trans-isopropyl N-[4-[5-[2-(tert-butylsulfamoyl)-4-[(4-hydroxyphenyl)methylcarbamoylamino]phenyl]thiazol-2-yl]cyclohexyl]carbamate Scheme 32

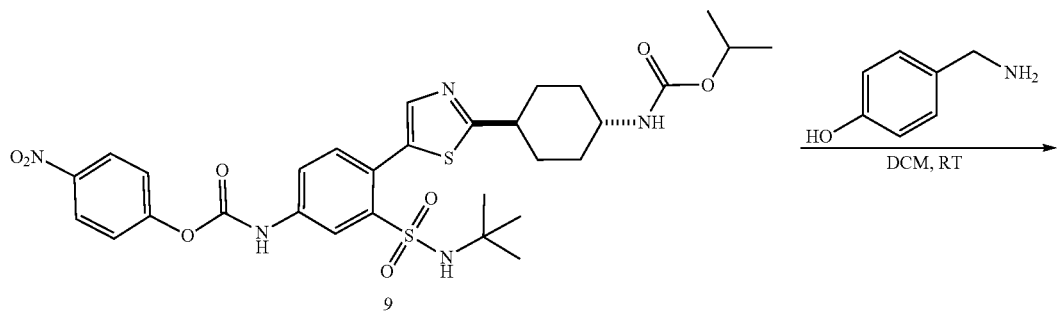

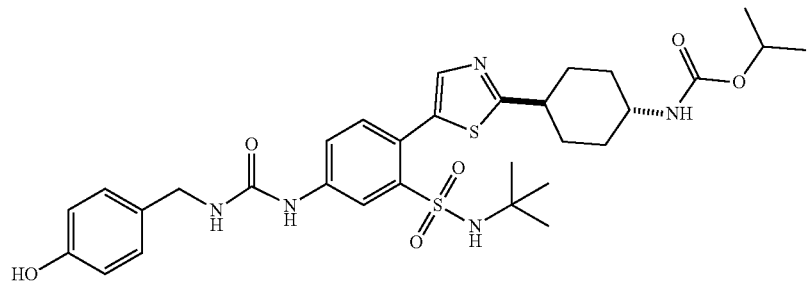

Ex. 73

Preparation of Ex 73.

To a solution 4-(aminomethyl) phenol (74.7 mg, 606.5 umol, 3 eq.) and DIEA (78.4 mg, 606.5 umol, 3 eq.) in DCM (2 mL) was added trans-(4-nitrophenyl)N-[3-(tert-butylsulfamoyl)-4-[2-[4-(isopropoxycarbonylamino)cyclohexyl]thiazol-5-yl]phenyl]carbamate (133.4 mg, 202.2 umol, 1 eq.) in DCM (2 mL). The mixture was stirred at 25° C. for 1 hr, then concentrated and the residue was purified by prep-HPLC (TFA condition) to give trans-isopropyl N-[4-[5-[2-(tert-butylsulfamoyl)-4-[(4-hydroxyphenyl)methylcarbamoylamino]phenyl]thiazol-2-yl]cyclohexyl]carbamate (23.56 mg, 35.99 umol, 17.80% yield, 98.357% purity) as a white solid. $^1$H NMR (400 MHz, METHANOL-d4) δ=8.24 (d, J=2.2 Hz, 1H), 7.77 (s, 1H), 7.69 (dd, J=2.2, 8.3 Hz, 1H), 7.36 (d, J=8.3 Hz, 1H), 7.16 (d, J=8.8 Hz, 2H), 6.75 (d, J=8.3 Hz, 2H), 4.85-4.74 (m, 1H), 4.30 (s, 2H), 3.45 (s, 1H), 3.15-2.97 (m, 1H), 2.23 (br d, J=12.3 Hz, 2H), 2.08 (br d, J=13.2 Hz, 2H), 1.79-1.63 (m, 2H), 1.48-1.34 (m, 2H), 1.22 (br d, J=6.1 Hz, 6H), 1.12 (s, 9H). ESI [M+H]=644.2

Example 74 Synthesis of trans-isopropyl N-[4-[5-[4-(benzylcarbamoylamino)-2-[(2-hydroxy-1,1-dimethyl-ethyl)sulfamoyl]phenyl]thiazol-2-yl]cyclohexyl]carbamate Scheme 33

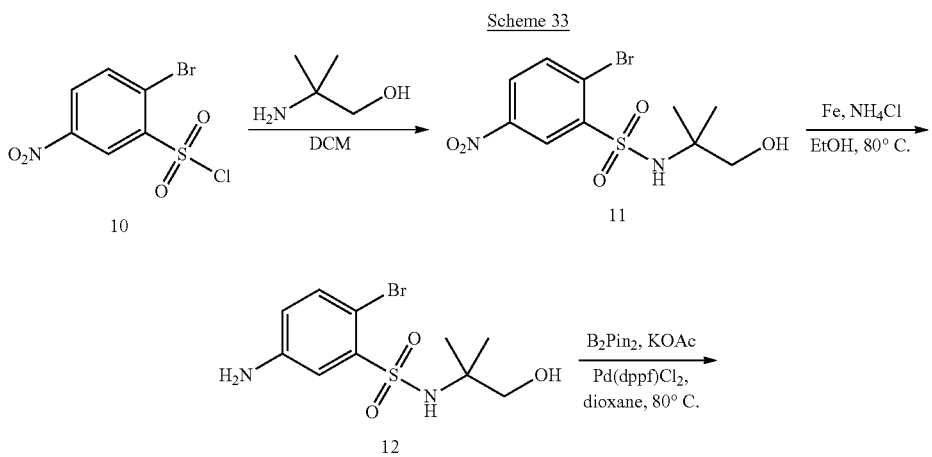

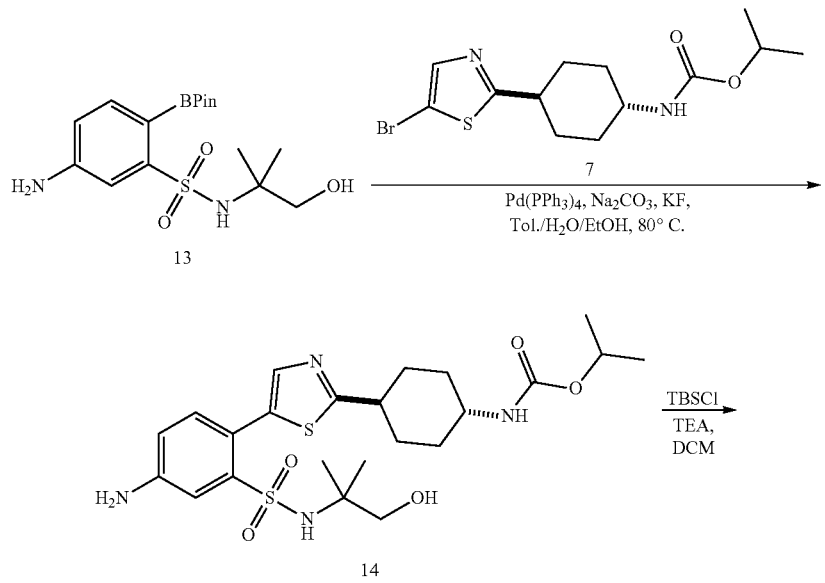

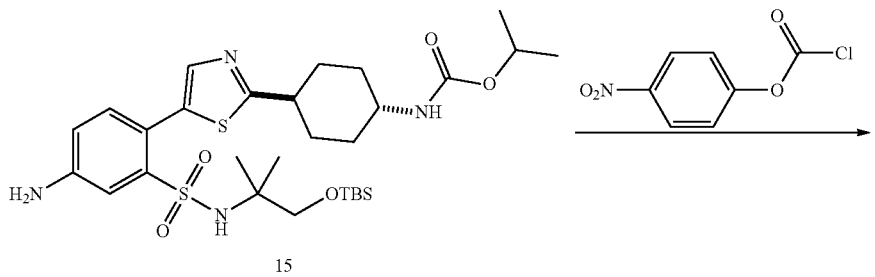

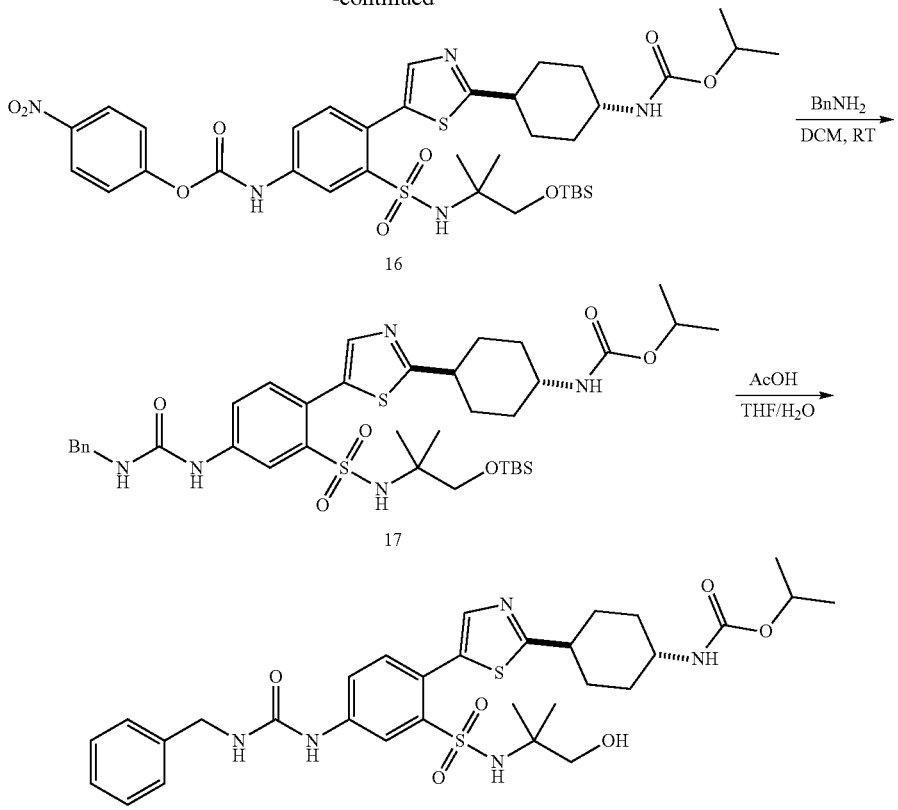

Ex. 74

Preparation of Compound 11.

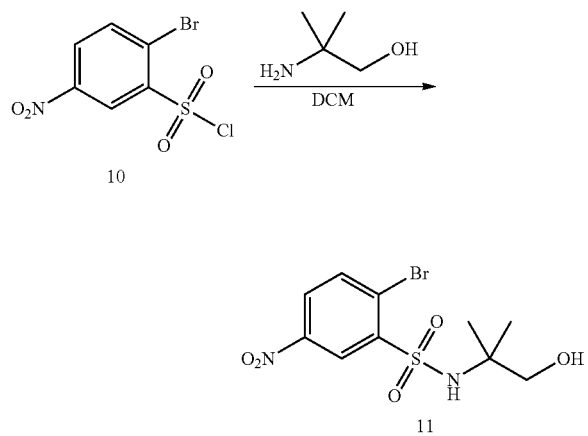

To a mixture of 2-amino-2-methyl-propan-1-ol (3 g, 33.7 mmol, 5.1 eq.) and DMAP (80 mg, 654.8 umol, 0.98 eq.) in DCM (50 mL) was added 2-bromo-5-nitro-benzenesulfonyl chloride (2 g, 6.66 mmol, 1 eq.). The mixture was stirred at 20° C. for 30 mins, then washed with 1N HCl (20 mL) and sat.aq.NaHCO₃ (20 mL). The organic layer was dried over Na₂SO₄, filtered and concentrated to give 2-bromo-N-(2-hydroxy-1,1-dimethyl-ethyl)-5-nitro-benzenesulfonamide (1.7 g, 4.8 mmol, 72.3% yield) as a yellow gum. ESI [M+H]=355.0/353.0

Preparation of Compound 12.

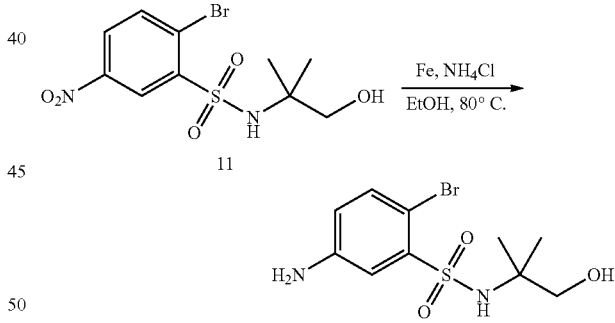

A mixture of 2-bromo-N-(2-hydroxy-1,1-dimethyl-ethyl)-5-nitro-benzenesulfonamide (1.7 g, 4.8 mmol, 1 eq.), Fe (1.5 g, 26.9 mmol, 5.6 eq.) and NH₄Cl (800 mg, 14.9 mmol, 3.1 eq.) in EtOH (15 mL)/H₂O (7.5 mL)/THF (7.5 mL) was stirred at 80° C. for 2 hrs. The reaction mixture was concentrated to remove EtOH, diluted with H₂O (100 mL) and extracted with EtOAc (100 mL×3). The combined organic layers were dried over Na₂SO₄, filtered and concentrated. The residue was purified by column chromatography (SiO₂, Petroleum ether:Ethyl acetate=100:1 to 1:1) to give 5-amino-2-bromo-N-(2-hydroxy-1,1-dimethyl-ethyl) benzenesulfonamide (1.1 g, 3.4 mmol, 70.7% yield) as a pale yellow solid. ESI [M+H]=325.0/323.0

Preparation of Compound 13.

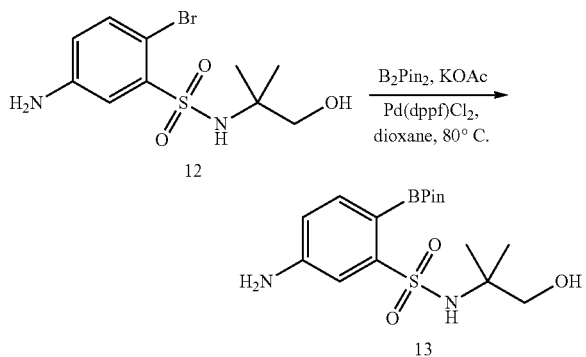

A mixture of 5-amino-2-bromo-N-(2-hydroxy-1,1-dimethyl-ethyl)benzenesulfonamide (400 mg, 1.24 mmol, 1 eq.), 4,4,5,5-tetramethyl-2-(4,4,5,5-tetramethyl-1,3,2-dioxaborolan-2-yl)-1,3,2-dioxaborolane (942.8 mg, 3.7 mmol, 3 eq.), Pd(dppf)Cl$_2$ (90.6 mg, 123.8 umol, 0.1 eq.) and KOAc (364.4 mg, 3.7 mmol, 3 eq.) in dioxane (4 mL) was stirred at 80° C. for 12 hrs under N$_2$ atmosphere and then concentrated. The residue was purified by column chromatography (SiO$_2$, Petroleum ether:Ethyl acetate=50:1 to 3:1) to give 5-amino-N-(2-hydroxy-1,1-dimethyl-ethyl)-2-(4,4,5,5-tetramethyl-1,3,2-dioxaborolan-2-yl)benzenesulfonamide (201 mg, crude) as a white solid. $^1$H NMR (400 MHz, METHANOL-d4) δ=7.53 (d, J=8.0 Hz, 1H), 7.28 (d, J=2.4 Hz, 1H), 6.75 (dd, J=6.4 Hz, 1H), 3.35 (s, 2H), 1.36 (s, 12H), 1.10 (s, 6H).

Preparation of Compound 14.

A mixture of 5-amino-N-(2-hydroxy-1,1-dimethyl-ethyl)-2-(4,4,5,5-tetramethyl-1,3,2-dioxaborolan-2-yl)benzenesulfonamide (140.7 mg, 380.1 umol, 1.2 eq.), trans-isopropyl N-[4-(5-bromothiazol-2-yl)cyclohexyl]carbamate (110 mg, 316.7 umol, 1 eq.), Na$_2$CO$_3$ (100.7 mg, 950.3 umol, 3 eq.), KF (27.6 mg, 475.1 umol, 1.5 eq.) and Pd(PPh$_3$)$_4$ (36.6 mg, 31.7 umol, 0.1 eq.) in toluene (1 mL)/EtOH (1 mL)/H$_2$O (0.3 mL) was stirred at 80° C. for 12 hrs under N$_2$ atmosphere. The reaction mixture was concentrated, diluted with H$_2$O (10 mL) and extracted with EtOAc (10 mL×2). The combined organic layers were dried over Na$_2$SO$_4$, filtered and concentrated. The residue was purified by prep-TLC (SiO$_2$, Ethyl acetate) to give trans-isopropyl N-[4-[5-[4-amino-2-[(2-hydroxy-1,1-dimethyl-ethyl)sulfamoyl]phenyl]thiazol-2-yl]cyclohexyl]carbamate (117 mg, crude) as a yellow solid. $^1$H NMR (400 MHz, METHANOL-d4) δ=7.63 (d, J=7.0 Hz, 1H), 7.44 (d, J=2.2 Hz, 1H), 7.15 (d, J=8.3 Hz, 1H), 6.83 (dd, J=2.4, 8.1 Hz, 1H), 4.85-4.78 (m, 1H), 3.50-3.39 (m, 1H), 3.25 (s, 2H), 3.03-2.91 (m, 1H), 2.21 (br t, J=6.1 Hz, 2H), 2.12-2.00 (m, 2H), 1.75-1.60 (m, 2H), 1.45-1.33 (m, 2H), 1.28-1.19 (s, 6H), 1.03 (s, 6H)

Preparation of Compound 15.

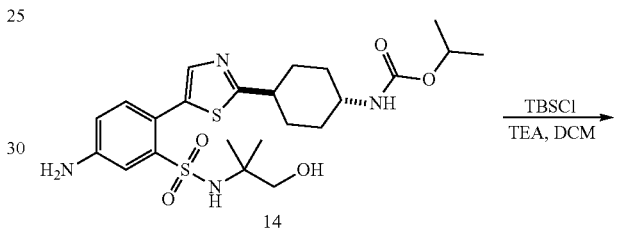

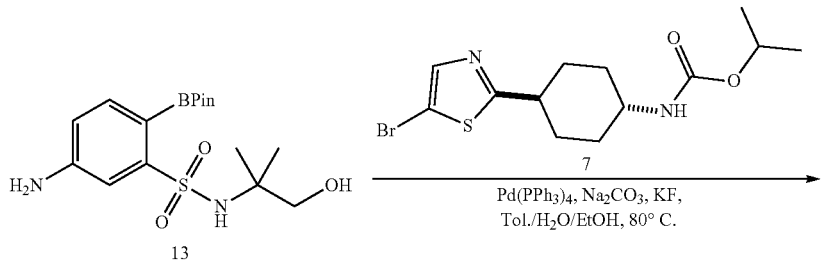

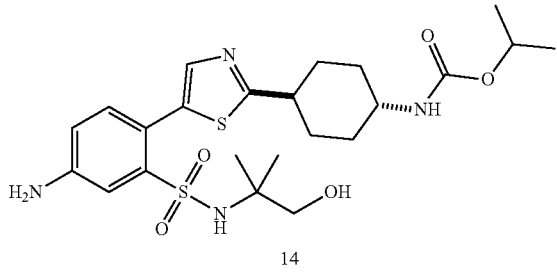

-continued

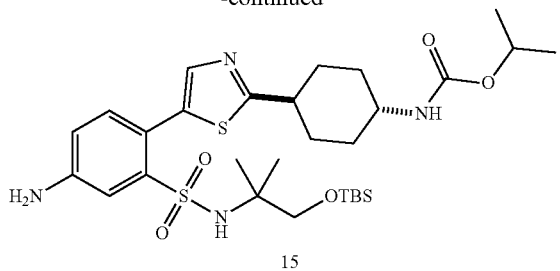

15

To a solution of trans-isopropyl N-[4-[5-[4-amino-2-[(2-hydroxy-1,1-dimethyl-ethyl) sulfamoyl]phenyl]thiazol-2-yl]cyclohexyl]carbamate (90 mg, 176.3 umol, 1 eq.) in DCM (1 mL) were added TEA (53.5 mg, 528.7 umol, 3 eq.), DMAP (2.2 mg, 17.6 umol, 0.1 eq.) and TBSCl (66.4 mg, 440.6 umol, 2.5 eq.). The mixture was stirred at 30° C. for 12 hrs and then concentrated. The residue was purified by prep-TLC (SiO₂, Petroleum ether:Ethyl acetate=2:1) to give trans-isopropyl N-[4-[5-[4-amino-2-[[2-[tert-butyl(dimethyl)silyl]oxy-1,1-dimethyl-ethyl]sulfamoyl]phenyl]thiazol-2-yl]cyclohexyl]carbamate (120 mg, crude) as a pale yellow solid. ESI [M+H]=625.2

Preparation of Compound 16.

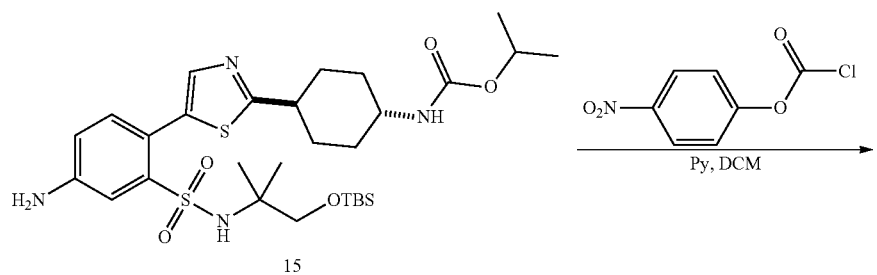

15

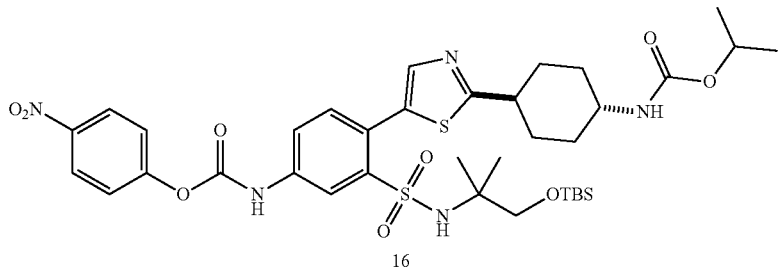

16

To a solution of trans-isopropyl N-[4-[5-[4-amino-2-[[2-[tert-butyl(dimethyl)silyl]oxy-1,1-dimethyl-ethyl]sulfamoyl]phenyl]thiazol-2-yl]cyclohexyl]carbamate (90 mg, 144 umol, 1 eq.) in DCM (1 mL) were added DMAP (1.8 mg, 14.4 umol, 0.1 eq.), pyridine (34.2 mg, 432 umol, 3 eq.) and (4-nitrophenyl) carbonochloridate (43.5 mg, 216 umol, 1.5 eq.). The mixture was stirred at 25° C. for 0.5 hr and used into the next step directly without further purification. ESI [M+H]=790.3

Preparation of Compound 17.

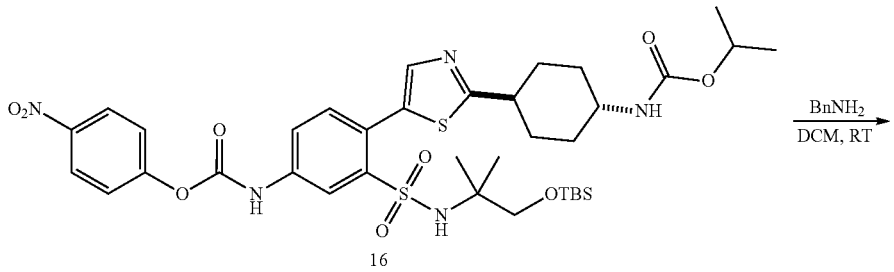

16

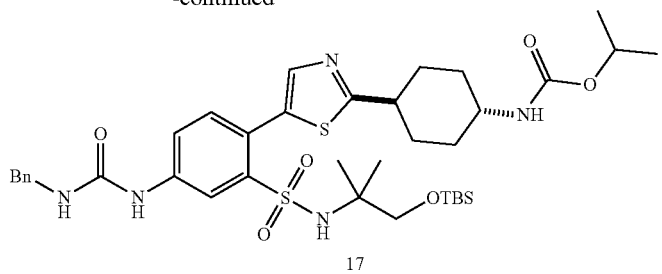

17

To a solution of phenylmethanamine (36 mg, 336 umol, 3 eq.) in DCM (1 mL) was added a solution of trans-(4-nitrophenyl)N-[3-[[2-[tert-butyl(dimethyl)silyl]oxy-1,1-dimethyl-ethyl]sulfamoyl]-4-[2-[4-(isopropoxycarbonylamino)cyclohexyl]thiazol-5-yl]phenyl]carbamate (88.5 mg, 112 umol, 1 eq.) in DCM (1 mL) and the mixture was stirred at 25° C. for 0.5 hr. The reaction mixture was diluted with H$_2$O (10 mL) and extracted with EtOAc (10 mL×2). The combined organic layers were dried over Na$_2$SO$_4$, filtered and concentrated. The residue was purified by prep-TLC (SiO$_2$, Petroleum ether:Ethyl acetate=1:1) to give trans-isopropyl N-[4-[5-[4-(benzylcarbamoylamino)-2-[[2-[tert-butyl(dimethyl)silyl]oxy-1,1-dimethyl-ethyl]sulfamoyl]phenyl]thiazol-2-yl]cyclohexyl]carbamate (93 mg, crude) as a yellow gum. ESI [M+H]=758.4

Preparation of Ex 74.

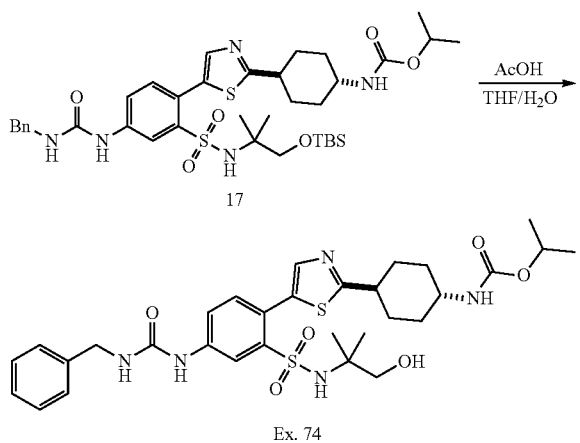

Ex. 74

A mixture of trans-isopropyl N-[4-[5-[4-(benzylcarbamoylamino)-2-[[2-[tert-butyl(dimethyl)silyl]oxy-1,1-dimethyl-ethyl]sulfamoyl]phenyl]thiazol-2-yl]cyclohexyl]carbamate (84.9 mg, 112 umol, 1 eq.) in AcOH (0.5 mL)/THF (0.5 mL)/H$_2$O (0.5 mL) was stirred at 80° C. for 0.5 hr. Then the mixture was concentrated and the residue was purified by prep-HPLC (TFA condition) to give trans-isopropyl N-[4-[5-[4-(benzylcarbamoylamino)-2-[(2-hydroxy-1,1-dimethyl-ethyl)sulfamoyl]phenyl]thiazol-2-yl]cyclohexyl] carbamate (5.86 mg, 9.10 umol, 8.13% yield, 100% purity) as a yellow solid. $^1$H NMR (400 MHz, METHANOL-d4) δ=8.25 (d, J=2.6 Hz, 1H), 7.81-7.66 (m, 2H), 7.40-7.30 (m, 5H), 7.28-7.22 (m, 1H), 4.82 (td, J=6.0, 12.5 Hz, 1H), 4.41 (s, 2H), 3.45 (br t, J=11.6 Hz, 1H), 3.28 (s, 2H), 3.00 (br t, J=11.8 Hz, 1H), 2.23 (br d, J=13.2 Hz, 2H), 2.11-2.00 (m, 2H), 1.77-1.60 (m, 2H), 1.48-1.32 (m, 2H), 1.22 (br d, J=6.1 Hz, 6H), 1.05 (s, 6H). ESI [M+H]=644.3

Example 75 Compound Primary Screening

1. Background

Primary screening was a phenotypic screen that utilized the synthetic lethal interaction between AID and RAD51 to identify compounds that were both potent and on target. AID expressing cells are dependent upon RAD51 for survival; inhibiting RAD51 in AID positive cells results in a cytotoxic effect. Based on such an effect, compounds that were potent in AID positive cells and were significantly less potent in AID negative cells were identified.

2. Materials and Supplies

Plastic ware and consumables needed for this experiment include: Cell Culture media; Evaporation Buffer media; 100% DMSO; 96 well U-bottom sterile culture plates; 250 mL bottle; 1.5 mL Opaque amber epi tubes; Epi Tube rack; 300 mL reservoirs; 25 mL reservoir; 25 mL serological pipette tips; 5 mL serological pipette tips P1000 Pipette Tips; and P200 Pipette Tips.

Equipment needed for this experiment include: Viaflo 384 liquid handler; Eppendorf serological pipette; Eppendorf P1000 Pipette; and Eppendorf P200 Pipette Daudi Cell Culture and WI-38 Cell Cultures were also needed for this experiment.

Lastly, compounds (e.g., the compounds of this invention) to be tested are needed.

3. Procedure

All steps were performed in a sterile environment inside the Biosafety cabinet.

The first step was to set up a cell killing assay in the Daudi cell line (AID positive). A 96 well u-bottom plate was prepared by writing the experiment number, plate number, date and initials in the top right corner of the plate lid. With a sterile 300 ml reservoir, and 25 ml serological pipette, evaporation buffer media was pipetted into reservoir in 25 ml increments.

Using the liquid handler, 150 ul of evaporation buffer media was pipetted from reservoir into rows A and H, and Columns 1 and 12 of the 96 well u-bottom plate. Cell cultures were counted to obtain the density of cells per ml, and the culture viability. The cell density information was used to obtain 1,000,000 cells from culture using a 5 mL serological pipette into an epi tube. The cell density information from the culture was used to calculate the number of cells and volume of media needed for the assay to seed 1250 cells in 130 ul of media per available culture well in the 96 well u-bottom plate. Rows B through F were used for cells (50 wells in total), with row G left for an empty media control. The calculation was overestimated by 10 mL to account for the dead volume in the 300 ml reservoir. Once the media volume was calculated, the appropriate volume of media was pipetted in 25 mL increments into the 250 mL bottle using a 25 mL serological pipette. The 250 ml bottle was capped tightly, and placed into a 37° C. water bath for 2 minutes. While the culture media was warming, 10 mL of fresh media was pipetted from the 500 mL culture media bottle into a sterile 25 mL reservoir. Using the Eppendorf multichannel pipette, 130 ul of media was pipted from the 25 mL reservoir into row G of the 96 well u-bottom plate. Once the 250 mL bottle of media was warmed, the volume of culture needed was pipetted into the bottle, and mixed gently with a 25 mL serological pipette as to not create bubbles, and then the contents of the bottle were pipetted into a new 300 mL reservoir. Using the liquid handler, 130 ul of culture was pipetted from the 300 mL reservoir into rows B through F of the 96 well u-bottom plate. Once the culture was added, the plate was placed into a 37° C. incubator until the compound master plate was prepared for use.

Two 96 well u-bottom plates were prepared by writing the master plate name in the upper right corner of the plate lid. Labeling one DMSO master and the other Media Master. The compounds of interest were obtained from the laboratory freezer, and placed into a 25 well storage box with a lid, and set the box aside. The compounds were vortexed after thawing but before use. Using an automatic multichannel pipette, 20 ul of 100% DMSO was pipetted into wells B3-B11 through G3-G11 of the DMSO master plate. For each compound on the master plate, 50 ul of the compound were pipetted in the appropriate well of row 2 (reference plate map to determine appropriate well). A serial dilution was prepared beginning by aspirating 20 ul from row 2 and mixing with row 3, repeating until row 11 was reached. Using the liquid handler, 194 ul of Daudi media was dispensed into wells B2-B11 through G2-G11 of the Media master plate. Using the liquid handler, 6 ul from the DMSO master plate was aspirated and dispensed into the media master plate, mixing 100 ul twice.

Compounds from master plate were then added to the culture plate. The culture plates were removed from the incubator, and set inside the biosafety cabinet. Using a liquid handler, 20 ul from wells B2 to B11 through G2 to G11 of master plate were aspirated, and dispensed into wells B2 to B11 through G2 to G11 of culture plate. This set was continued with each culture plate. Once the culture plates acquired their 20 ul of compound dilutions, they were placed back into the incubator, until their reads on Day 7 of experiment. Cell death was measured on Day 7 of the experiment using Cell-Titer Glo and a Promega Plate reader.

Percent cell death and $EC_{50}$ values were calculated by comparing the cell viability of the compound treated wells to the non-treated wells. Normalized RLU values were obtained by subtracting the media well values from each of the wells in the same column, and then dividing that value by the DMSO treated cells values. The percent kill was then calculated by subtracting the normalized RLU value from 1 and multiplying by 100. The average normalized percent kill value and standard error of the mean was then calculated. The kill values were then inputted into Prism with the corresponding standard errors. In Prism a non-linear regression line was plotted with the data points using a semi-log scale, and the $EC_{50}$ value was calculated. For compounds that showed good potency in the Daudi cell line, the assay was repeated using WI-38 cells (AID negative).

Screening Data

TABLE 1

| Compound No. | Structure | AID + $EC_{50}$ (µM)<br>A = ≤0.1 µM<br>B = ≤1 µM<br>C = >1 µM<br>ND = Not Determined | AID − $EC_{50}$ (µM)<br>A = ≤0.1 µM<br>B = ≤1 µM<br>C = >1 µM<br>ND = Not Determined |
|---|---|---|---|
| Ex. 1 | 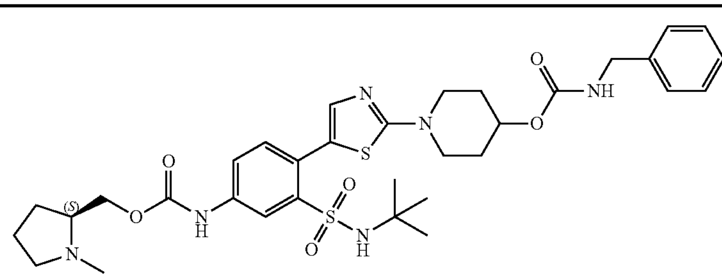 | C | ND |
| Ex. 2 | 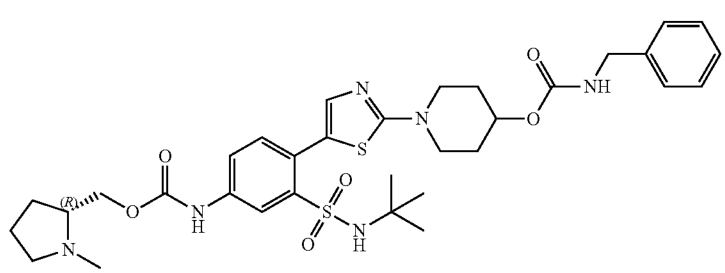 | C | ND |

TABLE 1-continued

| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 3 | 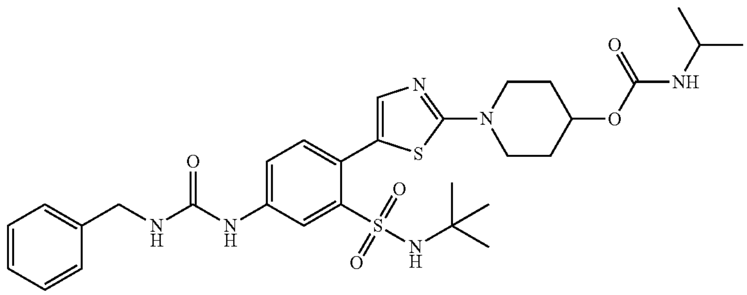 [SMILES: CC(C)NC(=O)OC1CCN(c2ncc(-c3ccc(NC(=O)NCc4ccccc4)cc3S(=O)(=O)NC(C)(C)C)s2)CC1] | A | C |
| Ex. 4 | 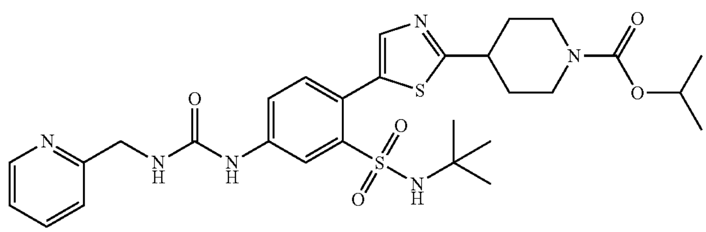 [SMILES: CC(C)OC(=O)N1CCC(c2ncc(-c3ccc(NC(=O)NCc4ccccn4)cc3S(=O)(=O)NC(C)(C)C)s2)CC1] | C | C |
| Ex. 5 | 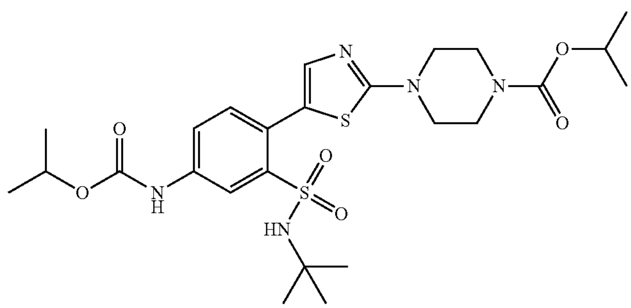 [SMILES: CC(C)OC(=O)Nc1ccc(-c2cnc(N3CCN(C(=O)OC(C)C)CC3)s2)c(S(=O)(=O)NC(C)(C)C)c1] | C | ND |
| Ex. 6 | 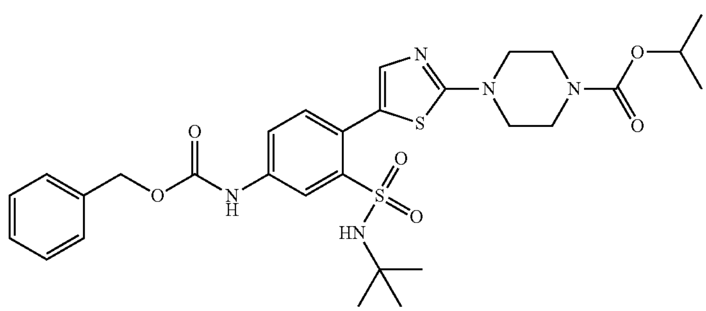 [SMILES: CC(C)OC(=O)N1CCN(c2ncc(-c3ccc(NC(=O)OCc4ccccc4)cc3S(=O)(=O)NC(C)(C)C)s2)CC1] | C | ND |
| Ex. 7 | 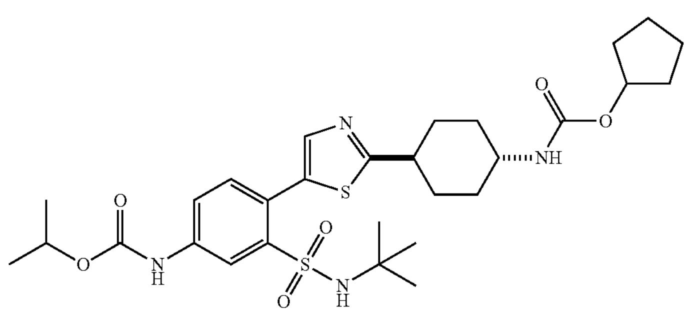 | B | ND |

TABLE 1-continued
| Compound No. | Structure | AID + EC$_{50}$ (μM) A = ≤0.1 μM B = ≤1 μM C = >1 μM ND = Not Determined | AID − EC$_{50}$ (μM) A = ≤0.1 μM B = ≤1 μM C = >1 μM ND = Not Determined |
|---|---|---|---|
| Ex. 8 | 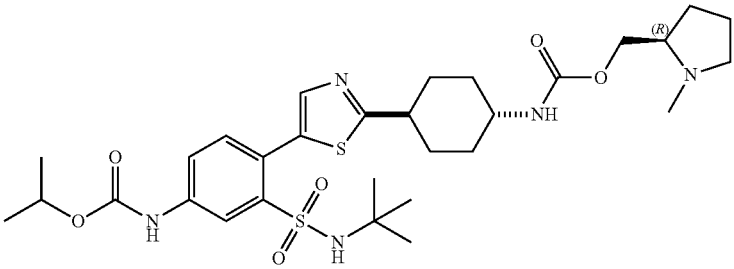 | C | ND |
| Ex. 9 | 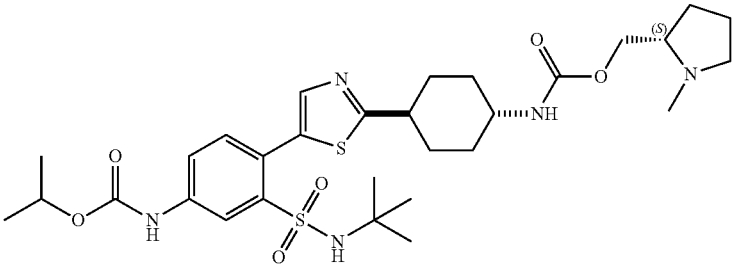 | B | ND |
| Ex. 10 | 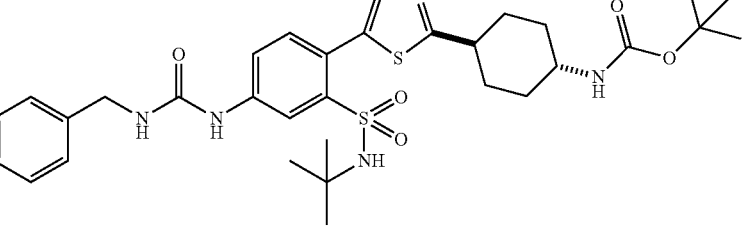 | A | C |
| Ex. 11 | 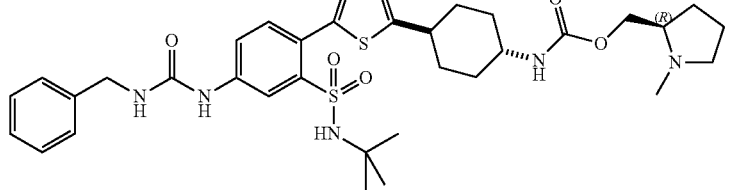 | B | ND |
| Ex. 12 | 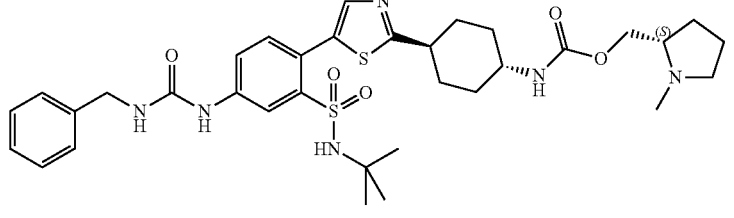 | B | ND |
| Ex. 13 | 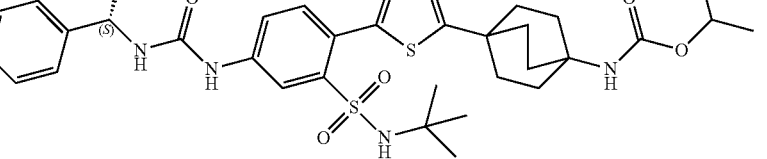 | A | C |

TABLE 1-continued
| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 14 | 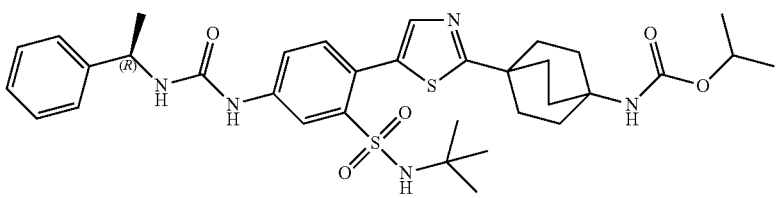 | A | C |
| Ex. 15 | 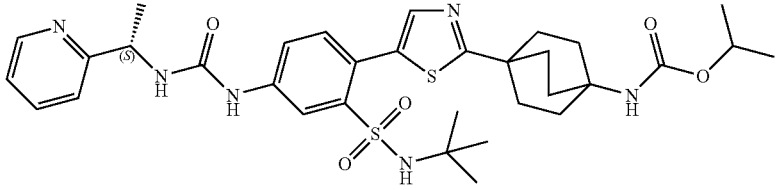 | A | C |
| Ex. 16 | 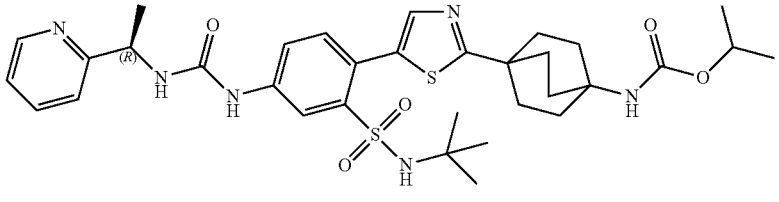 | A | C |
| Ex. 17 | 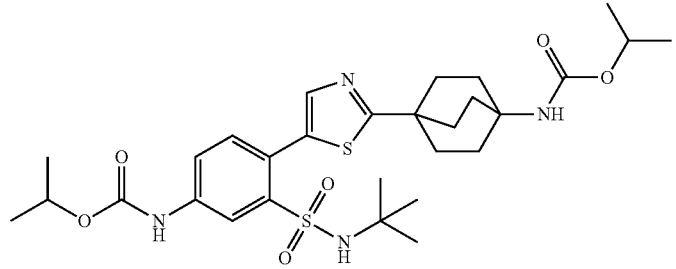 [SMILES: CC(C)OC(=O)Nc1ccc(-c2cnc(C34CCC(NC(=O)OC(C)C)(CC3)CC4)s2)c(S(=O)(=O)NC(C)(C)C)c1] | B | C |
| Ex. 18 | 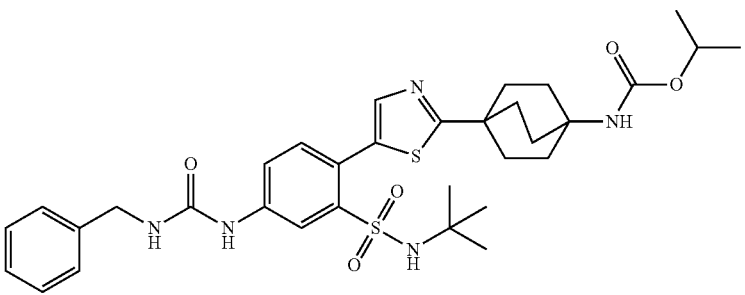 [SMILES: CC(C)OC(=O)NC12CCC(c3ncc(-c4ccc(NC(=O)NCc5ccccc5)cc4S(=O)(=O)NC(C)(C)C)s3)(CC1)CC2] | A | C |
| Ex. 19 | 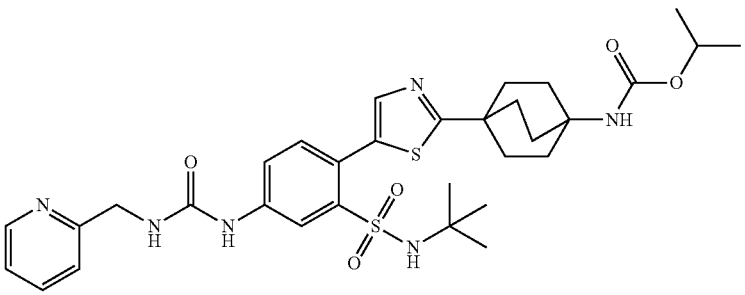 [SMILES: CC(C)OC(=O)NC12CCC(c3ncc(-c4ccc(NC(=O)NCc5ccccn5)cc4S(=O)(=O)NC(C)(C)C)s3)(CC1)CC2] | A | C |

TABLE 1-continued

| Compound No. | Structure | AID + EC₅₀ (µM)<br>A = ≤0.1 µM<br>B = ≤1 µM<br>C = >1 µM<br>ND = Not Determined | AID − EC₅₀ (µM)<br>A = ≤0.1 µM<br>B = ≤1 µM<br>C = >1 µM<br>ND = Not Determined |
|---|---|---|---|
| Ex. 20 | 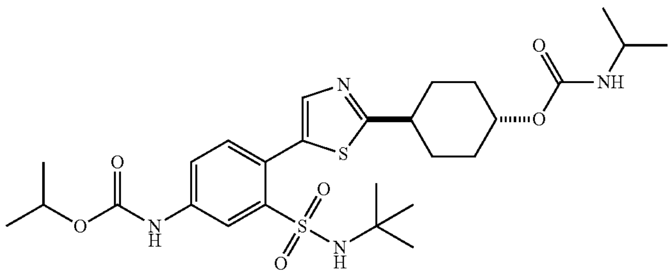 | C | ND |
| Ex. 21 | 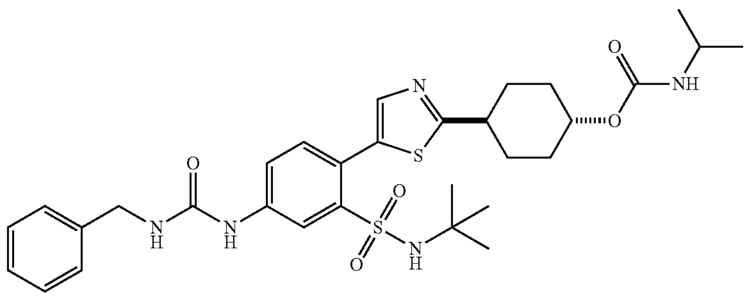 | A | ND |
| Ex. 22 | 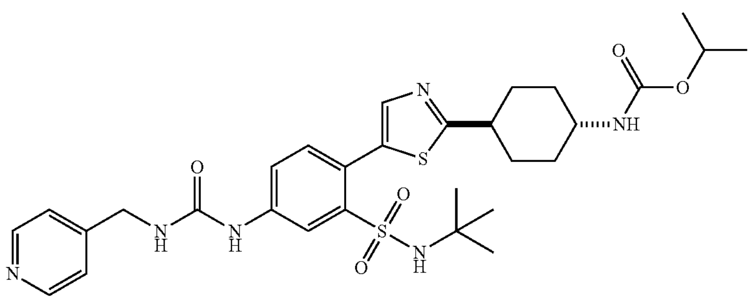 | B | ND |
| Ex. 23 | 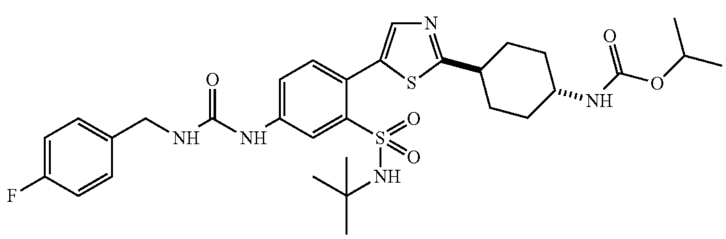 | A | ND |
| Ex. 24 | 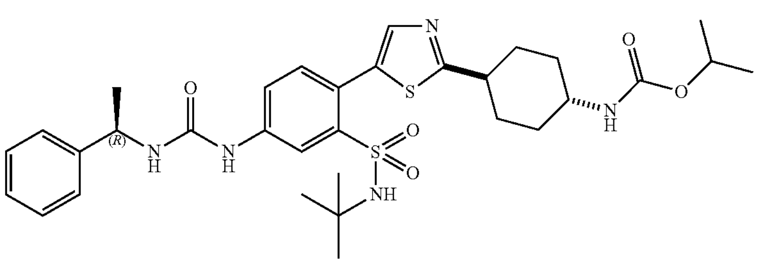 | A | C |

TABLE 1-continued

| Compound No. | Structure | AID + EC₅₀ (µM)<br>A = ≤0.1 µM<br>B = ≤1 µM<br>C = >1 µM<br>ND = Not Determined | AID − EC₅₀ (µM)<br>A = ≤0.1 µM<br>B = ≤1 µM<br>C = >1 µM<br>ND = Not Determined |
|---|---|---|---|
| Ex. 25 | 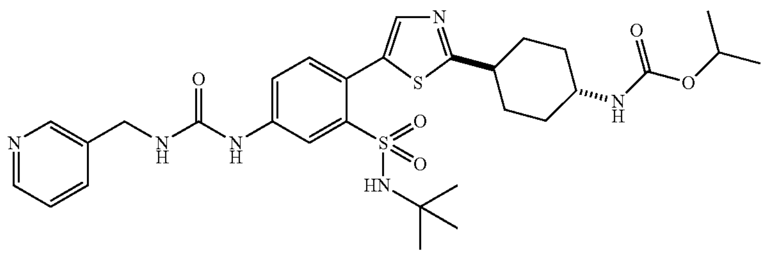 | A | ND |
| Ex. 26 | 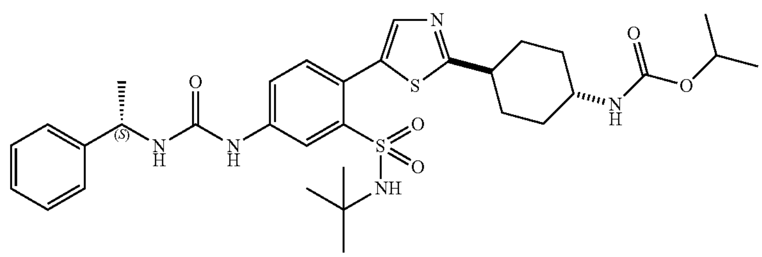 | A | C |
| Ex. 27 | 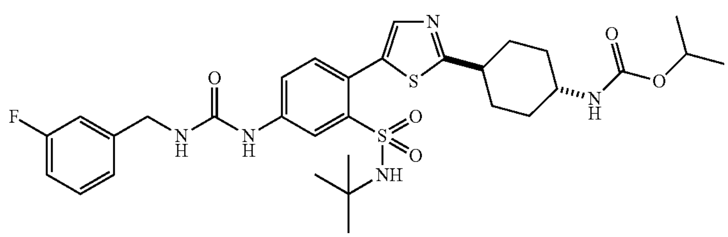 | A | C |
| Ex. 28 | 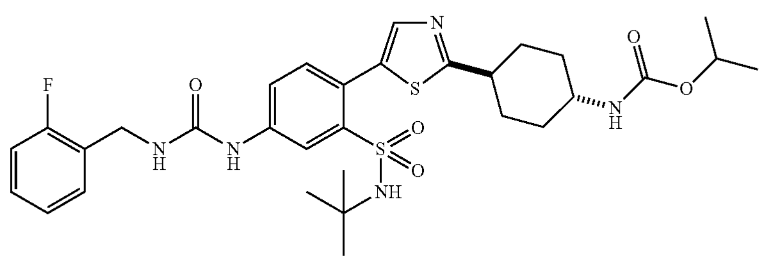 | A | ND |
| Ex. 29 | 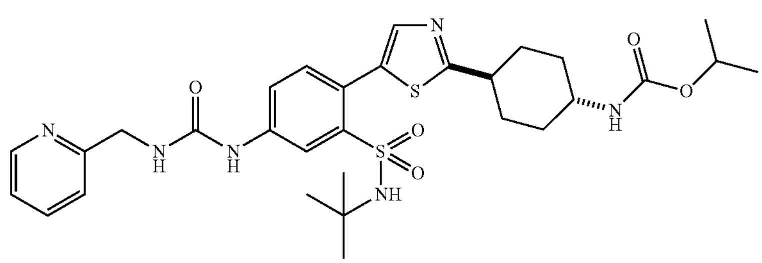 | A | C |

TABLE 1-continued

| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 30 | 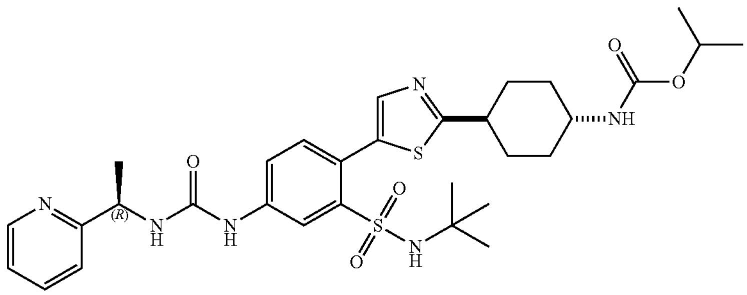 | A | C |
| Ex. 31 | 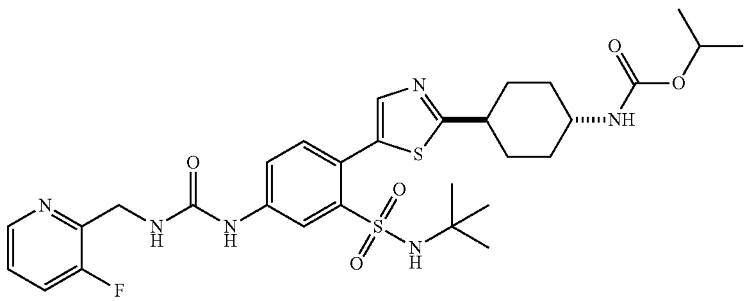 | A | C |
| Ex. 32 | 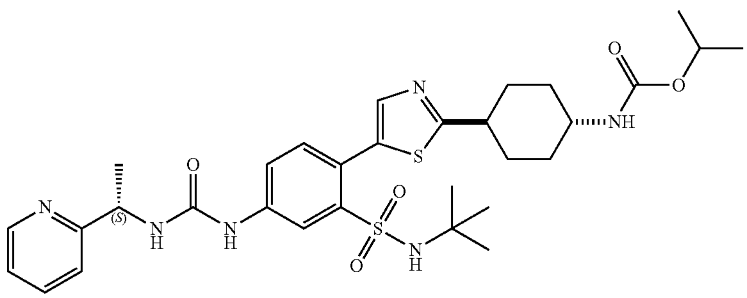 | A | C |
| Ex. 33 | 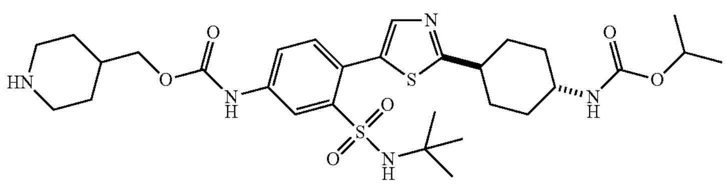 | C | ND |
| Ex. 34 | 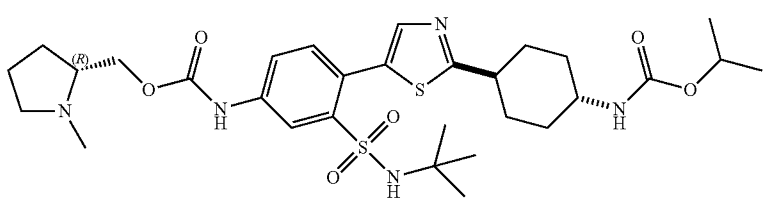 | B | ND |
| Ex. 35 | 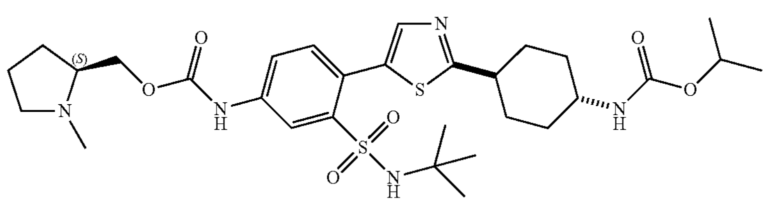 | B | ND |

TABLE 1-continued

| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 36 | 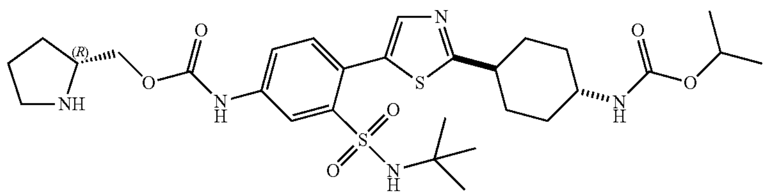 | B | ND |
| Ex. 37 | 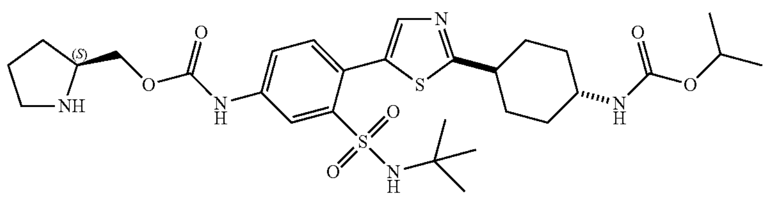 | B | ND |
| Ex. 38 | 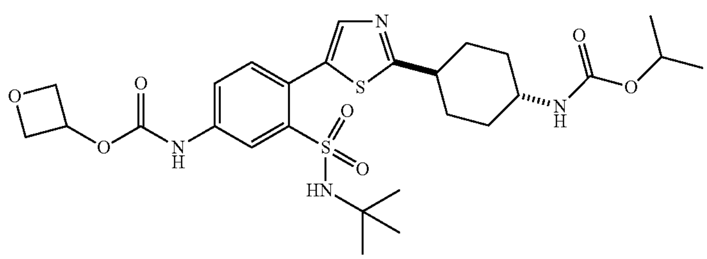 | A | C |
| Ex. 39 | 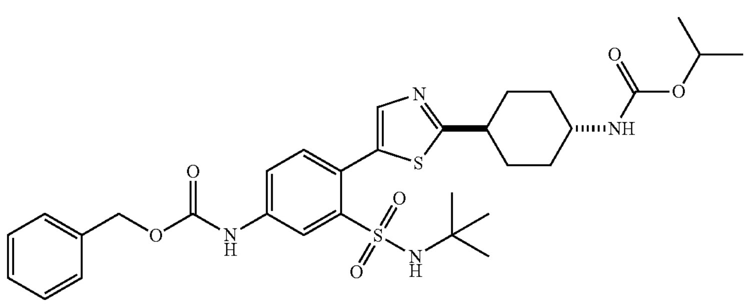 | A | C |
| Ex. 40 | 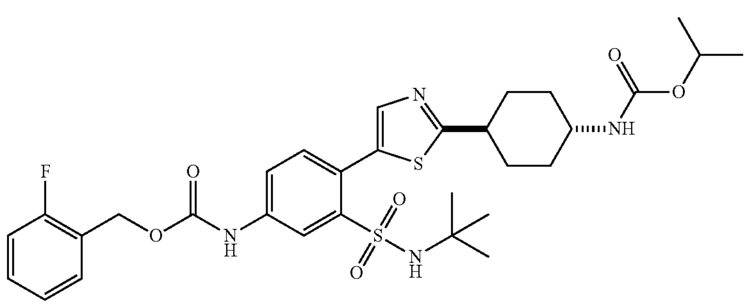 | A | C |

TABLE 1-continued

| Compound No. | Structure | AID + EC$_{50}$ (µM)<br>A = ≤0.1 µM<br>B = ≤1 µM<br>C = >1 µM<br>ND = Not Determined | AID − EC$_{50}$ (µM)<br>A = ≤0.1 µM<br>B = ≤1 µM<br>C = >1 µM<br>ND = Not Determined |
|---|---|---|---|
| Ex. 41 | 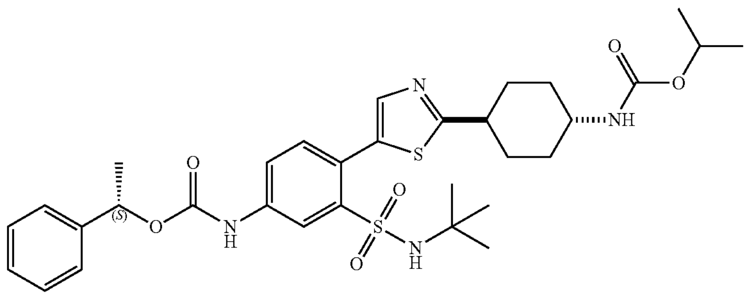 | A | C |
| Ex. 42 | 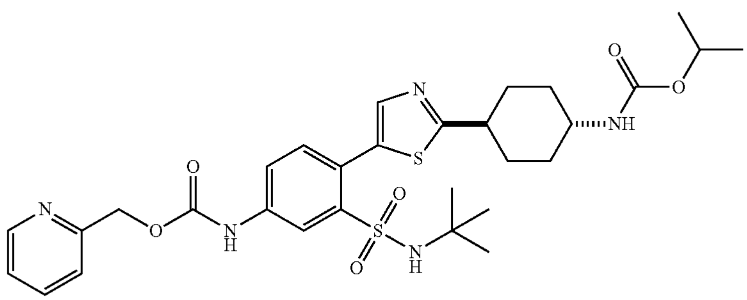 | A | C |
| Ex. 43 | 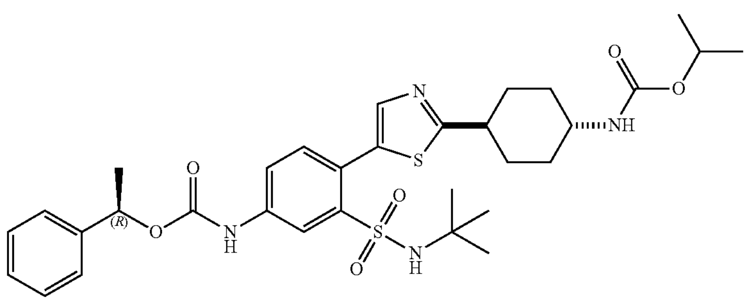 | B | C |
| Ex. 44 | 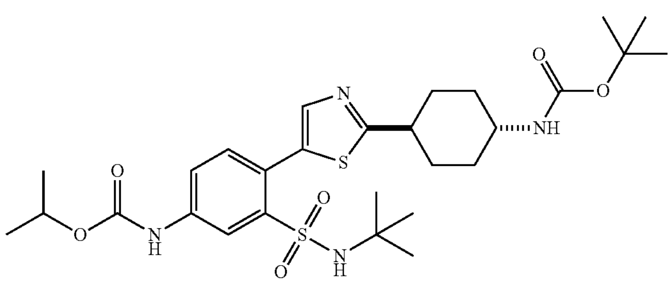 | C | ND |
| Ex. 45 | 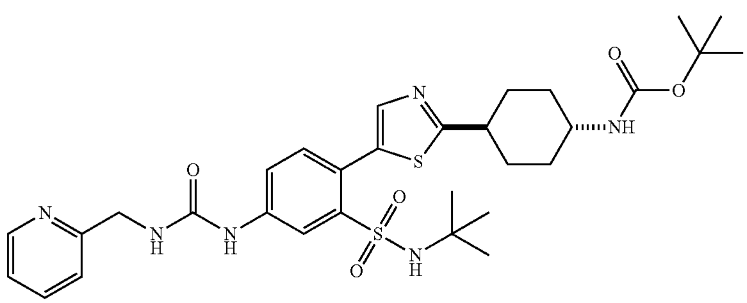 | A | ND |

TABLE 1-continued

| Compound No. | Structure | AID + EC₅₀ (µM) $A = \le 0.1\ \mu M$ $B = \le 1\ \mu M$ $C = >1\ \mu M$ ND = Not Determined | AID − EC₅₀ (µM) $A = \le 0.1\ \mu M$ $B = \le 1\ \mu M$ $C = >1\ \mu M$ ND = Not Determined |
| --- | --- | --- | --- |
| Ex. 46 | 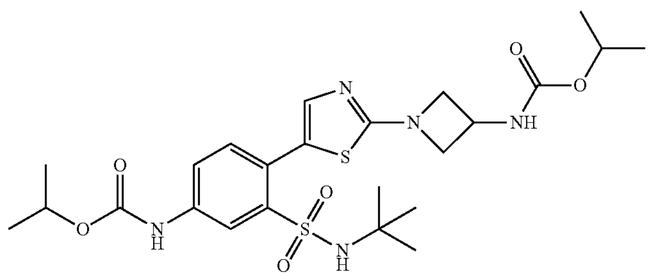 [SMILES: CC(C)OC(=O)Nc1ccc(-c2cnc(N3CC(NC(=O)OC(C)C)C3)s2)c(S(=O)(=O)NC(C)(C)C)c1] | C | C |
| Ex. 47 | 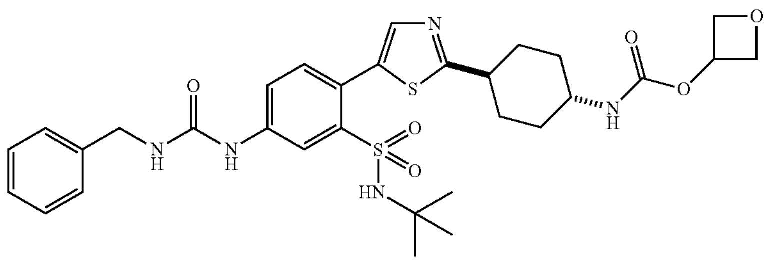 | A | C |
| Ex. 48 | 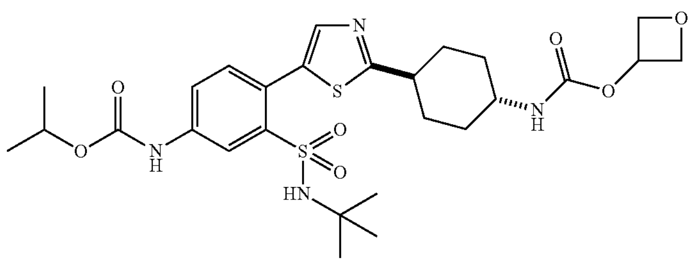 | B | C |
| Ex. 49 | 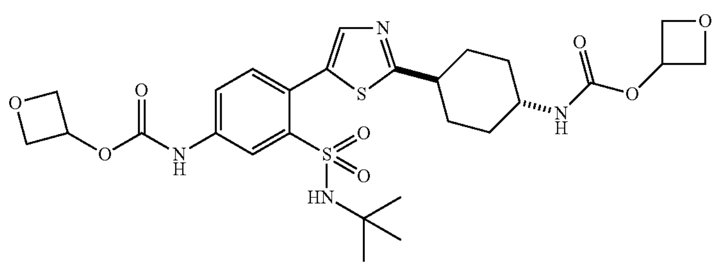 | B | C |
| Ex. 50 | 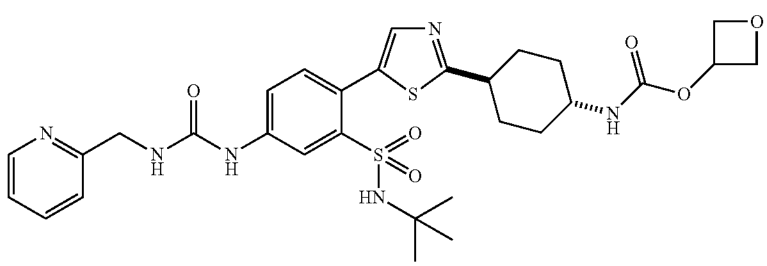 | A | C |

TABLE 1-continued
| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 51 | 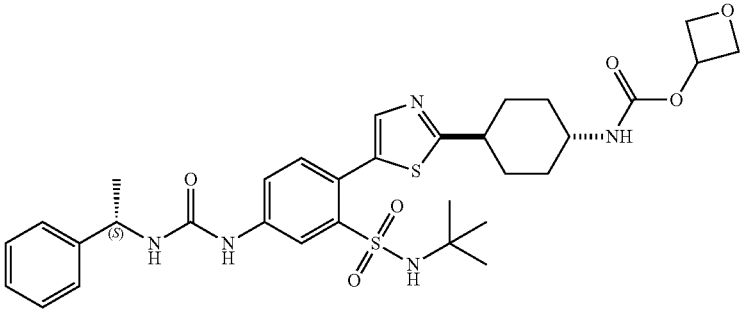 | A | C |
| Ex. 52 | 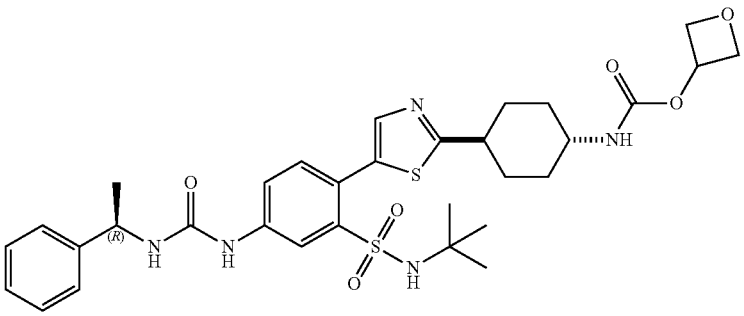 | A | C |
| Ex. 53 | 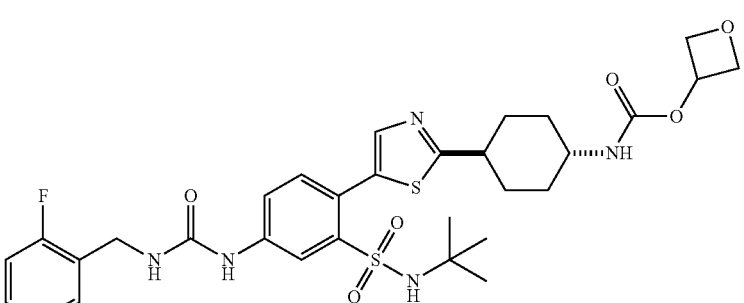 | A | C |
| Ex. 54 | 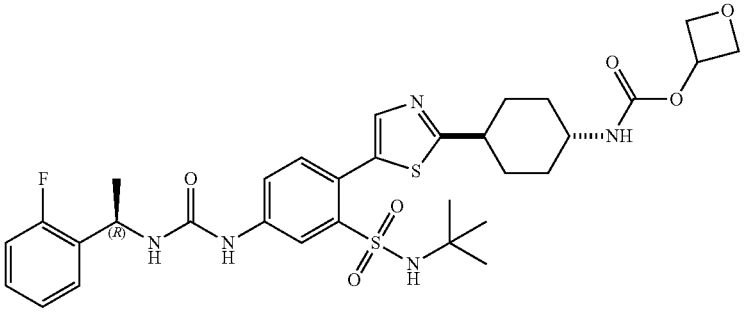 | A | C |

TABLE 1-continued

| Compound No. | Structure | AID + EC$_{50}$ (μM)<br>A = ≤0.1 μM<br>B = ≤1 μM<br>C = >1 μM<br>ND = Not Determined | AID − EC$_{50}$ (μM)<br>A = ≤0.1 μM<br>B = ≤1 μM<br>C = >1 μM<br>ND = Not Determined |
|---|---|---|---|
| Ex. 55 | 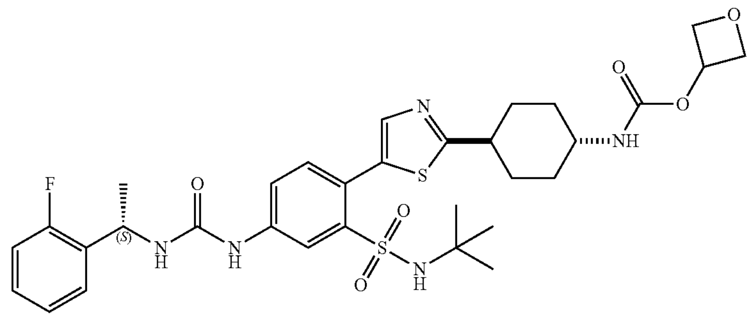 | A | C |
| Ex. 56 | 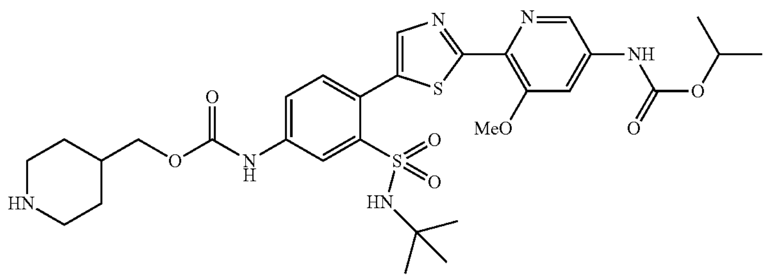 [SMILES: COc1cc(NC(=O)OC(C)C)cnc1-c1ncc(-c2ccc(NC(=O)OCC3CCNCC3)cc2S(=O)(=O)NC(C)(C)C)s1] | B | ND |
| Ex. 57 | 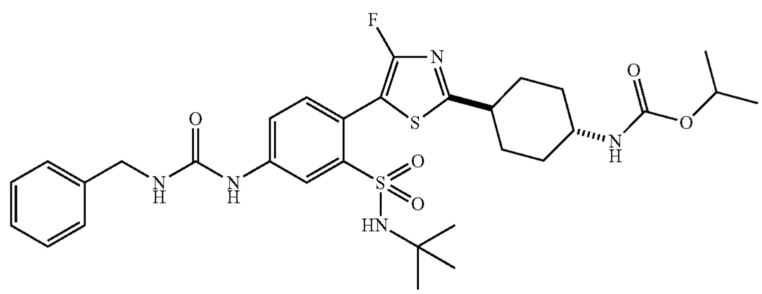 | A | C |
| Ex. 58 | 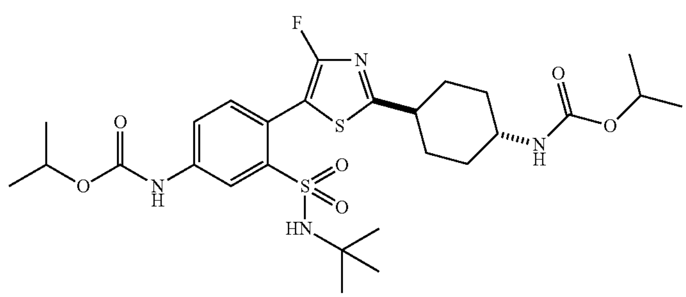 | B | C |
| Ex. 59 | 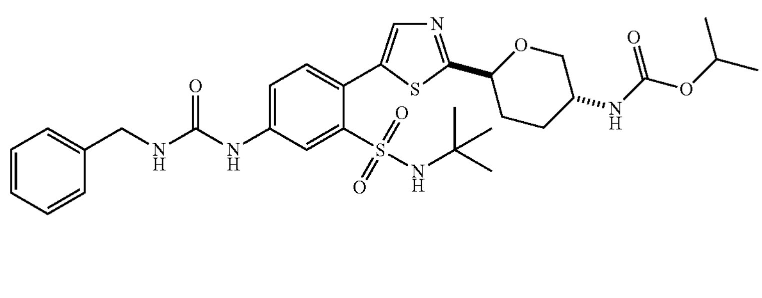 | A | C |

TABLE 1-continued

| Compound No. | Structure | AID + EC$_{50}$ (μM) A = ≤0.1 μM B = ≤1 μM C = >1 μM ND = Not Determined | AID − EC$_{50}$ (μM) A = ≤0.1 μM B = ≤1 μM C = >1 μM ND = Not Determined |
|---|---|---|---|
| Ex. 59A | 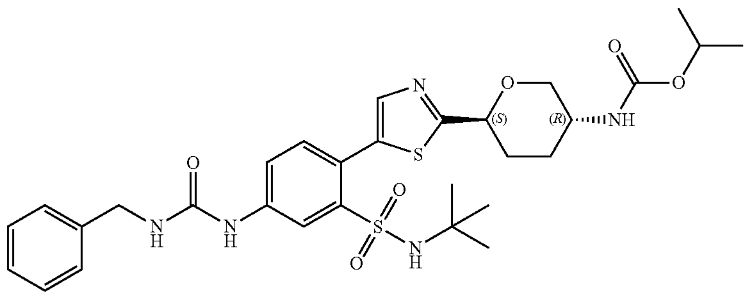 | B | C |
| Ex. 59B | 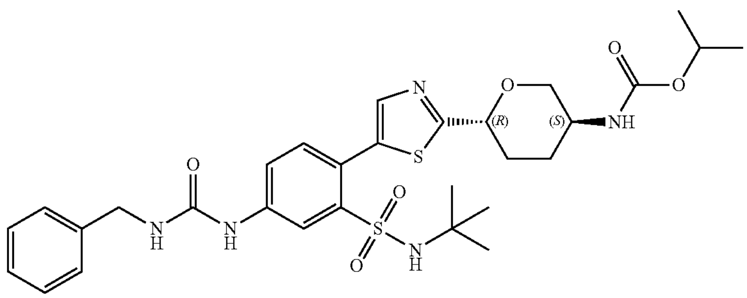 | A | C |
| Ex. 60 | 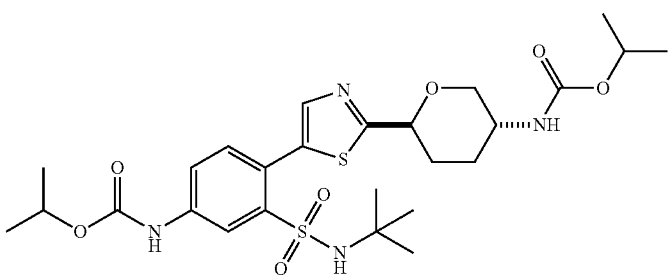 | B | C |
| Ex. 60A | 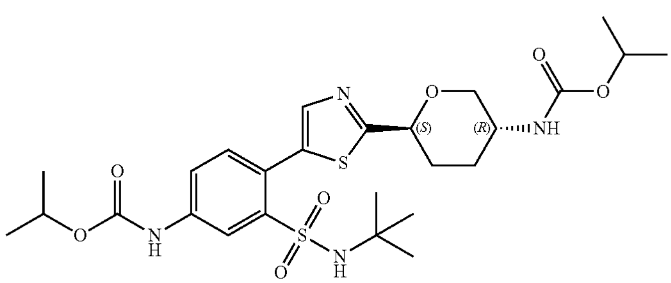 | C | C |
| Ex. 60B | 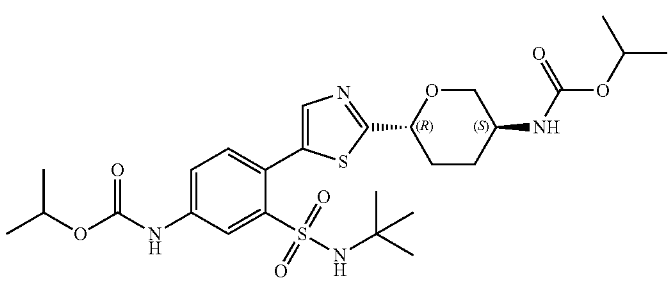 | B | C |

TABLE 1-continued

| Compound No. | Structure | AID + EC$_{50}$ (µM)<br>A = ≤0.1 µM<br>B = ≤1 µM<br>C = >1 µM<br>ND = Not Determined | AID − EC$_{50}$ (µM)<br>A = ≤0.1 µM<br>B = ≤1 µM<br>C = >1 µM<br>ND = Not Determined |
|---|---|---|---|
| Ex. 61 | 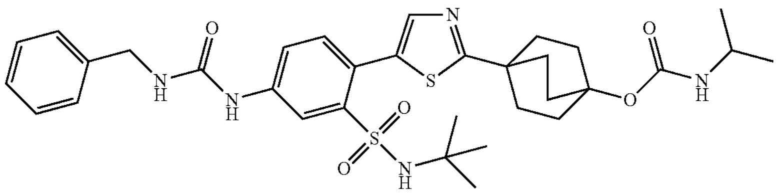 [SMILES: CC(C)NC(=O)OC12CCC(c3ncc(-c4ccc(NC(=O)NCc5ccccc5)cc4S(=O)(=O)NC(C)(C)C)s3)(CC1)CC2] | C | C |
| Ex. 62 | 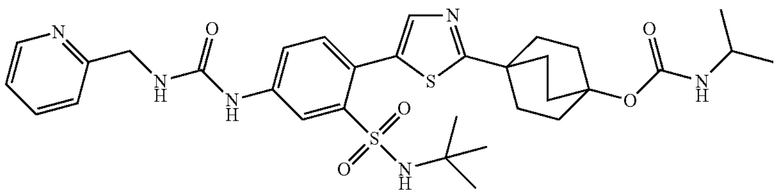 [SMILES: CC(C)NC(=O)OC12CCC(c3ncc(-c4ccc(NC(=O)NCc5ccccn5)cc4S(=O)(=O)NC(C)(C)C)s3)(CC1)CC2] | C | C |
| Ex. 63 | 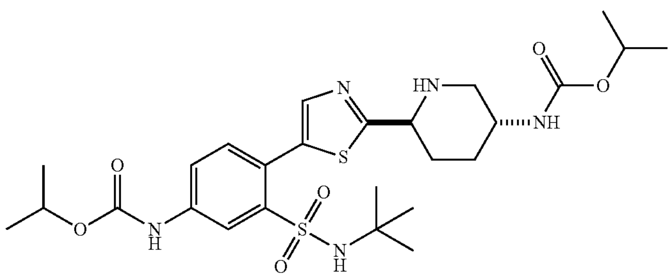 | B | ND |
| Ex. 64 | 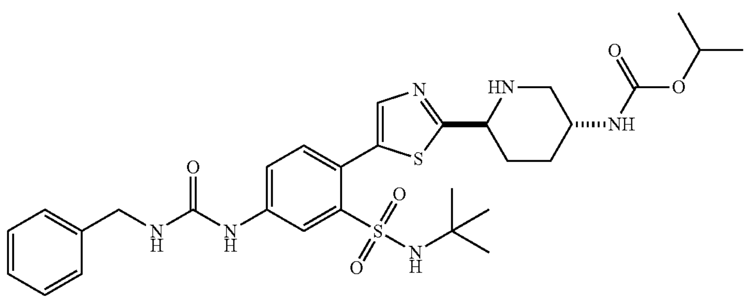 | A | C |
| Ex. 65 | 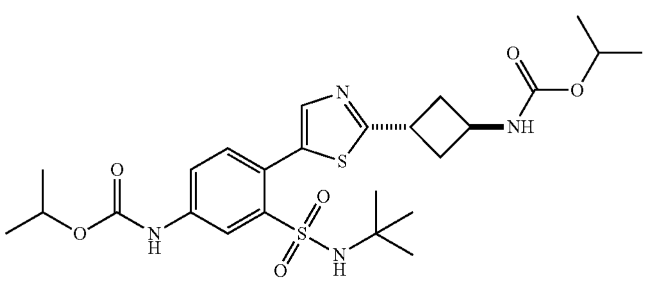 | B | C |
| Ex. 66A | 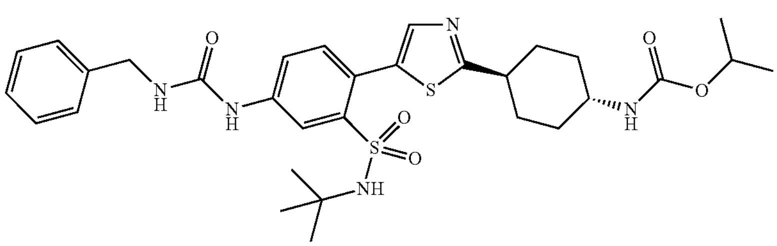 [SMILES: CC(C)OC(=O)N[C@H]1CC[C@H](c2ncc(-c3ccc(NC(=O)NCc4ccccc4)cc3S(=O)(=O)NC(C)(C)C)s2)CC1] | A | C |

TABLE 1-continued

| Compound No. | Structure | AID + EC$_{50}$ (μM)  A = ≤0.1 μM  B = ≤1 μM  C = >1 μM  ND = Not Determined | AID − EC$_{50}$ (μM)  A = ≤0.1 μM  B = ≤1 μM  C = >1 μM  ND = Not Determined |
|---|---|---|---|
| Ex. 66B | 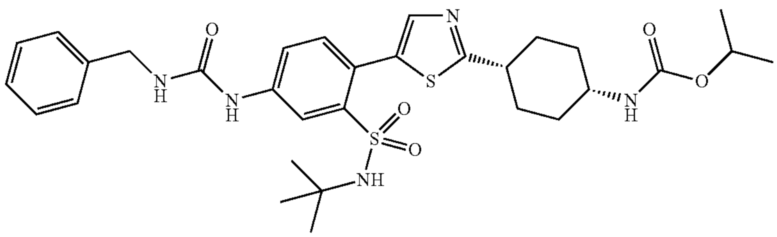 [SMILES: CC(C)OC(=O)N[C@H]1CC[C@@H](c2ncc(-c3ccc(NC(=O)NCc4ccccc4)cc3S(=O)(=O)NC(C)(C)C)s2)CC1] | B | ND |
| Ex. 67A | 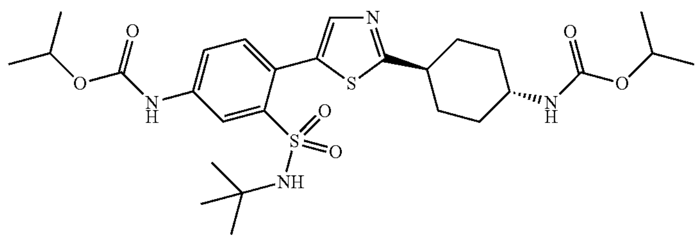 [SMILES: CC(C)OC(=O)Nc1ccc(-c2cnc([C@H]3CC[C@H](NC(=O)OC(C)C)CC3)s2)c(S(=O)(=O)NC(C)(C)C)c1] | B | C |
| Ex. 67B | 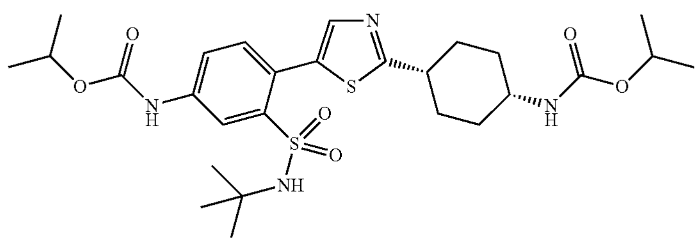 [SMILES: CC(C)OC(=O)Nc1ccc(-c2cnc([C@H]3CC[C@@H](NC(=O)OC(C)C)CC3)s2)c(S(=O)(=O)NC(C)(C)C)c1] | C | ND |
| Ex. 68 | 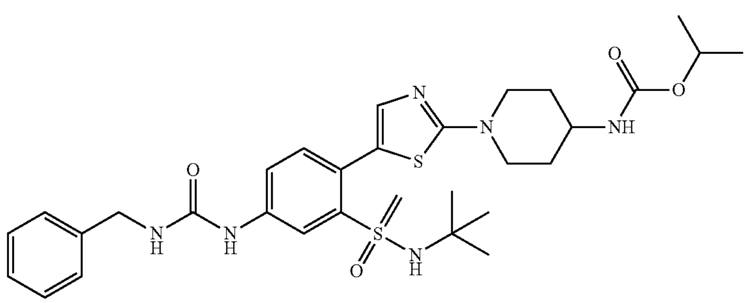 [SMILES: C=S(=O)(NC(C)(C)C)c1cc(NC(=O)NCc2ccccc2)ccc1-c1cnc(N2CCC(NC(=O)OC(C)C)CC2)s1] | B | ND |
| Ex. 69 | 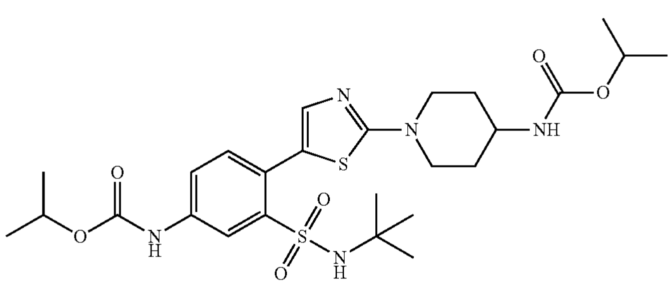 [SMILES: CC(C)OC(=O)Nc1ccc(-c2cnc(N3CCC(NC(=O)OC(C)C)CC3)s2)c(S(=O)(=O)NC(C)(C)C)c1] | C | ND |

TABLE 1-continued
| Compound No. | Structure | AID + EC$_{50}$ (μM) A = ≤0.1 μM B = ≤1 μM C = >1 μM ND = Not Determined | AID – EC$_{50}$ (μM) A = ≤0.1 μM B = ≤1 μM C = >1 μM ND = Not Determined |
|---|---|---|---|
| Ex. 70 | 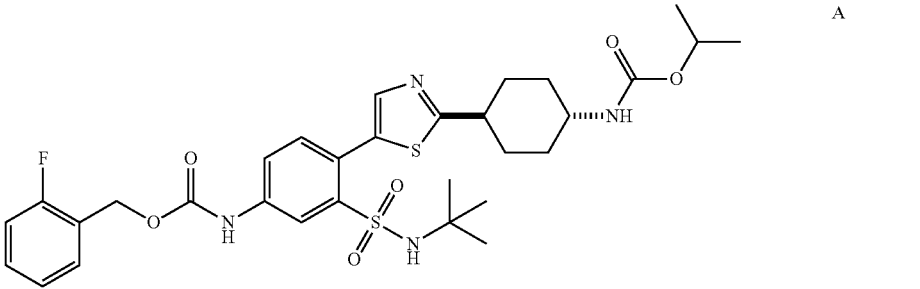 | A | C |
| Ex. 71 | 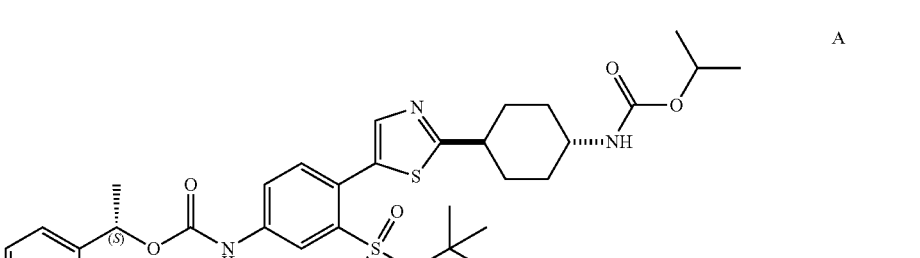 | A | C |
| Ex. 72 | 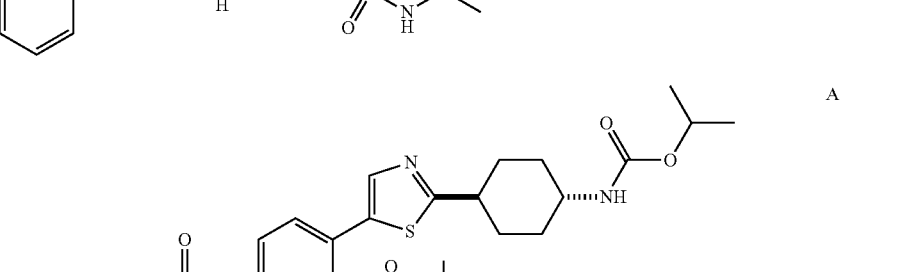 | A | C |
| Ex. 73 | 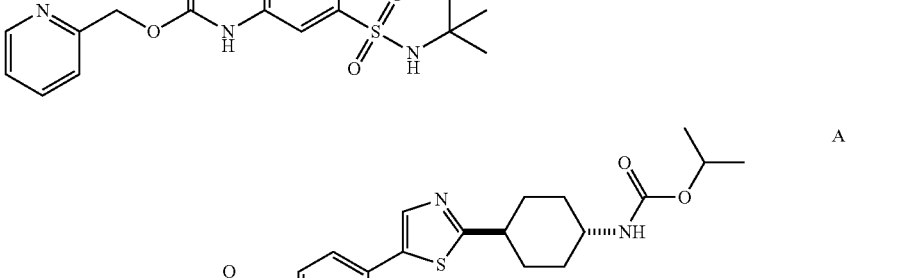 | A | C |
| Ex. 74 | 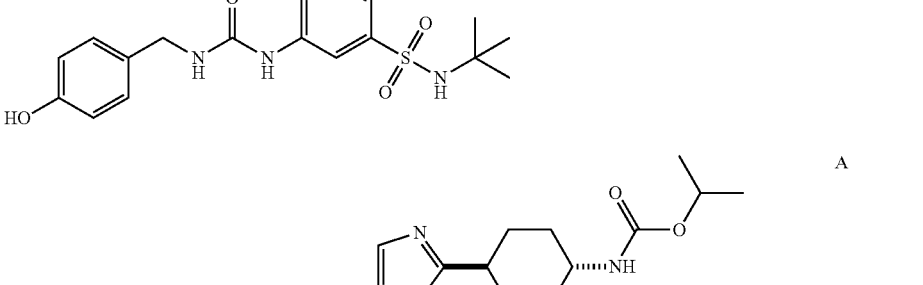 | A | C |

Example 76. Bi-Directional Caco-2 Permeability

Bi-directional Caco-2 permeability was assayed. Caco-2 cells were seeded onto permeable polycarbonate supports and allowed to differentiate for about 3 weeks prior to being used in the assays. The cells were then exposed to the compounds from either the apical or basolateral sides and incubated at 37 C for up to 90 minutes under light agitation. Compound transport was then measured using LC/MS/MS analysis at 30, 60, and 90 minutes.

TABLE 2

| Example No. | AB Papp (cm/sec × $10^6$) | BA Papp (cm/sec × $10^6$) | BA/AB Ratio | AB Recovery % | BA Recovery % |
|---|---|---|---|---|---|
| Ex. 5 | 5.9 | 2.2 | 0.4 | 34.7 | 80.8 |
| Ex. 7 | 1.7 | 2.1 | 1.2 | 55.9 | 92 |
| Ex. 10 | 1.2 | 1.5 | 1.3 | 59.9 | 87.2 |
| Ex. 17 | 2.8 | 2.1 | 0.8 | 47.2 | 81.9 |
| Ex. 20 | 9.4 | 10.4 | 1.1 | 44.8 | 96.6 |
| Ex. 21 | 3.6 | 10.7 | 3 | 58.6 | 78.3 |
| Ex. 22 | 1.1 | 21 | 18.7 | 83.1 | 89 |
| Ex. 27 | 0.7 | 0.5 | 0.7 | 92 | 107.1 |
| Ex. 28 | 1.9 | 3.3 | 1.7 | 66.9 | 81 |
| Ex. 29 | 10.9 | 24.1 | 2.2 | 93.9 | 90.9 |
| Ex. 30 | 11.5 | 15.7 | 1.4 | 79.8 | 115.6 |
| Ex. 31 | 12.8 | 13.6 | 1.1 | 70.5 | 92.3 |
| Ex. 34 | 0.4 | 45.2 | 103.9 | 98.2 | 96.8 |
| Ex. 35 | 0.4 | 41 | 99.1 | 98.8 | 107.5 |
| Ex. 38 | 17.9 | 22.9 | 1.3 | 73.3 | 82.3 |
| Ex. 44 | 3.2 | 4.2 | 1.3 | 36.2 | 69.4 |
| Ex. 45 | 7.6 | 10.8 | 1.4 | 73.6 | 84.4 |
| Ex. 47 | 8.7 | 12.4 | 1.4 | 65.3 | 80.7 |
| Ex. 48 | 23.1 | 16 | 0.7 | 80.1 | 90.3 |
| Ex. 50 | 2 | 29.1 | 14.6 | 87.7 | 98.1 |
| Ex. 51 | 9.9 | 10.5 | 1.1 | 65 | 85.7 |
| Ex. 52 | 7.4 | 10.9 | 1.5 | 64.1 | 91.7 |
| Ex. 53 | 9.3 | 9.7 | 1 | 63.1 | 90.9 |
| Ex. 55 | 6.5 | 7 | 1.1 | 65.2 | 83.8 |
| Ex. 57 | 1.3 | 3.5 | 2.7 | 61.9 | 86.8 |
| Ex. 58 | 5.1 | 3.4 | 0.7 | 52.3 | 83.5 |
| Ex. 59 | 3.1 | 15 | 4.8 | 61.5 | 91.5 |
| Ex. 59A | 3.1 | 9.6 | 3.1 | 55.6 | 85.5 |
| Ex. 59B | 4.6 | 9.7 | 2.1 | 56.2 | 82 |
| Ex. 60 | 15.6 | 13.3 | 0.9 | 59.8 | 90.8 |
| Ex. 60A | 12 | 11.2 | 0.9 | 55.3 | 86 |
| Ex. 60B | 11.6 | 13.5 | 1.2 | 51.2 | 84.3 |
| Ex. 63 | 10.5 | 26.7 | 2.5 | 83.6 | 90 |
| Ex. 64 | 2.2 | 27.4 | 12.5 | 79.7 | 95.9 |
| Ex. 66A | 2.9 | 3.9 | 1.4 | 64.9 | 81.2 |
| Ex. 67A | 10.5 | 6.9 | 0.7 | 50.7 | 78.6 |

Example 77. Human Liver Microsome Stability

The stability of the claimed compounds was determined in the presences of human liver microsomes. The compounds were incubated with the microsomes at 37° C. for 45 minutes. Samples were analyzed using LC-MS/MS. Data analysis included half-life, clearance rate, and the percentage of hepatic blood flow (% QH) for each of the compounds in the different species. Below are liver microsome assat data of representative compounds, which show that the claimed compounds have superior metabolic stability.

TABLE 3

| | Human Liver Microsome Stability | | |
|---|---|---|---|
| | Half Life (min) | Clearance (μg/min/mg) | % QH |
| Ex. 29 | 20.5 | 68.0 | 78.8 |
| Ex. 31 | 22.4 | 61.9 | 77.3 |
| Ex. 66A | 77.6 | 18.2 | 49.6 |
| Ex. 67A | >300 | <4.6 | <20.3 |

Example 78. Cell Line Screen

The activity of the claimed compounds was measured in a variety of cell lines with different expression levels of activation induced cytidine deaminase (AICDA). The potency assay was repeated in all of the listed cell lines and the $EC_{50}$ values recorded.

TABLE 4

| Cell Line (Cancer Type) | AICDA Expression | EC$_{50}$ (nM) Ex. 29 | EC$_{50}$ (nM) Ex. 31 | EC$_{50}$ (nM) Ex. 66A | EC$_{50}$ (nM) Ex. 67A |
|---|---|---|---|---|---|
| Daudi (Lymphoma) | High | 43 | 20 | 18 | 311 |
| WSU-FSCCL (Lymphoma) | Negative | 67 | <40 | 25 | 344 |
| U-698-M (Lymphoma) | High | 113 | 31 | 88 | 791 |
| CCRF-SB (Leukemia) | High | 1283 | 2164 | 183 | 932 |
| KYSE-70 (Head and Neck) | Low | 4660 | 4701 | 2639 | 2629 |
| SNU-1 (Gastric) | Negative | n.d. | n.d. | 609 | 2927 |
| KG-1 (Leukemia) | Negative | >10000 | 8785 | 3067 | 2995 |
| KYSE-510 (Head and Neck) | Negative | >10000 | >10000 | 4516 | 3403 |
| SNU-5 (Gastric) | Low | n.d. | n.d. | 2941 | 3845 |
| TOV-1120D (Ovary) | Negative | 9172 | n.d. | 2377 | 4924 |
| OV56 (Ovary) | Low | 9086 | n.d. | 5944 | 7228 |
| ARPE19/HPV16 (HPV Immortalized RPE) | Negative | >10000 | >10000 | >10000 | >10000 |
| WI-38 (Normal Human Lung Fibroblast) | Negative | >10000 | >10000 | >10000 | >10000 | n.d. not determined

Example 79. Pharmacokinetic (PK)

PK studies in mice were used to determine the fate of the compounds in a whole organism. Rats were treated with the compounds either orally of via IV at the indicated doses and followed for up to 24 hours. Plasma samples were taken at different time points and analyzed by LC-MS.

TABLE 5

| po @ 80 mg/kg (Formulation: 30% PEG400, 10% Vitamin E TPGS in water) | | Ex. 29 | Ex. 31 | Ex. 66A | Ex. 67A |
|---|---|---|---|---|---|
| Rat Female | T$_{1/2}$ (hr) | 4.66 | 4.75 | 2.59 | 11.5 |
| | F (%) @ 5 mg/kg | 8.39 | 2.77 | 3.31 | 86.5 |
| Rat Male | T$_{1/2}$ (hr) | 3.97 | 3.79 | 1.86 | 6.46 |
| | F (%) @ 5 mg/kg | 3.69 | 1.49 | 2.55 | 46.9 |

What is claimed is:

1. A method of treating lymphoma, comprising administering to a subject in need thereof an effective amount of a compound represented by the following structural formula:

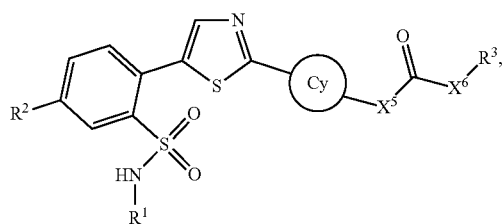

or a pharmaceutically acceptable salt thereof, wherein:
the thiazole ring is optionally substituted with F or Cl;
Cy is $(C_3-C_7)$cycloalkyl, bridged $(C_6-C_{12})$cycloalkyl, or a 4-10 membered heterocyclic ring, each of which is optionally substituted with one or more groups selected from the group consisting of halogen, OH, $(C_1-C_4)$alkyl, and $(C_1-C_4)$alkoxy;

when $X^5$ is connected with a nitrogen ring atom of Cy, $X^5$ is absent;
when $X^5$ is connected with a carbon ring atom of Cy, $X^5$ is $NR^a$ or O;
$X^6$ is $NR^a$ or O;
$R^1$ is $(C_1-C_5)$alkyl optionally substituted with OH;
$R^3$ is $(C_1-C_5)$alkyl, —CH$_2$-phenyl, $(C_3-C_7)$cycloalkyl, —CH$_2$—$(C_3-C_7)$cycloalkyl, —CH$_2$-monocyclic 3-7 membered heterocyclic ring, or monocyclic 3-7 membered heterocyclic ring, wherein the $(C_1-C_5)$ alkyl, $(C_3-C_7)$cycloalkyl, phenyl, or monocyclic 3-7 membered heterocyclic ring represented by $R^3$ or in the group represented by $R^3$ is optionally substituted with one or more groups selected from the group consisting of halogen, OH, $(C_1-C_4)$alkyl, halomethyl, halomethoxy, CN, and $(C_1-C_4)$alkoxy;
$R^2$ is —NR$^a$C(O)O(C$_1$-C$_4$)alkyl, —NR$^a$C(O)NR$^a$(C$_1$-C$_4$)alkyl, —NR$^a$C(O)O(C$_2$-C$_4$)alkenyl, —NR$^a$C(O)NR$^a$(C$_2$-C$_4$)alkenyl, —NR$^a$C(O)O—(C$_3$-C$_6$)cycloalkyl, —NR$^a$C(O)NR$^a$—(C$_3$-C$_7$)cycloalkyl, —NR$^a$C(O)O-phenyl, —NR$^a$C(O)NR$^a$-phenyl, —NR$^a$C(O)O-monocyclic 3-7 membered heterocyclic ring, —NR$^a$C(O)NR$^a$-monocyclic 3-7 membered heterocyclic ring, —NR$^a$C(O)O-monocyclic 5-6 membered heteroaromatic ring, or —NR$^a$C(O)NR$^a$-monocyclic 5-6 membered heteroaromatic ring;
wherein the $(C_1-C_4)$alkyl and the $(C_2-C_4)$alkenyl in the group represented by $R^2$ are each optionally and independently substituted with one or more groups selected from the group consisting of halogen, N$_3$, OR$^a$, NR$^a$R$^a$, $(C_3-C_6)$cycloalkyl, phenyl, a monocyclic 3-7 membered heterocyclic ring, and a monocyclic 5-6 membered heteroaromatic ring;
wherein the $(C_3-C_7)$cycloalkyl in the group represented by $R^2$ is optionally substituted with one or more groups selected from the group consisting of halogen, CH$_3$, =O, OR$^a$, and NR$^a$R$^a$;
wherein the phenyl in the group represented by $R^2$ is optionally substituted with one or more groups selected from the group consisting of halogen, CH$_3$, halomethyl, halomethoxy, CN, OR$^a$, and N$_3$;

wherein the heterocyclic ring in the group represented by R² is optionally substituted with one or more groups selected from the group consisting of =O, halogen, ORᵃ, CH₃, halomethyl, and halomethoxy;

wherein the heteroaromatic ring in the group represented by R² is optionally substituted with one or more groups selected from the group consisting of halogen, CN, CH₃, halomethyl, halomethoxy, ORᵃ, and NRᵃRᵃ; and each Rᵃ is independently H or CH₃.

2. The method of claim 1, wherein the compound is represented by the following structural formula:

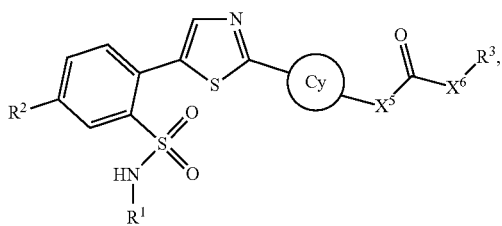

or a pharmaceutically acceptable salt thereof, wherein:
the thiazole ring is optionally substituted with F or Cl;
Cy is cyclohexyl or a 6-membered monocyclic heterocyclic ring;
X⁵ and X⁶ are each independently NRᵃ or O;
R¹ is (C₁-C₅)alkyl;
R³ is (C₁-C₅)alkyl or monocyclic 3-7-membered heterocyclic ring;
R² is —NRᵃC(O)O(C₁-C₄)alkyl, —NRᵃC(O)NRᵃ(C₁-C₄)alkyl, —NRᵃC(O)O(C₂-C₄)alkenyl, —NRᵃC(O)NRᵃ(C₂-C₄)alkenyl, —NRᵃC(O)—O(C₃-C₆)cycloalkyl, —NRᵃC(O)NRᵃ—(C₃-C₆)cycloalkyl, —NRᵃC(O)O-phenyl, —NRᵃC(O)NRᵃ-phenyl, —NRᵃC(O)O-monocyclic 3-7 membered heterocyclic ring, —NRᵃC(O)NRᵃ-monocyclic 3-7 membered heterocyclic ring, —NRᵃC(O)O-monocyclic 5-6 membered heteroaromatic ring, or —NRᵃC(O)NRᵃ-monocyclic 5-6 membered heteroaromatic ring;
wherein the (C₁-C₄)alkyl and the (C₂-C₄)alkenyl in the group represented by R² are each optionally and independently substituted with one or more halogen, N₃, ORᵃ, NRᵃRᵃ, (C₃-C₆)cycloalkyl, phenyl, monocyclic 3-7-membered heterocyclic ring, or monocyclic 5-6-membered heteroaromatic ring;
wherein the (C₃-C₆)cycloalkyl in the group represented by R² is optionally substituted with one or more halogen, CH₃, ORᵃ, or NRᵃRᵃ;
wherein the phenyl in the group represented by R² is optionally substituted with one or more halogen, CH₃, halomethyl, halomethoxy, ORᵃ, or N₃;
wherein the heterocyclic ring in the group represented by R² is optionally substituted with one or more =O, halogen, CH₃, halomethyl, or halomethoxy;
wherein the heteroaromatic ring in the group represented by R² is optionally substituted with one or more halogen, CH₃, halomethyl, halomethoxy, ORᵃ, or NRᵃRᵃ; and
each Rᵃ is independently H or CH₃.

3. The method of claim 1, wherein Cy is
cyclopropyl, cyclobutyl, cyclopentyl, cyclohexyl, cycloheptyl,
azetidinyl, azepanyl, diazaspiro[4.4]nonyl, diazaspiro[3.5]nonyl, diazepanyl, dihydroimidazolyl, dihydrofuranyl, dihydropyranyl, dihydropyridinyl, dihydropyrimidinyl, dihydrothienyl, dihydrothiophenyl, dihydrothiopyranyl, hexahydropyridazinyl, hexahydropyrimidinyl, hydantoinyl, indolinyl, isoindolinyl, morpholinyl, oxiranyl, oxetanyl, piperidinyl, piperazinyl, pyrrolidinonyl, pyrrolidinyl, tetrahydrofuranyl, tetrahydroimidazolyl, tetrahydroindolyl, tetrahydropyranyl, tetrahydrothienyl, tetrahydropyridinyl, tetrahydropyrimidinyl, tetrahydrothiophenyl, tetrahydrothiopyranyl, thiomorpholinyl, tropanyl, valerolactamyl,
bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, adamantly,
azanorbornyl, quinuclidinyl, isoquinuclidinyl, tropanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, azabicyclo [3.3.1]nonanyl, diazabicyclo[2.2.1]heptanyl, diazabicyclo[3.2.1]octanyl, octahydropyrrolo[3,4-b]pyrrolyl, or octahydropyrrolo[3,4-c]pyrrolyl.

4. The method of claim 1, wherein the compound is represented by the following structural formula:

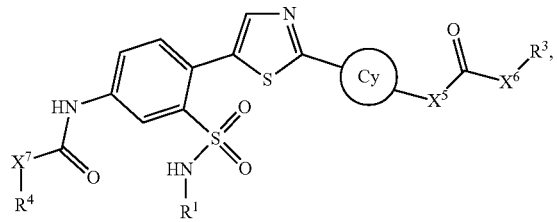

or a pharmaceutically acceptable salt thereof, wherein:
X⁷ is NH or O;
R⁴ is (C₁-C₄)alkyl, (C₃-C₆)cycloalkyl, or a monocyclic 3-7 membered heterocyclic ring;
wherein the (C₁-C₄)alkyl represented by R⁴ is optionally substituted with one or more groups selected from the group consisting of halogen, N₃, ORᵃ, NRᵃRᵃ, (C₃-C₆)cycloalkyl, phenyl, a monocyclic 3-7 membered heterocyclic ring, and a monocyclic 5-6 membered heteroaromatic ring,
wherein the (C₃-C₆)cycloalkyl or the monocyclic 3-7 membered heterocyclic ring represented by R⁴ or the (C₃-C₆)cycloalkyl or the monocyclic 3-7 membered heterocyclic ring in the group represented by R⁴ is optionally substituted with one or more groups selected from the group consisting of halogen, ORᵃ, =O, and CH₃,
wherein the phenyl in the group represented by R⁴ is optionally substituted with one or more groups selected from the group consisting of halogen, CH₃, halomethyl, halomethoxy, OR, and N₃;
wherein the heteroaromatic ring in the group represented by R⁴ is optionally substituted with one or more groups selected from the group consisting of halogen and CH₃.

5. The method of claim 4, wherein:
X⁷ is NH or O;
R³ is (C₁-C₅)alkyl;
R⁴ is (C₁-C₄)alkyl optionally substituted with one or more halogen, ORᵃ, NRᵃRᵃ, (C₃-C₆)cycloalkyl, phenyl, monocyclic 3-7-membered heterocyclic ring, or monocyclic 5-6-membered heteroaromatic ring;
wherein the phenyl is optionally substituted with one or more halogen, $CH_3$, halomethyl, halomethoxy, $OR^a$, or $N_3$;
wherein the 3-7-membered heterocyclic ring is optionally substituted with one or more =O, halogen, or $CH_3$; and
wherein the 5-6-membered heteroaromatic ring is optionally substituted with one or more halogen or $CH_3$.

6. The method of claim 4, wherein $R^4$ is $(C_1-C_3)$alkyl, $(C_3-C_6)$cycloalkyl, or a monocyclic 3-7 membered heterocyclic ring, wherein the $(C_1-C_3)$alkyl is optionally substituted with (i) phenyl optionally substituted by one or more halogen or $CH_3$; (ii) a monocyclic 5-6 membered heteroaromatic ring optionally substituted by one or more halogen or $CH_3$; or (iii) a monocyclic 3-7 membered heterocyclic ring optionally substituted by one or more halogen or $CH_3$.

7. The method of claim 4, wherein $R^4$ is $(C_1-C_3)$alkyl, $CH_2$-phenyl, $CH_2$-5-6 membered heteroaromatic ring, or $CH_2$-3-7 membered monocyclic heterocyclic ring, wherein the phenyl, 5-6 membered heteroaromatic ring, or 3-7 membered monocyclic heterocyclic ring in the group represented by $R^4$ is optionally substituted by one or more groups selected from the group consisting of halogen and $CH_3$.

8. The method of claim 4, wherein $R^4$ is $(C_1-C_3)$alkyl optionally substituted with (i) phenyl optionally substituted by one or more halogen, $CH_3$, halomethyl, halomethoxy, $OR^a$, or $N_3$; (ii) a monocyclic 5-6-membered heteroaromatic ring optionally substituted by one or more halogen or $CH_3$; or (iii) a monocyclic 3-7 membered heterocyclic ring optionally substituted by one or more =O or $CH_3$.

9. The method of claim 4, wherein $R^4$ is (i) $(C_1-C_3)$alkyl; (ii) $CH_2$-phenyl optionally substituted by halogen, $CH_3$, halomethyl, halomethoxy, $OR^a$, or $N_3$; (iii) $CH(CH_3)$-phenyl optionally substituted by halogen, $CH_3$, halomethyl, halomethoxy, $OR^a$, or $N_3$; (iv) $CH_2$-5-6 membered heteroaromatic ring optionally substituted by halogen or $CH_3$; or (v) $CH_2$-3-7 membered monocyclic heterocyclic ring optionally substituted by =O or $CH_3$.

10. The method of claim 4, wherein $R^4$ is

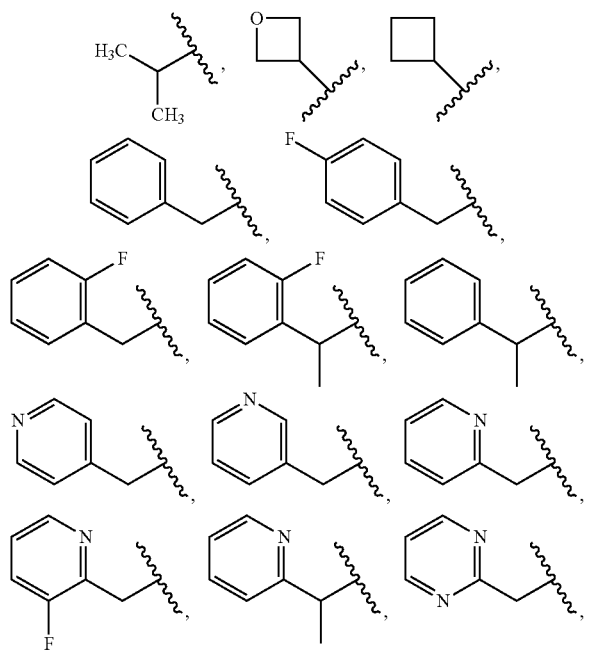

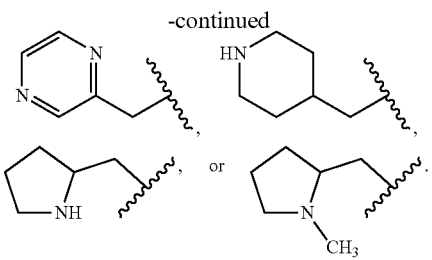

11. The method of claim 4, wherein the compound is represented by a structural formula selected from:

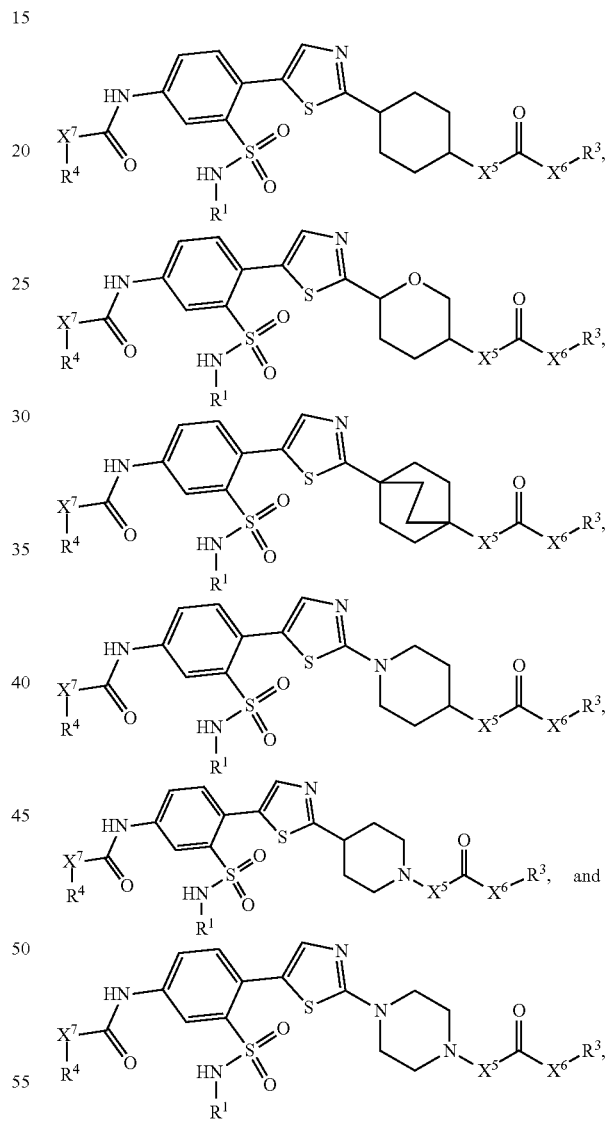

or a pharmaceutically acceptable salt thereof.

12. The method of claim 1, wherein Cy is azetidinyl or pyrrolidinyl, and the nitrogen ring atom is connected with the thiazole ring.

13. The method of claim 1, wherein Cy is 1,7-diazaspiro[4.4]nonyl, 2,7-diazaspiro[4.4]nonyl, 2,7-diazaspiro[3.5]nonyl, 1,4-diazepanyl, 2,5-diazabicyclo[2.2.1]heptanyl, 3,8-diazabicyclo[3.2.1]octanyl, octahydropyrrolo[3,4-b]pyrrolyl, or octahydropyrrolo[3,4-c]pyrrolyl, and the two nitrogen ring atoms are connected with the thiazole ring and the $X^5C(O)X^6R^3$ moiety, respectively.

14. The method of claim 1, wherein $R^3$ is $(C_1-C_4)$alkyl, $(C_4-C_6)$cycloalkyl, $CH_2$-phenyl, $CH_2$-monocyclic 4-6 membered heterocyclic ring, or monocyclic 4-6 membered heterocyclic ring, wherein the phenyl or monocyclic 4-6 membered heterocyclic ring represented by $R^3$ or in the group represented by $R^3$ is optionally substituted with one or more groups selected from the group consisting of halogen, OH, $OCH_3$, and $CH_3$.

15. The method of claim 1, wherein $R^3$ is isopropyl, tert-butyl, cyclobutyl, cyclopentyl, benzyl, oxetanyl, tetrahydro-2H-pyranyl, or $CH_3$

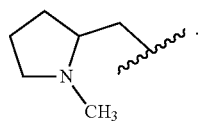

16. The method of claim 1, wherein $R^3$ is isopropyl or oxetanyl.

17. The method of claim 1, wherein R is tert-butyl.

18. The method of claim 4, wherein the compound is represented by a structural formula selected from:

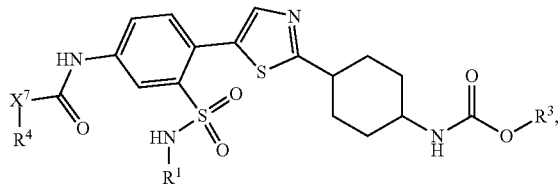

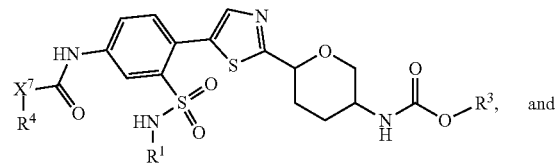

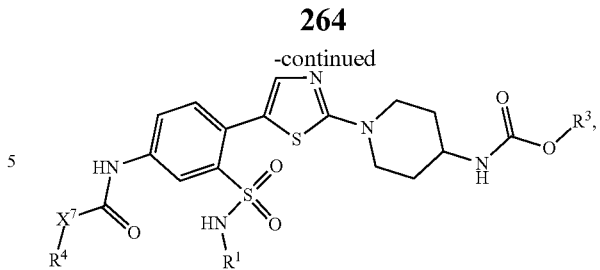

or a pharmaceutically acceptable salt thereof.

19. The method of claim 1, wherein the compound is of the following structure:

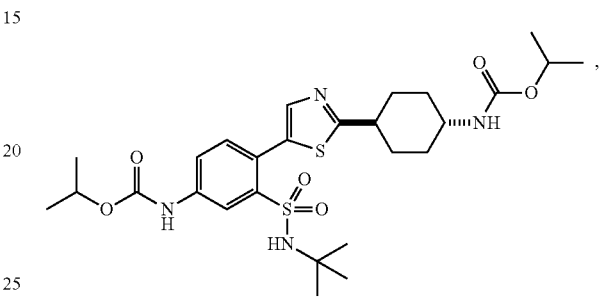

or a pharmaceutically acceptable salt thereof.

20. The method of claim 1, wherein the compound is of the following structure:

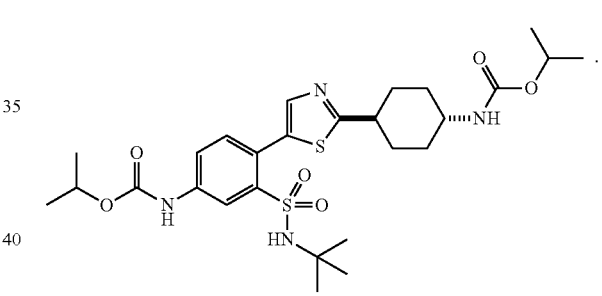

21. The method of claim 1, wherein the lymphoma is a B-cell lymphoma.

22. The method of claim 21, wherein the B-cell lymphoma is diffuse large B-cell lymphoma.

23. The method of claim 1, wherein the lymphoma is a Non-Hodgkin's lymphoma.

* * * * *